(12) United States Patent
Reich et al.

(10) Patent No.: US 8,268,814 B2
(45) Date of Patent: Sep. 18, 2012

(54) SUBSTITUTED SULFONAMIDE COMPOUNDS

(75) Inventors: Melanie Reich, Aachen (DE); Ellen Klegraf, Brig (CH); Stefan Oberboersch, Aachen (DE); Stefan Schunk, Aachen (DE); Ruth Jostock, Stolberg (DE); Sabine Hees, Aachen (DE); Tieno Germann, Aachen (DE); Michael Engels, Turnhout (BE)

(73) Assignee: Gruenenthal GmbH, Aachen (DE)

( * ) Notice: Subject to any disclaimer, the term of this patent is extended or adjusted under 35 U.S.C. 154(b) by 89 days.

(21) Appl. No.: 12/421,230

(22) Filed: Apr. 9, 2009

(65) Prior Publication Data

US 2009/0275558 A1    Nov. 5, 2009

Related U.S. Application Data

(60) Provisional application No. 61/043,507, filed on Apr. 9, 2008.

(30) Foreign Application Priority Data

Apr. 9, 2008 (EP) .................................. 08007026

(51) Int. Cl.
*A61K 31/55* (2006.01)
*A61K 31/44* (2006.01)
*A61K 31/40* (2006.01)
*C07D 223/16* (2006.01)
*C07D 221/02* (2006.01)
*C07D 209/00* (2006.01)

(52) U.S. Cl. ........ 514/218; 514/300; 514/412; 540/593; 546/112; 546/113; 548/452

(58) Field of Classification Search .................. 514/218, 514/300, 412; 540/593; 546/112, 113; 548/452
See application file for complete search history.

(56) References Cited

U.S. PATENT DOCUMENTS 6,350,755 B1 * 2/2002 deSolms et al. ............... 514/281
2009/0186899 A1 * 7/2009 Merla et al. ................... 514/249
2009/0203672 A1 * 8/2009 Merla et al. ............. 514/217.05

FOREIGN PATENT DOCUMENTS

WO    WO 2007/140383 A2    12/2007

OTHER PUBLICATIONS

Mori MA, Araújo RC, Reis FC, Sgai DG, Fonseca RG, Barros CC, Merino VF, Passadore M, Barbosa AM, Ferrari B, Carayon P, Castro CH, Shimuta SI, Luz J, Bascands JL, Schanstra JP, Even PC, Oliveira SM, Bader M, and Pesquero JB, "Kinin B1 receptor deficiency leads to leptin hypersensitivity and resistance to obesity," Diabetes, Jun. 2008, 57(6), 1491-1500.*
Greene TW and Wuts PGM. Protective Groups in Organic Synthesis, 3rd ed., 1999.*

J. Fred Hess, et al, "Generation and Characterization of a Humanized bradykinin B1 Receptor Mouse", Biol. Chem., Feb. 2006, pp. 195-201, vol. 387.
R. Hayashi, et al., "Bradykinin Stimulates IL-6 and IL-8 Production by Human Lung Fibroblasts through ERK- and p38 MAPK-dependent Mechanisms", European Respiratory Journal, 2000, pp. 452-458, vol. 16.
Bichoy H. Gabra, et al, "The Kinin System Mediates Hyperalgesia through the Inducible Bradykinin B1 Receptor Subtype: Evidence in Various Experimental Animal Models of Type 1 and Type 2 Diabetic Neuropathy", Biol. Chem., Feb. 2006, pp. 127-143, vol. 387.
Joao B. Calixto, et al., "Kinin $B_1$ Receptors: Key G-Protein-Coupled Receptors and Their Role in Inflammatory and Painful Processes", British Journal of Pharmacology, 2004, pp. 803-818, vol. 143.
Sara H. Bengtson, et al., "Kinin Receptor Expression During *Staphylococcus aureus* Infection", Blood, 2006, pp. 2055-2063, vol. 108.
Antoni Stadnicki, et al., "Immunolocalization and Expression of Kinin $B_1R$ and $B_2R$ Receptors in Human Inflammatory Bowel Disease", AJP Gastrointest Liver Physiol, Aug. 2005, pp. G361-G366, vol. 289.
A. Prat, et al., "Bradykinin $B_1$ Receptor Expression and Function on T Lymphocytes in Active Multiple Sclerosis", Dec. 10, 1999, pp. 2087-2092, vol. 53, No. 9, American Academy of Neurology.
Joao B. Pesquero, et al., Genetically Altered Animal Models in the Kallikrein-Kinin System, Biol. Chem., Feb. 2006, pp. 119-126, vol. 387.
Joao B. Pesquero, et al., "Hypoalgesia and Altered Inflammatory Responses in Mice Lacking Kinin B1 Receptors", PNAS, Jul. 5, 2000, pp. 8140-8145, vol. 97, No. 14.
Giselle F. Passos, et al., "Kinin $B_1$ Receptor Up-Regulation after Lipopolysaccharide Administration: Role of Proinflammatory Cytokines and Neutrophil Influx[1]", The Journal of Immunology, 2004, pp. 1839-1847, vol. 172.
L. M. Fredrik Leeb-Lundberg, et al., "International Union of Pharmacology. XLV. Classification of the KInin Receptor Family: from Molecular Mechanisms to Pathophysiological Consequences", Pharmacological Reviews, 2005, pp. 27-77, vol. 57, No. 1.

(Continued)

*Primary Examiner* — Paul Zarek
(74) *Attorney, Agent, or Firm* — Crowell & Moring LLP

(57) ABSTRACT

Substituted sulfonamide compounds corresponding to formula I

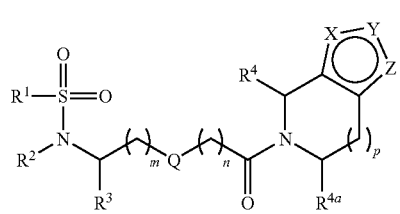

processes for the preparation thereof, pharmaceutical compositions containing such compounds, and the use of such compounds for treating and/or inhibiting pain or other conditions at least partly mediated by the bradykinin 1 receptor.

20 Claims, No Drawings

OTHER PUBLICATIONS

European Search Report including partial translation dated Aug. 21, 2008 (Five (5) pages).
English translation of International Search dated Jun. 25, 2009 and PCT/ISA/237 Form (Eleven (11) pages).
Robert W. Colman, "Regulation of angiogenesis by the kallikrein-kinin system", Current Pharmaceutical Design, vol. 12, No. 21, pp. 2599-2607, 2006.
Parenti et al., "The bradykinin/B1 receptor promotes angiogenesis by up-regulation of endogenous FGF-2 in endothelium via the nitric oxide synthase pathway", FASEB J 2001; 15: 1497-1489.
Prat et al., "Bradykinin $B_1$ receptor expression and function on T lymphocytes in active multiple sclerosis", Neurology, 1999, 53(9), 2087-2092.
Göbel et al., "Blockade of the kinin receptor B1 protects from autoimmune CNS disease by reducing leukocyte trafficking", Journal of Autoimmunity, 2010, 1-9.
Rodi et al., "Targeting kinin receptors for the treatment of neurological diseases", Current Pharmaceutical Design, 2005, 11, 1313-1326.
Austinat et al., "Blockade of bradykinin receptor B1 but not bradykinin receptor B2 provides protection from cerebral infarction and brain edema", Stroke, 2009, 40(1), 285-293.

* cited by examiner

SUBSTITUTED SULFONAMIDE COMPOUNDS

CROSS REFERENCE TO RELATED APPLICATIONS

This application claims priority from U.S. provisional patent application No. 61/043,507 and from European patent application no. EP 08007026.1, both filed Apr. 9, 2008, the entire disclosures of which are incorporated herein by reference.

BACKGROUND OF THE INVENTION

The present invention relates to substituted sulfonamide compounds, processes for the preparation thereof, pharmaceutical compositions containing these compounds, and the use of such substituted sulfonamide compounds in pharmaceutical compositions for treatment or inhibition of pain and/or other conditions at least partially mediated by the bradykinin 1 receptor.

In contrast to the constitutive expression of the bradykinin 2 receptor (B2R), in most tissues the bradykinin 1 receptor (B1R) is not expressed or expressed only weakly. Nevertheless, expression of B1R can be induced on various cells. For example, in the course of inflammation reactions a rapid and pronounced induction of B1R takes place on neuronal cells, but also various peripheral cells, such as fibroblasts, endothelial cells, granulocytes, macrophages and lymphocytes. In the course of inflammation reactions, a switch from a B2R to a B1R dominance thus occurs on the cells involved. The cytokines interleukin-1 (IL-1) and tumour necrosis factor alpha (TNFα) are involved to a considerable degree in this upwards regulation of BIR (Passos et al. J. Immunol. 2004, 172, 1839-1847). After activation with specific ligands, B1R-expressing cells then themselves can secrete inflammation-promoting cytokines such as IL-6 and IL-8 (Hayashi et al., Eur. Respir. J. 2000, 16,452-458). This leads to inwards migration of further inflammation cells, e.g. neutrophilic granulocytes (Pesquero et al., PNAS 2000, 97, 8140-8145). The bradykinin B1R system can contribute towards chronification of diseases via these mechanisms. This is demonstrated by a large number of animal studies (overviews in Leeb-Lundberg et al., Pharmacol. Rev. 2005, 57, 27-77 und Pesquero et al., Biol. Chem. 2006, 387, 119-126). On humans too, an enhanced expression of B1R, e.g. on enterocytes and macrophages in the affected tissue of patients with inflammatory intestinal diseases (Stadnicki et al., Am. J. Physiol. Gastrointest. Liver Physiol. 2005, 289, G361-366) or on T lymphocytes of patients with multiple sclerosis (Pratet et al., Neurology. 1999; 53, 2087-2092) or an activation of the bradykinin B2R-B1R system in the course of infections with *Staphylococcus aureus* (Bengtson et al., Blood 2006, 108, 2055-2063) is found. Infections with *Staphylococcus aureus* are responsible for syndromes such as superficial infections of the skin up to septic shock.

Based on the described pathophysiological relationships, there is a great therapeutic potential for the use of B1R antagonists on acute and, in particular, chronically inflammatory diseases. These include diseases of the respiratory tract (bronchial asthma, allergies, COPD/chronic obstructive pulmonary disease, cystic fibrosis etc.), inflammatory intestinal diseases (ulcerative colitis, CD/Crohn's disease etc.), neurological diseases (multiple sclerosis, neurodegeneration etc.), inflammations of the skin (atopic dermatitis, psoriasis, bacterial infections etc.) and mucous membranes (Behcet's disease, pelvitis, prostatitis etc.), rheumatic diseases (rheumatoid arthritis, osteoarthritis etc.), septic shock and reperfusion syndrome (following cardiac infarction, stroke).

The bradykinin receptor system is moreover also involved in regulation of angiogenesis and has potential as an angiogenesis inhibitor in cancer cases and macular degeneration on the eye. B1R knockout mice also are protected from induction of obesity by a particularly fat-rich diet (Pesquero et al., Biol. Chem. 2006, 387, 119-126). B1R antagonists are therefore also suitable for treatment of obesity.

B1R antagonists are suitable in particular for treatment of pain, in particular inflammation pain and neuropathic pain (Calixto et al., Br. J. Pharmacol. 2004, 1-16), and here in particular diabetic neuropathy (Gabra et al., Biol. Chem. 2006, 387, 127-143). They are furthermore suitable for treatment of migraine.

In the development of B1R modulators, however, there is the problem that the human and the rat B1R receptor differ so widely that many compounds which are good B1R modulators on the human receptor have only a poor or no affinity for the rat receptor. This makes pharmacological studies on animals considerably difficult, since many studies are usually conducted on the rat. However, if no activity exists on the rat receptor, neither the action nor side effects can be investigated on the rat. This has already led to transgenic animals with human B1 receptors being produced for pharmacological studies on animals (Hess et al., Biol. Chem. 2006; 387(2): 195-201). Working with transgenic animals, however, is more expensive than working with the unmodified animals. Since in the development of pharmaceutical compositions, however, precisely long-term toxicity studies on the rat belong to the standard studies, but this is inappropriate in the event of an absence of activity on the receptor, an important established instrument for checking safety is lacking for the development of such compounds. There is therefore a need for novel B1R modulators, B1R modulators which bind both to the rat receptor and to the human receptor offering particular advantages.

SUMMARY OF THE INVENTION

It Is therefore an object of the present invention to provide new compounds which are suitable in particular as pharmacological active compounds in pharmaceutical compositions.

A particular object of the invention is to provide new active compounds which are useful in treating and/or inhibiting disorders or diseases which are at least partly mediated by B1R receptors.

These and other objects are achieved by the substituted sulfonamide compounds as described and claimed hereinafter.

The invention therefore provides substituted sulfonamide compounds corresponding to formula I

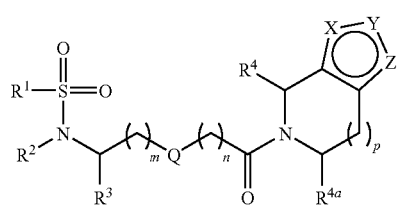

wherein
m and n each independently represent 0, 1 or 2;
p represents 0, 1 or 2;
Q represents a single bond, —$CH_2$— or —O—;

X represents N, NR$^5$, O, S or CR$^8$;
Y represents N, NR$^6$, O, S or CR$^9$;
Z represents N, NR$^7$, O, S or CR$^{10}$;
R$^1$ represents CH(aryl)$_2$, aryl, heteroaryl, or a CH(aryl)$_2$, aryl or heteroaryl bonded via a C$_{1-3}$-alkylene group;
R$^2$ and R$^3$ are defined as described under (i) or (ii):
(i) R$^2$ represents H, C$_{1-6}$-alkyl, C$_{3-8}$-cycloalkyl, bicyclic 8- to 12-membered carbocyclyl, CH(aryl)$_2$, aryl or heteroaryl; or denotes a C$_{3-8}$-cycloalkyl, bicyclic 8- to 12-membered carbocyclyl, CH(aryl)$_2$, aryl or heteroaryl bonded via a C$_{1-6}$-alkylene group, C$_{2-6}$-alkenylene group or C$_{2-6}$-alkynylene group; and R$^3$ represents H, —C(=O)—NR$^{11}$R$^{12}$, —C(=O)—OR$^{13}$, C$_{1-6}$-alkyl, aryl or heteroaryl; or denotes an aryl or heteroaryl bonded via a C$_{1-6}$-alkylene group, C$_{2-6}$-alkenylene group or C$_{2-6}$-alkynylene group, wherein R$^2$ and R$^3$ do not both simultaneously represent H, or
(ii) R$^2$ and R$^3$ together with the —N—(CH—)- group joining them form an unsubstituted or mono- or polysubstituted, e.g. di-, tri- or tetrasubstituted, 4-, 5-, 6- or 7-membered heterocyclic ring, which can be fused with an aryl or heteroaryl group, wherein said heterocyclic ring may be saturated or mono- or polyunsaturated, but not aromatic, and optionally may contain, in addition to the N hetero atom to which R$^2$ is bonded, at least one, e.g. 1 or 2, further hetero atom(s) or hetero atom group(s) selected from the group consisting of N, NR$^{14}$, O, S, S=O or S(=O)$_2$; wherein
R$^{14}$ denotes H, C$_{1-6}$-alkyl, —C(=O)—R$^{15}$, C$_{3-8}$-cycloalkyl, aryl, heteroaryl or a C$_{3-8}$-cycloalkyl, aryl or heteroaryl bonded via a C$_{1-3}$-alkylene group, and
R$^{15}$ denotes C$_{1-6}$-alkyl, C$_{3-8}$-cycloalkyl, aryl, heteroaryl or a C$_{3-8}$-cycloalkyl, aryl or heteroaryl bonded via a C$_{1-3}$-alkylene group,
R$^4$ and R$^{4a}$ each independently represent H, C$_{1-6}$-alkyl, C$_{3-8}$-cycloalkyl, aryl, heteroaryl or a C$_{3-8}$-cycloalkyl, aryl or heteroaryl bonded via a C$_{1-3}$-alkylene group;
R$^5$, R$^6$ and R$^7$ each independently represent H, C$_{1-6}$-alkyl, aryl or heteroaryl;
R$^8$, R$^9$ and R$^{10}$ each independently represent H, —CF$_3$, —C(=O)—NR$^{11}$R$^{12}$, —C$_{1-6}$-alkylene-C(=O)—NR$^{11}$R$^{12}$, —C$_{1-6}$C-alkylene-NR$^{11}$R$^{12}$, C$_{3-8}$-cycloalkyl, 3- to 8-membered heterocycloalkyl, aryl or heteroaryl or a C$_{3-8}$-cycloalkyl, 3- to 8-membered heterocycloalkyl, aryl or heteroaryl bonded via a C$_{1-6}$-alkylene group, wherein preferably at least one of the groups R$^4$, R$^{4a}$, R$^5$, R$^6$, R$^7$, R$^8$, R$^9$ and R$^{10}$ does not represent H,
R$^{11}$ and R$^{12}$ are defined as described under (iii) or (iv):
(iii) R$^{11}$ and R$^{12}$ each independently denote H, C$_{1-6}$-alkyl, C$_{2-6}$-alkenyl, C$_{3-8}$-cycloalkyl, 3- to 8-membered heterocycloalkyl, aryl or heteroaryl or a C$_{3-8}$-cycloalkyl, 3- to 8-membered heterocycloalkyl, aryl or heteroaryl bonded via a C$_{1-3}$-alkylene group; or
(iv) R$^{11}$ and R$^{12}$ together with the nitrogen atom joining them form an unsubstituted or mono- or polysubstituted, e.g. di-, tri- or tetrasubstituted, 4-, 5-, 6- or 7-membered heterocyclic ring, which optionally may be fused with a saturated, mono- or polyunsaturated or aromatic, unsubstituted or mono- or polysubstituted 4-, 5-, 6- or 7-membered ring system, wherein said heterocyclic ring may be saturated, or mono- or polyunsaturated, but not aromatic, and optionally may contain, in addition to the N hetero atom to which the groups R$^{11}$ and R$^{12}$ are bonded, at least one, e.g. 1 or 2, further hetero atom(s) or hetero atom group(s) selected from the group consisting of N, NR$^{16}$, O, S, S=O and S(=O)$_2$, and said ring system optionally may contain one or more, e.g. 1 or 2, hetero atom(s) or hetero atom group(s) selected from the group consisting of N, NR$^{17}$, O, S, S=O and S(=O)$_2$, wherein
R$^{16}$ is selected from the group consisting of H, C$_{1-6}$-alkyl, C$_{3-8}$-cycloalkyl, aryl, heteroaryl or an aryl, heteroaryl or C$_{3-8}$-cycloalkyl bonded via a C$_{1-3}$-alkylene group; and
R$^{17}$ is selected from the group consisting of H, C$_{1-6}$-alkyl, C$_{3-8}$-cycloalkyl, aryl, heteroaryl or an aryl, heteroaryl or C$_{3-8}$-cycloalkyl bonded via a C$_{1-3}$-alkylene group;
R$^{13}$ represents H, C$_{1-6}$-alkyl, C$_{3-8}$-cycloalkyl, 3- to 8-membered heterocycloalkyl, aryl or heteroaryl or a C$_{3-8}$-cycloalkyl, 3- to 8-membered heterocycloalkyl, aryl or heteroaryl bonded via a C$_{1-3}$-alkylene group;
wherein said C$_{1-6}$-alkyl, C$_{2-6}$-alkenyl, C$_{1-3}$-alkylene, C$_{1-6}$-alkylene, C$_{2-6}$-alkenylene, C$_{2-6}$-alkynylene, C$_{3-8}$-cycloalkyl, heterocycloalkyl, bicyclic 8- to 12-membered carbocyclyl, aryl and heteroaryl groups may each be unsubstituted or mono- or polysubstituted by identical or different substituents, and wherein said C$_{1-6}$-alkyl, C$_{2-6}$-alkenyl, C$_{1-3}$-alkylene, C$_{1-6}$-alkylene, C$_{2-6}$-alkenylene and C$_{2-6}$-alkynylene groups may be branched or unbranched;
optionally in the form of an individual enantiomer or an individual diastereomer, or the racemate, or the enantiomers, or the diastereomers, or mixtures of enantiomers and/or diastereomers, and in each case in the form of their bases, their physiologically acceptable salts and/or their N-oxides.

In the context of the present invention, the term "halogen" preferably represents the groups F, Cl, Br and I, and particularly preferably represents the groups F, Cl and Br.

In the context of this invention, the expression "C$_{1-6}$-alkyl" includes acyclic saturated hydrocarbon groups having 1, 2, 3, 4, 5 or 6 C atoms, which can be branched- or straight-chain (unbranched) and unsubstituted or substituted one or more times, for example 2, 3, 4 or 5 times, by identical or different substituents. The alkyl groups can preferably be selected from the group consisting of methyl, ethyl, n-propyl, iso-propyl, n-butyl, iso-butyl, sec-butyl, tert-butyl, n-pentyl, iso-pentyl, neo-pentyl and hexyl. Particularly preferred alkyl groups can be selected from the group consisting of methyl, ethyl, n-propyl, iso-propyl, n-butyl, sec-butyl, iso-butyl and tert-butyl.

In the context of this invention, the expression "C$_{2-6}$-alkenyl" includes acyclic unsaturated hydrocarbon groups having 2, 3, 4, 5 or 6 C atoms, which can be branched or straight-chain (unbranched) and unsubstituted or substituted one or more times, for example 2, 3, 4 or 5 times, by identical or different substituents. In this context, the alkenyl groups contain at least one C=C double bond. Alkenyl groups can preferably be selected from the group consisting of vinyl, prop-1-enyl, allyl, 2-methylprop-1-enyl, but-1-enyl, but-2-enyl, but-3-enyl, but-1,3-dienyl, 2-methylprop-1-enyl, but-2-en-2-yl, but-1-en-2-yl, pentenyl and hexenyl. Particularly preferred alkenyl groups can be selected from the group consisting of vinyl, prop-1-enyl, allyl, 2-methylprop-1-enyl, but-1-enyl, but-2-enyl, but-3-enyl, but-1,3-dienyl, 2-methylprop-1-enyl, but-2-en-2-yl and but-1-en-2-yl.

In the context of this invention, the expression "C$_{3-8}$-cycloalkyl" denotes cyclic saturated hydrocarbons having 3, 4, 5, 6, 7 or 8 carbon atoms, which can be unsubstituted or substituted one or more times, for example by 2, 3, 4 or 5 identical or different substituents, on one or more ring members. C$_{3-8}$-Cycloalkyl can preferably be selected from the group consisting of cyclopropyl, cyclobutyl, cyclopentyl, cyclohexyl, cycloheptyl and cyclooctyl.

The expression "3- to 8-membered heterocycloalkyl" designates saturated heterocyclic rings which can contain as ring members, selected independently of one another, 1, 2, 3, 4 or 5 identical or different hetero atoms, preferably from the group N, O or S. In the case where the heterocycloalkyl is bonded to a hetero atom, for example N, bonding to the heterocycloalkyl is preferably via one of the carbon ring members of the heterocycloalkyl.

3- to 8-membered heterocycloalkyls can be, in particular, 4-, 5- or 6-membered. Examples of 3- to 8-membered heterocycloalkyls include azetidinyl, pyrrolidinyl, piperidinyl, piperazinyl, morpholinyl, tetrahydropyranyl, dioxanyl and dioxolanyl, which can optionally be substituted as explained below.

In the context of this invention, the expression "aryl" denotes aromatic hydrocarbons, in particular phenyls and naphthyls. The aryl groups can also be condensed with further saturated, (partially) unsaturated or aromatic ring systems. Each aryl group can be unsubstituted or substituted one or more times, for example 2, 3, 4 or 5 times, wherein the substituents on the aryl can be identical or different and can be in any desired and possible position of the aryl. Aryl can advantageously be selected from the group consisting of phenyl, 1-naphthyl and 2-naphthyl, which can in each case be unsubstituted or substituted one or more times, for example by 2, 3, 4 or 5 groups.

In the context of the present invention, the expression "heteroaryl" represents a 5-, 6- or 7-membered cyclic aromatic group which contains at least 1, if appropriate also 2, 3, 4 or 5 hetero atoms, wherein the hetero atoms can be identical or different and the heteroaryl can be unsubstituted or substituted one or more times, for example 2, 3, 4 or 5 times, by identical or different substituents. The substituents can be bonded in any desired and possible position of the heteroaryl. The heterocyclic ring can also be part of a bi- or polycyclic, in particular a mono-, bi- or tricyclic system, which can then be more than 7-membered in total, preferably up to 14-membered. Preferred hetero atoms are selected from the group consisting of N, O and S. The heteroaryl group can preferably be selected from the group consisting of pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, benzoxazolyl, benzoxadiazolyl, imidazothiazolyl, dibenzofuranyl, dibenzothienyl, phthalazinyl, pyrazolyl, imidazolyl, thiazolyl, oxazolyl, oxadiazolyl, triazole, tetrazole, isoxazoyl, pyridinyl (pyridyl), pyridazinyl, pyrimidinyl, pyrazinyl, pyranyl, indazolyl, purinyl, indolizinyl, quinolinyl, isoquinolinyl, quinazolinyl, quinoxalinyl, carbazolyl, phenazinyl, phenothiazinyl and oxadiazolyl, in particular from the group consisting of thienyl (thiophenyl), pyridinyl (pyridyl), pyrimidinyl, thiazolyl, imidazolyl, oxazolyl, quinazolyl and quinolinyl, wherein bonding to the general structure I can be via any desired and possible ring member of the heteroaryl group. The heteroaryl group can be particularly preferably selected from the group consisting of furyl, thienyl and pyridinyl.

In the context of the present invention, the expression "bicyclic 8- to 12-membered carbocyclyl" represents cyclic hydrocarbon compounds which comprise two condensed ring systems, wherein the two ring systems together contain 8-12 ring members and no hetero atoms. In this context the two ring systems can have different ring sizes and different degrees of saturation, i.e. the two rings can each in itself be either aromatic, saturated or partly unsaturated. In particular, bicyclic 8- to 12-membered carbocyclyls are understood as meaning compounds which comprise an aromatic ring system with a fused-on saturated ring system. In this context bonding to the general structure I can be via any desired and possible ring member of the carbocyclyl group, but preferably via a ring member of an unsaturated ring. The bicyclic 8- to 12-membered carbocyclyl can be particularly preferably selected from the group consisting of 2,3-dihydro-1H-indenyl or 1,2,3,4-tetrahydronaphthyl.

In the context of the present invention, the expression "$C_{1-3}$-alkylene group" or "$C_{1-6}$-alkylene group" includes acyclic saturated hydrocarbon groups having 1, 2 or 3 or, respectively, having 1, 2, 3, 4, 5 or 6 C atoms, which can be branched- or straight-chain (unbranched) and unsubstituted or substituted one or more times, for example 2, 3, 4 or 5 times, by identical or different substituents and which link a corresponding group to the main general structure. The alkylene groups can preferably be selected from the group consisting of —$CH_2$—, —$CH_2$—$CH_2$—, —$CH(CH_3)$—, —$CH_2$—$CH_2$—$CH_2$—, —$CH(CH_3)$—$CH_2$—, —$CH(CH_2CH_3)$—, —$CH_2$—$(CH_2)_2$—$CH_2$—, —$CH(CH_3)$—$CH_2$—$CH_2$—, —$CH_2$—$CH(CH_3)$—$CH_2$—, —$CH(CH_3)$—$CH(CH_3)$—, —$CH(CH_2CH_3)$—$CH_2$—, —$C(CH_3)_2$—$CH_2$—, —$CH(CH_2CH_2CH_3)$—, —$C(CH_3)(CH_2CH_3)$—, —$CH_2$—$(CH_2)_3$—$CH_2$—, —$CH(CH_3)$—$CH_2$—$CH_2$—$CH_2$—, —$CH_2$—$CH(CH_3)$—$CH_2$—$CH_2$—, —$CH(CH_3)$—$CH_2$—$CH(CH_3)$—, —$CH(CH_3)$—$CH(CH_3)$—$CH_2$—, —$C(CH_3)_2$—$CH_2$—$CH_2$—, —$CH_2$—$C(CH_3)_2$—$CH_2$—, —$CH(CH_2CH_3)$—$CH_2$—$CH_2$—, —$CH_2$—$CH(CH_2CH_3)$—$CH_2$—, —$C(CH_3)_2$—$CH(CH_3)$—, —$CH(CH_2CH_3)$—$CH(CH_3)$—, —$C(CH_3)(CH_2CH_3)$—$CH_2$—, —$CH(CH_2CH_3)$—$CH_2$—, —$C(CH_2CH_3)_2$—$CH_2$—, —$CH(CH_2CH_2CH_3)$—, —$C(CH_3)(CH_2CH_2CH_3)$—, —$C(CH_2CH_3)_2$— and —$CH_2$—$(CH_2)_4$—$CH_2$—. The alkylene groups can be particularly preferably selected from the group consisting of —$CH_2$—, —$CH_2$—$CH_2$— and —$CH_2$—$CH_2$—$CH_2$—.

In the context of the present invention, the expression "$C_{2-6}$-alkenylene group" includes acyclic hydrocarbon groups having 2, 3, 4, 5 or 6 C atoms, which are unsaturated one or more times, for example 2, 3 or 4 times, and can be branched- or straight-chain (unbranched) and unsubstituted or substituted one or more times, for example 2, 3, 4 or 5 times, by identical or different substituents and which link a corresponding group to the main general structure. In this context the alkenylene groups contain at least one C=C double bond. The alkenylene groups can preferably be selected from the group consisting of —CH=CH—, —CH=CH—$CH_2$—, —$C(CH_3)$=$CH_2$—, —CH=CH—$CH_2$—$CH_2$—, —$CH_2$—CH=CH—$CH_2$—, —CH=CH—$CH_2$—$CH_2$—, —CH=CH—, —$C(CH_3)$=CH—$CH_2$—, —CH=$C(CH_3)$—$CH_2$—, —$C(CH_3)$=$C(CH_3)$—, —$C(CH_2CH_3)$=CH—, —CH=CH—$CH_2$—$CH_2$—$CH_2$—, —$CH_2$—CH=$CH_2$—$CH_2$—$CH_2$—, —CH=CH=CH—$CH_2$—$CH_2$— and —CH=$CH_2$—CH—CH=$CH_2$—.

In the context of the invention, the expression "$C_{2-6}$-alkynylene group" includes acyclic hydrocarbon groups having 2, 3, 4, 5 or 6 C atoms, which are unsaturated one or more times, for example 2, 3 or 4 times, and can be branched- or straight-chain (unbranched) and unsubstituted or substituted one or more times, for example 2, 3, 4 or 5 times, by identical or different substituents and which link a corresponding group to the main general structure. In this context the alkynylene groups contain at least one C≡C triple bond. The alkynylene groups can preferably be selected from the group consisting of —C≡C—, —C≡C—$CH_2$—, —C≡C—$CH_2$—$CH_2$—, —C≡C—$CH(CH_3)$—, —$CH_2$—C≡C—$CH_2$—, —C≡C—C≡C—, —C≡C—$C(CH_3)_2$—, —C≡C—$CH_2$—$CH_2$—$CH_2$—, —$CH_2$—C≡C—$CH_2$—$CH_2$—, —C≡C—$C_1$—C—$CH_2$— and —C≡C—$CH_2$—C≡C—.

In the context of the present invention, the expression "aryl or heteroaryl bonded via a $C_{1-3}$-alkylene group, a $C_{1-6}$-alkylene group, $C_{2-6}$-alkenylene group or $C_{2-6}$-alkynylene group"

means that the $C_{1-3}$-alkylene groups, $C_{1-6}$-alkylene groups, $C_{2-6}$-alkenylene groups, $C_{2-6}$-alkynylene groups and aryl or heteroaryl have the meanings defined above and the aryl or heteroaryl is bonded to the main general structure via a $C_{1-3}$-alkylene group, $C_{1-6}$-alkylene group, $C_{2-6}$-alkenylene group or $C_{2-6}$-alkynylene group. There may be mentioned by way of example benzyl, phenethyl and phenylpropyl.

In the context of the present invention, the expression "$C_{3-8}$-cycloalkyl and heterocyclyl bonded via a $C_{1-3}$-alkylene group, $C_{1-6}$-alkylene group, $C_{2-6}$-alkenylene group or $C_{2-6}$-alkynylene group" means that the $C_{1-3}$alkylene group, $C_{1-6}$-alkylene group, $C_{2-6}$-alkenylene group, $C_{2-6}$-alkynylene group, $C_{3-8}$-cycloalkyl and heterocyclyl have the meanings defined above and $C_{3-8}$-cycloalkyl and heterocyclyl are bonded to the main general structure via a $C_{1-3}$-alkylene group, $C_{1-6}$-alkylene group, $C_{2-6}$-alkenylene group or $C_{2-6}$-alkynylene group.

In connection with "alkyl", "alkenyl", "alkylene", "alkenylene", "alkynylene" and "cycloalkyl", in the context of this invention the term "substituted" is understood as meaning replacement of a hydrogen by F, Cl, Br, I, CN, $NH_2$, NH—$C_{1-6}$-alkyl, NH—$C_{1-6}$-alkylene-OH, $C_{1-6}$-alkyl, $N(C_{1-6}$-alkyl$)_2$, $N(C_{1-6}$-alkylene-OH$)_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2H$, $CO_2$—$C_{1-6}$-alkyl or benzyl, where groups substituted several times are to be understood as meaning those groups which are substituted several times, for example two or three times, either on different or on the same atoms, for example three times on the same C atom, as in the case of $CF_3$ or —$CH_2CF_3$, or at different places, as in the case of CH(Cl)—CH=CH—$CHCl_2$. Substitution several times can be by identical or different substituents, such as, for example, in the case of CH(OH)—CH=CH—$CHCl_2$.

With respect to "aryl" and "heteroaryl", in the context of this invention "substituted" is understood as meaning replacement one or more times, for example 2, 3, 4 or 5 times, of one or more hydrogen atoms of the corresponding ring system by F, Cl, Br, I, CN, $NH_2$, NH—$C_{1-6}$-alkyl, NH—$C_{1-6}$-alkylene-OH, $N(C_{1-6}$-alkyl$)_2$, $N(C_{1-6}$-alkylene-OH$)_2$, NH-aryl$^1$, N(aryl$^1$)$_2$, $N(C_{1-6}$-alkyl)aryl$^1$, pyrrolinyl, piperazinyl, morpholinyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —$O$—$C(CH_3)_2$—$CH_2$—, —$CH_2$—O—$CH_2$—O—, —O—$CH_2$—O—$CH_2$—, unsubstituted $C_{1-6}$-alkyl, pyrrolidinyl, imidazolyl, piperidinyl, benzyloxy, phenoxy, phenyl, naphthyl, pyridinyl, —$C_{1-3}$-alkylene-aryl$^1$, benzyl, thienyl, furyl, wherein aryl$^1$ represents phenyl, furyl, thienyl or pyridinyl, on one or various atoms, wherein the abovementioned substituents—unless stated otherwise—can optionally be substituted in their turn by the aforementioned substituents. Substitution of aryl and heteroaryl several times can be by identical or different substituents. Preferred substituents for aryl and heteroaryl can be selected from the group consisting of —$CH_2$—O—$CH_2$—O—, —O—$CH_2$—O—$CH_2$—, —O—$C_{1-3}$-alkyl, unsubstituted $C_{1-6}$-alkyl, F, Cl, Br, I, $CF_3$, $OCF_3$, OH, SH, phenyl, naphthyl, furyl, thienyl and pyridinyl, in particular from the group consisting of —$CH_2$—O—$CH_2$—O—, —O—$CH_2$—O—$CH_2$—, F, Cl, Br, $CF_3$, $CH_3$ and $OCH_3$.

In connection with "3- to 8-membered heterocycloalkyl", the term "substituted" is understood as meaning replacement of a hydrogen on one or more ring members by F, Cl, Br, I, —CN, $NH_2$, NH—$C_{1-6}$-alkyl, NH—$C_{1-6}$-alkylene-OH, $C_{1-6}$-alkyl, $N(C_{1-6}$-alkyl$)_2$, $N(C_{1-6}$-alkylene-OH$)_2$, pyrrolinyl, piperazinyl, morpholinyl, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2H$, $CO_2$—$C_{1-6}$-alkyl or benzyl. Replacement several times can be by identical or different substituents. A hydrogen bonded to an N ring member can be replaced by a $C_{1-6}$-alkyl, $C_{3-8}$-cycloalkyl, aryl, heteroaryl or a $C_{3-8}$-cycloalkyl, aryl or heteroaryl bonded via a $C_{1-3}$-alkylene group, wherein these alkyl, cycloalkyl, alkylene and aryl and heteroaryl groups can be unsubstituted or substituted as defined above. Examples of substituted 3- to 8-membered heterocycloalkyl groups are 1-methylpiperidin-4-yl, 1-phenylpiperidin-4-yl, 1-benzylpiperidin-4-yl, 1-methylpyrrolidin-3-yl, 1-phenylpyrrolidin-3-yl, 1-benzylpyrrolin-3-yl, 1-methylazetidin-3-yl, 1-phenyl-azetidin-3-yl or 1-benzylazetidin-3-yl.

In connection with the "heterocyclic ring", in the context of this invention the term "substituted" is understood as meaning replacement of a hydrogen bonded to a carbon ring atom by F, Cl, Br, I, CN, $NH_2$, NH—$C_{1-6}$-alkyl, NH—$C_{1-6}$-alkylene-OH, $C_{1-6}$-alkyl, $N(C_{1-6}$-alkyl$)_2$, $N(C_{1-6}$-alkylene-OH$)_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2H$, $CO_2$—$C_{1-6}$-alkyl or benzyl. If a heterocyclic group is substituted several times, e.g 1, 2, 3 or 4 times, the substituents can be on one and/or more carbon ring atoms. In preferred embodiments, one or more hydrogens on one or more carbon ring atoms are exchanged for F, e.g. —($CF_2$)—.

In connection with the "saturated or at least partly unsaturated ring system" which is fused with the heterocyclic ring formed by $R^{11}$ and $R^{12}$, in the context of this invention the term "substituted" means replacement of a hydrogen bonded to a carbon ring atom by F, Cl, Br, I, CN, $NH_2$, NH—$C_{1-6}$-alkyl, NH—$C_{1-6}$-alkylene-OH, $C_{1-6}$-alkyl, $N(C_{1-6}$-alkyl$)_2$, $N(C_{1-6}$-alkylene-OH$)_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2H$, $CO_2$—$C_{1-6}$-alkyl or benzyl. If the ring system is substituted several times, the substituents can be on one and/or more carbon ring atoms. In connection with the "aromatic ring system", which is fused with the heterocyclic ring formed by $R^{11}$ and $R^{12}$, in the context of this invention the term "substituted" is understood as meaning the corresponding substitution as defined for aryl and heteroaryl.

With respect to "bicyclic 8- to 12-membered carbocyclyl", in the context of this invention "substituted" is understood as meaning replacement one or more times of hydrogen atoms of the corresponding ring systems of the bicyclic carbocyclyl. In this context the substituents bonded to a saturated or partly unsaturated ring system of the carbocyclyl are independently selected from the group of substituents for cycloalkyl defined above, that is to say from F, Cl, Br, I, CN, $NH_2$, NH—$C_{1-6}$-alkyl, NH—$C_{1-6}$-alkylene-OH, $C_{1-6}$-alkyl, $N(C_{1-6}$-alkyl$)_2$, $N(C_{1-6}$-alkylene-OH$)_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2H$, $CO_2$—$C_{1-6}$-alkyl, or benzyl, wherein in the case of replacement several times several hydrogen atoms of one ring member and/or one hydrogen atom on several ring members are replaced. Substituents which are bonded to an aromatic ring system of the carbocyclyl are independently selected from the group of substituents for aryl or heteroaryl defined above, that is to say from F, Cl, Br, I, CN, $NH_2$, NH—$C_{1-6}$-alkyl, NH—$C_{1-6}$-alkylene-OH, $N(C_{1-6}$-alkyl$)_2$, $N(C_{1-6}$-alkylene-OH$)_2$, NH-aryl$^1$, N(aryl$^1$)$_2$, $N(C_{1-6}$-alkyl)aryl$^1$, pyrrolinyl, piperazinyl, morpholinyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—

C(CH₃)₂—CH₂—, unsubstituted $C_{1-6}$-alkyl, pyrrolidinyl, imidazolyl, piperidinyl, benzyloxy, phenoxy, phenyl, naphthyl, pyridinyl, —$C_{1-3}$-alkylene-aryl¹, benzyl, thienyl, furyl, wherein aryl¹ represents phenyl, furyl, thienyl or pyridinyl.

Preferred substituents for aromatic ring members of the bicyclic 8- to 12-membered carbocyclyl can be selected from the group consisting of —O—$C_{1-3}$-alkyl, unsubstituted $C_{1-6}$-alkyl, F, Cl, Br, I, CF₃, OCF₃, OH, SH, phenyl, naphthyl, furyl, thienyl and pyridinyl, in particular from the group consisting of F, Cl, Br, CF₃, CH₃ and OCH₃.

In the context of the present description, the symbol

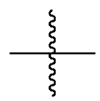

used in formulas designates a linking of a corresponding group to the particular main general structure.

Persons skilled in the art will understand that identical groups which are used for definition of different substituents, such as, for example, the groups $R^{11}$ and $R^{12}$ in the groups —(C=O)—$NR^{11}R^{12}$, —$C_{1-6}$-alkylene-C(=O)—$NR^{11}R^{12}$, —$C_{1-6}$-alkylene-$NR^{11}R^{12}$, can in each case be independent of one another.

In a preferred embodiment of the compounds according to the general formula I according to the invention, the groups $R^2$ and $R^3$ together with the —N—(CH—)- group joining them form a heterocyclic ring corresponding to formula A:

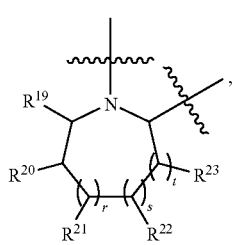

(A)

wherein r, s and t each independently represent 0 or 1; and $R^{19}$, $R^{20}$, $R^{21}$, $R^{22}$ and $R^{23}$ each independently represent H or two vicinal groups from $R^{19}$, $R^{20}$, $R^{21}$, $R^{22}$ and $R^{23}$ form a 5- or 6-membered fused-on aryl or heteroaryl group, which can be unsubstituted or substituted one or more times by identical or different substituents.

Persons skilled in the art will understand that the partial structure of formula (I) represented by the heterocyclic ring (A) can assume the following forms for the particular values 0 and 1 of the indices r, s and t:

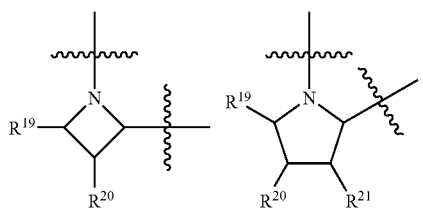

-continued

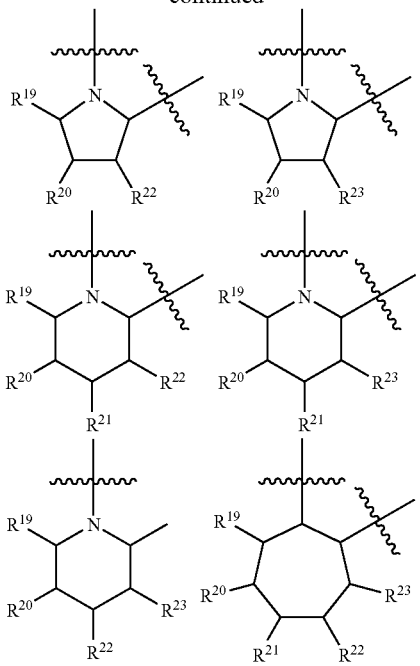

Persons skilled in the art furthermore will understand that if two vicinal (adjacent) groups from $R^{19}$, $R^{20}$, $R^{21}$, $R^{22}$ and $R^{23}$ form a (fused-on) ring which is aromatic or is unsaturated on one or both of the carbon atoms linked with the vicinal groups, this/these carbon atom(s) can no longer carry a hydrogen.

For example, the following form results for a heterocyclic ring according to (A) in which one of the indices r, s or t=0 and the other two are each=1, and the adjacent groups $R^{19}$ and $R^{20}$ form a fused-on benzene ring:

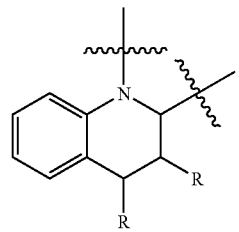

wherein R represents the corresponding group from $R^{21}$, $R^{22}$ and $R^{23}$.

The following form results for a heterocyclic ring according to (A) in which one of the indices r, s or t=0, and the other two are each=1, and the adjacent groups $R^{20}$ and $R^{21}$ or $R^{22}$ form a fused-on benzene ring:

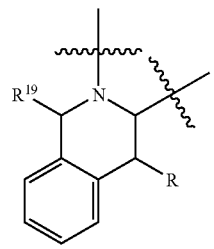

wherein R represents the corresponding group from $R^{22}$ or $R^{23}$.

The following form results for a heterocyclic ring (A) in which one of the indices r, s or t=0, and the other two are each=1, and two adjacent groups of $R^{21}$, $R^{22}$ and $R^{23}$ form a fused-on benzene ring:

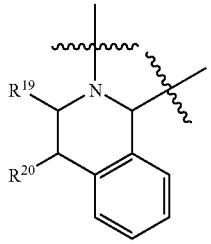

If the ring sizes of the heterocyclic groups according to (A) described above allow, i.e. for compounds in which r+s+t=2 or 3, in each case two pairs of adjacent groups can also form a fused-on ring, for example:

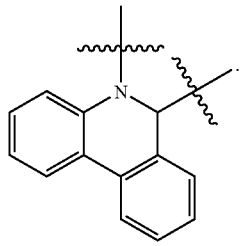

In the compounds according to the invention, preferably at least one of the groups $R^4$, $R^{4a}$, $R^5$, $R^6$, $R^7$, $R^8$, $R^9$ and $R^{10}$ is not H, i.e. the following partial structure (B)

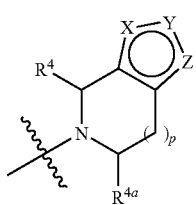

(B)

contains at least one substituent which differs from H. For example, 1, 2 or 3, in particular 1 or 2 of the groups $R^4$, $R^{4a}$, $R^5$, $R^6$, $R^7$, $R^8$, $R^9$ and $R^{10}$ can differ from hydrogen.

In a further preferred embodiment of the present invention, in the substituted sulfonamide compounds according to the invention, X, Y and Z are selected such that one or none of these variables represents a substituted nitrogen atom (i.e. $NR^5$, $NR^6$ or $NR^7$).

In the context of this invention, the term "physiologically acceptable salt" is understood as meaning salts of the compounds according to the invention with inorganic or organic acids, which are physiologically acceptable—in particular when used on humans and/or mammals. Examples of suitable acids include hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, 1,1-dioxo-1,2-dihydro1λ⁶-benzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethylbenzoic acid, α-liponic acid, acetylglycine, hippuric acid, phosphoric acid and/or aspartic acid. The salts of hydrochloric acid (hydrochlorides) and of citric acid (citrates) are particularly preferred. This term is furthermore also understood as meaning those compounds which are obtained by quaternization of a nitrogen atom present in the structure (e.g. pyridyl, N-methylpiperidinyl). Such compounds can be obtained, for example, by alkylation with generation of the corresponding cation, with counter-ions such as, for example, Cl— and F—.

In a preferred embodiment of the present invention, in the substituted sulfonamide compounds according to the invention $R^1$ represents CH(phenyl)$_2$, phenyl, naphthyl, Indolyl, benzofuranyl, benzothiophenyl (benzothienyl), benzoxazolyl, benzoxadiazolyl, pyrrolyl, furanyl, thienyl, thiazolyl, imidazolyl, oxazolyl, quinazolyl, quinolinyl, pyridinyl, pyridazinyl, pyrimidinyl, pyrazinyl, imidazothiazolyl, carbazolyl, dibenzofuranyl, dibenzothiophenyl (dibenzothienyl), benzyl or 2-phenylethyl, preferably CH(aryl)$_2$, phenyl, naphthyl, benzothiophenyl, benzoxadiazolyl, thiophenyl, pyridinyl, imidazothiazolyl or dibenzofuranyl, particularly preferably phenyl or naphthyl, in each case unsubstituted or substituted one or more times by identical or different substituents independently selected from the group consisting of —O—C$_{1-3}$-alkyl, —C$_{1-6}$-alkyl, —F, —Cl, —Br, —I, —CF$_3$, —OCF$_3$, —OH, —SH, phenyl, naphthyl, furyl, thienyl and pyridinyl.

In a further preferred embodiment of the present invention, in the substituted sulfonamide compounds according to the invention $R^1$ represents phenyl or naphthyl, wherein the phenyl or naphthyl is unsubstituted or substituted one or more times, for example 2, 3, 4 or 5 times, by identical or different substituents selected from the group consisting of methyl, methoxy, CF$_3$, OCF$_3$, F, Cl and Br.

In a further preferred embodiment, $R^1$ in the sulfonamide compounds according to the invention is selected from the group consisting of 4-methoxy-2,3,6-trimethylphenyl, 4-methoxy-2,6-dimethylphenyl, 4-methoxy-2,3,5-trimethylphenyl, 2,4,6-trimethylphenyl, 2-chloro-6-methylphenyl, 2,4,6-trichlorophenyl, 2-chloro-6-(trifluoromethyl)phenyl, 2,6-dichloro-4-methoxyphenyl, 2,4-dichloro-6-methylphenyl, 2-methylnaphthyl, 2-chloronaphthyl, 2-fluoronaphthyl, 2-chloro-4-(trifluoromethoxy)phenyl, 4-chloro-2,5-dimethylphenyl, 2,3-dichlorophenyl, 2,4-dichlorophenyl, 3,4-dichlorophenyl, 2,6-dichlorophenyl, 2-(trifluoromethyl)phenyl, 3-(trifluoromethyl)phenyl, 4-(trifluoromethyl)phenyl, 2-methoxyphenyl, 3-methoxyphenyl, 4-methoxyphenyl, 1-naphthyl and 2-naphthyl.

In a further preferred embodiment, $R^1$ in the sulfonamide compounds according to the invention is selected from the group consisting of 4-methoxy-2,3,6-trimethylphenyl, 4-methoxy-2,6-dimethylphenyl, 2-chloro-6-methylphenyl, 4-chloro-2,5-dimethylphenyl, 2-(trifluoromethyl)phenyl, 3-(trifluoromethyl)phenyl, 4-(trifluoromethyl)phenyl, 1-naphthyl and 2-naphthyl, preferably from the group consisting of 4-methoxy-2,6-dimethylphenyl, 4-chloro-2,5-dimethylphenyl, 2-(trifluoromethyl)phenyl, 3-(trifluoromethyl)phenyl, 4-(trifluoromethyl)phenyl, 1-naphthyl and 2-naphthyl.

In a further preferred embodiment, $R^1$ in the sulfonamide compounds according to the invention is a 4-methoxy-2,6-dimethylphenyl group.

In a further preferred embodiment of the present invention, in the substituted sulfonamide compounds according to the invention $R^2$ represents H, C$_{1-6}$-alkyl, C$_{3-6}$-cycloalkyl, 8- to 10-membered benzo-fused cycloalkyl, CH(phenyl)$_2$, aryl or heteroaryl, or a $C_{3-6}$-cycloalkyl, 8- to 10-membered benzo-fused cycloalkyl, CH(phenyl)$_2$, aryl or heteroaryl bonded via a $C_{1-6}$-alkylene group, $C_{2-6}$-alkenylene group or $C_{2-6}$-alkynylene group, wherein the groups $C_{1-6}$-alkyl, $C_{3-6}$-cycloalkyl, $C_{1-6}$-alkylene, $C_{2-6}$-alkenylene, $C_{2-6}$-alkynylene and aryl are in each case unsubstituted or substituted one or more times, wherein aryl in particular is unsubstituted or substituted one or more times by identical or different substituents independently selected from the group consisting of —CH$_2$—O—CH$_2$—O—, —O—CH$_2$—O—CH$_2$—, $C_{1-6}$-alkyl, $C_{1-6}$-alkyl-O—, F, Cl, Br, I, CF$_3$, OCF$_3$, OH and SH.

In a further preferred embodiment of the present invention, in the substituted sulfonamide compounds according to the invention R$^2$ represents H, $C_{1-6}$-alkyl, cyclopropyl, CH(phenyl)$_2$, phenyl, thienyl, pyridyl, pyrimidinyl, thiazolyl, imidazolyl, oxazolyl, quinazolyl, quinolinyl or a phenyl, thienyl, pyridyl, pyrimidinyl, thiazolyl, imidazolyl, oxazolyl, quinazolyl or quinolinyl bonded via a $C_{1-6}$-alkylene group, wherein the phenyl, thienyl, pyridyl, pyrimidinyl, thiazolyl, imidazolyl, oxazolyl, quinazolyl and quinolinyl is in each case unsubstituted or substituted one or more times by identical or different substituents independently selected from the group consisting of —CH$_2$—O—CH$_2$—O, —O—CH$_2$—O—CH$_2$—, methyl, ethyl, n-propyl, iso-propyl, n-butyl, iso-butyl, sec-butyl, tert-butyl, methoxy, F, Cl, Br, I, CF$_3$, OCF$_3$ and OH.

In a further preferred embodiment of the present invention, in the substituted sulfonamide compounds according to the invention R$^2$ represents H, methyl, ethyl, n-propyl, iso-propyl, n-butyl, iso-butyl, sec-butyl, tert-butyl or cyclopropyl.

In a further preferred embodiment of the present invention, in the substituted sulfonamide compounds according to the invention R$^2$ represents H, methyl, ethyl or cyclopropyl.

Preferably, R$^3$ in the sulfonamide compounds according to the invention can represent H, —C(=O)—NR$^{11}$R$^{12}$, —C(=O)—OR$^{13}$, $C_{1-6}$-alkyl, aryl or heteroaryl; wherein the groups $C_{1-6}$-alkyl, aryl and heteroaryl are in each case unsubstituted or substituted one or more times, wherein the aryl and heteroaryl in particular are unsubstituted or substituted one or more times by identical or different substituents independently selected from the group consisting of $C_{1-6}$-alkyl, $C_{1-6}$-alkyl-O—, F, Cl, Br, I, CF$_3$, OCF$_3$, OH and SH.

In a further preferred embodiment of the sulfonamide compounds according to the invention, R$^3$ represents H, —C(=O)—NR$^{11}$R$^{12}$, —C(=O)—OR$^{13}$, phenyl, naphthyl, thienyl, pyridyl, pyrimidyl, thiazolyl, imidazolyl, oxazolyl, quinazolyl or quinolinyl, wherein the phenyl, naphthyl, thienyl, pyridyl, pyrimidyl, thiazolyl, imidazolyl, oxazolyl, quinazolyl or quinolinyl is each case unsubstituted or substituted one or more times by identical or different substituents independently selected from the group consisting of methyl, ethyl, n-propyl, iso-propyl, n-butyl, iso-butyl, sec-butyl, tert-butyl, methoxy, F, Cl, Br, I, CF$_3$, OCF$_3$ and OH.

In a further preferred embodiment of the sulfonamide compounds according to the invention, R$^3$ represents H or unsubstituted phenyl.

In a further preferred embodiment of the sulfonamide compounds according to the invention, R$^2$ and R$^3$ together with the —N—(CH—)- group joining them form an unsubstituted or mono or polysubsubstituted, e.g. di-, tri- or tetrasubstituted, 4-, 5-, 6- or 7-membered, preferably 5-, 6- or 7-membered heterocyclic ring, which may contain an oxygen atom as a ring-member and which can be fused with one or two 6-membered aromatic ring(s) (benzo group).

In a further preferred embodiment of the sulfonamide compounds according to the invention, R$^2$ and R$^3$ together with the —N—(CH—)- group joining them form a 5- or 6-membered unsubstituted, mono- or disubstituted heterocyclic ring, which may contain an oxygen atom and which can be fused with a 6-membered aromatic ring (benzo group).

In a further preferred embodiment of the sulfonamide compounds according to the invention, R$^4$ and R$^{4a}$ each independently represent H, $C_{1-6}$-alkyl, $C_{3-8}$-cycloalkyl, phenyl, naphthyl, furyl, thienyl or pyridinyl or a phenyl, naphthyl, furyl, thienyl or pyridinyl bonded via a $C_{1-3}$-alkylene group; wherein the phenyl, naphthyl, furyl, thienyl or pyridinyl is unsubstituted or substituted one or more times by identical or different substituents independently selected from the group consisting of —O—$C_{1-3}$-alkyl, —$C_{1-6}$-alkyl, —F, —Cl, —Br, —I, —CF$_3$, —OCF$_3$, —OH, —SH, phenyl, naphthyl, furyl, thienyl and pyridinyl.

In a further preferred embodiment of the sulfonamide compounds according to the invention, R$^4$ and R$^{4a}$ each independently represent H, methyl, ethyl, n-propyl, iso-propyl, n-butyl, iso-butyl, sec-butyl, tert-butyl, phenyl, naphthyl, furyl, thienyl, pyridinyl, benzyl or phenethyl, wherein the phenyl, naphthyl, furyl, thienyl, pyridinyl or the aromatic part of benzyl and phenethyl is in each case unsubstituted or substituted one or more times by identical or different substituents independently selected from the group consisting of —O—$C_{1-3}$-alkyl, —$C_{1-6}$-alkyl, —F, —Cl, —Br, —I, —CF$_3$, —OCF$_3$, —OH, —SH, phenyl, naphthyl, furyl, thienyl and pyridinyl.

In a further preferred embodiment of the sulfonamide compounds according to the invention, R$^4$ and R$^{4a}$ each independently represent H, methyl, ethyl, phenyl or pyridinyl, wherein the phenyl and pyridinyl is each case unsubstituted or substituted one or more times by identical or different substituents independently selected from the group consisting of methoxy, methyl, —F, —Cl, —Br, —I, —CF$_3$ and —OCF$_3$.

In a further preferred embodiment of the sulfonamide compounds according to the invention, R$^{4a}$ represents H or phenyl, in particular H.

In a further preferred embodiment of the sulfonamide compounds according to the invention, R$^4$ represents a group selected from the group consisting of H, methyl, ethyl, phenyl and pyridinyl, wherein the phenyl and pyridinyl is each case unsubstituted or substituted one or more times by identical or different substituents independently selected from the group consisting of methoxy, methyl, —F, —Cl, —Br, —I, —CF$_3$ and —OCF$_3$, and R$^{4a}$ represents H.

In a further preferred embodiment of the sulfonamide compounds according to the invention, R$^5$, R$^6$ and R$^7$ each independently represent H, methyl, ethyl, n-propyl, iso-propyl, n-butyl, iso-butyl, sec-butyl, tert-butyl or phenyl.

In a further preferred embodiment of the sulfonamide compounds according to the invention, R$^8$, R$^9$ and R$^{10}$ each independently represent H, —CF$_3$, —C(=O)—NR$^{11}$R$^{12}$, —$C_{1-6}$-alkylene-C(=O)—NR$^{11}$R$^{12}$, —$C_{1-6}$-alkylene-NR$^{11}$R$^{12}$, phenyl, naphthyl, furyl, thienyl or pyridinyl or a phenyl, naphthyl, furyl, thienyl or pyridinyl bonded via a $C_{1-6}$-alkylene group, wherein the phenyl, naphthyl, furyl, thienyl or pyridinyl are unsubstituted or substituted one or more times by identical or different substituents independently selected from the group consisting of —O—$C_{1-3}$-alkyl, —$C_{1-6}$-alkyl, —F, —Cl, —Br, —I, —CF$_3$, —OCF$_3$, —OH, —SH, phenyl, naphthyl, furyl, thienyl and pyridinyl.

In a further preferred embodiment of the sulfonamide compounds according to the invention, R$^8$, R$^9$ and R$^{10}$ each independently represent H, —CF$_3$, —C(=O)—NR$^{11}$R$^{12}$, —(CH$_2$)—NR$^{11}$R$^{12}$—(CH$_2$)$_2$—NR$^{11}$R$^{12}$, —(CH$_2$)$_3$—NR$^{11}$R$^{12}$, —(CH$_2$)—(C=O)—NR$^{11}$R$^{12}$, —(CH$_2$)$_2$—(C=O)—NR$^{11}$R$^{12}$—(CH$_2$)$_3$—(C=O)—NR$^{11}$R$^{12}$, phenyl, naphthyl, furyl, thienyl or pyridinyl or a phenyl, naphthyl, furyl, thienyl or pyridinyl bonded via a —(CH$_2$)—, —(CH$_2$)$_2$— or —(CH$_2$)$_3$— group, wherein the phenyl, naphthyl, furyl, thienyl or pyridinyl is unsubstituted or substituted one or more times by identical or different substituents independently selected from the group consisting of —O—C$_{1-3}$-alkyl, —C$_{1-6}$-alkyl, —F, —Cl, —Br, —I, —CF$_3$, —OCF$_3$, —OH, —SH, phenyl, naphthyl, furyl, thienyl and pyridinyl.

In a further preferred embodiment of the sulfonamide compounds according to the invention, R$^8$, R$^9$ and R$^{10}$ each independently represent H, —CF$_3$, —C(=O)—N$^{11}$R$^{12}$, —(CH$_2$)—NR$^{11}$R$^{12}$, —(CH$_2$)$_2$—NR$^{11}$R$^{12}$, —(CH$_2$)$_3$—NR$^{11}$R$^{12}$—(CH$_2$)—(C=O)—NR$^{11}$R$^{12}$, —(CH$_2$)$_2$—(C=O)—NR$^{11}$R$^{12}$, —(CH$_2$)$_3$—(C=O)—NR$^{11}$R$^{12}$ phenyl or pyridinyl or a phenyl or pyridinyl bonded via a —(CH$_2$)—, —(CH$_2$)$_2$— or —(CH$_2$)$_3$— group, wherein the phenyl and pyridinyl is unsubstituted or substituted one or more times by identical or different substituents independently selected from the group consisting of methoxy, methyl, —F, —Cl, —Br, —I, —CF$_3$ and —OCF$_3$.

In a further preferred embodiment of the sulfonamide compounds according to the invention, R$^{11}$ and R$^{12}$ each independently represent H, substituted or unsubstituted C$_{1-6}$-alkyl or C$_{3-8}$-cycloalkyl; or the group —NR$^{11}$R$^{12}$ represents the heterocylic ring corresponding to the formula IIaa

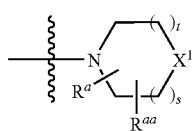

IIaa wherein

X' represents O, S, NR$^{18}$CH$_2$, C(H)(halogen) or C(halogen)$_2$, wherein halogen preferably denotes F, Cl or Br, R$^{18}$ represents H; C$_{1-6}$-alkyl, C$_{3-8}$-cycloalkyl; aryl, preferably phenyl or naphthyl; or heteroaryl, preferably a 5- to 6-membered heteroaryl having 1 or 2 N hetero atoms, in particular pyridinyl; or R$^{18}$ represents a C$_{3-8}$-cycloalkyl bonded via a C$_{1-3}$-alkylene group, an aryl, preferably phenyl or naphthyl, bonded via a C$_{1-3}$-alkylene group; or a heteroaryl, preferably a 5- to 6-membered heteroaryl having 1 or 2 N hetero atoms, in particular pyridinyl, bonded via a C$_{1-3}$-alkylene group; and R$^a$ and R$^{aa}$ each independently represent H, methyl, ethyl, F, Cl or Br;

s and t each independently represent 0, 1 or 2, with the proviso that s+t=0, 1, 2 or 3, wherein said C$_{1-6}$-alkyl, C$_{3-8}$-cycloalkyl, C$_{1-3}$-alkylene, aryl and heteroaryl groups may each be unsubstituted or substituted one or more times by identical or different substituents independently selected from the group consisting of —O—C$_{1-3}$-alkyl, —C$_{1-6}$-alkyl, —F, —Cl, —Br, —I, —CF$_3$, —OCF$_3$, —OH, —SH, phenyl, naphthyl, furyl, thienyl and pyridinyl.

In a further preferred embodiment of the sulfonamide compounds according to the invention, R$^{11}$ and R$^{12}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or the group —NR$^{11}$R$^{12}$ represents a heterocyclic ring selected from the group consisting of:

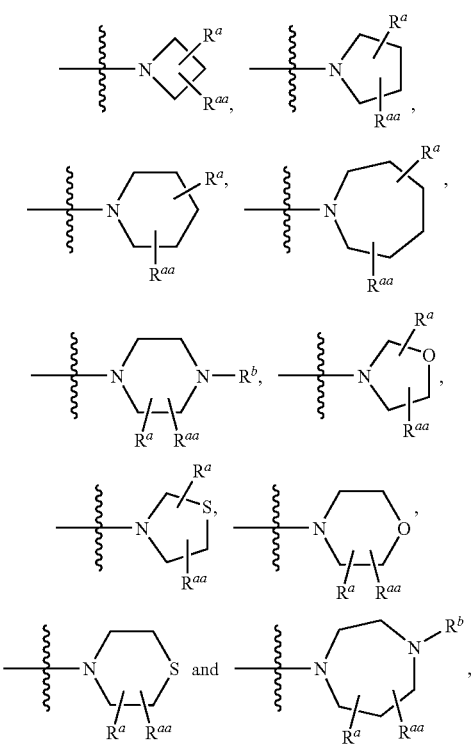

wherein R$^a$ and R$^{aa}$ each independently represent H, methyl, ethyl, F, Cl or Br and R$^b$ represents methyl, phenyl or pyridinyl, wherein the phenyl or pyridinyl can be bonded via a C$_{1-6}$-alkylene bridge and is unsubstituted or substituted one or more times, for example 2 times or 3 times, by identical or different substituents independently selected from the group consisting of methyl, methoxy, F and Cl.

In the —C$_{1-6}$-alkylene-NR$^{11}$R$^{12}$ group, the abovementioned —NR$^{11}$R$^{12}$ groups are in each case linked with the base structure via a —C$_{1-6}$-alkylene-bridge, in particular via a —(CH$_2$)—, —(CH$_2$)$_2$— or —(CH$_2$)$_3$— group.

In the definitions mentioned, the —(C=O)—NR$^{11}$R$^{12}$ group can preferably represent a group which is selected from the group consisting of

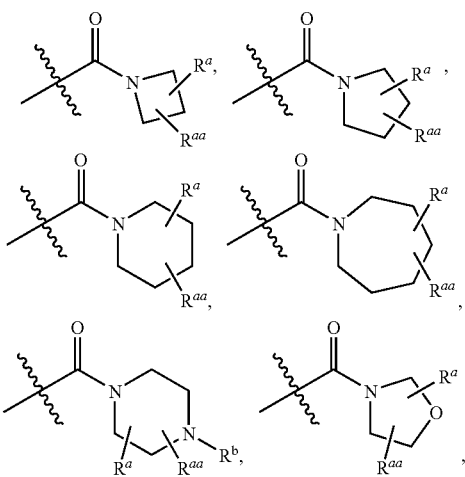

-continued

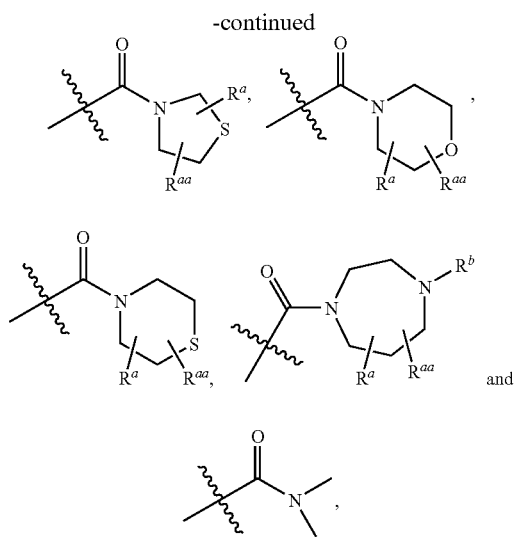

wherein $R^a$ and $R^{aa}$ each independently represent H, methyl, ethyl, F, Cl or Br and $R^b$ represents methyl, phenyl or pyridinyl, wherein the phenyl or pyridinyl can be bonded via a $C_{1-6}$-alkylene bridge and is unsubstituted or substituted one or more times, for example 2 times or 3 times, by identical or different substituents independently selected from the group consisting of methyl, methoxy, F and Cl.

In the —$C_{1-6}$-alkylene-C(=O)—$NR^{11}R^{12}$ definition mentioned, the abovementioned groups are in each case linked with the base structure via a $C_{1-6}$-alkylene bridge, in particular via a —$(CH_2)$—, —$(CH_2)_2$— or —$(CH_2)_3$— group.

In the definitions mentioned herein, the —$NR^{11}R^{12}$ group can represent in particular a group which is selected from the group consisting of

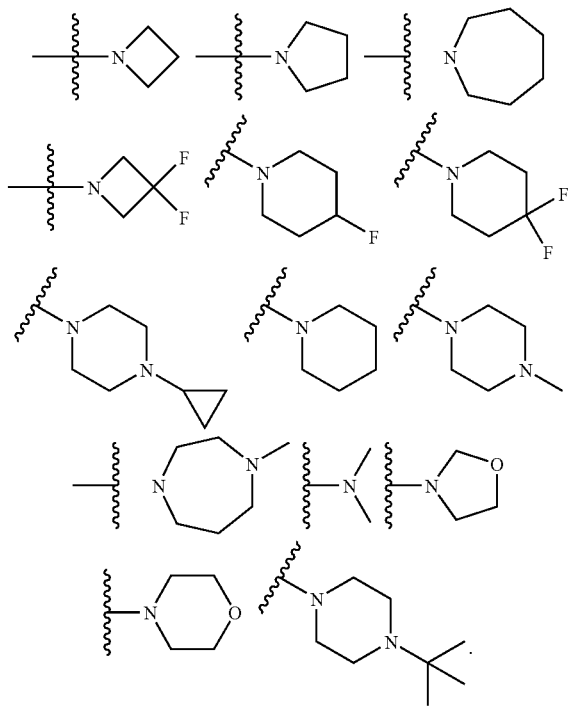

In a further preferred embodiment of the sulfonamide compounds according to the invention, $R^{13}$ represents H, methyl, ethyl, n-propyl, iso-propyl, n-butyl, iso-butyl, sec-butyl, tert-butyl, benzyl or phenethyl.

In a further preferred embodiment of the sulfonamide compounds according to the invention, $R^{14}$ represents H, methyl, ethyl, n-propyl, iso-propyl, n-butyl, iso-butyl, sec-butyl, tert-butyl, cyclopropyl, —C(=O)—$R^{15}$, phenyl, furyl, thiophenyl or pyridinyl or a phenyl, furyl, thiophenyl or pyridinyl bonded via a $C_{1-3}$-alkylene group.

In a further preferred embodiment of the sulfonamide compounds according to the invention, $R^{15}$ represents methyl, ethyl, phenyl, furyl, thiophenyl or pyridinyl or a phenyl, furyl, thiophenyl or pyridinyl bonded via a $C_{1-3}$-alkylene group.

In a further preferred embodiment of the sulfonamide compounds according to the invention, $R^{16}$ represents H, methyl, ethyl, phenyl, furyl, thiophenyl or pyridinyl or a phenyl, furyl, thiophenyl or pyridinyl bonded via a $C_{1-3}$-alkylene group.

In a further preferred embodiment of the sulfonamide compounds according to the invention, $R^{17}$ represents H, methyl, ethyl, phenyl, furyl, thiophenyl or pyridinyl or a phenyl, furyl, thiophenyl or pyridinyl bonded via a $C_{1-3}$-alkylene group.

Preferred sulfonamide compounds according to the invention are also compounds in which the following partial structure

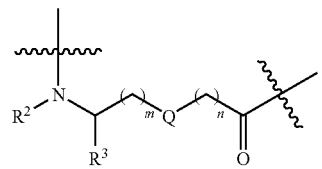

is selected from the group consisting of

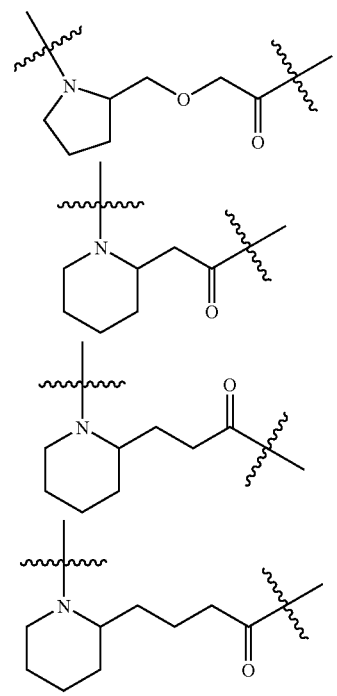

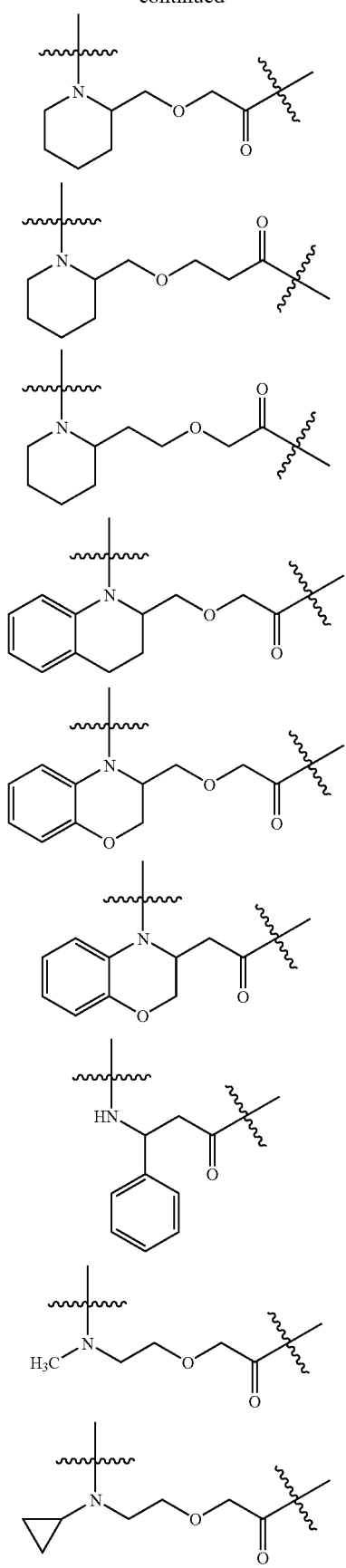
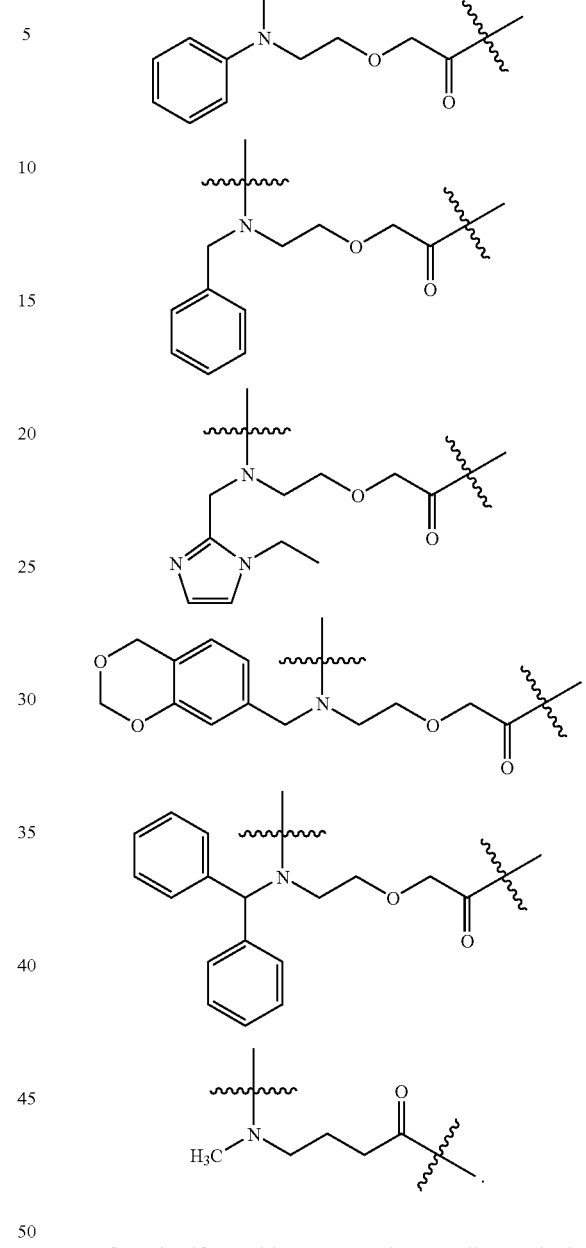
Preferred sulfonamide compounds according to the invention are those in which p represents 0 and X, Y and Z are selected such that the following partial structure
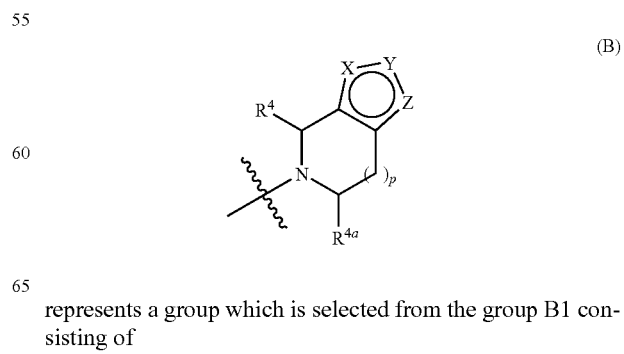
(B)
represents a group which is selected from the group B1 consisting of

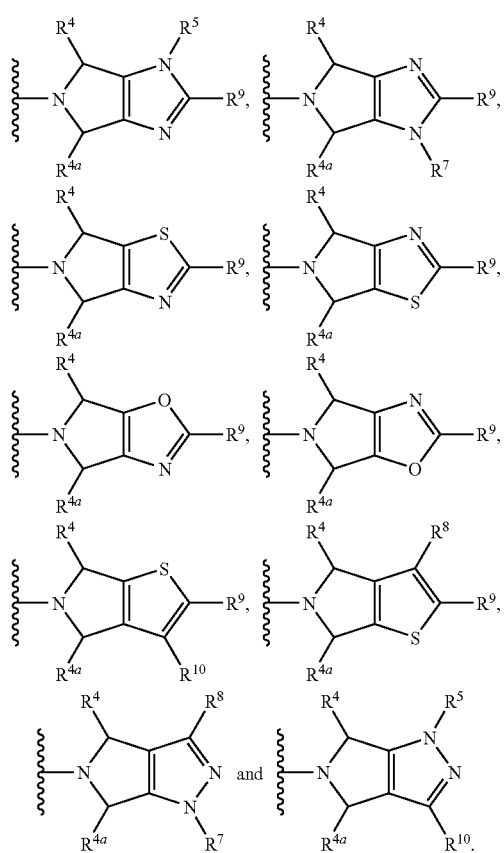

Preferred sulfonamide compounds according to the invention are furthermore those in which p represent 1 and X, Y and Z are selected such that the partial structure (B) represents a group which is selected from the group B2 consisting of

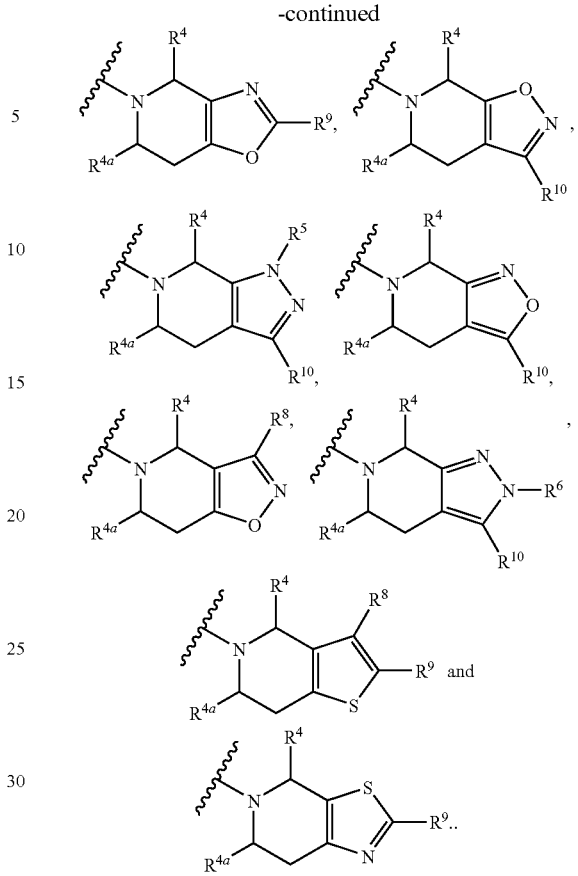

Preferred sulfonamide compounds according to the invention are furthermore those in which p represents 2, and X, Y and Z are selected such that the partial structure (B) represents the following group:

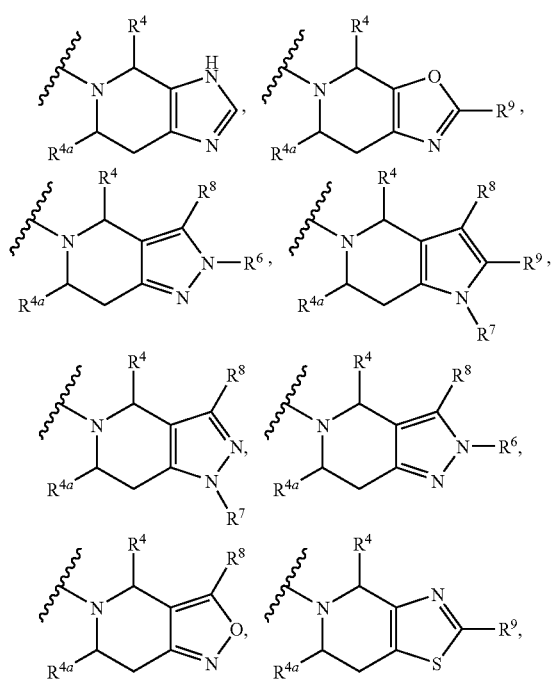

Preferred sulfonamide compounds according to the invention are furthermore those in which preferably p=1, and
X represents $CR^8$,
Y represents $CR^9$, and
Z represents S;
or
X represents S,
Y represents $CR^9$, and
Z represents N;
or
X represents $CR^8$,
Y represents N, and
Z represents O;
or
X represents $CR^8$,
Y represents $CR^9$, and
Z represents $NR^7$;
or X represents S,
Y represents $CR^9$, and
Z represents $CR^{10}$;
or
X represents N,
Y represents $CR^9$, and
Z represents $NR^7$;
or
X represents O,
Y represents $CR^9$, and
Z represents N;
or
X represents $NR^5$,
Y represents N, and
Z represents $CR^{10}$;
or
X represents $CR^8$,
Y represents N, and
Z represents $NR^7$.

Particularly preferred sulfonamide compounds according to the invention are furthermore those in which p represents 1 and X, Y and Z are selected such that the partial structure (B) represents a group which is selected from the group consisting of

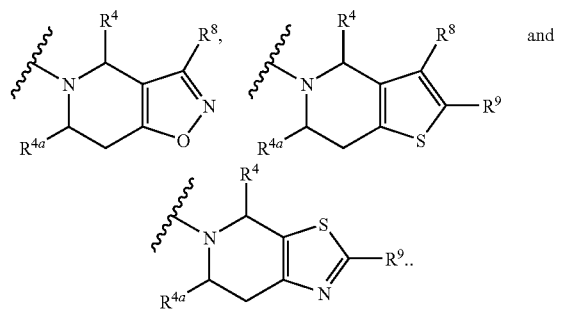

In a further preferred embodiment of the sulfonamide compounds according to the invention, m, n and Q in the partial structure

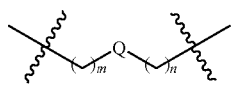

are selected such that this partial structure is selected from the group consisting of a single bond, $-(CH_2)-$; $-(CH_2)_2-$; $-(CH_2)_3-$; $-(CH_2)-O-(CH_2)-$; $-(CH_2)_2-O-(CH_2)$; $-(CH_2)-O-(CH_2)_2$; $-(CH_2)_2-O-(CH_2)_2$ and $-(CH_2)-O-$.

In a further preferred embodiment of the sulfonamide compounds according to the invention, p represents 0 or 1, preferably 1.

Substituted sulfonamide compounds corresponding to formula I according to the invention which are likewise preferred are those wherein
m and n each independently represent 0, 1 or 2;
p represents 0, 1 or 2;
Q represents a single bond, $-CH_2-$ or $-O-$;
X represents N, $NR^5$, O, S or $CR^8$;
Y represents N, $NR^6$, O, S or $CR^9$;
Z represents N, $NR^7$, O, S or $CR^{10}$;

$R^1$ represents $CH(phenyl)_2$, phenyl, naphthyl, indolyl, benzofuranyl, benzothiophenyl (benzothienyl), benzoxazolyl, benzoxadiazolyl, pyrrolyl, furanyl, thienyl, thiazolyl, imidazolyl, oxazolyl, quinazolyl, quinolinyl, pyridinyl, pyridazinyl, pyrimidinyl, pyrazinyl, imidazothiazolyl, carbazolyl, dibenzofuranyl, dibenzothiophenyl (dibenzothienyl), benzyl or 2-phenylethyl, in each case unsubstituted or substituted one or more times by identical or different substituents independently selected from the group consisting of $-O-C_{1-3}$-alkyl, $-C_{1-6}$-alkyl, $-F$, $-Cl$, $-Br$, $-I$, $-CF_3$, $-OCF_3$, $-OH$, $-SH$, phenyl, naphthyl, furyl, thienyl and pyridinyl;

$R^2$ represents H, $C_{1-6}$-alkyl, $C_{3-6}$-cycloalkyl, 8- to 10-membered benzo-fused cycloalkyl, $CH(phenyl)_2$, aryl or heteroaryl, or a $C_{3-6}$-cycloalkyl, 8- to 10-membered benzo-fused cycloalkyl, $CH(phenyl)_2$, aryl or heteroaryl bonded via a $C_{1-6}$-alkylene group, $C_{2-6}$-alkenylene group or $C_{2-6}$-alkynylene group, wherein the groups $C_{1-6}$-alkyl, $C_{3-6}$-cycloalkyl, $C_{1-6}$-alkylene, $C_{2-6}$-alkenylene, $C_{2-6}$-alkynylene and aryl are in each case unsubstituted or substituted one or more times, wherein aryl in particular is unsubstituted or substituted one or more times by identical or different substituents which are independently selected from the group consisting of $-CH_2-O-CH_2-O-$, $-O-CH_2-O-CH_2-$, $C_{1-6}$-alkyl, $C_{1-6}$-alkyl-O-, F, Cl, Br, I, $CF_3$, $OCF_3$, OH and SH;

$R^3$ represents H, $-C(=O)-NR^{11}R^{12}$, $-C(=O)-OR^{13}$, $C_{1-6}$-alkyl, aryl or heteroaryl, wherein the groups $C_{1-6}$-alkyl, aryl and heteroaryl are in each case unsubstituted or substituted one or more times, wherein the aryl and heteroaryl in particular are unsubstituted or substituted one or more times by identical or different substituents independently selected from the group consisting of $C_{1-6}$-alkyl, $C_{1-6}$-alkyl-O-, F, Cl, Br, I, $CF_3$, $OCF_3$, OH and SH, wherein $R^2$ and $R^3$ do not both represent H; or $R^2$ and $R^3$ together with the $-N-(CH-)-$ group joining them form a 4-, 5-, 6- or 7-membered heterocyclic ring, which may contain an oxygen atom as a ring-member and can be fused with one or two 6-membered aromatic ring(s) (e.g., a benzo group);

$R^4$ and $R^{4a}$ each independently represent H, $C_{1-6}$-alkyl, $C_{3-8}$-cycloalkyl, phenyl, naphthyl, furyl, thienyl or pyridinyl or a phenyl, naphthyl, furyl, thienyl or pyridinyl bonded via a $C_{1-3}$-alkylene group, wherein the phenyl, naphthyl, furyl, thienyl or pyridinyl is unsubstituted or substituted one or more times by identical or different substituents independently selected from the group consisting of $-O-C_{1-3}$-alkyl, $C_{1-6}$-alkyl, $-F$, $-Cl$, $-Br$, $-I$, $-CF_3$, $-OCF_3$, $-OH$, $-SH$, phenyl, naphthyl, furyl, thienyl and pyridinyl;

$R^5$, $R^6$ and $R^7$ each independently represent H, $C_{1-4}$-alkyl or phenyl;

$R^8$, $R^9$ and $R^{10}$ each independently represent H, $-CF_3$, $-C(=O)-NR^{11}R^{12}$, $-C_{1-6}$-alkylene-C$(=O)-NR^{11}R^{12}$, $-C_{1-6}$-alkylene-$NR^{11}R^{12}$, phenyl, naphthyl, furyl, thienyl or pyridinyl or a phenyl, naphthyl, furyl, thienyl or pyridinyl bonded via a $C_{1-6}$-alkylene group, wherein the phenyl, naphthyl, furyl, thienyl or pyridinyl is unsubstituted or substituted one or more times by identical or different substituents independently selected from the group consisting of $-O-C_{1-3}$-alkyl, $-C_{1-6}$-alkyl, $-F$, $-Cl$, $-Br$, $-I$, $-CF_3$, $-OCF_3$, $-OH$, $-SH$, phenyl, naphthyl, furyl, thienyl and pyridinyl;

wherein preferably at least one of the groups $R^4$, $R^{4a}$, $R^5$, $R^6$, $R^7$, $R^8$, $R^9$ and $R^{10}$ does not represent H, $R^{11}$ and $R^{12}$ each independently represent H, substituted or unsubstituted $C_{1-6}$-alkyl or $C_{3-8}$-cycloalkyl; or the group —$NR^{11}R^{12}$ represents the heterocylic ring corresponding to formula IIaa

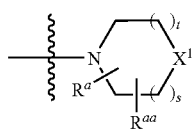

wherein $X^1$ represents O, S, $NR^{18}$, $CH_2$, C(H)(halogen) or C(halogen)$_2$, wherein halogen preferably denotes F, Cl or Br, $R^{18}$ represents H; $C_{1-6}$-alkyl, $C_{3-8}$-cycloalkyl; aryl, preferably phenyl or naphthyl; or heteroaryl, preferably a 5- to 6-membered heteroaryl having 1 or 2 N hetero atoms, in particular pyridinyl; or $R^{18}$ represents a $C_{3-8}$-cycloalkyl bonded via a $C_{1-3}$-alkylene group, an aryl, preferably phenyl or naphthyl, bonded via a $C_{1-3}$-alkylene group; or a heteroaryl, preferably a 5- to 6-membered heteroaryl having 1 or 2 N hetero atoms, in particular pyridinyl, bonded via a $C_{1-3}$-alkylene group, wherein the abovementioned groups $C_{1-6}$-alkyl, $C_{3-8}$-cycloalkyl, $C_{1-3}$-alkylene, aryl and heteroaryl may optionally each be unsubstituted or substituted one or more times by identical or different substituents independently selected from the group consisting of —O—$C_{1-3}$-alkyl, —$C_{1-6}$-alkyl, —F, —Cl, —Br, —I, —$CF_3$, —$OCF_3$, —OH, —SH, phenyl, naphthyl, furyl, thienyl and pyridinyl, $R^a$ and $R^{aa}$ each independently represent H, methyl, ethyl, F, Cl or Br, and s and t each independently represent 0, 1 or 2, with the proviso that s+t=0, 1, 2 or 3, $R^{13}$ represents H, methyl, ethyl, n-propyl, iso-propyl, n-butyl, iso-butyl, sec-butyl, tert-butyl, benzyl or phenethyl, optionally in the form of an individual enantiomer or of an individual diastereomer, of the racemate, of the enantiomers, of the diastereomers, mixtures of enantiomers and/or diastereomers, and in each case in the form of their bases, their physiologically acceptable salts and/or their N-oxides.

Substituted sulfonamide compounds corresponding to formula I according to the invention which are likewise preferred are those in which m and n each independently represent 0, 1 or 2;

p represents 0, 1 or 2;

Q represents a single bond, —$CH_2$— or —O—;

X represents N, $NR^5$, O, S or $CR^8$;

Y represents N, $NR^6$, O, S or $CR^9$;

Z represents N, $NR^7$, O, S or $CR^{10}$;

$R^1$ represents phenyl or naphthyl, wherein the phenyl or naphthyl is unsubstituted or substituted one or more times, for example 2, 3, 4 or 5 times, by identical or different substituents selected from the group consisting of methyl, methoxy, $CF_3$, $OCF_3$, F, Cl and Br;

$R^2$ represents H, $C_{1-6}$-alkyl, cyclopropyl, CH(phenyl)$_2$, phenyl, thienyl, pyridyl, pyrimidinyl, thiazolyl, imidazolyl, oxazolyl, quinazolyl, quinolinyl or a phenyl, thienyl, pyridyl, pyrimidinyl, thiazolyl, imidazolyl, oxazolyl, quinazolyl or quinolinyl bonded via a $C_{1-6}$-alkylene group, wherein the phenyl, thienyl, pyridyl, pyrimidinyl, thiazolyl, imidazolyl, oxazolyl, quinazolyl and quinolinyl is in each case unsubstituted or substituted one or more times by identical or different substituents independently selected from the group consisting of methyl, ethyl, n-propyl, iso-propyl, n-butyl, iso-butyl, sec-butyl, tert-butyl, methoxy, F, Cl, Br, I, $CF_3$, $OCF_3$ and OH;

$R^3$ represents H, —C(=O)—$NR^{11}R^{12}$, —C(=O)—$OR^{13}$, phenyl, naphthyl, thienyl, pyridyl, pyrimidyl, thiazolyl, imidazolyl, oxazolyl, quinazolyl or quinolinyl, wherein the phenyl naphthyl, thienyl, pyridyl, pyrimidyl, thiazolyl, imidazolyl, oxazolyl, quinazolyl or quinolinyl is each case unsubstituted or substituted one or more times by identical or different substituents independently selected from the group consisting of methyl, ethyl, n-propyl, iso-propyl, n-butyl, iso-butyl, sec-butyl, tert-butyl, methoxy, F, Cl, Br, I, $CF_3$, $OCF_3$ and OH, and wherein $R^2$ and $R^3$ do not both simultaneously represent H; or $R^2$ and $R^3$ together with the —N—(CH—)- group joining them form a 4-, 5-, 6- or 7-membered, preferably 5-, 6- or 7-membered heterocyclic ring, which may contain an oxygen atom and which optionally may be fused with one or two 6-membered aromatic ring(s) (e.g., benzo groups);

$R^4$ and $R^{4a}$ each independently represent H, methyl, ethyl, n-propyl, iso-propyl, n-butyl, iso-butyl, sec-butyl, tert-butyl, phenyl, naphthyl, furyl, thienyl, pyridinyl, benzyl or phenethyl, wherein the phenyl, naphthyl, furyl, thienyl, pyridinyl or the aromatic part of benzyl and phenethyl is in each case unsubstituted or substituted one or more times by identical or different substituents independently selected from the group consisting of —O—$C_{1-3}$-alkyl, —$C_{1-6}$-alkyl, —F, —Cl, —Br, —I, —$CF_3$, —$OCF_3$, —OH, —SH, phenyl, naphthyl, furyl, thienyl and pyridinyl;

$R^5$, $R^6$ and $R^7$ each independently represent H, methyl, ethyl, n-propyl, iso-propyl, n-butyl, iso-butyl, sec-butyl, tert-butyl or phenyl;

$R^8$, $R^9$ and $R^{10}$ each independently represent H, —$CF_3$, —C(=O)—$NR^{11}R^{12}$, —($CH_2$)—$NR^{11}R^{12}$, —($CH_2$)$_2$—$NR^{11}R^{12}$, —($CH_2$)$_3$—$NR^{11}R^{12}$, —($CH_2$)—(C=O)—$NR^{11}R^{12}$, —($CH_2$)$_2$—(C=O)—$NR^{11}R^{12}$, —($CH_2$)$_3$—(C=O)—$NR^{11}R^{12}$, phenyl, naphthyl, furyl, thienyl or pyridinyl or a phenyl, naphthyl, furyl, thienyl or pyridinyl bonded via a —($CH_2$)—, —($CH_2$)$_2$— or —($CH_2$)$_3$— group, wherein phenyl, naphthyl, furyl, thienyl or pyridinyl is unsubstituted or substituted one or more times by identical or different substituents independently selected from the group consisting of —O—$C_{1-3}$-alkyl, —$C_{1-6}$-alkyl, —F, —Cl, —Br, —I, —$CF_3$, —$OCF_3$, —OH, —SH, phenyl, naphthyl, furyl, thienyl and pyridinyl;

wherein at least one of the groups $R^4$, $R^{4a}$, $R^5$, $R^6$, $R^7$, $R^8$, $R^9$ and $R^{10}$ does not represent H;

$R^{11}$ and $R^{12}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or the group —$NR^{11}R^{12}$ represents a heterocyclic ring selected from the group consisting of

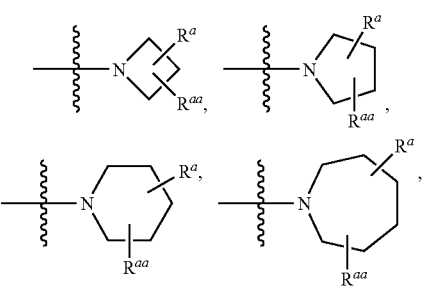

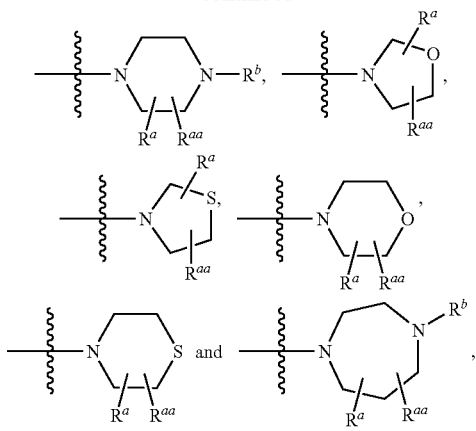

wherein $R^a$ and $R^{aa}$ each independently represent H, methyl, ethyl, F, Cl or Br, and $R^b$ represents methyl, phenyl or pyridinyl, wherein the phenyl or pyridinyl can be bonded via a $C_{1-6}$-alkylene bridge and is unsubstituted or substituted one or more times, for example 2 times or 3 times, by identical or different substituents independently selected from the group consisting of methyl, methoxy, F and Cl.

$R^{13}$ represents H, methyl, ethyl, n-propyl, iso-propyl, n-butyl, iso-butyl, sec-butyl, tert-butyl, benzyl or phenethyl, optionally in the form of an individual enantiomer or of an individual diastereomer, of the racemate, of the enantiomers, of the diastereomers, mixtures of enantiomers and/or diastereomers, and in each case in the form of their bases, their physiologically acceptable salts and/or their N-oxides.

Substituted sulfonamide compounds corresponding to formula I according to the invention which are likewise preferred are those wherein m and n each independently represent 0, 1 or 2;

Q represents a single bond, —$CH_2$— or —O—;

p and X, Y, Z are selected such that the following partial structure

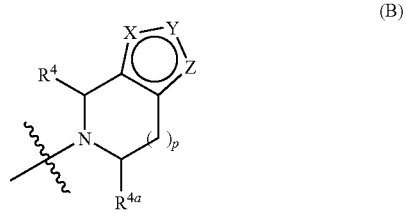

(B)

represents a group which is selected from the abovementioned group B1 or B2, $R^1$ represents phenyl or naphthyl, wherein the phenyl or naphthyl is unsubstituted or substituted one or more times, for example 2, 3, 4 or 5 times, by identical or different substituents selected from the group consisting of methyl, methoxy, $CF_3$, $OCF_3$, F, Cl and Br;

$R^2$ represents H, methyl, ethyl, n-propyl, iso-propyl, n-butyl, iso-butyl, sec-butyl, tert-butyl or cyclopropyl;

$R^3$ represents H or phenyl, wherein the phenyl may be unsubstituted or substituted one or more times by identical or different substituents independently selected from the group consisting of methyl, ethyl, n-propyl, iso-propyl, n-butyl, iso-butyl, sec-butyl, tert-butyl, methoxy, F, Cl, Br, I, $CF_3$, $OCF_3$ and OH; wherein $R^2$ and $R^3$ do not both simultaneously represent H; or $R^2$ and $R^3$ together with the —N—(CH—)-group joining them form a 4-, 5-, 6- or 7-membered, preferably 5-, 6- or 7-membered, heterocyclic ring, which optionally may contain an oxygen atom and which optionally may be fused with one or two 6-membered aromatic ring(s) (e.g., benzo groups);

$R^4$ and $R^{4a}$ each independently represent H, methyl, ethyl, n-propyl, iso-propyl, n-butyl, iso-butyl, sec-butyl, tert-butyl, phenyl, naphthyl, furyl, thienyl, pyridinyl, benzyl or phenethyl, wherein the phenyl, naphthyl, furyl, thienyl, pyridinyl or the aromatic part of benzyl and phenethyl is in each case unsubstituted or substituted one or more times by identical or different substituents independently selected from the group consisting of —O—$C_{1-3}$-alkyl, $C_{1-6}$-alkyl, —F, —Cl, —Br, —I, —$CF_3$, —$OCF_3$, —OH, —SH, phenyl, naphthyl, furyl, thienyl and pyridinyl;

$R^5$, $R^6$ and $R^7$ each independently represent H, methyl, ethyl, n-propyl, iso-propyl, n-butyl, iso-butyl, sec-butyl; tert-butyl and phenyl;

$R^8$, $R^9$ and $R^{10}$ each independently represent H, —$CF_3$, —C(=O)—$NR^{11}R^{12}$, —$(CH_2)$—$NR^{11}R^{12}$, —$(CH_2)_2$—$NR^{11}R^{12}$, —$(CH_2)_3$—$NR^{11}R^{12}$, —$(CH_2)$—(C=O)—$NR^{11}R^{12}$—$(CH_2)_2$—(C=O)—$NR^{11}R^{12}$, —$(CH_2)_3$—(C=O)—$NR^{11}R^{12}$, phenyl, naphthyl, furyl, thienyl or pyridinyl, or a phenyl, naphthyl, furyl, thienyl or pyridinyl bonded via a —$(CH_2)$—, —$(CH_2)_2$— or —$(CH_2)_3$— group, wherein the phenyl, naphthyl, furyl, thienyl or pyridinyl may be unsubstituted or substituted one or more times by identical or different substituents independently selected from the group consisting of —O—$C_{1-3}$-alkyl, —$C_{1-6}$-alkyl, —F, —Cl, —Br, —I, —$CF_3$, —$OCF_3$, —OH, —SH, phenyl, naphthyl, furyl, thienyl and pyridinyl;

wherein at least one of the groups $R^4$, $R^{4a}$, $R^5$, $R^6$, $R^7$, $R^3$, $R^9$ and $R^{10}$ does not represent H;

$R^{11}$ and $R^{12}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or the group —$NR^{11}R^{12}$ represents a heterocyclic ring selected from the group consisting of:

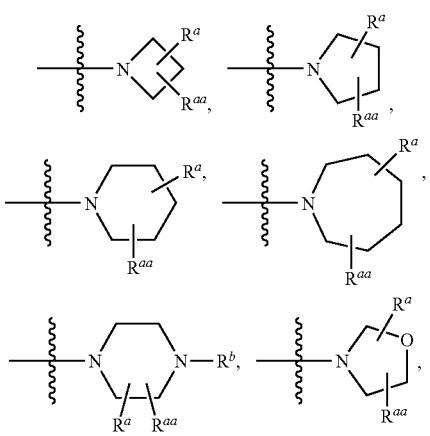

-continued

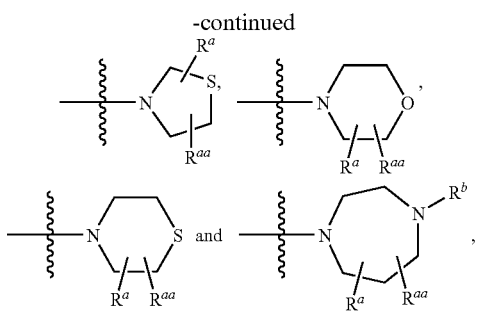

wherein
$R^a$ and $R^{aa}$ each independently represent H, methyl, ethyl, F, Cl or Br, and
$R^b$ represents methyl, phenyl or pyridinyl, wherein the phenyl or pyridinyl optionally may be bonded via a $C_{1-6}$-alkylene bridge and may be unsubstituted or substituted one or more times, for example 2 times or 3 times, by identical or different substituents independently selected from the group consisting of methyl, methoxy, F and Cl;
optionally in the form of an individual enantiomer or of an individual diastereomer, of the racemate, of the enantiomers, of the diastereomers, mixtures of enantiomers and/or diastereomers, and in each case in the form of their bases, their physiologically acceptable salts and/or their N-oxides.

Particularly preferred substituted sulfonamide compounds corresponding to formula I according to the invention are those in which
m and n each independently represent 0, 1 or 2;
p represents 1;
Q represents a single bond, —$CH_2$— or —O—;
p and X, Y and Z are selected such that the following partial structure

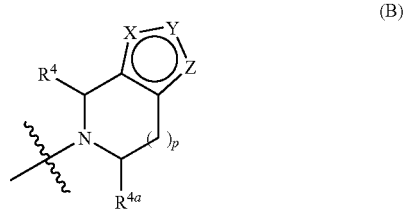

(B)

represents a group which is selected from the group consisting of

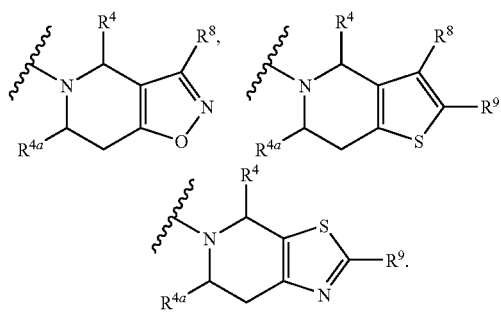

$R^1$ represents phenyl or naphthyl, wherein the phenyl or naphthyl may be unsubstituted or substituted one or more times, for example 2, 3, 4 or 5 times, by identical or different substituents selected from the group consisting of methyl, methoxy, $CF_3$, $OCF_3$, F, Cl and Br;
$R^2$ represents H, methyl, ethyl, n-propyl, iso-propyl, n-butyl, iso-butyl, sec-butyl, tert-butyl or cyclopropyl;
$R^3$ represents H or phenyl, wherein the phenyl may be unsubstituted or substituted one or more times by identical or different substituents independently selected from the group consisting of methyl, ethyl, n-propyl, iso-propyl, n-butyl, iso-butyl, sec-butyl, tert-butyl, methoxy, F, Cl, Br, I, $CF_3$, $OCF_3$ and OH; wherein $R^2$ and $R^3$ do not both simultaneously represent H; or
$R^2$ and $R^3$ together with the —N—(CH—)-group joining them form a 4-, 5-, 6- or 7-membered, preferably 5-, 6- or 7-membered, heterocyclic ring, which optionally may be fused with one or two 6-membered aromatic ring(s) (e.g., benzo group);
$R^4$ represents H, methyl, ethyl, n-propyl, iso-propyl, n-butyl, iso-butyl, sec-butyl, tert-butyl, phenyl, naphthyl, furyl, thienyl, pyridinyl, benzyl or phenethyl, wherein the phenyl, naphthyl, furyl, thienyl, pyridinyl or the aromatic part of benzyl and phenethyl may be unsubstituted or substituted one or more times by identical or different substituents independently selected from the group consisting of —O—$C_{1-3}$-alkyl, —$C_{1-6}$-alkyl, —F, —Cl, —Br, —I, —$CF_3$, —$OCF_3$, —OH, —SH, phenyl, naphthyl, furyl, thienyl and pyridinyl;
$R^{4a}$ represents H or phenyl, wherein the phenyl may be unsubstituted or substituted one or more times by identical or different substituents independently selected from the group consisting of —O—$C_{1-3}$-alkyl, —$C_{1-6}$-alkyl, —F, —Cl, —Br, —I, —$CF_3$, —$OCF_3$, —OH, —SH, phenyl, naphthyl, furyl, thienyl and pyridinyl;
$R^8$ and $R^9$ each independently represent H, —C(=O)—$NR^{11}R^{12}$, —$(CH_2)$—$NR^{11}R^{12}$, —$(CH_2)_2$—$NR^{11}R^{12}$, —$(CH_2)_3$—$NR^{11}R^{12}$, —$(CH_2)$—(C=O)—$NR^{11}R^{12}$, —$(CH_2)_2$—(C=O)—$NR^{11}R^{12}$, —$(CH_2)_3$—(C=O)—$NR^{11}R^{12}$, phenyl, naphthyl, furyl, thienyl or pyridinyl or a phenyl, naphthyl, furyl, thienyl or pyridinyl bonded via a —$(CH_2)$—, —$(CH_2)_2$— or —$(CH_2)_3$— group, wherein phenyl, naphthyl, furyl, thienyl or pyridinyl may be unsubstituted or substituted one or more times by identical or different substituents independently selected from the group consisting of —O—$C_{1-3}$-alkyl, —$C_{1-6}$-alkyl, —F, —Cl, —Br, —I, —$CF_3$, —$OCF_3$, —OH, —SH, phenyl, naphthyl, furyl, thienyl and pyridinyl;
wherein at least one of the groups $R^4$, $R^{4a}$, $R^8$ and $R^9$ does not represent H; and the group —$NR^{11}R^{12}$ represents a group which is selected from the group consisting of:

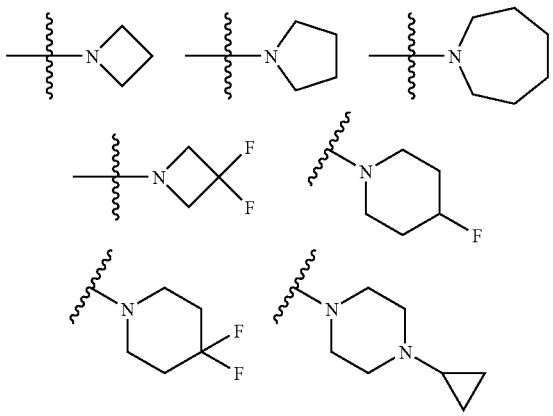

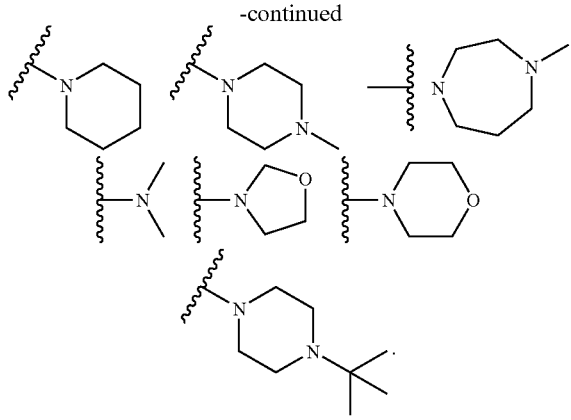

optionally in the form of an individual enantiomer or of an individual diastereomer, of the racemate, of the enantiomers, of the diastereomers, mixtures of enantiomers and/or diastereomers, and in each case in the form of their bases, their physiologically acceptable salts and/or their N-oxides.

Very particularly preferred sulfonamide compounds according to the invention are selected from the group consisting of:

1 3-(1-(4-methoxy-2,6-dimethylphenylsulfonyl)piperidin-2-yl)-1-(3-(pyridin-4-yl)-6,7-dihydroisoxazolo[4,5-c]pyridin-5(4H)-yl)propan-1-one
2 2-((1-(4-methoxy-2,6-dimethylphenylsulfonyl)piperidin-2-yl)methoxy)-1-(3-(pyridin-4-yl)-6,7-dihydroisoxazolo[4,5-c]pyridin-5(4H)-yl)ethanone
3 I—N-(3-oxo-1-phenyl-3-(3-(pyridin-4-yl)-6,7-dihydroisoxazolo[4,5-c]pyridin-5(4H)-yl)propyl)naphthalene-2-sulfonamide
4 3-(1-(4-chloro-2,5-dimethylphenylsulfonyl)piperidin-2-yl)-1-(3-(piperidine-1-carbonyl)-6,7-dihydroisoxazolo[4,5-c]pyridin-5(4H)-yl)propan-1-one
5 1-(3-(piperidin-1-ylmethyl)-6,7-dihydroisoxazolo[4,5-c]pyridin-5(4H)-yl)-2-(1-(3-(trifluoromethyl)phenylsulfonyl)piperidin-2-yl)ethanone
6 3-(1-(4-chloro-2,5-dimethylphenylsulfonyl)piperidin-2-yl)-1-(3-(piperidin-1-ylmethyl)-6,7-dihydroisoxazolo[4,5-c]pyridin-5(4H)-yl)propan-1-one
7 2-((1-(4-methoxy-2,6-dimethylphenylsulfonyl)piperidin-2-yl)methoxy)-1-(4-p-tolyl-6,7-dihydrothieno[3,2-c]pyridin-5(4H)-yl)ethanone
8 2-((1-(4-methoxy-2,6-dimethylphenylsulfonyl)piperidin-2-yl)methoxy)-1-(4-m-tolyl-6,7-dihydrothieno[3,2-c]pyridin-5(4H)-yl)ethanone
9 2-((1-(4-methoxy-2,6-dimethylphenylsulfonyl)piperidin-2-yl)methoxy)-1-(3-(piperidin-1-ylmethyl)-6,7-dihydroisoxazolo[4,5-c]pyridin-5(4H)-yl)ethanone
10 3-(1-(4-chloro-2,5-dimethylphenylsulfonyl)piperidin-2-yl)-1-(4-m-tolyl-6,7-dihydrothieno[3,2-c]pyridin-5(4H)-yl)propan-1-one
11 3-(1-(4-chloro-2,5-dimethylphenylsulfonyl)piperidin-2-yl)-1-(4-o-tolyl-6,7-dihydrothieno[3,2-c]pyridin-5(4H)-yl)propan-1-one
12 2-((1-(4-methoxy-2,6-dimethylphenylsulfonyl)piperidin-2-yl)methoxy)-1-(4-o-tolyl-6,7-dihydrothieno[3,2-c]pyridin-5(4H)-yl)ethanone
13 4-methoxy-N,2,6-trimethyl-N-(2-(2-oxo-2-(3-(piperidin-1-ylmethyl)-6,7-dihydroisoxazolo[4,5-c]pyridin-5(4H)-yl)ethoxy)ethyl)benzenesulfonamide
14 2-((1-(4-methoxy-2,6-dimethylphenylsulfonyl)piperidin-2-yl)methoxy)-1-(3-(piperidin-1-carbonyl)-6,7-dihydroisoxazolo[4,5-c]pyridin-5(4H)-yl)ethanone
15 2-((1-(4-methoxy-2,6-dimethylphenylsulfonyl)piperidin-2-yl)methoxy)-1-(4-phenyl-6,7-dihydrothieno[3,2-c]pyridin-5(4H)-yl)ethanone
16 3-(1-(4-chloro-2,5-dimethylphenylsulfonyl)piperidin-2-yl)-1-(4-phenyl-6,7-dihydrothieno[3,2-c]pyridin-5(4H)-yl)propan-1-one
17 I—N-(3-oxo-1-phenyl-3-(3-(piperidin-1-ylmethyl)-6,7-dihydroisoxazolo[4,5-c]pyridin-5(4H)-yl)propyl)naphthalene-2-sulfonamide
18 N-(2-(2-(4-ethyl-6,7-dihydrothieno[3,2-c]pyridin-5(4H)-yl)-2-oxoethoxy)ethyl)-4-methoxy-N,2,6-trimethylbenzenesulfonamide
19 1-(4-(4-fluorophenyl)-6,7-dihydrothieno[3,2-c]pyridin-5(4H)-yl)-2-(1-(3-(trifluoromethyl)phenylsulfonyl)piperidin-2-yl)ethanone
20 N-((1R)-3-oxo-1-phenyl-3-(4-p-tolyl-6,7-dihydrothieno[3,2-c]pyridin-5(4H)-yl)propyl)naphthalene-2-sulfonamide
21 N-((1R)-3-(4-(4-fluorophenyl)-6,7-dihydrothieno[3,2-c]pyridin-5(4H)-yl)-3-oxo-1-phenylpropyl)naphthalene-2-sulfonamide
22 1-(4-(4-fluorophenyl)-6,7-dihydrothieno[3,2-c]pyridin-5(4H)-yl)-2-((1-(4-methoxy-2,6-dimethylphenylsulfonyl)piperidin-2-yl)methoxy)ethanone
23 1-(4-ethyl-6,7-dihydrothieno[3,2-c]pyridin-5(4H)-yl)-4-(1-(4-methoxy-2,6-dimethylphenylsulfonyl)piperidin-2-yl)butan-1-one
24 1-(3-(4-chlorophenyl)-6,7-dihydroisoxazolo[4,5-c]pyridin-5(4H)-yl)-2-((1-(4-methoxy-2,6-dimethylphenylsulfonyl)piperidin-2-yl)methoxy)ethanone
25 1-(3-(4-fluorophenyl)-6,7-dihydroisoxazolo[4,5-c]pyridin-5(4H)-yl)-2-((1-(4-methoxy-2,6-dimethylphenylsulfonyl)piperidin-2-yl)methoxy)ethanone
26 I—N-(3-oxo-1-phenyl-3-(2-(piperidin-1-ylmethyl)-6,7-dihydrothieno[3,2-c]pyridin-5(4H)-yl)propyl)naphthalene-2-sulfonamide
27 2-((1-(4-methoxy-2,6-dimethylphenylsulfonyl)piperidin-2-yl)methoxy)-1-(2-(piperidin-1-ylmethyl)-6,7-dihydrothieno[3,2-c]pyridin-5(4H)-yl)ethanone
28 4-methoxy-N,2,6-trimethyl-N-(2-(2-oxo-2-(2-(piperidin-1-ylmethyl)-6,7-dihydrothieno[3,2-c]pyridin-5(4H)-yl)ethoxy)ethyl)benzenesulfonamide
29 2-((1-(4-methoxy-2,6-dimethylphenylsulfonyl)piperidin-2-yl)methoxy)-1-(3-(morpholinomethyl)-6,7-dihydroisoxazolo[4,5-c]pyridin-5(4H)-yl)ethanone
30 4-methoxy-N,2,6-trimethyl-N-(2-(2-(3-(morpholinomethyl)-6,7-dihydroisoxazolo[4,5-c]pyridin-5(4H)-yl)-2-oxoethoxy)ethyl)benzenesulfonamide
31 1-(3-((dimethylamino)methyl)-6,7-dihydroisoxazolo[4,5-c]pyridin-5(4H)-yl)-2-((1-(4-methoxy-2,6-dimethylphenylsulfonyl)piperidin-2-yl)methoxy)ethanone
32 N-(2-(2-(3-((dimethylamino)methyl)-6,7-dihydroisoxazolo[4,5-c]pyridin-5(4H)-yl)-2-oxoethoxy)ethyl)-4-methoxy-N,2,6-trimethylbenzenesulfonamide
33 3-(1-(4-chloro-2,5-dimethylphenylsulfonyl)piperidin-2-yl)-1-(4-(6-chloropyridin-3-yl)-6,7-dihydrothieno[3,2-c]pyridin-5(4H)-yl)propan-1-one
34 3-(1-(4-chloro-2,5-dimethylphenylsulfonyl)piperidin-2-yl)-1-(4-(3-(trifluoromethyl)phenyl)-6,7-dihydrothieno[3,2-c]pyridin-5(4H)-yl)propan-1-one
35 3-(1-(4-chloro-2,5-dimethylphenylsulfonyl)piperidin-2-yl)-1-(4-(3-fluorophenyl)-6,7-dihydrothieno[3,2-c]pyridin-5(4H)-yl)propan-1-one
36 2-((1-(4-methoxy-2,6-dimethylphenylsulfonyl)piperidin-2-yl)methoxy)-1-(4-(pyridin-4-yl)-6,7-dihydrothieno[3,2-c]pyridin-5(4H)-yl)ethanone 37 1-(2-(pyridin-4-yl)-6,7-dihydrothiazolo[5,4-c]pyridin-5(4H)-yl)-2-(1-(3-(trifluoromethyl)phenylsulfonyl)piperidin-2-yl)ethan-1-one 38 2-((1-(4-methoxy-2,6-dimethylphenylsulfonyl)piperidin-2-yl)methoxy)-1-(2-(pyridin-4-ylmethyl)-6,7-dihydrothiazolo[5,4-c]pyridin-5(4H)-yl)ethan-1-one 39 4-methoxy-N,2,6-trimethyl-N-(2-(2-oxo-2-(2-(pyridin-4-ylmethyl)-6,7-dihydrothiazolo[5,4-c]pyridin-5(4H)-yl)ethoxy)ethyl)benzenesulfonamide 40 1-(2-(pyridin-4-ylmethyl)-6,7-dihydrothiazolo[5,4-c]pyridin-5(4H)-yl)-2-(1-(3-(trifluoromethyl)phenylsulfonyl)piperidin-2-yl)ethan-1-one 41 3-(1-(4-methoxy-2,6-dimethylphenylsulfonyl)piperidin-2-yl)-1-(2-(pyridin-4-ylmethyl)-6,7-dihydrothiazolo[5,4-c]pyridin-5(4H)-yl)propan-1-one 42 N-(3-oxo-1-phenyl-3-(2-(pyridin-4-ylmethyl)-6,7-dihydrothiazolo[5,4-c]pyridin-5(4H)-yl)propyl)naphthalene-2-sulfonamide 43 4-(1-(4-methoxy-2,6-dimethylphenylsulfonyl)piperidin-2-yl)-1-(2-(pyridin-4-ylmethyl)-6,7-dihydrothiazolo[5,4-c]pyridin-5(4H)-yl)butan-1-one 44 1-(2-((4-methylpiperazin-1-yl)methyl)-6,7-dihydrothieno[3,2-c]pyridin-5(4H)-yl)-2-(1-(3-(trifluoromethyl)phenylsulfonyl)piperidin-2-yl)ethan-1-one 45 3-(1-(4-methoxy-2,6-dimethylphenylsulfonyl)piperidin-2-yl)-1-(2-((4-methylpiperazin-1-yl)methyl)-6,7-dihydrothieno[3,2-c]pyridin-5(4H)-yl)propan-1-one 46 N-(3-(2-((4-methylpiperazin-1-yl)methyl)-6,7-dihydrothieno[3,2-c]pyridin-5(4H)-yl)-3-oxo-1-phenylpropyl)naphthalene-2-sulfonamide 47 4-(1-(4-methoxy-2,6-dimethylphenylsulfonyl)piperidin-2-yl)-1-(2-((4-methylpiperazin-1-yl)methyl)-6,7-dihydrothieno[3,2-c]pyridin-5(4H)-yl)butan-1-one 48 2-((1-(4-methoxy-2,6-dimethylphenylsulfonyl)piperidin-2-yl)methoxy)-1-(2-(pyridin-4-yl)-6,7-dihydrothiazolo[5,4-c]pyridin-5(4H)-yl)ethan-1-one 49 4-methoxy-N,2,6-trimethyl-N-(2-(2-oxo-2-(2-(pyridin-4-yl)-6,7-dihydrothiazolo[5,4-c]pyridin-5(4H)-yl)ethoxy)ethyl)benzenesulfonamide 50 2-((1-(4-methoxy-2,6-dimethylphenylsulfonyl)piperidin-2-yl)methoxy)-1-(2-((4-methylpiperazin-1-yl)methyl)-6,7-dihydrothieno[3,2-c]pyridin-5(4H)-yl)ethan-1-one 51 4-methoxy-N,2,6-trimethyl-N-(2-(2-(2-((4-methylpiperazin-1-yl)methyl)-6,7-dihydrothieno[3,2-c]pyridin-5(4H)-yl)-2-oxoethoxy)ethyl)benzenesulfonamide 52 3-(1-(4-methoxy-2,6-dimethylphenylsulfonyl)piperidin-2-yl)-1-(2-(pyridin-4-yl)-6,7-dihydrothiazolo[5,4-c]pyridin-5(4H)-yl)propan-1-one 53 4-(1-(4-methoxy-2,6-dimethylphenylsulfonyl)piperidin-2-yl)-1-(2-(pyridin-4-yl)-6,7-dihydrothiazolo[5,4-c]pyridin-5(4H)-yl)butan-1-one 54 1-(4-pyridin-4-yl-4,5,6,7-tetrahydro-thieno[3,2-c]pyridin-5-yl)-2-[1-[[3-(trifluoromethyl)phenyl]sulfonyl]-piperidin-2-yl]-ethanone 55 3-[1-[(4-chloro-2,5-dimethyl-phenyl)sulfonyl]-piperidin-2-yl]-1-(4-pyridin-4-yl-4,5,6,7-tetrahydro-thieno[3,2-c]pyridin-5-yl)-propan-1-one 56 N-[2-[2-[2-(azetidin-1-yl-methyl)-4,5,6,7-tetrahydro-thieno[3,2-c]pyridin-5-yl]-2-oxo-ethoxy]-ethyl]-2-chloro-N-cyclopropyl-6-methyl-benzenesulfonic acid amide 57 2-chloro-N-cyclopropyl-N-[2-[2-[2-[(3,3-difluoro-azetidin-1-yl)-methyl]-4,5,6,7-tetrahydro-thieno[3,2-c]pyridin-5-yl]-2-oxo-ethoxy]-ethyl]-6-methyl-benzenesulfonic acid amide 58 2-[[(2S)-1-[(4-methoxy-2,6-dimethyl-phenyl)sulfonyl]-piperidin-2-yl]-methoxy]-1-[2-(piperidin-1-yl-methyl)-4,5,6,7-tetrahydro-thiazolo[5,4-c]pyridin-5-yl]-ethanone 59 2-[[(2S)-1-[(2-chloro-6-methyl-phenyl)sulfonyl]-piperidin-2-yl]-methoxy]-1-[2-(piperidin-1-yl-methyl)-4,5,6,7-tetrahydro-thieno[3,2-c]pyridin-5-yl]-ethanone 60 2-chloro-N-cyclopropyl-6-methyl-N-[2-[2-oxo-2-[2-(piperidin-1-yl-methyl)-4,5,6,7-tetrahydro-thieno[3,2-c]pyridin-5-yl]-ethoxy]-ethyl]-benzenesulfonic acid amide 61 2-[[(2S)-1-[(4-methoxy-2,6-dimethyl-phenyl)sulfonyl]-1,2,3,4-tetrahydro-quinolin-2-yl]-methoxy]-1-[2-(piperidin-1-yl-methyl)-4,5,6,7-tetrahydro-thieno[3,2-c]pyridin-5-yl]-ethanone 62 2-[[(2S)-1-[(4-methoxy-2,6-dimethyl-phenyl)sulfonyl]-piperidin-2-yl]-methoxy]-1-[2-(pyrrolidin-1-yl-methyl)-4,5,6,7-tetrahydro-thieno[3,2-c]pyridin-5-yl]-ethanone 63 2-[[(2S)-1-[(4-methoxy-2,6-dimethyl-phenyl)sulfonyl]-pyrrolidin-2-yl]-methoxy]-1-[2-(piperidin-1-yl-methyl)-4,5,6,7-tetrahydro-thieno[3,2-c]pyridin-5-yl]-ethanone 64 2-[[(2S)-1-[(4-methoxy-2,6-dimethyl-phenyl)sulfonyl]-piperidin-2-yl]-methoxy]-1-[2-[(4-methyl-[1,4]diazepan-1-yl)-methyl]-4,5,6,7-tetrahydro-thieno[3,2-c]pyridin-5-yl]-ethanone 66 4-Methoxy-N,2,6-trimethyl-N-[2-[2-oxo-2-(4-phenyl-4,5,6,7-tetrahydro-1H-imidazo[4,5-c]pyridin-5-yl)-ethoxy]-ethyl]-benzenesulfonic acid amide 68 4-[1-[(2-Chloro-6-methyl-phenyl)sulfonyl]-piperidin-2-yl]-1-[2-[(4-methyl-piperazin-1-yl)-methyl]-4,5,6,7-tetrahydro-thieno[3,2-c]pyridin-5-yl]-butan-1-one 69 4-[1-[(2-Chloro-6-methyl-phenyl)sulfonyl]-piperidin-2-yl]-1-(4-phenyl-4,5,6,7-tetrahydro-1H-imidazo[4,5-c]pyridin-5-yl)-butan-1-one 71 4-[1-[(4-Methoxy-2,6-dimethyl-phenyl)sulfonyl]-piperidin-2-yl]-1-(4-phenyl-4,5,6,7-tetrahydro-1H-imidazo[4,5-c]pyridin-5-yl)-butan-1-one 73 1-[2-[(4-Methyl-piperazin-1-yl)-methyl]-4,5,6,7-tetrahydro-thieno[3,2-c]pyridin-5-yl]-4-[1-(naphthalen-1-ylsulfonyl)-piperidin-2-yl]-butan-1-one 74 4-[1-(Naphthalen-1-ylsulfonyl)-piperidin-2-yl]-1-(4-phenyl-4,5,6,7-tetrahydro-1H-imidazo[4,5-c]pyridin-5-yl)-butan-1-one 75 1-[2-[(4-Methyl-piperazin-1-yl)-methyl]-4,5,6,7-tetrahydro-thieno[3,2-c]pyridin-5-yl]-4-[1-(naphthalen-2-ylsulfonyl)-piperidin-2-yl]-butan-1-one 76 4-[1-(Naphthalen-2-ylsulfonyl)-piperidin-2-yl]-1-(4-phenyl-4,5,6,7-tetrahydro-1H-imidazo[4,5-c]pyridin-5-yl)-butan-1-one 78 N-(4H-[1,3]Benzodioxin-7-yl-methyl)-4-methoxy-2,6-dimethyl-N-[2-[2-[2-[(4-methyl-piperazin-1-yl)-methyl]-4,5,6,7-tetrahydro-thieno[3,2-c]pyridin-5-yl]-2-oxo-ethoxy]-ethyl]-benzenesulfonic acid amide 81 N-Benzyl-4-Methoxy-2,6-dimethyl-N-[2-[2-[2-[(4-methyl-piperazin-1-yl)-methyl]-4,5,6,7-tetrahydro-thieno[3,2-c]pyridin-5-yl]-2-oxo-ethoxy]-ethyl]-benzenesulfonic acid amide 82 N-Benzyl-4-Methoxy-2,6-dimethyl-N-[2-[2-oxo-2-(4-phenyl-4,5,6,7-tetrahydro-1H-imidazo[4,5-c]pyridin-5-yl)-ethoxy]-ethyl]-benzenesulfonic acid amide 83 4-Methoxy-2,6-Dimethyl-N-[2-[2-[2-[(4-methyl-piperazin-1-yl)-methyl]-4,5,6,7-tetrahydro-thieno[3,2-c]pyridin-5-yl]-2-oxo-ethoxy]-ethyl]-N-phenyl-benzenesulfonic acid amide 84 4-Methoxy-2,6-Dimethyl-N-[2-[2-oxo-2-(4-phenyl-4,5,6,7-tetrahydro-1H-imidazo[4,5-c]pyridin-5-yl)-ethoxy]-ethyl]-N-phenyl-benzenesulfonic acid amide 85 2-[[1-[(4-Methoxy-2,6-dimethyl-phenyl)sulfonyl]-1,2,3,4-tetrahydro-quinolin-2-yl]-methoxy]-1-[2-[(4-methyl-piperazin-1-yl)-methyl]-4,5,6,7-tetrahydro-thieno[3,2-c]pyridin-5-yl]-ethanone 86 2-[[1-[(4-Methoxy-2,6-dimethyl-phenyl)sulfonyl]-1,2,3,4-tetrahydro-quinolin-2-yl]-methoxy]-1-(4-phenyl-4,5,6,7-tetrahydro-1H-imidazo[4,5-c]pyridin-5-yl)-ethanone 87 1-[2-[(4-Methyl-piperazin-1-yl)-methyl]-4,5,6,7-tetrahydro-thieno[3,2-c]pyridin-5-yl]-4-[1-[[2-(trifluoromethyl)-phenyl]sulfonyl]-piperidin-2-yl]-butan-1-one 88 1-(4-Phenyl-4,5,6,7-tetrahydro-1H-imidazo[4,5-c]pyridin-5-yl)-4-[1-[[2-(trifluoromethyl)-phenyl]sulfonyl]-piperidin-2-yl]-butan-1-one 91 2-[[4-[(4-Methoxy-2,6-dimethyl-phenyl)sulfonyl]-3,4-dihydro-2H-[1,4]benzoxazin-3-yl]-methoxy]-1-[2-[(4-methyl-piperazin-1-yl)-methyl]-4,5,6,7-tetrahydro-thieno[3,2-c]pyridin-5-yl]-ethanone 92 2-[[4-[(4-Methoxy-2,6-dimethyl-phenyl)sulfonyl]-3,4-dihydro-2H-[1,4]benzoxazin-3-yl]-methoxy]-1-(4-phenyl-4,5,6,7-tetrahydro-1H-imidazo[4,5-c]pyridin-5-yl)-ethanone 93 1-[2-[(4-Methyl-piperazin-1-yl)-methyl]-4,5,6,7-tetrahydro-thieno[3,2-c]pyridin-5-yl]-2-[[4-[[2-(trifluoromethyl)-phenyl]sulfonyl]-3,4-dihydro-2H-[1,4]benzoxazin-3-yl]-methoxy]-ethanone 94 1-(4-Phenyl-4,5,6,7-tetrahydro-1H-imidazo[4,5-c]pyridin-5-yl)-2-[[4-[[2-(trifluoromethyl)-phenyl]sulfonyl]-3,4-dihydro-2H-[1,4]benzoxazin-3-yl]-methoxy]-ethanone 95 4-Methoxy-N,2,3,6-tetramethyl-N-[2-[2-[2-[(4-methyl-piperazin-1-yl)-methyl]-4,5,6,7-tetrahydro-thieno[3,2-c]pyridin-5-yl]-2-oxo-ethoxy]-ethyl]-benzenesulfonic acid amide 96 4-Methoxy-N,2,3,6-tetramethyl-N-[2-[2-oxo-2-(4-phenyl-4,5,6,7-tetrahydro-1H-imidazo[4,5-c]pyridin-5-yl)-ethoxy]-ethyl]-benzenesulfonic acid amide 97 1-[2-[(4-Methyl-piperazin-1-yl)-methyl]-4,5,6,7-tetrahydro-thieno[3,2-c]pyridin-5-yl]-2-[[1-[[2-(trifluoromethyl)-phenyl]sulfonyl]-piperidin-2-yl]-methoxy]-ethanone 98 1-(4-Phenyl-4,5,6,7-tetrahydro-1H-imidazo[4,5-c]pyridin-5-yl)-2-[[1-[[2-(trifluoromethyl)-phenyl]sulfonyl]-piperidin-2-yl]-methoxy]-ethanone 99 3-[[1-[(4-Methoxy-2,6-dimethyl-phenyl)sulfonyl]-piperidin-2-yl]-methoxy]-1-[2-[(4-methyl-piperazin-1-yl)-methyl]-4,5,6,7-tetrahydro-thieno[3,2-c]pyridin-5-yl]-propan-1-one 100 3-[[1-[(4-Methoxy-2,6-dimethyl-phenyl)sulfonyl]-piperidin-2-yl]-methoxy]-1-(4-phenyl-4,5,6,7-tetrahydro-1H-imidazo[4,5-c]pyridin-5-yl)-propan-1-one 101 2-[2-[1-[(4-Methoxy-2,6-dimethyl-phenyl)sulfonyl]-piperidin-2-yl]-ethoxy]-1-[2-[(4-methyl-piperazin-1-yl)-methyl]-4,5,6,7-tetrahydro-thieno[3,2-c]pyridin-5-yl]-ethanone 102 2-[2-[1-[(4-Methoxy-2,6-dimethyl-phenyl)sulfonyl]-piperidin-2-yl]-ethoxy]-1-(4-phenyl-4,5,6,7-tetrahydro-1H-imidazo[4,5-c]pyridin-5-yl)-ethanone 103 N-Methyl-N-[4-[2-[(4-methyl-piperazin-1-yl)-methyl]-4,5,6,7-tetrahydro-thieno[3,2-c]pyridin-5-yl]-4-oxo-butyl]-3-(trifluoromethyl)-benzenesulfonic acid amide 104 N-Methyl-N-[4-Oxo-4-(4-phenyl-4,5,6,7-tetrahydro-1H-imidazo[4,5-c]pyridin-5-yl)-butyl]-3-(trifluoromethyl)-benzenesulfonic acid amide 105 1-[2-[(4-Methyl-piperazin-1-yl)-methyl]-4,5,6,7-tetrahydro-thieno[3,2-c]pyridin-5-yl]-2-[4-(naphthalen-2-ylsulfonyl)-3,4-dihydro-2H-[1,4]benzoxazin-3-yl]-ethanone 106 2-[4-(Naphthalen-2-ylsulfonyl)-3,4-dihydro-2H-[1,4]benzoxazin-3-yl]-1-(4-phenyl-4,5,6,7-tetrahydro-1H-imidazo[4,5-c]pyridin-5-yl)-ethanone 107 4-Methoxy-N,2,6-trimethyl-N-[2-[2-oxo-2-(2-phenyl-4,5,6,7-tetrahydro-oxazolo[5,4-c]pyridin-5-yl)-ethoxy]-ethyl]-benzenesulfonic acid amide 108 4-Methoxy-N,2,6-trimethyl-N-[2-[2-[1-methyl-3-(trifluoromethyl)-1,4,5,6-tetrahydro-pyrrolo[3,4-c]pyrazol-5-yl]-2-oxo-ethoxy]-ethyl]-benzenesulfonic acid amide 109 2-[[1-[(4-Methoxy-2,6-dimethyl-phenyl)sulfonyl]-piperidin-2-yl]-methoxy]-1-(2-phenyl-4,5,6,7-tetrahydro-oxazolo[5,4-c]pyridin-5-yl)-ethanone 110 2-[[1-[(4-Methoxy-2,6-dimethyl-phenyl)sulfonyl]-piperidin-2-yl]-methoxy]-1-[1-methyl-3-(trifluoromethyl)-1,4,5,6-tetrahydro-pyrrolo[3,4-c]pyrazol-5-yl]-ethanone 111 4-[1-[(2-Chloro-6-methyl-phenyl)sulfonyl]-piperidin-2-yl]-1-(2-phenyl-4,5,6,7-tetrahydro-oxazolo[5,4-c]pyridin-5-yl)-butan-1-one 112 4-[1-[(2-Chloro-6-methyl-phenyl)sulfonyl]-piperidin-2-yl]-1-[1-phenyl-3-(trifluoromethyl)-1,4,5,6-tetrahydro-pyrrolo[3,4-c]pyrazol-5-yl]-butan-1-one 113 4-[1-[(2-Chloro-6-methyl-phenyl)sulfonyl]-piperidin-2-yl]-1-[1-methyl-3-(trifluoromethyl)-1,4,5,6-tetrahydro-pyrrolo[3,4-c]pyrazol-5-yl]-butan-1-one 114 4-[1-[(4-Methoxy-2,6-dimethyl-phenyl)sulfonyl]-piperidin-2-yl]-1-(2-phenyl-4,5,6,7-tetrahydro-oxazolo[5,4-c]pyridin-5-yl)-butan-1-one 115 4-[1-[(4-Methoxy-2,6-dimethyl-phenyl)sulfonyl]-piperidin-2-yl]-1-[1-phenyl-3-(trifluoromethyl)-1,4,5,6-tetrahydro-pyrrolo[3,4-c]pyrazol-5-yl]-butan-1-one 116 4-[1-[(4-Methoxy-2,6-dimethyl-phenyl)sulfonyl]-piperidin-2-yl]-1-[1-methyl-3-(trifluoromethyl)-1,4,5,6-tetrahydro-pyrrolo[3,4-c]pyrazol-5-yl]-butan-1-one 117 4-[1-(Naphthalen-1-ylsulfonyl)-piperidin-2-yl]-1-(2-phenyl-4,5,6,7-tetrahydro-oxazolo[5,4-c]pyridin-5-yl)-butan-1-one 118 1-[1-Methyl-3-(trifluoromethyl)-1,4,5,6-tetrahydro-pyrrolo[3,4-c]pyrazol-5-yl]-4-[1-(naphthalen-1-ylsulfonyl)-piperidin-2-yl]-butan-1-one 119 4-[1-(Naphthalen-2-ylsulfonyl)-piperidin-2-yl]-1-(2-phenyl-4,5,6,7-tetrahydro-oxazolo[5,4-c]pyridin-5-yl)-butan-1-one 120 1-[1-Methyl-3-(trifluoromethyl)-1,4,5,6-tetrahydro-pyrrolo[3,4-c]pyrazol-5-yl]-4-[1-(naphthalen-2-ylsulfonyl)-piperidin-2-yl]-butan-1-one 121 N-[(1-Ethyl-1H-imidazol-2-yl)-methyl]-4-methoxy-2,6-dimethyl-N-[2-[2-oxo-2-(2-phenyl-4,5,6,7-tetrahydro-oxazolo[5,4-c]pyridin-5-yl)-ethoxy]-ethyl]-benzenesulfonic acid amide 122 N-[(1-Ethyl-1H-imidazol-2-yl)-methyl]-4-methoxy-2,6-dimethyl-N-[2-[2-oxo-2-[1-phenyl-3-(trifluoromethyl)-1,4,5,6-tetrahydro-pyrrolo[3,4-c]pyrazol-5-yl]-ethoxy]-ethyl]-benzenesulfonic acid amide 123 N-[(1-Ethyl-1H-imidazol-2-yl)-methyl]-4-methoxy-2,6-dimethyl-N-[2-[2-[1-methyl-3-(trifluoromethyl)-1,4,5,6-tetrahydro-pyrrolo[3,4-c]pyrazol-5-yl]-2-oxo-ethoxy]-ethyl]-benzenesulfonic acid amide 124 N-(4H-[1,3]Benzodioxin-7-yl-methyl)-4-methoxy-2,6-dimethyl-N-[2-[2-oxo-2-(2-phenyl-4,5,6,7-tetrahydro-oxazolo[5,4-c]pyridin-5-yl)-ethoxy]-ethyl]-benzenesulfonic acid amide 125 2-[[(2S)-1-[(4-methoxy-2,6-dimethyl-phenyl)sulfonyl]-1,2,3,4-tetrahydro-quinolin-2-yl]-methoxy]-1-(3-pyridin-4-yl-4,5,6,7-tetrahydro-isoxazolo[4,5-c]pyridin-5-yl)-ethanone 126 2-((1-(4-methoxy-2,6-dimethylphenylsulfonyl)piperidin-2-yl)methoxy)-1-(4-phenyl-3-(piperidin-1-ylmethyl)-6,7-dihydroisoxazolo[4,5-c]pyridin-5(4H)-yl)ethanone optionally in the form of their physiologically acceptable salts.

The numbering of the individual embodiments of the compounds according to the invention used above is retained in the following explanations of the present invention, in particular in the description of the examples.

The compounds according to the invention have an antagonistic action on the human B1R receptor or the B1R receptor of the rat. In a preferred embodiment of the invention, the compounds according to the invention have an antagonistic action both on the human B1R receptor (hB1R) and on the B1R receptor of the rat (rB1R).

Compounds which show an inhibition of at least 15%, 25%, 50%. 70%, 80% or 90% on the human B1R receptor and/or on the B1R receptor of the rat in the FLIPR assay at a concentration of 10 μm are particularly preferred. Compounds which show an inhibition on the human B1R receptor and on the B1R receptor of the rat of at least 70%, in particular of at least 80% and particularly preferably of at least 90% at a concentration of 10 μm are very particularly preferred.

The agonistic or antagonistic action of substances can be quantified on the bradykinin 1 receptor (B1R) of the human and rat species with ectopically expressing cell lines (CHO K1 cells) and with the aid of a $Ca^{2+}$-sensitive dyestuff (Fluo-4) in a fluorescent imaging plate reader (FLIPR). The figure in % activation is based on the $Ca^{2+}$ signal after addition of Lys-Des-$Arg^9$-bradykinin (0.5 nM) or Des-$Arg^9$-bradykinin (100 nM). Antagonists lead to a suppression of the $Ca^{2+}$ inflow after addition of the agonist. % inhibition compared with the maximum achievable inhibition is stated.

The substances according to the invention act, for example, on the B1R relevant in connection with various diseases, so that they are suitable as a pharmaceutical active compound in pharmaceutical compositions. The invention therefore also provides pharmaceutical compositions containing at least one substituted sulfonamide compound according to the invention and optionally suitable additives and/or auxiliary substances and/or optionally further active compounds.

The pharmaceutical compositions according to the invention optionally contain, in addition to at least one substituted sulfonamide compound according to the invention, suitable additives and/or auxiliary substances, that is to say also carrier materials, fillers, solvents, diluents, dyestuffs and/or binders, and can be administered as liquid pharmaceutical composition forms in the form of injection solutions, drops or juices or as semi-solid pharmaceutical composition forms in the form of granules, tablets, pellets, patches, capsules, plasters/spray-on plasters or aerosols. The choice of auxiliary substances etc. and the amounts thereof to be employed depend on whether the pharmaceutical composition is to be administered orally, perorally, parenterally, intravenously, intraperitoneally, intradermally, intramuscularly, nasally, buccally, rectally or topically, for example to the skin, the mucous membranes or into the eyes. Formulations in the form of tablets, coated tablets, capsules, granules, drops, juices and syrups are suitable for oral administration, and solutions, suspensions, easily reconstitutable dry formulations and sprays are suitable for parenteral, topical and inhalatory administration. Sulfonamide compounds according to the invention in a depot, in dissolved form or in a plaster, optionally with the addition of agents which promote penetration through the skin, are suitable formulations for percutaneous administration. Formulation forms which can be used orally or percutaneously can release the substituted sulfonamide compounds according to the invention in a delayed manner. The substituted sulfonamide compounds according to the invention can also be used in parenteral long-term depot forms, such as e.g. implants or implanted pumps. In principle, other further active compounds known to the person skilled in the art can be added to the pharmaceutical compositions according to the invention.

The amount of active compound to be administered to patients varies as a function of the weight of the patient, of the mode of administration, the indication and the severity of the disease. 0.00005 to 50 mg/kg, preferably 0.01 to 5 mg/kg of at least one substituted sulfonamide compound according to the invention are conventionally administered.

In a preferred form of the pharmaceutical composition, a substituted sulfonamide compound according to the invention contained therein is present as the pure diastereomer and/or enantiomer, as a racemate or as a non-equimolar or equimolar mixture of the diastereomers and/or enantiomers.

B1R is involved in particular in the pain event. The substituted sulfonamide compounds according to the invention can accordingly be used for the preparation of a pharmaceutical composition for treatment of pain, in particular acute, visceral, neuropathic, chronic or inflammatory pain.

The invention therefore also provides the use of a substituted sulfonamide compound according to the invention for the preparation of a pharmaceutical composition for treatment of pain, in particular acute, visceral, neuropathic, chronic or inflammatory pain.

The invention also provide the use of a substituted sulfonamide compound according to the invention for the preparation of a pharmaceutical composition for treatment of diabetes, diseases of the respiratory tract, for example bronchial asthma, allergies, COPD/chronic obstructive pulmonary disease or cystic fibrosis; inflammatory intestinal diseases, for example ulcerative colitis or CD/Crohn's disease; neurological diseases, for example multiple sclerosis or neurodegeneration; inflammations of the skin, for example atopic dermatitis, psoriasis or bacterial infections; rheumatic diseases, for example rheumatoid arthritis or osteoarthritis; septic shock; reperfusion syndrome, for example following cardiac infarction or stroke, obesity; and as an angiogenesis inhibitor.

In this context, in one of the above uses it may be preferable for a substituted sulfonamide compound which is used to be present as the pure diastereomer and/or enantiomer, as a racemate or as a non-equimolar or equimolar mixture of the diastereomers and/or enantiomers.

The invention also provides a method for the treatment, in particular in one of the abovementioned indications, of a non-human mammal or a human requiring treatment thereof, by administration of a therapeutically active dose of a substituted sulfonamide compound according to the invention, or of a pharmaceutical composition according to the invention.

The invention also provides a method for the treatment of pain, in particular of acute, visceral, neuropathic, chronic or inflammatory pain, of a non-human mammal or a human requiring treatment thereof, by administration of a therapeutically active dose of a substituted sulfonamide compound according to the invention, or of a pharmaceutical composition according to the invention.

The invention also provides a process for the preparation of the substituted sulfonamide compounds according to the invention as described in the following description, examples and claims. The general synthesis process for preparation of the compounds according to the invention is first described.

The following abbreviations are used herein:
9-BBN=9-borabicyclo[3,3,1]nonane
BOP=1-benzotriazolyloxy-tris-(dimethylamino)-phosphonium hexafluorophosphate
Bu=butyl
CDI=1,1'-carbonyldiimidazole
DBU=1,8-diazabicyclo(5.4.0)undec-7-ene
DCC=dicyclohexylcarbodiimide
DCE=1,2-dichloroethane
MC=methylene chloride
DIPEA=N,N-Diisopropylamine
DMAP=4-dimethylaminopyridine
DMF=N,N-dimethylformamide
DMS=dimethyl sulfide
DMSO=dimethylsulfoxide
EDCI=N-(3-dimethylaminopropyl)-N'-ethylcarbodiimide hydrochloride
Et=ethyl
HATU=N-[(dimethylamino)-1H-1,2,3-triazolo[4,5-b]pyridino-1-ylmethylenemethan-aminium hexafluorophosphate N-oxide
HBTU=O-(benzotriazol-1-yl)-N,N,N',N'-tetramethyluronium hexafluorophosphate
HOAt=1-hydroxy-7-azabenzotriazole
HOBt=1-hydroxybenzotriazole, where appropriate as the hydrate
Me=methyl
Ms=methanesulfonyl
PFPTFA=pentafluorophenyl trifluoroacetate
PFP=pentafluorophenol
PyBOP=benzotriazol-1-yl-oxy-tris-pyrrolidino-phosphonium hexafluorophosphate
TBTU=O-(benzotriazol-1-yl)-N,N,N',N'-tetramethyluronium tetrafluoroborate
TFA=trifluoroacetic acid
THF=tetrahydrofuran
TLC=thin layer chromatography
TEMPO=2,2,6,6-Tetramethylpiperidine-1-oxyl
TMSOTf=trimethylsilyl triflate
PTSA=p-toluenesulfonic acid The protecting group (PG) is a suitable nitrogen-protecting group, preferably ethyloxycarbonyl, tert-butyloxycarbonyl (Boc), benzyloxycarbonyl (Cbz), acetyl (Ac) or benzyl (Bn).

Preferred protecting groups for carboxylic acids are selected in such a form that the protected hydroxy group forms a methyl carboxylic ester (—$CO_2Me$), ethyl carboxylic ester (—$CO_2Et$) or a tert-butoxy carboxylic ester (—$CO_2tertBu$).

Preferred protecting groups for alcohols are silyl based protecting groups, such as trimethylsilyl (TMS), triethysilyl (TES), tert-butyldimethylsilyl (TBDMS).

Protecting groups can be introduced and removed by conventional literature methods known to the person skilled in the art, as described, for example, in (a) Philip J. Kocienski, Protecting Groups, 3$^{rd}$ edition, Georg Thieme Verlag, 2005 (ISBN 3-13-135603-0), particularly pages 187-314, 487-631, & 393-425 and (b) Peter G. M. Wuts, Theodora W. Greene, Greene's Protective Groups in Organic Synthesis, 4$^{th}$ edition, Wiley-Interscience, 2007 (ISBN-13: 978-0-471-69754-1), particularly pages 16-366, 533-646 & 696-926. It can be seen by those skilled in the art that in some cases the sequence of the reaction steps can be modified where appropriate.

The separation of diastereomers and/or enantiomers is carried out by conventional methods known to the person skilled in the art, for example by recrystallization, chromatography or, in particular, HPLC chromatography or crystallization with an optionally chiral acid or base and separation of the salts or chiral HPLC chromatography (Fogassy et al., Optical Resolution Methods, Org. Biomol. Chem. 2006, 4, 3011-3030).

The process for the preparation of the compounds of type (I) according to the invention is reproduced in the following Equation 1:

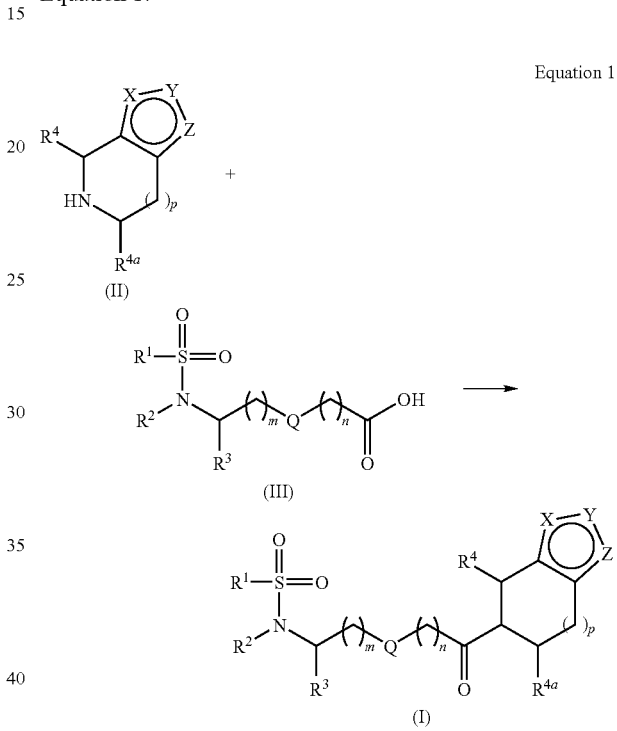

Equation 1

The amines (II) are preferably reacted in an amide formation using carboxylic acids (III) in the presence of dehydrating agents, such as sodium sulfate or magnesium sulfate, phosphorus oxide or reagents such as, for example, CDI, DCC (optionally bonded to a polymer), TBTU, HATU, EDCI, PyBOP or PFPTFA, also in the presence of HOAt or HOBt and an organic base, for example DIPEA, triethylamine or pyridine, in an organic solvent, such as THF, MC, diethyl ether, dioxane, DMF or acetonitrile, to give the compounds corresponding to formula (I) according to the invention. However, the amide bond can also be effected by conversion of the particular acid into the corresponding acid chloride or acid anhydride and subsequent reaction with the particular amine. The preparation of the acid chloride can be carried out by reaction with $SOCl_2$, $PCl_3$, $PCl_5$ or 1-chloro-N,N,2-trimethyl-1-propenylamine, optionally in a solvent, such as THF, MC, diethyl ether, dioxane, DMF or acetonitrile.

1. Amine Units:
The amine units employed, compounds corresponding to formula (II), are commercially available, known from the literature, for example from EP1270557, WO2006105945 and W. T. Ashton et al., *Bioorg. Med. Chem. Lett.*, 15 (2005), 2253-2258, or can be prepared as described in the following.

General Process for the Synthesis of the Amine Units
Synthesis of the amines corresponding to formula (IIa) and (IIb)
Equation 2
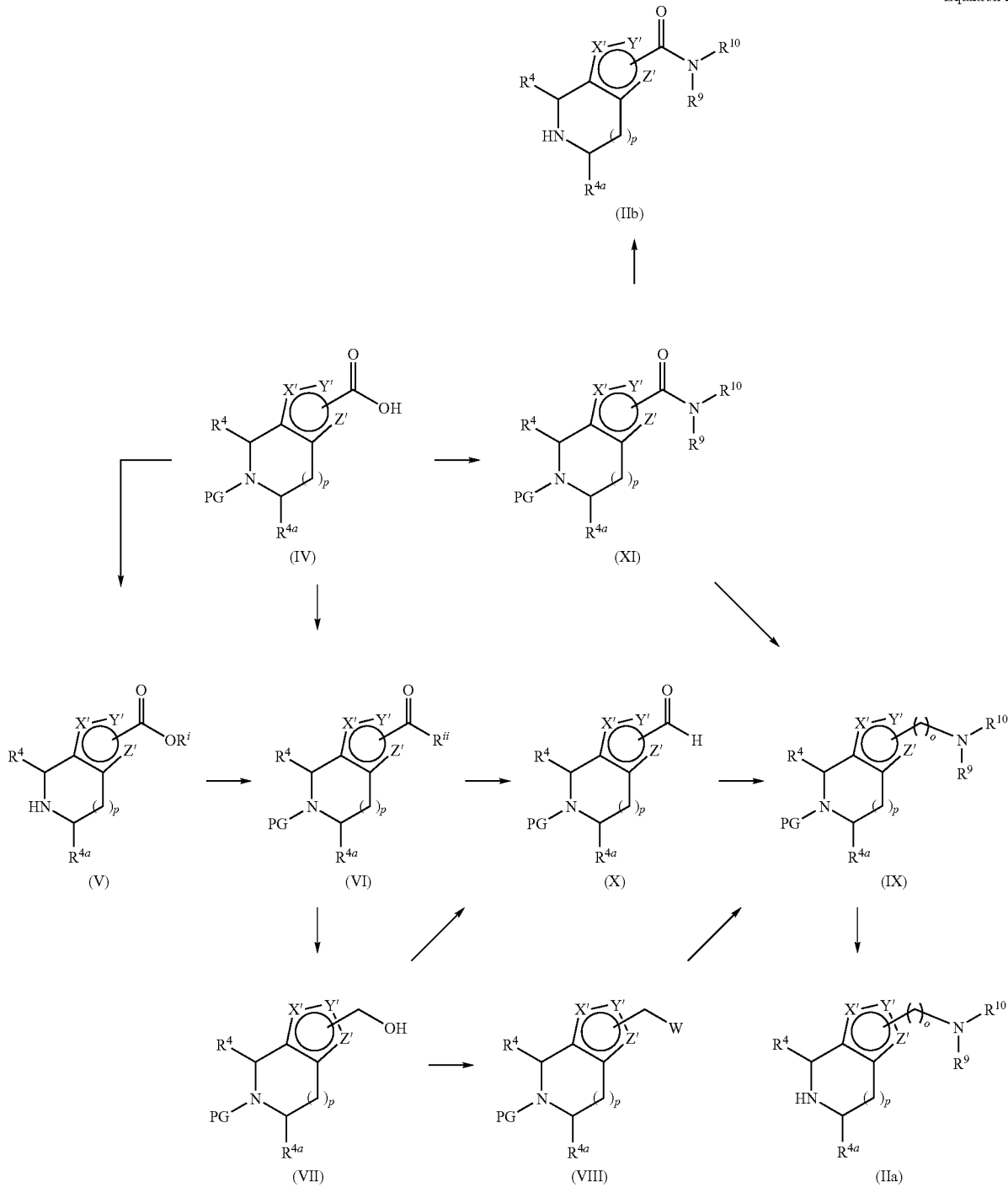
PG = a suitable amine-protecting group, for example Boc, Cbz, Ac, Ethoxycarbonyl.
W = halogen (Cl, Br, I), Oms or another suitable leaving group.
$R^i$ = preferably Me, Et.
$R^{ii}$ = preferably OMe, OEt, N(Me)OMe (Weinreb amide).
X' = Y' = Z' = O, S, N, C.
o = 1-6

Compounds corresponding to formula (IV) can optionally be prepared from the corresponding unprotected amines by introduction of a suitable amine-protecting group by methods known to the person skilled in the art.

Compounds corresponding to formula (IV) are reacted in at least one solvent, preferably selected from the group consisting of methanol, ethanol, propanol, isopropanol, dioxane, diethyl ether, THF, MC, DMF and DMSO, with an alcohol using at least an acid chloride or an acid anhydride or an acid, preferably from the group consisting of thionyl chloride, acetyl chloride, acetic anhydride, sulfuric acid and hydrochloric acid, at temperatures of from preferably 0° C. to 120° C. to give compounds having the general formula (V).

Compounds corresponding to formula (VI) are obtained from compounds corresponding to formula (V) by introduction of the corresponding amine-protecting group.

Compounds corresponding to formula (V) (optionally in the form of the corresponding hydrochloride) are reacted in at least one solvent, preferably selected from the group consisting of water, methanol, ethanol, isopropanol, acetonitrile, MC, THF, dioxane, toluene, DMF and DMSO, with at least one suitable reagent, preferably selected from the group consisting of di-tert-butyl dicarbonate, O-(tert-butoxycarbonyl) hydroxylamine, 1,2,2,2-tetrachloroethyl tert-butyl carbonate, O-tert-butyl S-pyridin-2-yl carbonothioate, tert-butyl carbonazidate, 1-(tert-butoxycarbonyl)benzotriazole, in the presence of an excess of base, preferably selected from the group consisting of caesium carbonate, calcium carbonate, potassium carbonate, potassium bicarbonate, sodium bicarbonate, sodium hydroxide, potassium hydroxide, triethylamine, diisopropylethylamine and pyridine, at temperatures of from preferably 0° C. to 80° C. to give compounds corresponding to formula (VI).

Alternatively, compounds corresponding to formula (VI) in which $R^{ii}$=N(Me)OMe (Weinreb amide) are obtained from carboxylic acids corresponding to formula (IV) by reaction with N,O-dimethylhydroxylamine hydrochloride in a suitable reaction medium, preferably diethyl ether, THF, acetonitrile, methanol, ethanol, DMF or MC or corresponding mixtures, optionally in the presence of a coupling reagent, preferably selected from the group consisting of BOP, DCC (optionally bonded to a solid phase), EDCI, HATU, HBTU, HOAt, optionally in the presence of at least one inorganic base, preferably selected from the group consisting of potassium carbonate and caesium carbonate, or an organic base, preferably selected from the group consisting of triethylamine, pyridine, N-methylmorpholine, 4,4-dimethylaminopyridine and diisopropylethylamine, preferably at temperatures of from preferably −70° C. to 100° C. However, the amide bond can also be effected by conversion of the acid into the corresponding acid chloride or acid anhydride and subsequent reaction with the particular amine. The acid chloride can prepared by reaction with $SOCl_2$, $PCl_3$, $PCl_5$ or 1-chloro-N,N,2-trimethyl-1-propenylamine, optionally in a solvent, such as THF, MC, diethyl ether, dioxane, DMF or acetonitrile, at a temperature of between −78° C. and 100° C.

Compounds corresponding to formula (VI) are reacted in at least one solvent, preferably selected from the group consisting of THF, diethyl ether, toluene or MC, with at least one reducing agent, preferably selected from the group consisting of diisobutylaluminium hydride, lithium aluminium hydride, lithium tri-tert-butoxyaluminium hydride, sodium bis(2-methoxyethoxy)aluminium hydride, sodium borohydride, aluminium hydride, at temperatures of from preferably −78° C. to 50° C. to give compounds corresponding to formula (VII).

Compounds corresponding to formula (VII) are obtained from compounds corresponding to formula (VII) by introduction of a suitable leaving group, such as, for example, halogen or mesylate.

Preferred compounds corresponding to formula (VII) are reacted in at least one solvent, preferably selected from the group consisting of MC, dioxane, diethyl ether, THF, acetonitrile and DMF, with a sulfonyl chloride, preferably selected from the group consisting of methylsulfonyl chloride, trifluoromethylsulfonyl chloride, tolylsulfonyl chloride, and at least one base, preferably selected from the group consisting of caesium carbonate, calcium carbonate, potassium carbonate, triethylamine, diisopropylethylamine and pyridine, at temperatures of from preferably 0° C. to 80° C. to give compounds corresponding to formula (VII) (W=OMs).

Compounds corresponding to formula (VII) are reacted in at least one solvent, preferably selected from the group consisting of MC, dioxane, diethyl ether, THF, acetonitrile, toluene and DMF, with a suitable amine in the presence of an excess of a base, preferably selected from the group consisting of caesium carbonate, calcium carbonate, potassium carbonate, potassium bicarbonate, sodium bicarbonate, triethylamine, diisopropylethylamine and pyridine, at temperatures of from preferably 0° C. to 80° C. to give compounds corresponding to formula (IX).

Alternatively, compounds corresponding to formula (IX) can be obtained from compounds corresponding to formula (X), which are in turn synthesized from compounds corresponding to formula (VI).

The liberation of the aldehyde function to give compounds corresponding to formula (X) is carried out by reaction of the compounds (VI) with a suitable reducing agent. In this context, diisobutylaluminium hydride, lithium aluminium hydride, lithium tri-tert-butoxyaluminium hydride, sodium bis(2-methoxyethoxy)aluminium hydride or bis(cyclopentadienyl)zirconium hydridochloride (Schwartz's reagent) in solvents, such as THF, diethyl ether, toluene or MC, can be employed. The reaction times can be between preferably 5 minutes and 7 hours, and the reaction temperature can vary between preferably −78° C. and 50° C.

Additionally compounds corresponding to formula (X) can be obtained from compounds corresponding to formula (VII) by oxidation in the presence of a suitable oxidising agent, such as TEMPO/NaOCl, manganese(IV) oxide, pyridinium dichromate, pyridinium chlorochromate, $(COCl)_2$/DMSO/triethylamine or Dess-Martin periodinone, where necessary in the presence of acetic acid or sodium acetate, in a suitable solvent such as dichloromethane, chloroform, diethylether or mixtures thereof, at temperatures of preferably −78° C. to 200° C.

In the reductive amination, compounds corresponding to formula (X) are reacted with an amine and the imine formed is then reduced to give the amine (IX) (o=1). Suitable reducing agents are, for example, $NaBH_4$, $NaBH(OAc)_3$, $NaCNBH_3$, $NH_4CNBH_3$, polymer-bonded cyanoborohydride, borane-pyridine complex or triethylsilane. The reaction can be carried out in solvents, such as, for example, methanol, ethanol, MC, DCE, acetonitrile, THF, toluene, water, DMSO, DMF, 1-methyl-2-pyrrolidin-2-one or mixtures of the solvents. Auxiliary reagents, such as, for example, HCl (gaseous or as an aqueous solution), acetic acid, TFA, $ZnCl_2$, 1,3-dimethyl-2-imidazolidine, $MgSO_4$, $Na_2SO_4$ or a molecular sieve, are often also used. However, the imine formed can also be converted into the amine by catalytic hydrogenation on catalysts, such as, for example, $PtO_2$ or Pd/C, in solvents, such as, for example, methanol or ethanol.

In the case where o=2-6, compounds corresponding to formula (X) are reacted with methoxy-methyl-triphenylphosphine in a suitable organic solvent, preferably THF, in the presence of a suitable base, preferably potassium tert-butylate, at temperatures of between preferably −10 and 40° C. to give the correspondingly lengthened aldehydes. Where appropriate, this step is repeated often in a corresponding manner, before the aldehydes are reacted in a reductive amination, as described above, to give compounds corresponding to formula (IX) (o=2-6).

Alternatively, compounds corresponding to formula (IX) can be obtained from compounds corresponding to formula (XI), which are in turn synthesized from compounds corresponding to formula (IV).

Compounds corresponding to formula (IV) are reacted with amines in a reaction medium such as diethyl ether, THF, acetonitrile, methanol, ethanol, DMF, MC or corresponding mixtures, optionally in the presence of at least one coupling reagent, such as BOP, DCC (optionally bonded to a solid phase), HATU, HBTU, HOAt and EDCI, optionally in the presence of at least one inorganic base, such as potassium carbonate or caesium carbonate, or an organic base, such as triethylamine, pyridine, N-methylmorpholine, 4,4-dimethylaminopyridine and diisopropylethylamine, at temperatures of from preferably −70° C. to 100° C. to give compounds corresponding to formula (XI). Alternatively, the carboxylic acid can be converted into the corresponding acid chloride or acid anhydride and reacted with the corresponding amine.

Compounds corresponding to formula (XI) are reduced to give compounds corresponding to formula (IX). Suitable reducing agents are, for example, $NaBH_4$, $LiBH_4$, L-Selectride, superhydride, $NaBH(Oac)_3$, $NaCNBH_3$, polymer-bonded cyanoborohydride, $NH_4CNBH_3$, $Bu_4NBH_4$, sodium (dimethylamino)trihydroborate, 9-BBN, diborane, borane-THF complex, borane-diethyl ether complex, borane-DMS complex, borane-diethylaniline complex, borane-dimethylamine complex, borane-ethylphenylpropylamine complex, borane-diisopropylamine complex, borane-pyridine complex, lithium aluminium hydride, alane, diisobutylaluminium hydride, lithium tri-tert-butoxyaluminium hydride, sodium bis(2-methoxyethoxy)aluminium hydride, diphenylsilane, methylphenylsilane, optionally in the present of $BF_3$ etherate, chlorotrimethylsilane, titanium tetrachloride, Meerwein's salt, zinc chloride, $RhH(CO)(PPh_3)_3$ or $Cp_2TiF_2$. The reaction can be carried out in solvents, such as, for example, methanol, ethanol, MC, DCE, dodecane, acetonitrile, THF, diethyl ether, dioxane, toluene, 1,2-dimethoxyethane or mixtures of the solvents, and at a temperature of from −78 to 100° C. The reaction time can be between 30 minutes and 70 hours.

Compounds corresponding to formula (IIa) are obtained from compounds corresponding to formula (IX) by splitting of the corresponding amine-protecting group by methods known to the person skilled in the art.

Compounds corresponding to formula (IIb) are obtained from compounds corresponding to formula (XI) by splitting of the corresponding amine-protecting group by methods known to the person skilled in the art.

Preferred protecting groups can be removed as follows:

BOC protecting groups can be removed in at least one solvent, preferably selected from the group consisting of acetonitrile, diethyl ether, THF, methanol, ethanol, MC, dioxane and DMF, with an acid, preferably selected from the group consisting of trifluoroacetic acid, hydrochloric acid, methanesulfonic acid and sulfuric acid, at temperatures of from preferably 0° C. to 110° C.

Cbz protecting groups can be removed under acidic conditions. This acidic splitting off can be carried out, for example, by reaction with an HBr/glacial acetic acid mixture, a mixture of TFA in dioxane/water or HCl in methanol or ethanol. However, reagents such as, for example, $Me_3Sil$, in solvents, such as, for example, MC, chloroform or acetonitrile, $BF_3$ etherate with the addition of ethanethiol or $Me_2S$ in solvents, such as, for example, MC, a mixture of aluminium chloride/anisole in a mixture of MC and nitromethane or triethylsilane/$PdCl_2$ in methanol, with the addition of triethylamine, are also suitable. A further method is the hydrogenolytic splitting off of the protecting group under increased pressure or normal pressure with the aid of catalysts, such as, for example, Pd on charcoal, $Pd(OH)_2$, $PdCl_2$, Raney nickel or $PtO_2$, in solvents, such as, for example, methanol, ethanol, 2-propanol, THF, acetic acid, ethyl acetate, chloroform, optionally with the addition of HCl, formic acid or TFA.

Educts corresponding to formula (IVa), (Va) and (VIa) are commercially available, known from the literature (for example: EP1270557; WO2006/105945; Venkatesan, A. M. et al., Journal of Medicinal Chemistry, 2006, 49, 15, 4623-4637; Kikuchi, C. et al., Bioorganic & Medicinal Chemistry Letters, 2002, 12, 18, 2549-2552; Haginoya, N. et al., Heterocycles, 2004, 63, 7, 1555-1562) or can be prepared as described in the following (Equation 3).

Equation 3

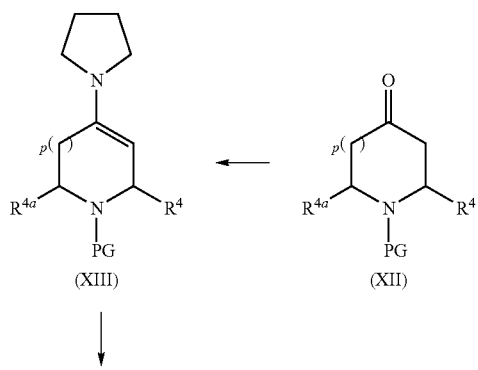

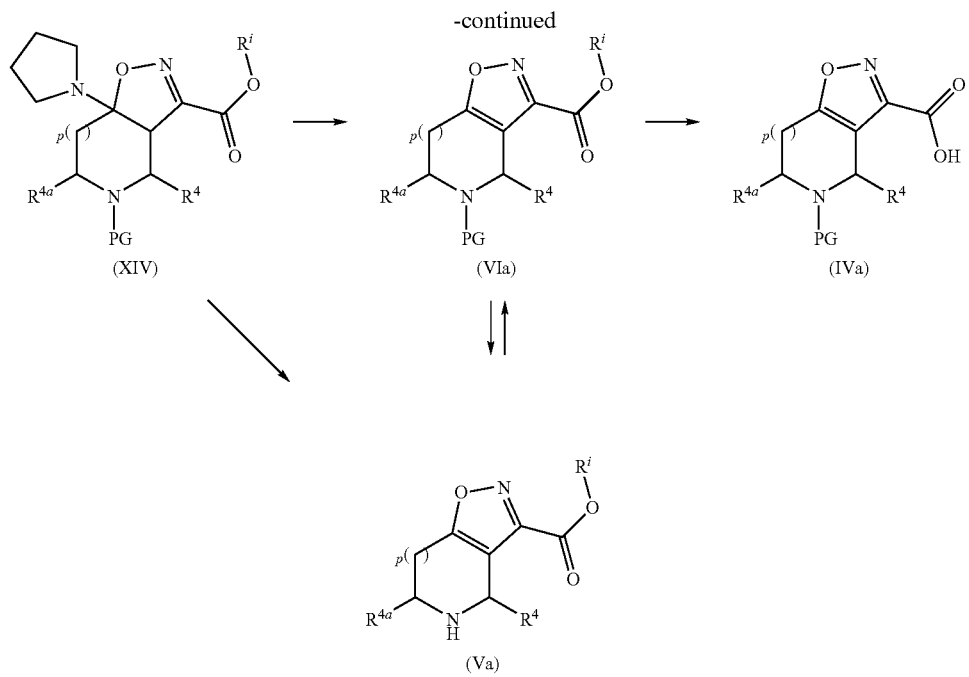

PG = a suitable amine-protecting group, for example Boc, Cbz, Ac
R$^i$ = preferably Me, Et Commercial compounds/compounds known from the literature corresponding to formula (XII) are reacted in a solvent, such as toluene or benzene, with pyrrolidine in the presence of a catalytic amount of acid, preferably in the presence of p-toluenesulfonic acid, under reflux using a water separator to give compounds corresponding to formula (XIII).

Compounds corresponding to formula (XIII) are reacted with a chlorohydroxyiminoacetic acid ester in a reaction medium, such as acetonitrile, MC, chloroform, DMF, dimethylacetamide, DMSO and corresponding mixtures, in the presence of at least one base, such as triethylamine, pyridine, 4,4-dimethylamino-pyridine, N-methylmorpholine and diisopropylethylamine, at a temperature of preferably 0-30° C. to give compounds corresponding to formula (XIV).

Compounds corresponding to formula (XIV) are reacted (depending on the amine-protecting group selected) in a solvent, such as acetonitrile, MC, chloroform, DMF, dimethylacetamide, DMSO, water, methanol, ethanol and corresponding mixtures, in the presence of a suitable acid, preferably TFA or sulfuric acid, to give compounds corresponding to formula (Va) or (VIa).

Compounds corresponding to formula (Va) can be reacted by splitting off of the protecting group (PG—amine-protecting group) by processes known to the person skilled in the art to give compounds corresponding to formula (VIa).

The preferred acetyl protecting groups can be removed, for example, in a solvent, such as methanol, ethanol, isopropanol, THF, water and corresponding mixtures, in the presence of an inorganic acid, such as HCl and/or sulfuric acid, under reflux.

Compounds corresponding to formula (VIa) can be reacted by introduction of a protecting group (PG—amine-protecting group) by processes known to the person skilled in the art to give compounds corresponding to formula (Va).

The preferred Boc protecting group can be introduced in a reaction medium, such as dioxane, ethanol, methanol, isopropanol, water, MC and corresponding mixtures, in the presence of an organic base, preferably triethylamine, diisopropyl-amine, pyridine, 4,4-dimethylaminopyridine and N-methylmorpholine, DIPEA, with di-tert-butyl dicarbonate at 0° C. and subsequently at preferably 20-30° C.

Compounds corresponding to formula (VIa) can be reacted by removing the protecting group (acid-protecting group) by processes known to those skilled in the art to give compounds corresponding to formula (IVa).

The hydrolysis of compounds corresponding to formula (VIa) can be carried out in a suitable solvent, such as THF, methanol, ethanol, isopropanol, water and corresponding mixtures, with an inorganic base, preferably potassium hydroxide, lithium hydroxide or sodium hydroxide, at a temperature of preferably 0-150° C.

Synthesis of the Amines Corresponding to Formula (IIc)

Equation 4

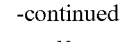

(XVI)

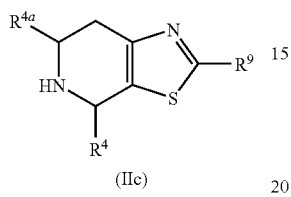

(IIc)

Compounds corresponding to formula (XV) known from the literature (U.S. Pat. Nos. 6,265,418, 6,599,895) are reacted in at least one solvent, preferably selected from the group consisting of methanol, ethanol, propanol, iso-propanol, dioxane, diethyl ether, THF, water and DMF, with a thioamide corresponding to formula $R^9CSNH_2$, wherein $R^9$ has the meaning given above, in the presence of an excess of a base, preferably selected from the group consisting of caesium carbonate, calcium carbonate, potassium carbonate, triethylamine, diisopropylethylamine and pyridine, at temperatures of from preferably 0° C. to 120° C. to give compounds corresponding to formula (XVI), it being possible for the thioamides $R^9CSNH_2$ employed to be obtained from the corresponding nitriles in at least one solvent, preferably selected from the group consisting of methanol, ethanol, propanol, iso-propanol, dioxane, diethyl ether and THF, in the presence of an excess of ammonia and in the presence of an excess of hydrogen sulfide at temperatures of from preferably 0° C. to 80° C.

Compounds corresponding to formula (XVI) can be reacted by removing the protecting group (amine-protecting group) by known processes to give compounds corresponding to formula (IIc). In the case of the protecting group (PG) =tert-butyloxycarbonyl (Boc), the compounds corresponding to formula (XVI) are reacted in at least one solvent, preferably selected from the group consisting of methanol, ethanol, MC, diethyl ether, THF, acetonitrile, dioxane, DMF and DMSO, with an acid, preferably selected from the group consisting of trifluoroacetic acid, sulfuric acid and hydrochloric acid, at temperatures of from preferably 0° C. to 80° C. to give compounds having the general formula (IIb).

In the case of the protecting group (PG)=ethyloxycarbonyl, the compounds corresponding to formula (XVI) are reacted in at least one solvent, preferably selected from the group consisting of methanol, ethanol, isopropanol, ethylene glycol, water, THF, dioxane, DMF and DMSO, with at least one base, preferably selected from the group consisting of sodium hydroxide, potassium hydroxide, potassium carbonate, barium hydroxide, lithium propanethiolate, hydrazine, methyllithium and potassium trimethylsilanolate, at temperatures of from preferably 0° C. to 120° C. to give compounds having the general formula (IIb).

Synthesis of the amines corresponding to formula (IId)

Equation 5

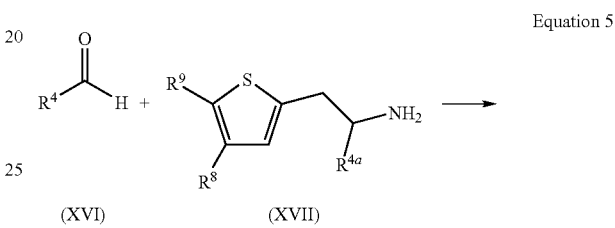

(XVI)         (XVII)

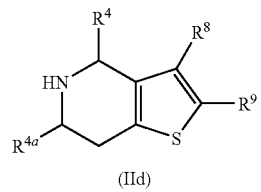

(IId)

The educts employed, compounds corresponding to formula (XVII) and (XVI), are commercially available or can be prepared by methods known from the literature.

Compounds having the general formula (IId) are obtained by reaction of compounds having the general formula (XVII) with compounds having the general formula (XVI) in solvents, such as ethanol, methanol, diethyl ether, MC, ethyl acetate, pyridine, benzene, toluene or a mixture of these solvents, optionally with the addition of triethylamine, sodium hydroxide, trifluoroacetic acid, and optionally with removal of the water formed during the reaction, for example by azeotropic distillation or by addition of a molecular sieve. The reaction times can be between preferably 1-75 hours and the reaction temperature can vary between preferably 20° C. and 110° C. However, the cyclization to give compounds corresponding to formula (IId) can also be achieved by reaction of compounds having the general formula (XVII) with the corresponding carboxylic acid and subsequent reduction of the cyclic imine primarily formed with reducing agents, such as, for example, sodium borohydride.

Synthesis of the amines corresponding to formula (IIe)

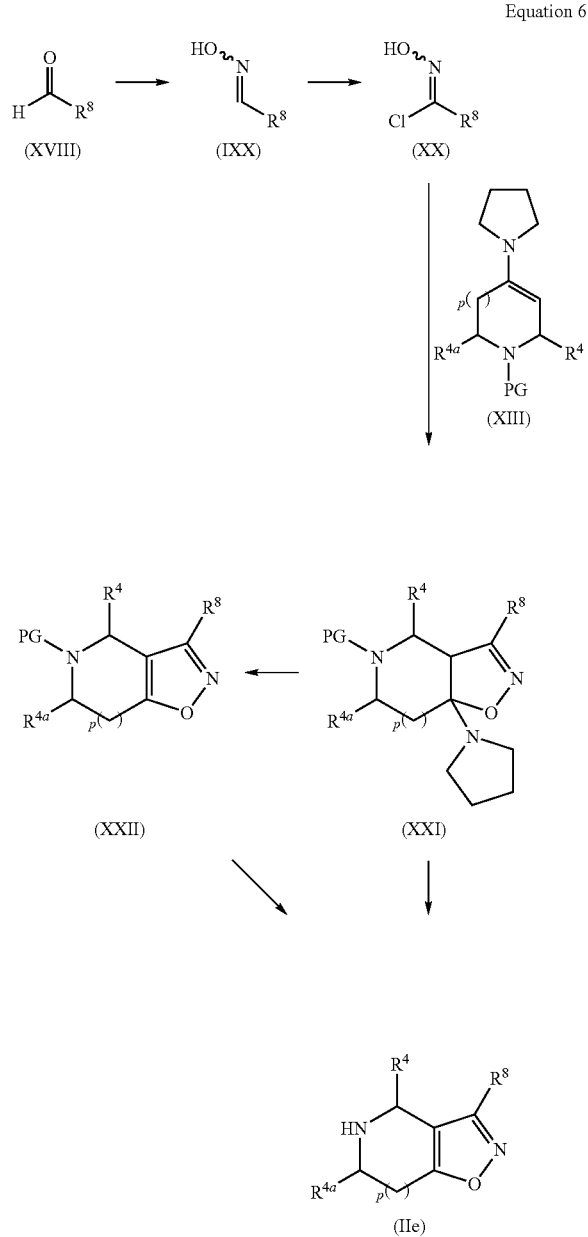

Equation 6

PG = a suitable amine-protecting group, for example Boc or Ac

If compounds corresponding to formula (XVIII) are not commercially available, they can be prepared from the corresponding carboxylic acids in the presence of a suitable reducing agent, or from the corresponding alcohols in the presence of a suitable oxidizing agent.

If compounds corresponding to formula (IXX) are not commercially available, these can be prepared from compounds corresponding to formula (XVIII) in the presence of hydroxylamine or hydroxylamine hydrochloride in a suitable reaction medium, such as, for example, methanol, ethanol, DMF, acetonitrile, DMSO or water and corresponding mixtures, optionally in the presence of a base, such as, for example, triethylamine, diisopropylethylamine, sodium acetate or sodium hydroxide, or in the presence of an ion exchanger (for example Amberlite) at preferred temperatures of between preferably 0° C. and 150° C.

Compounds corresponding to formula (IXX) can be reacted in the presence of N-chlorosuccinimide or alternative suitable reagents in a suitable reaction medium, such as, for example, DMF, acetonitrile, DMSO or chloroform and corresponding mixtures, at preferred temperatures of between preferably 0° C. and 150° C. to give compounds corresponding to formula (XX).

Compounds corresponding to formula (XIII) (see Equation 3) are reacted with compounds corresponding to formula (XX) in a reaction medium, such as DMSO, acetonitrile, MC, chloroform, DMF, dimethylacetamide and corresponding mixtures, in the presence of at least one base, such as triethylamine, pyridine, 4,4-dimethyl-aminopyridine, N-methylmorpholine and diisopropylethylamine, at a temperature of preferably 0-30° C. to give compounds corresponding to formula (XXI).

Compounds corresponding to formula (XXI) are reacted, depending on the amine-protecting group selected, in a solvent, such as acetonitrile, MC, chloroform, DMF, dimethylacetamide, DMSO, water, ethanol, methanol and corresponding mixtures, in the presence of a suitable acid, preferably TFA or sulfuric acid, under reflux to give compounds corresponding to formula (XXII) or (IIe).

Compounds corresponding to formula (XXII) can be reacted by removing the protecting group (PG—amine-protecting group) by processes known to the person skilled in the art to give compounds corresponding to formula (IIe).

The preferred acetyl protecting group can be removed, for example, in a solvent, such as methanol, ethanol, isopropanol, THF, water and corresponding mixtures, in the presence of an inorganic acid, such as HCl and/or sulfuric acid, under reflux.

2. Acid Units:

The acid units employed, compounds corresponding to formula (III), are known from the literature (e.g. from β-Amino Acids—Tetrahedron Report Number 617: M. Liu, M. P. Sibi, *Tetrahedron*, 58, (2002), 7991-8053) or can be prepared as described in the following.

B-Amino acids can be converted into the acid units corresponding to formula (III), optionally using suitable protecting groups, by introduction of a sulfonyl group analogously to the processes described in the following.

General Synthesis Process for The Preparation of the Acyclic Acid Units (IIIa)

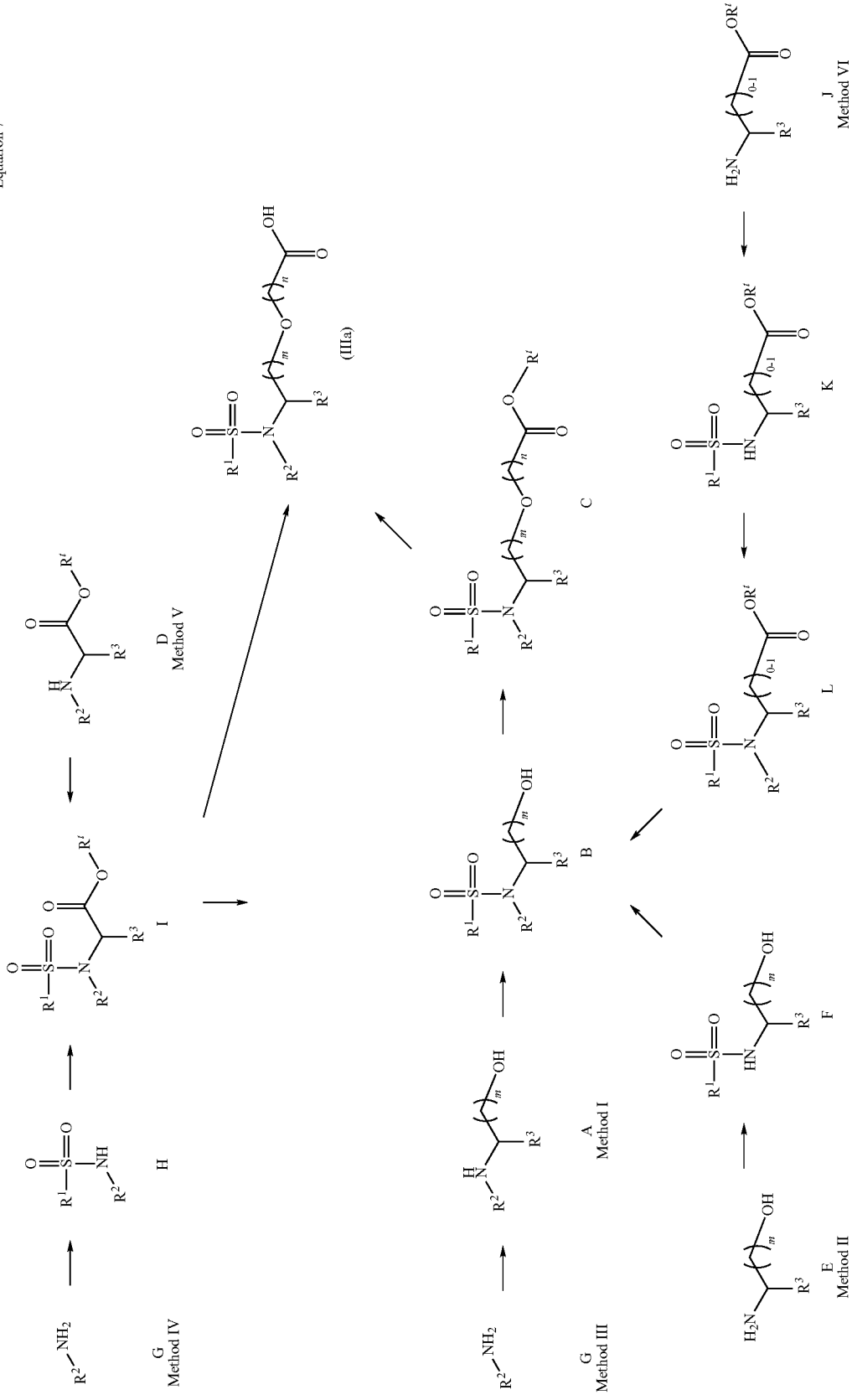

In Method 1, the racemic (R and S configuration) or enantiomerically pure (R or S configuration) amino alcohols A are reacted in a sulfonylation with sulfonyl chlorides, bromides or pentafluorophenolate $R^1SO_2X$ (X=Cl, Br, OPFP), optionally in the presence of an organic or inorganic base, for example potassium carbonate, sodium carbonate, sodium bicarbonate, diisopropylethylamine, triethylamine, pyridine, dimethylaminopyridine, diethylamine or DBU, preferably in an organic solvent, for example acetone, acetonitrile, MC or THF, and at a temperature of from 0° C. to the reflux temperature, to give the sulfonylated amino alcohols B. The sulfonylated amino alcohols B are reacted in an alkylation reaction with halogenated ester compounds using tetrabutylammonium chloride or bromide or tetrabutylammonium hydrogen sulfate in a phase transfer reaction using an organic solvent, such as THF, toluene, benzene or xylene, and an inorganic base, such as potassium hydroxide, sodium hydroxide, sodium carbonate, sodium bicarbonate, potassium carbonate, or in the presence of an organic or inorganic base, conventional inorganic bases are metal alcoholates, such as sodium methanolate, sodium ethanolate, potassium tert-butylate, lithium bases or sodium bases, such as lithium diisopropylamide, butyllithium, tert-butyllithium, sodium methylate, or metal hydrides, such as potassium hydride, lithium hydride, sodium hydride, conventional organic bases are diisopropylethylamine, triethylamine, in an organic solvent, such as MC, THF or diethyl ether, at 0° C. to the reflux temperature, to give the products of the general structure C.

In Method II, the racemic (R and S configuration) or enantiomerically pure (R or S configuration) amino alcohols E are reacted in a sulfonylation with sulfonyl chlorides, bromides or pentafluorophenolate $R^1SO_2X$ (X=Cl, Br, OPFP), optionally in the presence of an organic or inorganic base, for example potassium carbonate, sodium bicarbonate, diisopropylethylamine, triethylamine, pyridine, dimethylamino-pyridine, diethylamine or DBU, preferably in an organic solvent, for example acetone, acetonitrile, MC or THF, and at a temperature of from 0° C. to the reflux temperature, to give the sulfonylated amino alcohols F. The sulfonylated amino alcohols F are then reacted in an alkylation reaction with alkyl halides (RX, X=I, Br, Cl), mesylates or alternative alkylating reagents, optionally in the presence of an organic or inorganic base, for example sodium hydroxide, potassium carbonate, caesium carbonate, DBU or DIPEA, preferably in an organic solvent, for example dimethylformamide, acetone, THF, acetonitrile, dioxane or these solvents as mixtures, at a temperature of from 0° C. to the reflux temperature, to give the sulfonylated amino alcohols B. These are conversted to the ester compounds C as described in Method I.

In Methods I-III, the ester compounds C are reacted in an ester cleavage using organic acids, such as trifluoroacetic acid, or aqueous inorganic acids, such as hydrochloric acid, or using aqueous inorganic bases, such as lithium hydroxide, potassium hydroxide, sodium hydroxide, sodium carbonate, sodium bicarbonate, potassium carbonate, in organic solvents, such as methanol, dioxane, MC, THF, diethyl ether or these solvents as mixtures, at 0° C. to room temperature, to give the acid stages corresponding to formula (IIIa).

In Method III, commercial amines or amines accessible to those skilled in the art are alkylated with 2-bromoethanol or compounds in organic solvents, such as ethanol, methanol, ether, THF or MC, at a temperature of from 0° C. to the reflux temperature for up to 20 hours. The further process proceeds analogously to the other methods.

In Method IV, the amines are reacted in a sulfonylation with sulfonyl chlorides, bromides or pentafluorophenolate $R^1SO_2X$ (X=Cl, Br, OPFP), optionally in the presence of an organic or inorganic base, for example potassium carbonate, sodium carbonate, sodium bicarbonate, diisopropylethylamine, triethylamine, pyridine, dimethylaminopyridine, diethylamine or DBU, preferably in an organic solvent, for example acetone, acetonitrile, MC or THF, and at a temperature of from 0° C. to the reflux temperature, to give the sulfonylated compounds H.

The sulfonylated amines are then reacted in an alkylation reaction with methyl 2-bromoacetate or compounds H, optionally in the presence of an organic or inorganic base, for example sodium hydride, potassium carbonate, caesium carbonate, DBU or DIPEA, preferably in an organic solvent, for example dimethylformamide, acetone, THF, acetonitrile, dioxane or these solvents as mixtures, to give the sulfonylated amino esters 1.

The sulfonylated amino esters I are reacted in a reduction reaction to give a sulfonylated amino alcohol B using metal hydrides as reducing agents, such as, for example, $LiAlH_4$, $BH_3 \times DMS$ or $NaBH_4$, in an organic solvent, such as THF or diethyl ether. The further process of Method IV corresponds to the other methods.

In Method V, the amino acids or amino esters D are reacted in a sulfonylation with sulfonyl chlorides, bromides or pentafluorophenolate $R^1SO_2X$ (X=Cl, Br, OPFP), optionally in the presence of an organic or inorganic base, for example potassium carbonate, sodium carbonate, sodium bicarbonate, diisopropylethylamine, triethylamine, pyridine, dimethylaminopyridine, diethylamine or DBU, preferably in an organic solvent, for example acetone, acetonitrile, MC or THF, and at a temperature of from 0° C. to the reflux temperature, to give the sulfonylated amino acids/esters 1. The compounds I are reacted in an ester cleavage using organic acids, such as trifluoroacetic acid, or aqueous inorganic acids, such as hydrochloric acid, or using aqueous inorganic bases, such as lithium hydroxide, potassium hydroxide, sodium hydroxide, sodium carbonate, sodium bicarbonate, potassium carbonate, in organic solvents, such as methanol, dioxane, MC, THF, diethyl ether or these solvents as mixtures, at 0° C. to room temperature, to give the acid stages corresponding to formula (IIIa).

In Method VI, the amino acid or amino ester compounds J are reacted in a sulfonylation with sulfonyl chlorides, bromides or pentafluorophenolate $R^1SO_2X$ (X=Cl, Br, OPFP), optionally in the presence of an organic or inorganic base, for example potassium carbonate, sodium carbonate, sodium bicarbonate, diisopropylethylamine, triethylamine, pyridine, dimethylaminopyridine, diethylamine or DBU, preferably in an organic solvent, for example acetone, acetonitrile, MC or THF, and at a temperature of from 0° C. to the reflux temperature, to give the sulfonylated amino acids/esters K. The sulfonylated amino acids/esters K are reacted with an alcohol under Mitsunobu conditions, employing for example DEAD (Diethylazodicarboxylat), DIAD (Diisopropylazodicarboxylat) or fluorinated equivalents in the presence of triphenylphoshine (or a fluorinated equivalent or $PPh_3$ on solid support) in a suitable organic solvent, such as THF or fluorinated solvents, to give compounds corresponding to formula L. The sulfonylated compounds L are reacted in a reduction reaction to give a sulfonylated amino alcohol B using metal hydrides as reducing agents, such as, for example, $LiAlH_4$, $BH_3 \times DMS$ or $NaBH_4$, in an organic solvent, such as THF or diethyl ether. The further process of Method IV corresponds to the other methods.

General Synthesis Process for the Preparation of the Cyclic Acid Units (IIIb)

Equations 8
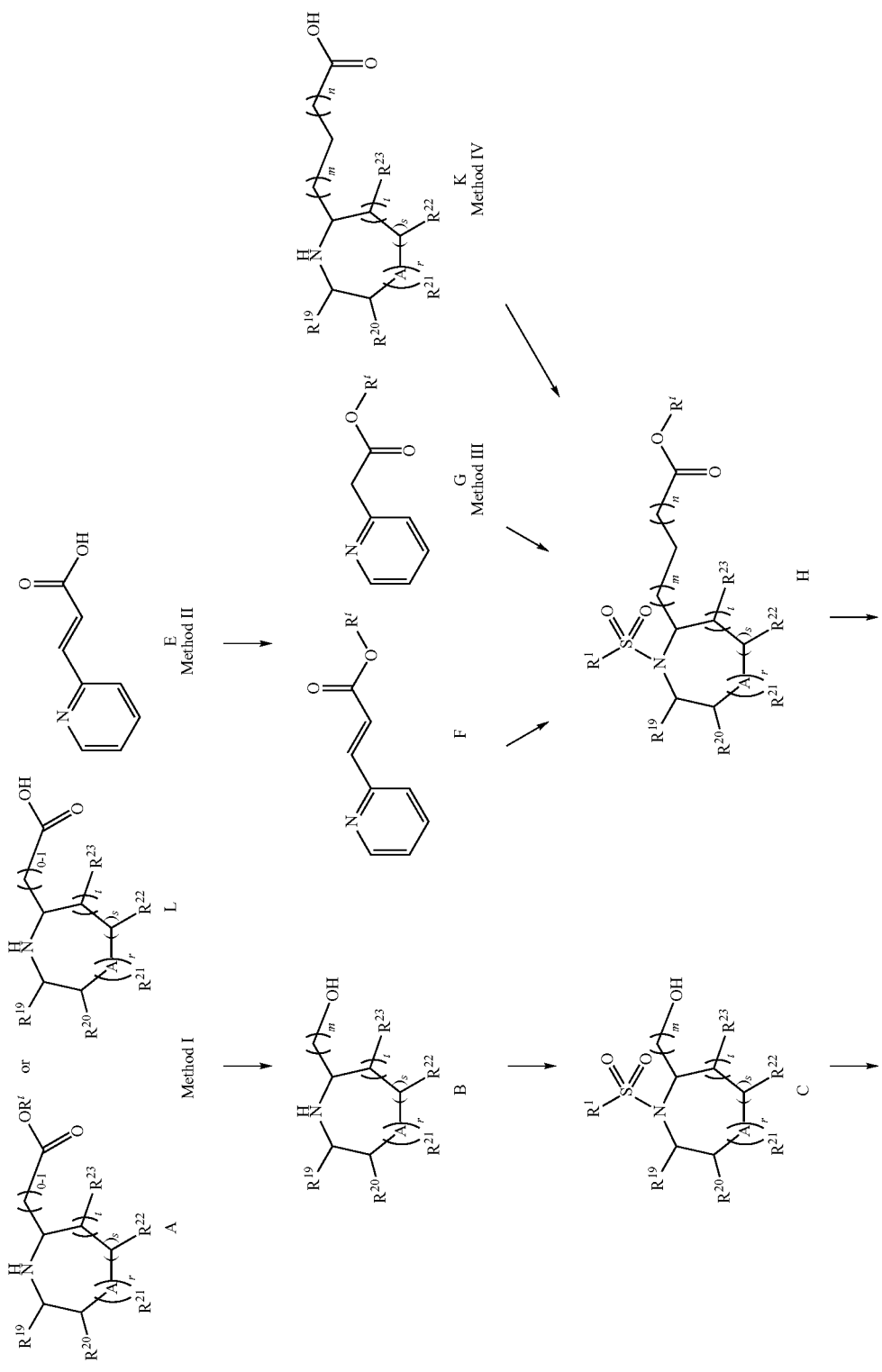

-continued
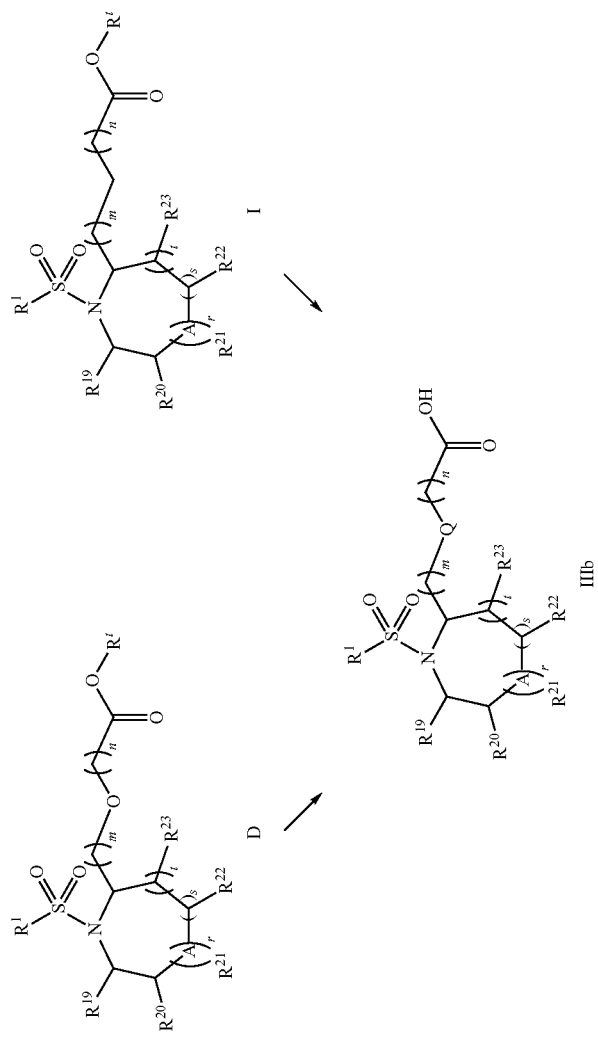
R$^t$ = preferably Me, Et, tert-Bu or H
A = N, O, S

In Method I, the racemic (R and S configuration) or enantiomerically pure (R or S configuration) amino acid esters A or amino acids L are reacted by a reduction to give an amino alcohol B using metal hydrides as reducing agents, such as, for example, $LiAlH_4$, $BF_3$ etherate, $BH_3 \times DMS$ or $NaBH_4$, in an organic solvent, such as THF or diethyl ether, at temperatures of from 0° C. to the reflux temperature. The amino alcohols B are reacted further in a sulfonylation with sulfonyl chlorides, bromides or pentafluorophenolate $R^1SO_2X$ (X=Cl, Br, OPFP), optionally in the presence of an organic or inorganic base, for example potassium carbonate, sodium bicarbonate, diisopropylethylamine, triethylamine, pyridine, dimethylamino-pyridine, diethylamine or DBU, preferably in an organic solvent, for example acetone, acetonitrile, MC or THF, and at a temperature of from 0° C. to the reflux temperature, to give the sulfonylated amino alcohols C.

The sulfonylated amino alcohols C are reacted in an alkylation reaction with halogenated ester compounds (or carboxylic acids) using tetrabutylammonium chloride or bromide or tetrabutylammonium hydrogen sulfate in a phase transfer reaction using an organic solvent, such as THF, toluene, benzene or xylene, and an inorganic base, such as potassium hydroxide, sodium hydroxide, sodium carbonate, sodium bicarbonate, potassium carbonate, or in the presence of an organic or inorganic base, conventional inorganic bases are metal alcoholates, such as sodium methanolate, sodium ethanolate, potassium tert-butylate, lithium bases or sodium bases, such as lithium diisopropylamide, butyllithium, tert-butyllithium, sodium methylate, or metal hydrides, such as potassium hydride, lithium hydride, sodium hydride, conventional organic bases are diisopropylethyl-amine, triethylamine, in an organic solvent, such as MC, THF or diethyl ether, at 0° C. to the reflux temperature, to give the products of the general structure D.

In Method II, 3-(pyridin-2-yl)acrylic acid E is esterified using dehydrating reagents, for example inorganic acids, such as $H_2SO_4$ or phosphorus oxides, or organic reagents, such as thionyl chloride, in organic solvents, such as THF, diethyl ether, methanol, ethanol or MC, to give stage F, at temperatures of from room temperature to the reflux temperature.

In Methods II and III, the ester stages F and G are hydrogenated in a hydrogenation under conditions known to the person skilled in the art in organic solvents, such as THF, chloroform, and in the presence of catalysts, such as platinum oxides, with hydrogen under normal pressure or increased pressure to give the intermediates H.

In Methods II-III, stage H is reacted further in a sulfonylation with sulfonyl chlorides, bromides or pentafluorophenolate $R^1SO_2X$ (X=Cl, Br, OPFP), optionally in the presence of an organic or inorganic base, for example potassium carbonate, sodium bicarbonate, diisopropylethylamine, triethylamine, pyridine, diethylamine or DBU, preferably in an organic solvent, for example acetonitrile, MC or THF, at 0° C. to the reflux temperature, to give the sulfonylated amino esters 1.

In Methods I-III, the ester compounds D and I (provided $R^t$ is not H—If $R^t$ is H, then D and I are equivalent to (IIIb) and do not need to be deprotected) are reacted in an ester cleavage using organic acids, such as trifluoroacetic acid, or aqueous inorganic acids, such as hydrochloric acid, or using aqueous inorganic bases, such as lithium hydroxide, potassium hydroxide, sodium hydroxide, sodium carbonate, sodium bicarbonate, potassium carbonate, in organic solvents, such as methanol, dioxane, MC, THF, diethyl ether or these solvents as mixtures, at 0° C. to room temperature, to give the acid stages corresponding to formula (IIIb).

In Method IV, the racemic (R and S configuration) or enantiomerically pure (R or S configuration) amino acids K are esterified using dehydrating reagents, for example inorganic acids, such as $H_2SO_4$ or phosphorus oxides, or organic reagents, such as thionyl chloride, in organic solvents, such as THF, diethyl ether, methanol, ethanol or MC, to give the amino esters H. The further course of the general process corresponds to Methods II-III.

It is obvious to a person skilled in the art that in each case where either an amine or an alcohol is depicted it may be replaced by a suitably protected compound, where appropriate. It should be noted that the protecting group has to be removed by a suitable standard deprotection procedure known to the person skilled in the art prior to those steps where modification of the functional group in question is desired (i.e. prior to conversion to yield the compounds corresponding to formula C, D and 1).

Pharmacological Studies

1 Functional Investigation on the Bradykinin 1 Receptor (B1R)

The agonistic or antagonistic action of substances can be determined on the bradykinin 1 receptor (B1R) of the human and rat species with the following assay. In accordance with this assay, the $Ca^{2+}$ inflow through the channel is quantified with the aid of a $Ca^{2+}$-sensitive dyestuff (type Fluo-4, Molecular Probes Europe BV, Leiden, Holland) in a fluorescent imaging plate reader (FLIPR, Molecular Devices, Sunnyvale, USA).

2 Method

Chinese hamster ovary cells (CHO K1 cells) transfected stably with the human B1R gene (hB1R cells) or the B1R gene of the rat (rB1R cells) are used. For functional studies, these cells are plated out on black 96-well plates with a clear base (BD Biosciences, Heidelberg, Germany or Greiner, Frickenhausen, Germany) in a density of 20,000-35,000 cells/well. The cells are left overnight at 37° C. and 5% $CO_2$ in culture medium (hB1R cells: Nutrient Mixture Ham's F12, Gibco Invitrogen GmbH, Karlsruhe, Germany or DMEM, Sigma-Aldrich, Taufkirchen, Germany; rB1R cells: D-MEM/F12, Gibco Invitrogen GmbH, Karlsruhe, Germany) with 10 vol. % FBS (foetal bovine serum, Gibco Invitrogen GmbH, Karlsruhe, Germany or PAN Biotech GmbH, Aidenbach, Germany). On the following day, the cells are loaded for 60 min at 37° C. with 2.13 μM Fluo-4 (Molecular Probes Europe BV, Leiden, Holland) in HBSS buffer (Hank's buffered saline solution, Gibco Invitrogen GmbH, Karlsruhe, Germany) with 2.5 mM probenecid (Sigma-Aldrich, Taufkirchen, Germany) and 10 mM HEPES (Sigma-Aldrich, Taufkirchen, Germany). The plates are then washed 2× with HBSS buffer, and HBSS buffer which additionally contains 0.1% BSA (bovine serum albumin; Sigma-Aldrich, Taufkirchen, Germany), 5.6 mM glucose and 0.05% gelatine (Merck KgaA, Darmstadt, Germany) is added. After a further incubation of 20 minutes at room temperature, the plates are inserted into the FLIPR for the $Ca^{2+}$ measurement.

Alternatively, the plates are washed with buffer A (15 mM HEPES, 80 mM NaCl, 5 mM KCl, 1.2 mM $CaCl_2$, 0.7 mM $MgSO_4$, 2 g/l glucose, 2.5 mM probenecid), buffer A is added and the plates are loaded with 2.5 μM Fluo-4 and 0.025% Pluronic F127 (Sigma-Aldrich, Taufkirchen, Germany). Thereafter, the cells are washed 2× with buffer A and incubated for 30 minutes with buffer A, which additionally contains 0.05% BSA and 0.05% gelatine, at room temperature and thereafter inserted into the FLIPR for the $Ca^{2+}$ measurement. The $Ca^{2+}$-dependent fluorescence is measured here before and after addition of substances ($\lambda_{ex}$=488 nm, $\lambda_{em}$=540 nm). Quantification is by measurement of the highest fluorescence intensity (FC, fluorescence counts) over time.

3 FLIPR Assay

The FLIPR protocol consists of 2 additions of substance. Test substances (10 µM) are first pipetted on to the cells and the $Ca^{2+}$ inflow is compared with the control (hB1R: Lys-Des-Arg$^9$-bradykinin >=50 nM; rB1R: Des-Arg$^9$-bradykinin 10 µM). This gives the figure in % activation based on the $Ca^{2+}$ signal after addition of Lys-Des-Arg$^9$-bradykinin (>=50 nM) or Des-Arg$^9$-bradykinin (10 µM). After incubation for 10-20 minutes, Lys-Des-Arg$^9$-bradykinin (hB1R) or Des-Arg$^9$-bradykinin (rB1R) in the concentration of the $EC_{80}$ is applied and the inflow of $Ca^{2+}$ is likewise determined. Antagonists lead to a suppression of the $Ca^{2+}$ inflow. % inhibition compared with the maximum achievable inhibition is calculated. In order to determine the $IC_{50}$ value, the substances are added in various concentrations. Duplicate or triplicate determinations (n=2 or n=3) are carried out, and these are repeated in at least one further independent experiment (N>=2).

The following examples serve to illustrate the invention in further detail, without limiting the scope of the inventive concept.

EXAMPLES

The chemicals and solvents employed were obtained commercially from the conventional suppliers (Acros, Aldrich, Fluka, Lancaster, Maybridge, TCI, Fluorochem, Tyger, ABCR, Fulcrum, FrontierScientific etc.) or were synthesised by the methods known to the person skilled in the art. The yields of the compounds prepared are not optimized. Commercially available materials, for example $Al_2O_3$ or silica gel [for example from E. Merck, Darmstadt, Germany], were used as the stationary phase for column chromatography. Thin-layer chromatography investigations were carried out with commercially available HPTLC pre-coated plates (for example silica gel 60 F 254 from E. Merck, Darmstadt). The mixing ratios of solvents, eluants or for chromatographic investigations are always given in volume/volume unless indicated otherwise. Unless indicated otherwise, analysis was carried out by mass spectroscopy (ESI-MS). The number of equivalents of reagents, as well as the solvent amount, the reaction temperature and the reaction time may vary slightly for reactions which have been carried out by an analogous method. Work-up and purification (mainly column chromatography) were adjusted in order to compensate for the characteristics of each compound synthesized by an analogous method.

Analytical method for individual compounds:

The analytical studies were carried out by mass spectroscopy.

Equipment and Methods for HPLC-MS Analytics:

HPLC: Waters Alliance 2795 with PDA Waters 2998; MS: Micromass Quattro MicroTM API; Column: Waters Atlantis® T3, 3 µm, 100 Å, 2.1×30 mm; temp:. 40° C., Eluent A: water+0.1% formic acid; Eluent B: acetonitrile+0.1% formic acid; Gradient: 0% B to 100% B in 8.8 min, 100% B for 0.4 min, 100% B to 0% B in 0.01 min, 0% B for 0.8 min; Flow: 1.0 mL/min; Ionisation: ES+, 25 V; Make up: 100 µL/min 70% methanol+0.2% formic acid; UV: 200-400 nm.

Those skilled in the art will understand that the acid and amine structural units employed within the scope of the syntheses of individual substances can also be used analogously in parallel synthesis according to the methods described.

I. Individual Substances

1. Acid units

The following acid units were synthesized and used for synthesizing the compounds according to the invention:

| Acid | Structure | Name |
|---|---|---|
| AC1 | 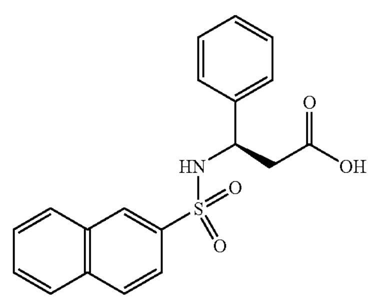 | (R)-3-(Naphthalene-2-sulfonamido)-3-phenylpropanoic acid |
| AC2 | 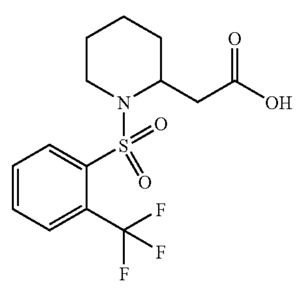 | 2-(1-(2-(Trifluoromethyl)phenylsulfonyl)piperidin-2-yl)acetic acid |

-continued

| Acid | Structure | Name |
|---|---|---|
| AC3 | 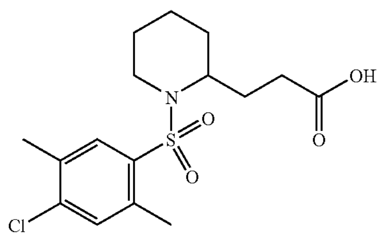 | 3-(1-(4-Chloro-2,5-dimethylphenylsulfonyl)piperidin-2-yl)propanoic acid |
| AC4 | 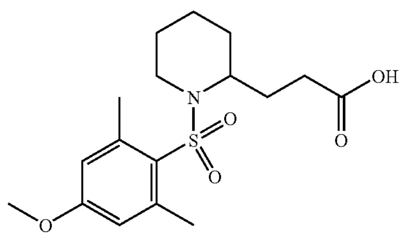 | 3-(1-(4-Methoxy-2,6-dimethylphenylsulfonyl)piperidin-2-yl)propanoic acid |
| AC5 | 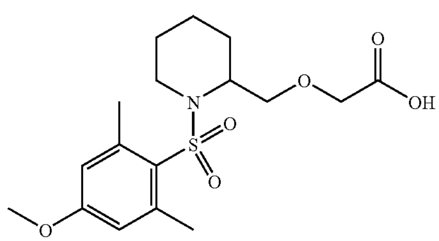 | 2-((1-(4-Methoxy-2,6-dimethylphenylsulfonyl)piperidin-2-yl)methoxy)acetic acid |
| AC6 | 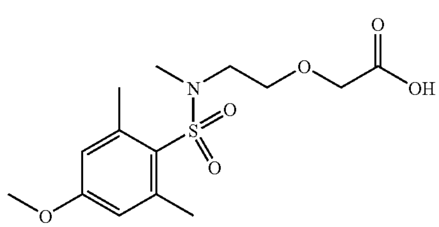 | 2-(2-(4-Methoxy-N,2,6-trimethylphenylsulfonamido)ethoxy)acetic acid |
| AC7 | 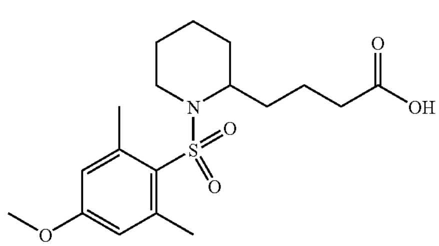 | 4-(1-(4-Methoxy-2,6-dimethylphenylsulfonyl)piperidin-2-yl)butanoic acid |
| AC27 | 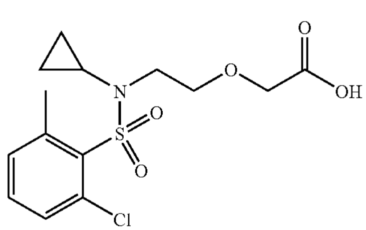 | 2-(2-(2-Chloro-N-cyclopropyl-6-methylphenylsulfonamido)ethoxy)acetic acid |

-continued

| Acid | Structure | Name |
|---|---|---|
| AC28 | 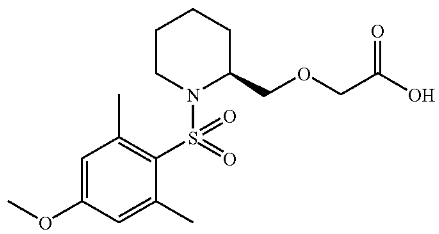 | (S)-2-((1-(4-Methoxy-2,6-dimethylphenylsulfonyl)piperidin-2-yl)methoxy)acetic acid |
| AC29 | 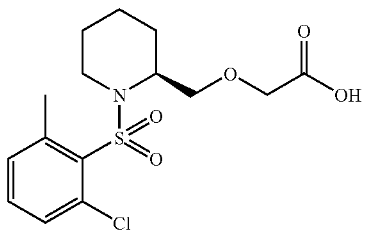 | (S)-2-((1-(2-Chloro-6-methylphenylsulfonyl)piperidin-2-yl)methoxy)acetic acid |
| AC30 | 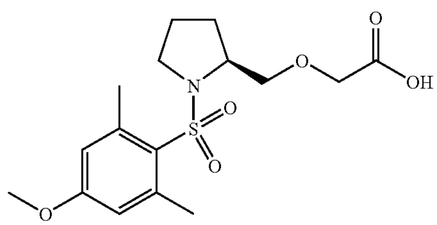 | (S)-2-((1-(4-Methoxy-2,6-dimethylphenylsulfonyl)pyrrolidin-2-yl)methoxy)acetic acid |
| AC31 | 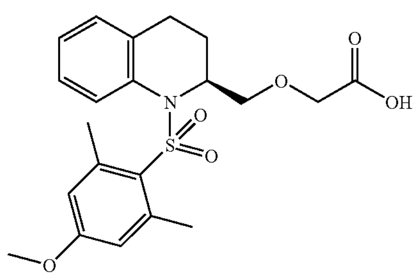 | (S)-2-((1-(4-Methoxy-2,6-dimethylphenylsulfonyl)-1,2,3,4-tetrahydroquinolin-2-yl)methoxy)acetic acid |

Synthesis of (3R)-(naphthalene-2-sulfonamido)-3-phenylpropionic acid (AC1)

Stage 1. (3R)-(Naphthalene-2-sulfonamido)-3-phenylpropionic acid tert-butyl Ester Triethylamine (1.8 ml, 13.55 mmol) and catalytic amounts of DMAP were added to a solution of (3R)-3-amino-3-phenylpropionic acid tert-butyl ester (1 g, 4.52 mmol) in methylene chloride (MC, 10 ml). 2-Naphthalenesulfonic acid chloride (1 g, 4.52 mmol), dissolved in MC (7 ml), was added, while cooling with ice. After stirring for 10 minutes, while cooling with ice, the mixture was slowly warmed to room temperature and stirred overnight. NaHCO₃ solution was added to the reaction mixture and the mixture was stirred. After separation of the phases, the aqueous phase was extracted with methylene chloride. This organic phase was washed with sat. NaCl solution, dried with MgSO₄, filtered and concentrated to dryness in vacuo. Purification was carried out by chromatography on silica gel (hexane/tert-butyl methyl ether 3/1). The yield was 1.6 g (86%).

Stage 2. (3R)-(Naphthalene-2-sulfonamido)-3-phenylpropionic Acid (AC1)

(3R)-(Naphthalene-2-sulfonamido)-3-phenylpropionic acid tert-butyl ester (1.6 g, 3.88 mmol) was dissolved in MC (40 ml), trifluoroacetic acid (5 ml, 64.9 mmol) was added and the mixture was stirred at room temperature overnight. The reaction mixture was then concentrated and the residue was codistilled twice with toluene. The yield was 1.3 g (100%).

Synthesis of 2-(1-(3-(trifluoromethyl)phenylsulfonyl)piperidin-2-yl)acetic Acid (AC2)

Stage 1. 2-(Piperidinyl-2-yl)acetic acid hydrochloride

PtO₂ (0.8 g, moistened with methanol) was added to a solution of 2-(pyridin-2-yl)acetic acid hydrochloride (20 g) in methanol (200 ml) and the mixture was stirred under a hydrogen atmosphere for 2 hours. The reaction was monitored by thin layer chromatography and the mixture was filtered over Celite when the conversion was complete. The filtrate was concentrated in vacuo. The yield was 20.5 g (quantitative).

Stage 2. 2-(Piperidinyl-2-yl)acetic acid methyl ester hydrochloride 2-(Piperidin-2-yl)acetic acid hydrochloride (20.5 g) was dissolved in methanol (200 ml) and the solution was cooled to 0° C. Thionyl chloride (16.3 g) was added dropwise at this temperature in the course of 10-15 minutes. The reaction mixture was then stirred under reflux at 65° C. for 2 hours and the reaction was observed by thin layer chromatography. When the reaction was complete, the mixture was concentrated in vacuo. The yield was 22 g (quantitative).

Stage 3. 1-(3-(Trifluoromethyl)phenylsulfonyl)piperidin-2-yl)acetic acid methyl ester 2-(Piperidin-2-yl)acetic acid methyl ester hydrochloride (1.7 g) was dissolved in MC (65 ml) and $K_2CO_3$ (2.66 g) was added. A solution of 3-(trifluoromethyl)-benzene-1-sulfonyl chloride (2.14 g) in methylene chloride (20 ml) was added dropwise to this mixture in the course of 10 minutes, The mixture was stirred at room temperature for 8 hours and the reaction was monitored by thin layer chromatography. When the reaction had ended, the mixture was filtered and the filtrate was washed with water (100 ml). After separation of the phases, the organic phase was concentrated in vacuo. Purification was carried out by chromatography on silica gel (20% ethyl acetate in hexane). The yield was 2.89 g (90%).

Stage 4. 2-(1-(3-(Trifluoromethyl)phenylsulfonyl) piperidin-2-yl)acetic acid (AC2)

KOH (8.12 g) was added to a solution of 1-(3-trifluoromethyl)phenylsulfonyl)-piperidin-2-yl)acetic acid methyl ester (26 g) in methanol (260 ml) and the mixture was stirred at room temperature for 6 hours. The reaction was observed by thin layer chromatography. When the reaction had ended, the reaction mixture was concentrated in vacuo and the resulting residue was taken up in water (200 ml). The solution was cooled to 0° C., adjusted to pH=2 with concentrated HCl and extracted with methylene chloride (2×200 ml). The combined organic phases were dried with $Na_2SO_4$ and concentrated to dryness in vacuo. The yield was 23.32 g (93%).

Synthesis of 3-(1-(4-chloro-2,5-dimethylphenylsulfonyl)piperidin-2-yl)propionic acid (AC3) Stage 1. 3-(2-Pyridyl)acrylic acid ethyl ester (Ethoxycarbonylmethyl)-triphenylphosphonium salt (341.5 g) was added to a solution of picolinaldehyde (31.1 ml) in toluene (350 ml) at room temperature and the mixture was stirred for a further 90 minutes. The reaction was observed by thin layer chromatography. When the reaction had ended, the toluene was distilled off, the residue was taken up in hexane (200 ml) and the mixture was stirred vigorously for 15 minutes. The solid which had precipitated was filtered out and washed thoroughly with hexane and the filtrate was concentrated in vacuo. Purification of the crude product was carried out by chromatography on silica gel (hexane). The yield was 50 g (86%).

Stage 2. 3-(Piperidin-2-yl)propionic acid ethyl ester hydrochloride 3-(2-Pyridyl)acrylic acid ethyl ester (16.88 g) was dissolved in methanol (160 ml), $PtO_2$ (0.717 g, moistened with methanol) was added and the mixture was stirred under a hydrogen atmosphere at 80 PSI for 3 hours. The reaction was monitored by thin layer chromatography. When the reaction had ended, the mixture was filtered over Celite. The filtrate was concentrated in vacuo. The yield was 17 g (97%).

Stage 3. 3-(1-(4-Chloro-2,5-dimethylphenylsulfonyl) piperidin-2-yl)propionic acid ethyl ester Triethylamine (30 g) was added dropwise to a solution of 3-(piperidin-2-yl)propionic acid ethyl ester hydrochloride (30 g) in methylene chloride (210 ml) at 0° C. and the mixture was then stirred at room temperature for 10 minutes. Chloro-2,5-dimethylbenzene-1-sulfonyl chloride (32.3 g) was then added slowly and the mixture was stirred for 2 hours. The reaction was observed by thin layer chromatography. Because of incomplete conversion, the mixture was stirred for a further 17 hours before the reaction was ended by addition of water (200 ml). The phases were separated and the aqueous phase was extracted with MC (150 ml). The combined organic phases were dried with $Na_2SO_4$, filtered and concentrated in vacuo. Purification of the crude product was carried out by chromatography on silica gel (5% ethyl acetate in hexane). The yield was 47.23 g (90%).

Stage 4. 3-(1-(4-Chloro-2,5-dimethylphenylsulfonyl) piperidin-2-yl)propionic acid (AC3)

KOH (10.5 g) was added to a solution of 3-(1-(4-chloro-2,5-dimethylphenyl-sulfonyl)piperidin-2-yl)propionic acid ethyl ester (33 g) in methanol/water (230 ml/100 ml) and the mixture was stirred at room temperature for 15 hours. The reaction was observed by thin layer chromatography. When the reaction was complete, the methanol was distilled off and the aqueous phase was extracted with ethyl acetate (2×75 ml). The aqueous phase was then adjusted to pH=4 with HCl, while cooling with ice, and extracted with MC. The combined organic phases were dried with $Na_2SO_4$ and concentrated in vacuo. The yield was 30.6 g (100%).

Synthesis of 3-(1-(4-methoxy-2,6-dimethylphenylsulfonyl)piperidin-2-yl)propionic acid (AC4)

The synthesis of this carboxylic acid was carried out analogously to acid unit AC3.

Synthesis of 2-((1-(4-methoxy-2,6-dimethylphenylsulfonyl)piperidin-2-yl)methoxy)acetic acid (AC5)

Stage 1. 4-Methoxy-2,6-dimethylbenzene-1-sulfonyl Chloride 3,5-Dimethylanisole (102.5 g, 753 mmol) was dissolved in MC (1,000 ml) and the solution was cooled to 0° C. Chlorosulfonic acid (251 ml, 3.763 mmol, in 250 ml of MC) was slowly added dropwise to this solution. After 10 minutes, the reaction mixture was poured on to ice (1,000 ml) and extracted with MC (1×250 ml). The combined organic phases were washed with water (1,000 ml) and NaCl solution (1,000 ml), dried with $Na_2SO_4$ and concentrated in vacuo. Purification of the crude product was carried out by chromatography on silica gel (heptane/MC, 5:1). The yield was 63.50 g (36%).

Stage 2. (1-(4-Methoxy-2,6-dimethylphenylsulfonyl) piperidin-2-yl)methanol $K_2CO_3$ (20.40 g, 147.6 mmol) and 4-methoxy-2,6-dimethylbenzene-1-sulfonyl chloride (19.05 g, 81.2 mmol) were added in succession to a suspension of piperidin-2-ylmethanol (8.50 g, 73.8 mmol) in acetone (350 ml). The reaction mixture was then stirred at 50° C. overnight. After cooling to room temperature, the mixture was filtered and the filtrate was concentrated in vacuo. The crude product was employed in the next stage without further purification. The yield was 27.25 g (quantitative).

Stage 3. tert-Butyl 2-((1-(4-methoxy-2,6-dimethylphenylsulfonyl)piperidin-2-yl)methoxy)acetate n-Bu$_4$NCl (7.52 g, 27.1 mmol) was added to a solution of (1-(4-methoxy-2,6-dimethylphenylsulfonyl)piperidin-2-yl) methanol (27.2 g, max. 73.8 mmol) in toluene/MC (150 ml/150 ml) and the mixture was cooled to 0° C. A 35% strength aqueous NaOH solution (300 ml) was then added. Bromoacetic acid tert-butyl ester (17.8 ml, 122 mmol) was then added dropwise to the reaction mixture and the mixture was stirred at room temperature for 3 hours. The organic phase was separated off, washed with water (3×300 ml), dried over Na$_2$SO$_4$ and concentrated in vacuo. Purification was carried out by chromatography on silica gel (heptane/ethyl acetate 3:1). The yield was 26.8 g (85% over 2 stages).

Stage 4. 2-((1-(4-Methoxy-2,6-dimethylphenylsulfonyl)piperidin-2-yl)methoxy)acetic acid (AC5)

A 6 M aqueous NaOH solution (200 ml, 1.200 mmol) was added to a solution of tert-butyl 2-((1-(4-methoxy-2,6-dimethylphenylsulfonyl)piperidin-2-yl)methoxy)-acetate (26.8 g, 62.7 mmol) in THF (200 ml) and methanol (200 ml) and the reaction was stirred at room temperature for 1 hour. The organic solvents were then distilled off and 6 M aqueous HCl (210 ml) was added to the residue at 0° C. The aqueous phase was extracted with methylene chloride (200 ml) and ethyl acetate (200 ml). The combined organic phases were dried with Na$_2$SO$_4$, filtered and concentrated in vacuo. The residue obtained was codistilled twice with diisopropyl ether. The yield was 21.92 g (94%).

Synthesis of 2-(2-(4-methoxy-N,2,6-trimethylphenylsulfonamido)ethoxy)acetic acid (AC6)

Stage 1. N-(2-Hydroxyethyl)-4-methoxy-N,2,6-trimethylbenzenesulfonamide

Triethylamine (213 ml, 1,512.5 mmol) was added to a solution of 2-(methylamino)ethanol (53.5 ml, 665.5 mmol) in MC (1,250 ml) and the mixture was cooled to 0° C. A solution of 4-methoxy-2,6-dimethylbenzene-1-sulfonyl chloride (142 g, 605 mmol) [see AC5, Stage 1] in MC (750 ml) was then slowly added dropwise. The reaction mixture was stirred at room temperature for 2 hours. The organic phase was then washed with aqueous 0.5 M HCl (800 ml) and water (2×1,000 ml). The combined organic phases were dried with Na$_2$SO$_4$, filtered and concentrated in vacuo. Purification was carried out by chromatography on silica gel (heptane/ethyl acetate 1:1). The yield was 116.3 g (70%).

Stage 2. tert.-Butyl 2-(2-(4-methoxy-N,2,6-trimethylphenylsulfonamido)-ethoxy)acetate n-Bu$_4$NCl (39 g, 140.1 mmol) was added to a solution of N-(2-hydroxyethyl)-4-methoxy-N,2,6-trimethylbenzenesulfonamide (116 g, 424.4 mmol) in toluene (750 ml) and the mixture was cooled to 0° C. Aqueous 35% strength NaOH solution (1,000 ml) was then added. Bromoacetic acid tert-butyl ester (93 ml, 636.6 mmol) was then added dropwise to the reaction mixture and the mixture was stirred at room temperature for 2 hours. The organic phase was separated off, washed with water (3×750 ml), dried over Na$_2$SO$_4$ and concentrated in vacuo. Purification was carried out by chromatography on silica gel (heptane/ethyl acetate 4:1). The yield was 124.6 g (76%).

Stage 3. 2-(2-(4-Methoxy-N,2,6-trimethylphenylsulfonamido)ethoxy)acetic acid (AC6)

tert-Butyl 2-(2-(4-methoxy-N,2,6-trimethylphenylsulfonamido)ethoxy)acetate (124.5 g, 321.3 mmol) was dissolved in THF (1,150 ml) and MeOH (1,900 ml), and an aqueous 6 M NaOH solution (1,300 ml) was added. The reaction mixture was stirred at room temperature for 1 hour and the organic solvents were then distilled off. The residue was taken up in aqueous 6 M HCl (2,000 ml) at 0° C. and the mixture was extracted with methylene chloride (2×1,000 ml). The combined organic phases were dried, filtered and concentrated to dryness in vacuo. The yield was 103.5 g (97%).

Synthesis of 4-(1-(4-methoxy-2,6-dimethylphenylsulfonyl)piperidin-2-yl)butanoic acid (AC7)

Stage 1. Methyl 4-(piperidin-2-yl)butanoic acid methyl ester hydrochloride

Hydrogen chloride in methanol 1.25 mol/l (58 ml, 72.43 mmol) was added to 4-piperidin-2-ylbutanoic acid hydrochloride (1.5 g, 7.243 mmol) and the mixture was refluxed for 6 hours, cooled to room temperature and stirred for 3 days. A thin layer chromatography control still showed educt, and the mixture was topped up with hydrogen chloride in methanol (4 ml) and refluxed for 3 hours. The reaction mixture was concentrated in vacuo and the residue was taken up in ethanol/ether 1/1 (5 ml). The solution was slowly added dropwise to ice-cooled ether (300 ml), the resulting suspension was stirred in an ice-bath for 1 hour and the solid was filtered out with suction, washed with ether and dried in vacuo. The yield was 1.21 g (75%).

Stage 2. Methyl 4-(1-(4-methoxy-2,6-dimethylphenylsulfonyl)piperidin-2-yl)butanoic acid methyl ester Methyl 4-(piperidin-2-yl)butanoic acid methyl ester hydrochloride (1.26 g, 5.683 mmol) was dissolved in methylene chloride (25 ml) and triethylamine (4 ml, 28.417 mmol) and a solution of 4-methoxy-2,6-dimethylbenzenesulfonic acid chloride (2.67 g, 11.37 mmol) [see AC5, stage 1) in methylene chloride (10 ml) was added. The mixture was stirred at room temperature overnight. 1 mol/l HCl solution (10 ml) was added to the reaction mixture, phase separation, extraction of the aqueous phase with methylene chloride (2×20 ml). The combined organic phases were washed with sat. sodium chloride solution (20 ml), dried over sodium sulfate and concentrated in vacuo. The crude product was purified by column chromatography (silica gel) with hexane/methylene chloride/ether (400/100/50). The yield was 1.65 g (75%).

Stage 3. 4-(1-(4-Methoxy-2,6-dimethylphenylsulfonyl)piperidin-2-yl)butanoic acid (AC7)

Methyl 4-(1-(4-methoxy-2,6-dimethylphenylsulfonyl)piperidin-2-yl)butanoic acid methyl ester (1.65 g, 4.3 mmol) was dissolved in water (10 ml) and methanol (35 ml), and lithium hydroxide was added (0.3 g, 12.9 mmol). The mixture was stirred at room temperature for 3 days, the methanol was then distilled off in vacuo and ethyl acetate (50 ml) and HCl solution (1 mol/l, 10 ml) were added to the residue. The phases were then separated, extraction was carried out with ethyl acetate (2×50 ml) and the combined organic phases were dried over sodium sulfate and concentrated in vacuo. The yield was 1.56 g (98%).

Synthesis of 2-(2-(2-chloro-N-cyclopropyl-6-methylphenylsulfonamido)-ethoxy)acetic acid (AC27)

Step (i): 2-(Cyclopropylamino)ethanol

Cyclopropylamine (5 g, 1 eq.) was dissolved in ethanol (60 ml) and 2-bromo ethanol (0.5 eq.) was added. The resulting reaction mixture was heated to 60° C. for 16 h. The reaction mixture was evaporated under reduced pressure and used directly in the next step without further purification. Yield: 70%

Step (ii): 2-Chloro-N-cyclopropyl-N-(2-hydroxyethyl)-6-methylbenzene-sulfonamide To 2-(cyclopropylamino)ethanol (2 eq.) was added triethylamine (2.5 eq.) and the mixture was cooled to 0° C. To this cold reaction mixture was added 2-chloro-6-methylbenzene sulfonyl chloride (1 eq.) and the mixture was stirred at 25° C. for 2 h. It was diluted with dichloromethane and the organic layer was washed with water and brine and finally dried over sodium sulfate. Evaporation of the organic layer under reduced pressure gave the crude product which was purified by column chromatography (10% ethyl acetate in hexane). Yield: 50%

Step (iii): tert-Butyl 2-(2-(2-chloro-N-cyclopropyl-6-methylphenylsulfonamido)-ethoxy)acetate To a cold solution of 2-chloro-N-cyclopropyl-N-(2-hydroxyethyl)-6-methylbenzenesulfonamide (1 eq.) in dichloromethane (15 ml) was added tetrabutylammonium chloride (0.1 eq.) and 35% sodium hydroxide solution (15 ml) at 0° C. tert-Butyl 2-bromoacetate (1.2 eq.) was added dropwise to this cold reaction mixture maintaining the same temperature. After addition was complete, the reaction mixture was stirred at room temperature for 16 h (monitored by TLC). It was diluted with dichloromethane and the organic layer was washed with water and brine and finally dried over sodium sulfate. Evaporation of the organic layer under reduced pressure gave the crude product which was purified by column chromatography (20% ethyl acetate in hexane). Yield: 70%

Step (iv): 2-(2-(2-Chloro-N-cyclopropyl-6-methylphenylsulfonamido)ethoxy)-acetic acid (AC27)

To a dichloromethane (10 ml/mmol) solution of tert-butyl 2-(2-(2-chloro-N-cyclopropyl-6-methylphenylsulfonamido) ethoxy)acetate (1 eq.) was added trifluoroacetic acid (13 eq.) at 0° C. and the resulting reaction mixture was stirred at ambient temperature for 2 h. The solvent was evaporated off and the residue dried under vacuum to remove traces of trifluoroacetic acid. The crude product was used in the next step without further purification. Yield: quantitative Synthesis of (S)-2-((1-(4-methoxy-2,6-dimethylphenylsulfonyl)piperidin-2-yl)methoxy)acetic acid (AC28)

Step (i): (S)-Piperidin-2-ylmethanol (S)-Piperidine-2-carboxylic acid (2 g, 15.5 mmol) was placed in tetrahydro-furan (20 ml); boron trifluoride etherate (2.1 ml, 117.1 mmol) was added, followed by boron dimethylsulfide in tetrahydrofuran (dropwise, 3 ml, 30.9 mmol). The reaction mixture was then refluxed for 16 h. Quenching was carried out with ice-cold methanol (10 ml); hydrogen chloride solution (conc. aq., 3 ml) was added dropwise, and refluxing was carried out for 30 min. After cooling, the mixture was rendered alkaline with dilute sodium hydroxide solution (4%) and extracted with dichloromethane (3×50 ml). The combined organic phases were dried over sodium sulfate and concentrated in vacuo. The crude product was used in the next stage without being purified further. Yield: 44%

Step (ii): (S)-(1-(4-Methoxy-2,6-dimethylphenylsulfonyl)piperidin-2-yl)-methanol (S)-Piperidin-2-ylmethanol (1.1 eq.) was dissolved in dichloromethane (4 ml/mmol) and cooled, and triethylamine (2.5 eq.) was added. A solution of 4-methoxy-2,6-dimethylbenzenesulfonyl chloride (1 eq.) in dichloromethane (2 ml/mmol) was added dropwise at 0° C., and then stirring was carried out for 90 min at room temperature. Hydrogen chloride solution (eq., 0.5 mol/l, 2 ml/mmol) was added, stirring was carried out for 15 min, and the phases were separated. The organic phase was washed with water, dried over sodium sulfate and concentrated in vacuo. The crude product was used in the next stage without being purified further. Yield: 20%

Step (iii): (S)-tert-Butyl 2-((1-(4-methoxy-2,6-dimethylphenylsulfonyl)piperidin-2-yl)methoxy)acetate Tetra-n-butylammonium chloride (0.33 eq.) and sodium hydroxide solution (5 ml/mmol, 35%) were added at 0° C. to a cooled solution of (S)-1-(4-methoxy-2,6-dimethylphenylsulfonyl)piperidin-2-yl)methanol (1 eq.) in toluene (5 ml/mmol). tert-Butyl 2-bromoacetate (1.5 eq.) was then added slowly at 0° C. After stirring for 90 min at room temperature, the phases were separated, and the organic phase was washed with water until pH neutral, dried over sodium sulfate and concentrated in vacuo. The crude product was used in the next stage without being purified further. Yield: 64%

Step (iv): (S)-2-((1-(4-Methoxy-2,6-dimethylphenylsulfonyl)piperidin-2-yl)methoxy)acetic acid (AC28)

(S)-tert-butyl 2-((1-(4-methoxy-2,6-dimethylphenylsulfonyl)piperidin-2-yl)-methoxy)acetate (1 eq.) was dissolved in dichloromethane (10 ml/mmol) and cooled, and trifluoroacetic acid (13 eq.) was added slowly at 0° C. After stirring for 2 h at room temperature, the reaction mixture was concentrated in vacuo and dried. The crude product was used in the next stage without being purified further. Yield: quantitative Synthesis of (S)-2-((1-(2-chloro-6-methylphenylsulfonyl)piperidin-2-yl)methoxy)acetic acid (AC29)

Synthesis of this acid unit was carried out in analogy to (S)-2-((1-(4-Methoxy-2,6-dimethylphenylsulfonyl)piperidin-2-yl)methoxy)acetic acid (AC28) employing 2-chloro-6-methylbenzene-1-sulfonyl chloride in step (ii).

Synthesis of (S)-2-((1-(4-methoxy-2,6-dimethylphenylsulfonyl)pyrrolidin-2-yl)methoxy)acetic acid (AC30)

Step 1: (S)-Pyrrolidin-2-ylmethanol

A solution of (S)-pyrrolidine-2-carboxylic acid (3 g, 26.0575 mmol) in tetrahydrofuran (290 ml) was cooled to 0°

C. and LiAlH$_4$ (3.4 g, 91.2012 mmol) was added very slowly. The reaction was then refluxed for 2 h. TLC revealed complete consumption of the starting material. The reaction mixture was cooled to room temperature and excess LiAlH$_4$ was quenched with saturated sodium sulfate solution, diluted with ethyl acetate and filtered through a bed of Celite. The filtrate was dried over sodium sulfate, concentrated and used in next step without further purification. Yield: 83%.

Step 2: (S)-(1-(4-Methoxy-2,6-dimethylphenylsulfonyl)pyrrolidin-2-yl)methanol

To a solution of (S)-pyrrolidin-2-ylmethanol (2.2 g, 8.54 mmol) in dichloro-methane (20 ml) was added triethylamine (2.9 ml, 21.36 mmol) and the mixture was cooled to 0° C. Then a solution of 4-methoxy-2,6-dimethyl-benzenesulfonyl chloride (2 g, 8.547 m.mole) in dichloromethane (10 ml) was added and the mixture was stirred at room temperature for 2 h. TLC showed complete consumption of the starting material. The reaction mixture was diluted in dichloromethane and was washed with water and brine. The organic layer was dried over sodium sulfate, concentrated and purified by column chromatography.
Yield: 55%.

Step 3: (S)-tert-Butyl 2-((1-(4-methoxy-2,6-dimethylphenylsulfonyl)pyrrolidin-2-yl)methoxy)acetate To a solution of (S)-(1-(4-methoxy-2,6-dimethylphenylsulfonyl)pyrrolidin-2-yl)methanol (2.7 g, 9.0303 mmol) in dichloromethane (45 ml) was added 35% aq NaOH solution (45 ml) followed by addition of tetra-n-butylammonium chloride (290 mg, 0.09308 mmol). The reaction mixture was stirred for 15 min at room temperature. Then it was cooled to 0° C. and tert-butyl 2-bromoacetate (1.7 ml, 10.83 mmol) was added and the mixture stirred for 2 h at room temperature. After completion of the reaction the organic layer was separated and washed with water and brine. The organic layer was dried over sodium sulfate and purified by column chromatography. Yield: 81%.

Step 4: (S)-2-((1-(4-Methoxy-2,6-dimethylphenylsulfonyl)pyrrolidin-2-yl)methoxy)acetic acid (AC30)

To a solution of (S)-tert-butyl 2-((1-(4-methoxy-2,6-dimethylphenylsulfonyl)-pyrrolidin-2-yl)methoxy)acetate (1 eq.) in dichloromethane (10 ml/mmol) was added trifluoroacetic acid (2 ml/mmol) at 0° C. and the resulting reaction mixture was stirred at 25° C. for 2 h. The solvent was evaporated off and it was dried under vacuum to remove traces of trifluoroacetic acid. The crude product was used directly for the next step. Yield: quantitative.

Synthesis of (S)-2-((1-(4-Methoxy-2,6-dimethylphenylsulfonyl)-1,2,3,4-tetrahydroquinolin-2-yl)methoxy)acetic acid [AC31]

Step (i): (S)-tert-Butyl 2-(hydroxymethyl)-3,4-dihydroquinoline-1(2H)-carboxylate (S)-1-(tert-Butoxycarbonyl)-1,2,3,4-tetrahydroquinoline-2-carboxylic acid (5 g, 18.03 mmol) was dissolved in tetrahydrofuran (40 ml) and the mixture was cooled. Boron hydride-tetrahydrofuran complex (27 ml, 1 mol/l in tetrahydrofuran) was cautiously added dropwise at 0° C. and the mixture was then stirred at room temperature for 15 h. The reaction mixture was cooled again and water (8 ml) was slowly added dropwise at 0° C. Potassium carbonate (4.21 g, 30.65 mmol) was then added and the mixture was stirred for 30 min. After phase separation the aqueous phase was extracted with diethyl ether (2×30 ml) and the combined organic phases were washed with saturated sodium chloride solution (30 ml), dried over sodium sulfate and concentrated in vacuo. The crude product was purified by column chromatography (silica gel) with hexane/ethyl acetate 2/1.
Yield: 3.98 g (83%)

Step (ii): (S)-(1,2,3,4-Tetrahydroquinolin-2-yl)methanol hydrochloride

Hydrogen chloride in methanol (1.25 mol/l, 60 ml) was added to (S)-tert-butyl 2-(hydroxymethyl)-3,4-dihydroquinoline-1(2H)-carboxylate (3.98 g, 15.1 mmol) and the mixture was refluxed for 2 h. The solvent was removed in vacuo, the residue was taken up in ethanol (5 ml) and the mixture was cooled. Diethylether (200 ml) was added and the mixture was stirred in an ice bath for 30 min. The precipitate was filtered out with suction, washed with diethylether and dried in vacuo.
Yield: 2.72 g, 90%

Step (iii): (S)-(1-(4-Methoxy-2,6-dimethylphenylsulfonyl)-1,2,3,4-tetrahydroquinolin-2-yl)methanol (a) Chlorosulfonic acid (2 eq.) in dichloromethane (0.2 ml/mmol) was added dropwise at 0° C. to a solution, cooled to, of 3,5-dimethylanisole (1 eq.) in dichloromethane (1.3 ml/mmol). When the reaction was complete (TLC monitoring), ice-water was added and the organic phase was extracted with water and saturated sodium chloride solution. The organic phase was dried over sodium sulfate and concentrated in vacuo. The sulfonyl chloride so obtained was reacted further directly without being purified further. Yield: 70%.

(b) Pyridine (5.5 ml, 68.11 mmol) was added dropwise to a cooled solution of (S)-(1,2,3,4-tetrahydroquinolin-2-yl) methanol hydrochloride (2.72 g, 13.62 mmol) in dichloromethane (50 ml) and triethylamine (5.66 ml, 40.87 mmol) at 0° C., followed by 4-dimethylaminopyridine (16 mg, catalytic). 4-Methoxy-2,6-dimethylbenzene-sulfonyl chloride (3.836 g, 16.35 mmol, synthesis see above), dissolved in dichloromethane (35 ml), was slowly added dropwise and the mixture was then warmed to room temperature and stirred for 15 h. The reaction mixture was washed with saturated copper sulfate solution (20 ml) and saturated sodium chloride solution (20 ml), dried over sodium sulfate and concentrated in vacuo. The crude product was purified by column chromatography (silica gel) with hexane/ethyl acetate 2/1. Yield: 1.22 g (24%).

Step (iv): (S)-tert-Butyl 2-((1-(4-methoxy-2,6-dimethylphenylsulfonyl)-1,2,3,4-tetrahydroquinolin-2-yl)methoxy)acetate tert-Butyl 2-bromoacetate (1.358 g, 6.972 mmol) and tetra-n-butylammonium hydrogen sulfate (110 mg, 0.332 mmol) were stirred in sodium hydroxide solution (26 ml, 50% aq) and toluene (20 ml). A solution of (S)-(1-(4-methoxy-2,6-dimethyl-phenylsulfonyl)-1,2,3,4-tetrahydroquinolin-2-yl) methanol (1.2 g, 3.32 mmol) in toluene (10 ml) was added slowly. The addition was exothermic, cooling was achieved with an ice bath. After stirring at room temperature for 1 h, the phases were separated and the aqueous phase was extracted with diethylether (2×50 ml). The combined organic phases were washed with saturated sodium chloride solution (30 ml), dried (Na$_2$SO$_4$) and concentrated in vacuo. The crude product was purified by column chromatography (silica gel) with hexane/ethyl acetate 5/1.
Yield: 1.03 g (65%).

Step (v): (S)-2-((1-(4-Methoxy-2,6-dimethylphenyl-sulfonyl)-1,2,3,4-tetrahydroquinolin-2-yl)methoxy)acetic acid (AC31)

(S)-tert-Butyl 2-((1-(4-methoxy-2,6-dimethylphenylsulfonyl)-1,2,3,4-tetrahydroquinoline-2-yl)methoxy)acetate (1 g, 2.103 mmol) was dissolved in dichloromethane (15 ml) and trifluoroacetic acid (3.24 ml, 42.05 mmol) was added slowly. After stirring at room temperature for 2 h, the solvent was removed in vacuo and the residue was co-evaporated twice more with 20 ml of toluene each time. Yield: 0.84 g (95%).

2.) Synthesis of Example Compounds by Reaction of Thiophenepiperidines with Carboxylic Acids A.) Reaction of Thiophenepiperidines with Carboxylic Acids

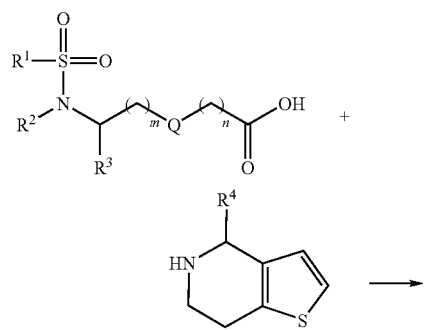

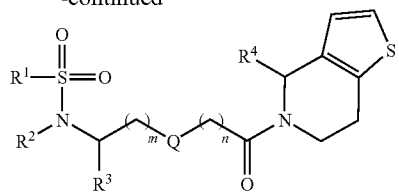

Method 1

The corresponding amine (1.1 eq.), HATU (1 eq.) and triethylamine (1.9 eq.) were added to a solution of the particular acid (1 eq.) in THF (5 ml) and the mixture was stirred at room temperature. The reaction was monitored by thin layer chromatography. When the conversion was complete, ethyl acetate (30 ml) was added to the reaction mixture and the mixture was extracted in each case twice with saturated $NH_4Cl$ solution and saturated $NaHCO_3$ solution. The combined organic phases were dried with $MgSO_4$ and concentrated to dryness in vacuo. Purification is carried out by chromatography on silica gel.

Method 2

Polystyrene-bonded dicyclohexylcarbodiimide (0.68 g, 2 eq., loading 1.36 mmol/g) was initially introduced into the reaction vessel and the acid (1.5 eq.), dissolved in MC, was added. The mixture was stirred at room temperature for 5 minutes. The amine (1 eq.) was then added. The mixture was stirred at room temperature for 3 days. The reaction mixture was filtered and washing was carried out with methylene chloride. The filtrate was concentrated to dryness in vacuo and the residue was purified by column chromatography on silica gel.

The example compounds listed in the following table were synthesized by Method 1 or 2.

| Ex. no. | Structure | Acid | Amine | Method | HPLC-MS |
|---|---|---|---|---|---|
| 15 | 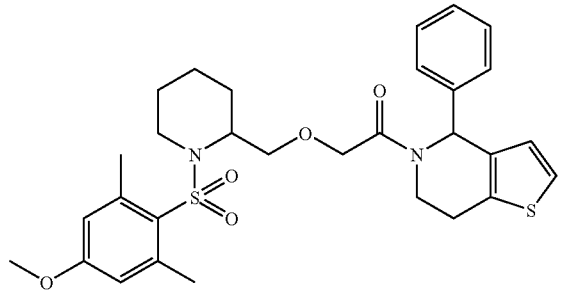 | AC5 | TP1 | 2 | MS, $R_t$ = 6.0 min, m/z = 569.2 [MH]$^+$ |
| 16 | 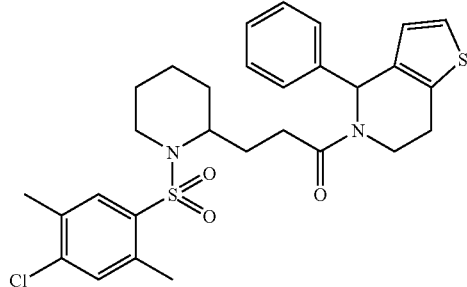 | AC3 | TP1 | 1 | MS, $R_t$ = 6.5 min, m/z = 557.1 [MH]$^+$ |

-continued

| Ex. no. | Structure | Acid | Amine | Method | HPLC-MS |
|---|---|---|---|---|---|
| 12 | 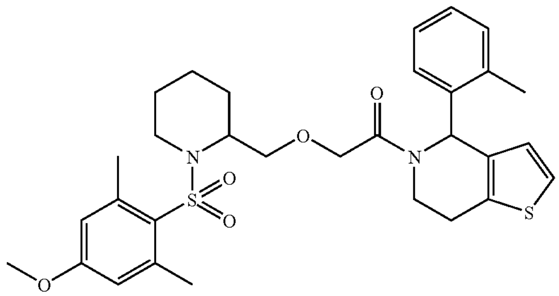 | AC5 | TP2 | 1 | MS, $R_t$ = 6.1 min, m/z = 583.3 [MH]$^+$ |
| 11 | 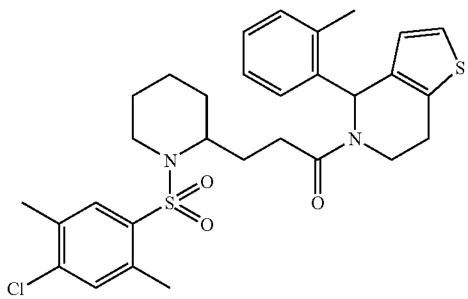 | AC3 | TP2 | 1 | MS, $R_t$ = 6.7 min, m/z = 571.2 [MH]$^+$ |
| 08 | 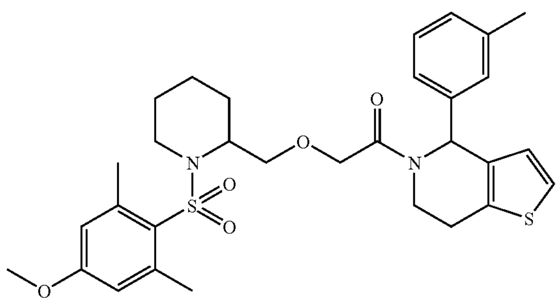 | AC5 | TP3 | 1 | MS, $R_t$ = 6.1 min, m/z = 583.2 [MH]$^+$ |
| 10 | 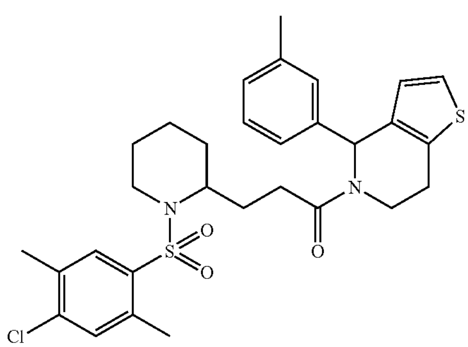 | AC3 | TP3 | 1 | MS, $R_t$ = 6.7 min, m/z = 571.2 [MH]$^+$ |
| 07 | 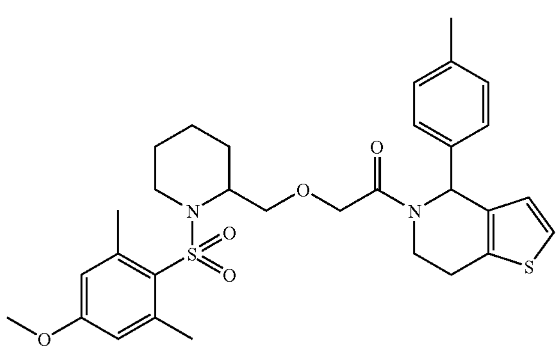 | AC5 | TP4 | 1 | MS, $R_t$ = 6.1 min, m/z = 583.3 [MH]$^+$ |

| Ex. no. | Structure | Acid | Amine | Method | HPLC-MS |
|---|---|---|---|---|---|
| 22 | 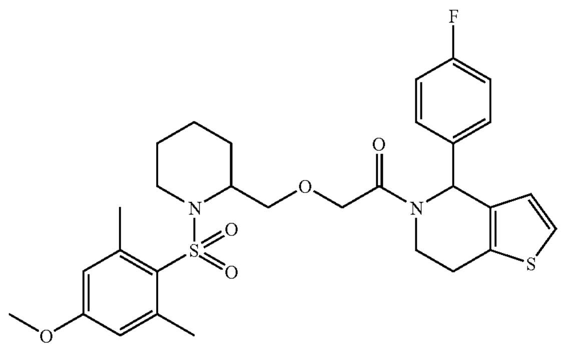 | AC5 | TP5 | 1 | MS, $R_t$ = 6.4 min, m/z = 587.1 [MH]$^+$ |
| 19 | 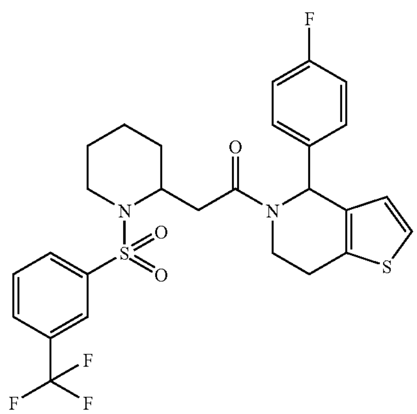 | AC2 | TP5 | 1 | MS, $R_t$ = 5.9 min, m/z = 567.1 [MH]$^+$ |
| 20 | 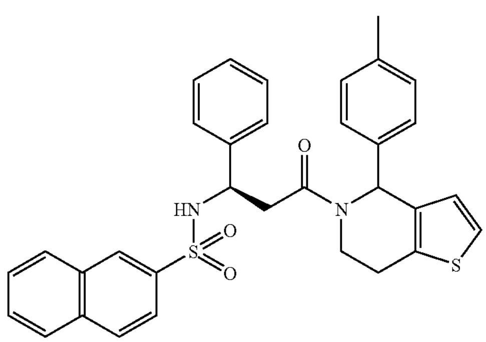 | AC1 | TP4 | 1 | MS, $R_t$ = 6.5 min, m/z = 567.1 [MH]$^+$ |
| 21 | 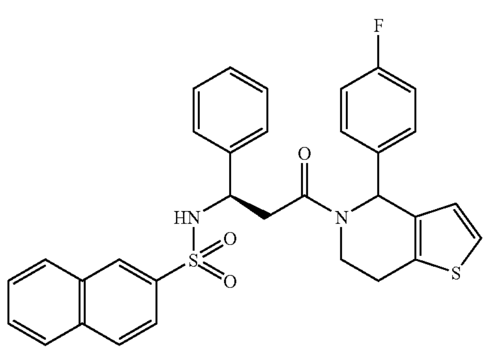 | AC1 | TP5 | 1 | MS, $R_t$ = 6.3 min, m/z = 571.0 [MH]$^+$ |

-continued

| Ex. no. | Structure | Acid | Amine | Method | HPLC-MS |
|---|---|---|---|---|---|
| 33 | 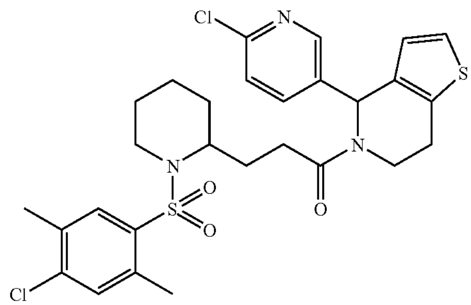 | AC3 | TP6 | 1 | MS, $R_t$ = 6.7 min, m/z = 591.9 [MH]$^+$ |
| 34 | 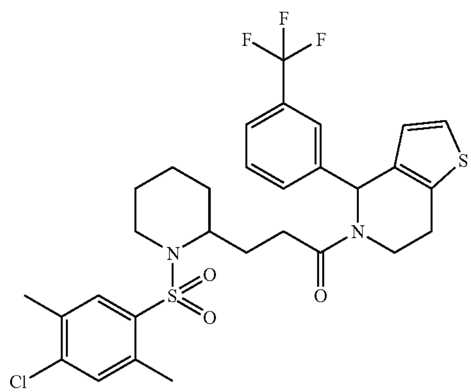 | AC3 | TP8 | 1 | MS, $R_t$ = 7.4 min, m/z = 625.0 [MH]$^+$ |
| 35 | 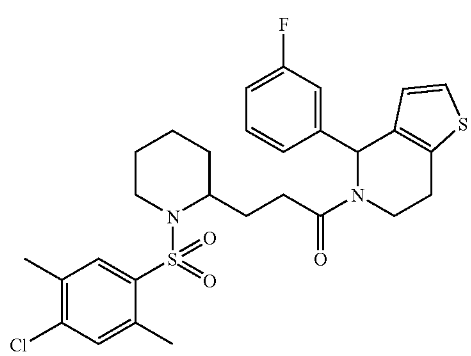 | AC3 | TP9 | 1 | MS, $R_t$ = 7.1 min, m/z = 575.0 [MH]$^+$ |
| 36 | 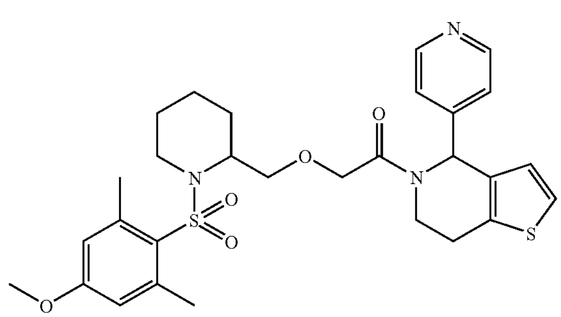 | AC5 | TP7 | 1 | MS, $R_t$ = 4.2 min, m/z = 570.0 [MH]$^+$ |

| Ex. no. | Structure | Acid | Amine | Method | HPLC-MS |
|---|---|---|---|---|---|
| 54 | 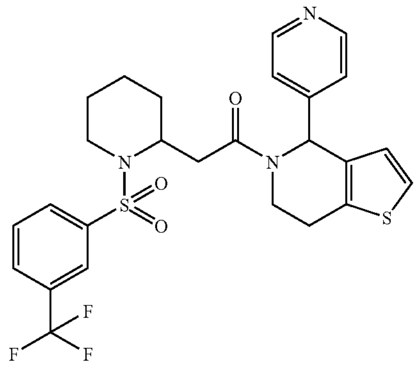 | AC2 | TP7 | 1 | MS, $R_t$ = 4.11 min, m/z = 549.2 [MH]+ |
| 55 | 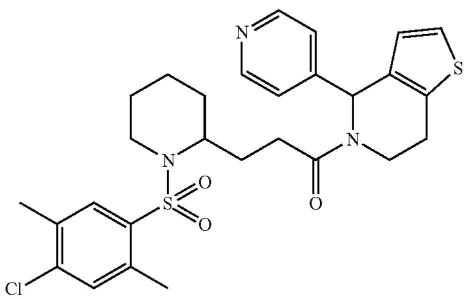 | AC3 | TP7 | 1 | MS, $R_t$ = 4.8 min, m/z = 557.9 [MH]+ |

Example 18

N-(2-(2-(4-Ethyl-6,7-dihydrothieno[3,2-c]pyridin-5(4H)-yl)-2-oxoethoxy)ethyl)-4-methoxy-N,2,6-trimethyl benzenesulfonamide

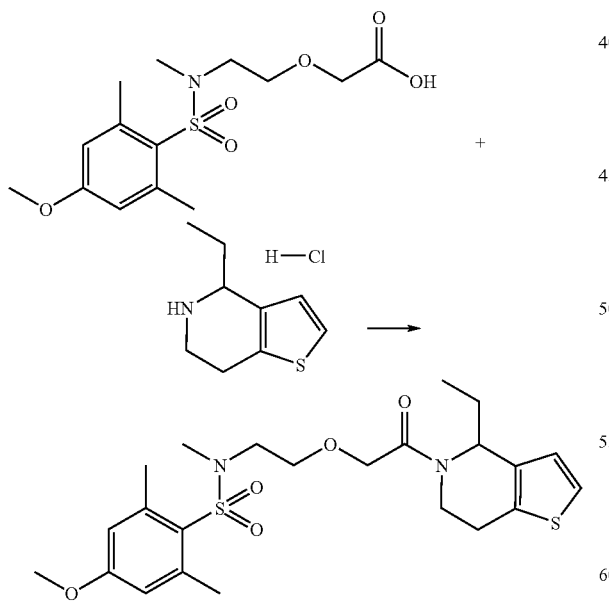

2-(2-(4-Methoxy-N,2,6-trimethylphenylsulfonamide)ethoxy)acetic acid (AC6) (120 mg, 362 mmol) and N-ethyl-N'-(3-dimethylaminopropyl)carbodiimide hydrochloride (EDCI) (103 mg, 543 mmol) were dissolved in MC (8 ml) under an inert gas and N-hydroxybenzotriazole (HOBt) (53 mg, 398 mmol), 4-ethyl-4,5,6,7-tetrahydrothieno[3,2-c]pyridine hydrochloride (110 mg, 543 mmol) and N-ethyldiisopropylamine (0.19 ml, 1.09 mmol) were added. The resulting reaction mixture was stirred at room temperature for 3 days. It was diluted with MC (30 ml) and washed with saturated sodium bicarbonate solution. The aqueous phase was extracted with MC (2×30 ml) and the combined organic phases were dried (MgSO$_4$) and concentrated in vacuo. The crude product was purified by column chromatography (silica gel) with ethyl acetate/hexane 200/10. The yield was 180 mg (100%, white, resin). MS, $R_t$=5.0 min, m/z=481.1 [MH]+

Example 23

1-(4-Ethyl-6,7-dihydrothieno[3,2-c]pyridin-5(4H)-yl)-4-(1-(4-methoxy-2,6-dimethylphenylsulfonyl)piperidin-2-yl)butan-1-one

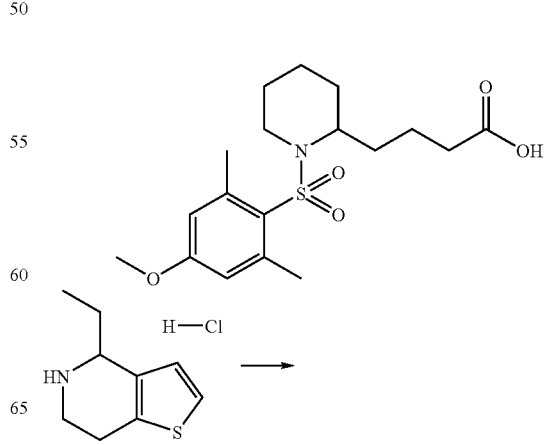

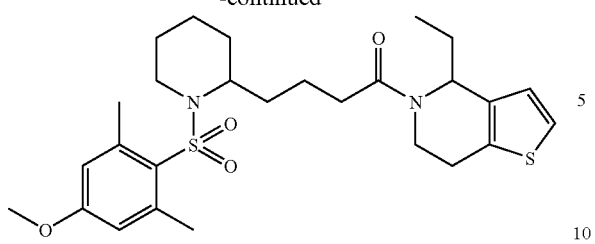

N-Ethyldiisopropylamine (0.21 ml, 1.218 mmol), 1-hydroxybenzotriazole hydrate (60 mg, 0.447 mol), 1-(3-dimethylaminopropyl)-3-ethylcarbodiimide hydrochloride (116 mg, 0.609 mmol) and 4-ethyl-4,5,6,7-tetrahydrothieno[3,2-c]pyridine hydrochloride (123 mg, 0.609 mmol) were added to a solution of 4-(1-(4-methoxy-2,6-dimethylphenylsulfonyl)piperidin-2-yl)butanoic acid (AC7) (0.15 g, 0.406 mmol) in MC (10 ml) and the mixture was stirred at room temperature for 15 hours. Saturated sodium bicarbonate solution (20 ml) was added to the mixture and the aqueous phase was then extracted with MC (2×30 ml). The combined organic phases were dried (MgSO$_4$) and concentrated in vacuo. The crude product was purified by column chromatography (silica gel) with hexane/ethyl acetate 2/1. The yield was 200 mg (94%, white, resin).

MS, R$_t$ 5.6 min, m/z=519.1 [MH]$^+$

B.) Synthesis of the Thiophenepiperidines
(Amines TP)

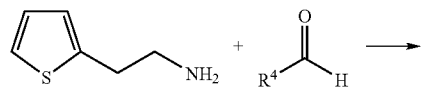

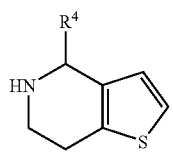

Method 1

Thiophenethylamine (5 g, 39.3 mmol) was dissolved in toluene (80 ml), the aldehyde (39.3 mmol) was added, and a molecular sieve (4 Å spheres) was added. The mixture was stirred under reflux for 3 days using a water separator. The molecular sieve was then filtered out and the filtrate was concentrated in vacuo. After addition of trifluoroacetic acid (112 ml), the mixture was stirred at room temperature for a further 3 days. The reaction mixture was concentrated on a rotary evaporator, the residue was dissolved in ether (200 ml), and the solution was washed with 2 M sodium hydroxide solution (100 ml). The combined organic phases were dried with MgSO$_4$, filtered and concentrated. The purity of the resulting compounds was checked by NMR and recrystallization was carried out if appropriate.

Method 2

Thiophenethylamine (39.3 mmol) was dissolved in ethanol (41 ml), and triethylamine (2.4 ml) and the aldehyde (39.3 mmol) were added. The mixture was stirred at room temperature for 15 hours. The reaction mixture was then concentrated in vacuo and trifluoroacetic acid (100 ml) was cautiously added to the residue. The mixture was stirred at room temperature for a further 3 days. The reaction mixture was then concentrated in vacuo. The residue was dissolved in ether (200 ml) and the solution was washed with 2 M sodium hydroxide solution (100 ml). The combined organic phases were dried over MgSO$_4$, filtered and concentrated. Purification was carried out by chromatography on silica gel. The purity of the products obtained was checked by NMR.

The thiophenepiperidines listed in the following table were synthesized by Method 1 or 2.

| Amine no. | Name | Structure | Method |
|---|---|---|---|
| TP1 | 4-Phenyl-4,5,6,7-tetrahydrothieno[3,2-c]pyridine | 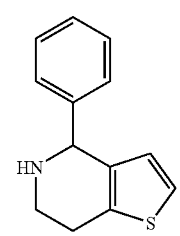 | 2 |
| TP2 | 4-o-Tolyl-4,5,6,7-tetrahydrothieno[3,2-c]pyridine | 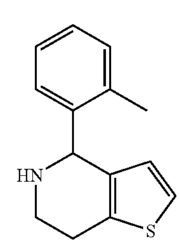 | 1 |

-continued

| Amine no. | Name | Structure | Method |
|---|---|---|---|
| TP3 | 4-m-Tolyl-4,5,6,7-tetrahydrothieno[3,2-c]pyridine | 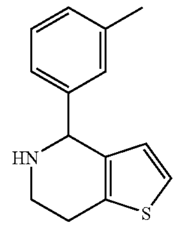 | 2 |
| TP4 | 4-p-Tolyl-4,5,6,7-tetrahydrothieno[3,2-c]pyridine | 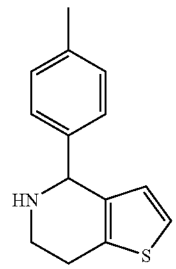 | 1 |
| TP5 | 4-(4-Fluorophenyl)-4,5,6,7-tetrahydrothieno[3,2-c]pyridine | 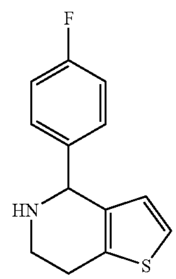 | 1 |
| TP6 | 4-(6-Chloropyridin-3-yl)-4,5,6,7-tetrahydrothieno[3,2-c]pyridine | 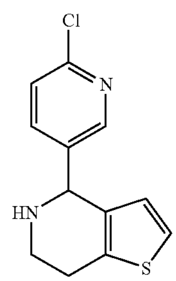 | 2 |
| TP7 | 4-(Pyridin-4-yl)-4,5,6,7-tetrahydrothieno[3,2-c]pyridine | 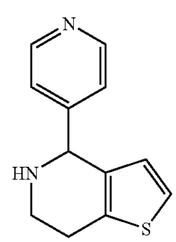 | 2 |
| TP8 | 4-(3-(Trifluoromethyl)phenyl)-4,5,6,7-tetrahydrothieno[3,2-c]pyridine | 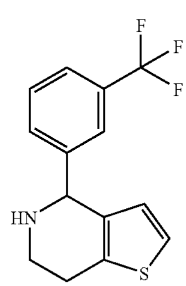 | 1 |

| Amine no. | Name | Structure | Method |
|---|---|---|---|
| TP9 | 4-(3-Fluorophenyl)-4,5,6,7-tetrahydrothieno[3,2-c]pyridine | 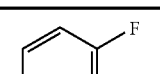 | 1 |

3.) Synthesis of Example Compounds by Reaction of Aminomethylated Thiophenepiperidines with Carboxylic Acids

A.) Reaction of Aminomethylated Thiophenepiperidines with Carboxylic Acids

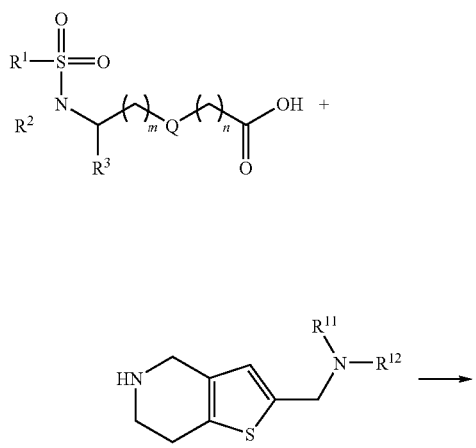

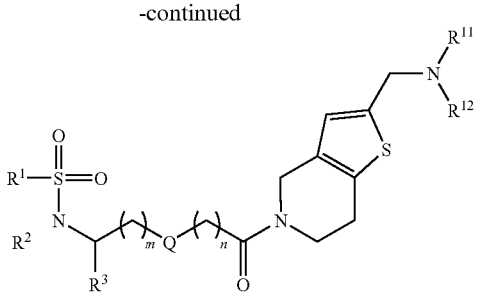

To a solution of the carboxylic acid (acid unit AC) (1 eq.) in dichloromethane (10 ml/mmol) was added diisopropyl ethylamine (2.5 eq.) at 0° C. followed by the addition of HOBt (1 eq.) and EDCI (1.5 eq.). The resultant solution was stirred at 25° C. for 15 min. It was again cool to 0° C. and the amine (amine unit TP) (1.3 eq.) dissolved in dichloromethane was added. The reaction mixture was stirred for 16 h at 25° C. The mixture was diluted with dichloromethane, washed with saturated ammonium chloride solution, brine, saturated sodium hydrogen carbonate and finally again with brine. The organic layer was dried over sodium sulfate and evaporated to dryness under reduced pressure to give the crude product. The crude material was purified by column chromatography.

The example compounds listed in the following table were prepared from the corresponding carboxylic acids (acid) and thiophenepiperidines (amine) in accordance with the general procedure described above.

| Example no. | Structure | Acid | Amine | Yield (%) | HPLC-MS |
|---|---|---|---|---|---|
| 62 | 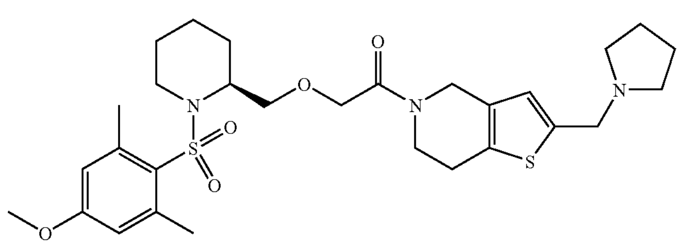 | AC28 | TP11 | 65 | MS, $R_t$ = 3.3 min, m/z = 576.2 [MH]+ |

-continued
| Example no. | Structure | Acid | Amine | Yield (%) | HPLC-MS |
|---|---|---|---|---|---|
| 64 | 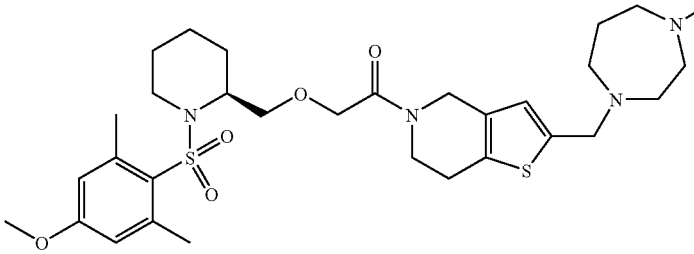 | AC28 | TP12 | 18 | MS, $R_t$ = 2.8 min, m/z = 619.3 [MH]$^+$ |
| 59 | 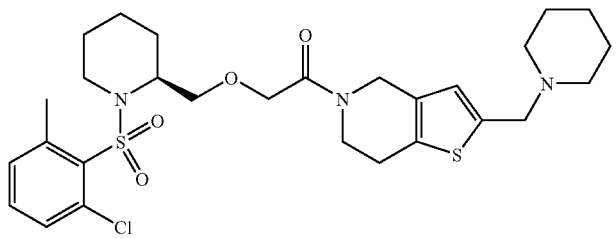 | AC28 | TP10 | 34 | MS, $R_t$ = 3.4 min, m/z = 580.2 [MH]$^+$ |
| 63 | 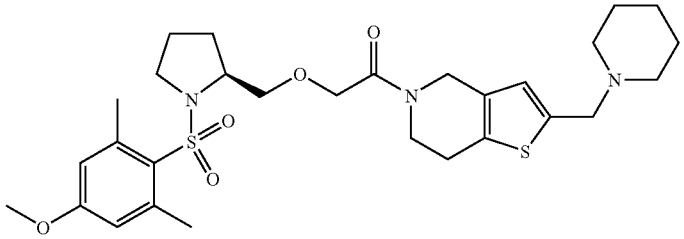 | AC30 | TP10 | 24 | MS, $R_t$ = 3.3 min, m/z = 576.2 [MH]$^+$ |
| 60 | 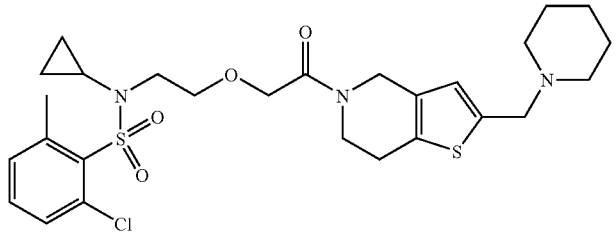 | AC27 | TP10 | 34 | MS, $R_t$ = 3.4 min, m/z = 566.1 [MH]$^+$ |
| 61 | 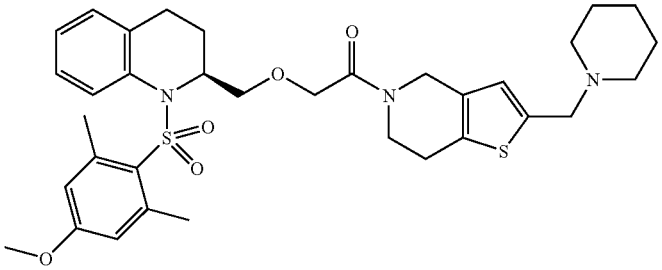 | AC31 | TP10 | 38 | MS, $R_t$ = 3.8 min, m/z = 638.2 [MH]$^+$ |

Example 26

(R)—N-(3-Oxo-1-phenyl-3-(2-(piperidin-1-ylmethyl)-6,7-dihydrothieno[3,2-c]pyridin-5(4H)-yl)propyl)naphthalene-2-sulfonamide

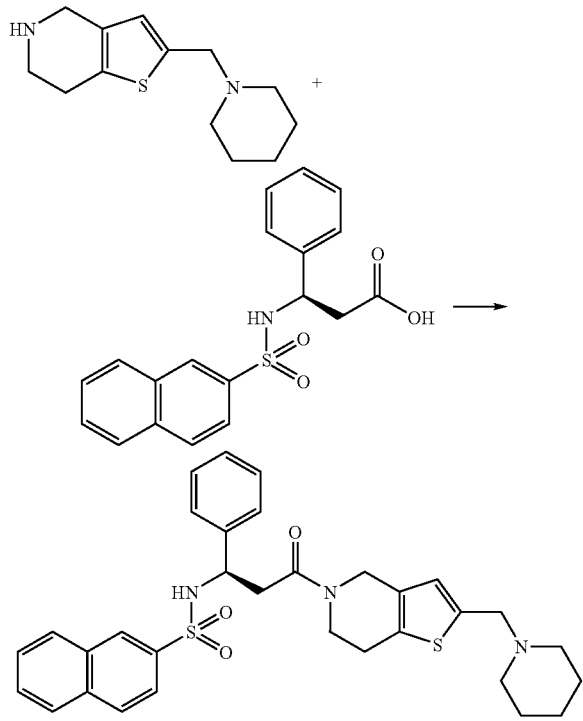

Diisopropylethylamine (0.78 ml, 4.44 mmol) was added to a solution of (3R)-(naphthalene-2-sulfonamido)-3-phenylpropionic acid (AC1) (174 mg, 0.49 mmol) in MC (1.5 ml) and the mixture was cooled to 0° C. HATU (186 mg, 0.49 mmol) and 2-(piperidin-1-ylmethyl)-4,5,6,7-tetrahydrothieno[3,2-c]pyridine (TP10) (105 mg, max. 0.42 mmol) were then added. The mixture was stirred at room temperature for 18 hours and then washed with NaHCO₃ solution. The aqueous phase was extracted with methylene chloride (2×10 ml) and the combined organic phases were dried with Na₂SO₄, filtered and concentrated in vacuo. Purification was carried out by chromatography on silica gel (MC/(7 M NH₃ in MeOH), gradient 1.0 after 2.2% (7 M NH₃ in MeOH)). The yield was 121 mg (50% over 3 stages). MS, R$_t$=3.3 min, m/z=574.2 [MH]⁺

Example 27

2-((1-(4-Methoxy-2,6-dimethylphenylsulfonyl)piperidin-2-yl)methoxy)-1-(2-(piperidin-1-ylmethyl)-6,7-dihydrothieno[3,2-c]pyridin-5(4H)-yl)ethanone

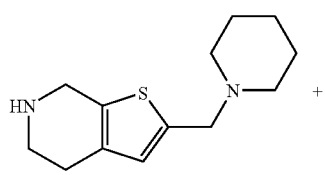

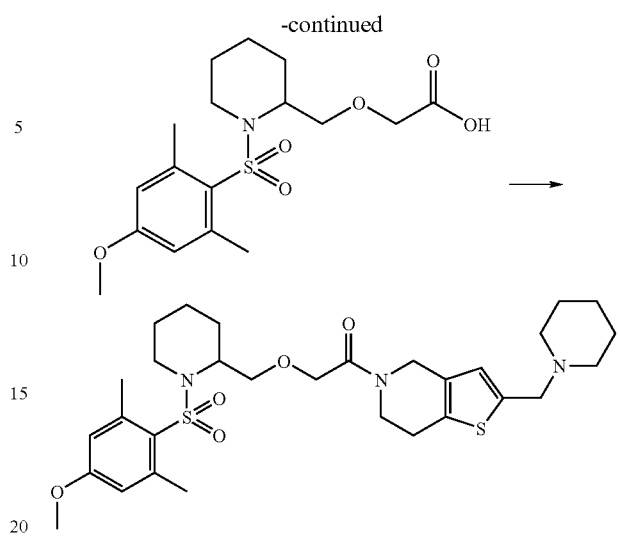

2-((1-(4-Methoxy-2,6-dimethylphenylsultonyl)piperidin-2-yl)methoxy)acetic acid (AC5) (396 mg, 1.07 mmol), diisopropylethylamine (372 µl, 2.13 mmol), HOAt (15 mg, 107 µmol) and EDCI (306 mg, 1.60 mmol) were added to a solution of 2-(piperidin-1-ylmethyl)-4,5,6,7-tetrahydrothieno[3,2-c]pyridine (TP10) (277 mg, max. 425 µm) in MC (25 ml) and the mixture was stirred at room temperature overnight. The reaction mixture was then concentrated in vacuo and the residue obtained was purified by chromatography on silica gel (MC/(7 M NH₃ in MeOH), 99:1). The product fractions were combined and evaporated to dryness. The residue was dissolved in dry acetonitrile (5 ml), the solution was dried by freeze drying and the solid was then dissolved in MC (10 ml). Solid NaHCO₃ (approx. 500 mg) was added to this solution and the mixture was stirred for 1 hour. The mixture was then filtered and the filtrate was concentrated in vacuo. The yield was 88 mg (35% over 2 stages). MS, R$_t$=3.6 min, m/z=590.2 [MH]⁺

Example 28

4-Methoxy-N,2,6-trimethyl-N-(2-(2-oxo-2-(2-(piperidin-1-yl-methyl)-6,7-dihydrothieno[3,2-c]pyridin-5(4H)-yl)ethoxy)ethyl)benzene-sulfonamide

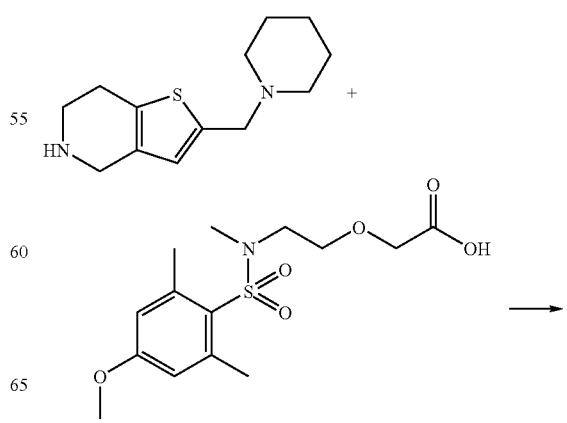

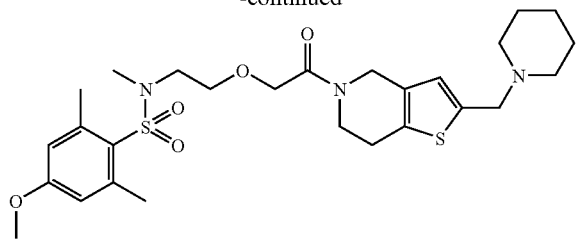

2-(2-(4-Methoxy-N,2,6-trimethylphenylsulfonamido)ethoxy)acetic acid (AC6) (353 mg, 1.06 mmol), diisopropylethylamine (372 µl, 2.13 mmol), HOAt (15 mg, 107 µmol) and EDCI (306 mg, 1.60 mmol) were added to a solution of 2-(piperidin-1-ylmethyl)-4,5,6,7-tetrahydrothieno[3,2-c]pyridine (TP10) (277 mg, max. 425 µm) in MC (25 ml) and the mixture was stirred at room temperature overnight. The reaction mixture was then concentrated in vacuo and the residue obtained was purified by chromatography on silica gel (MC/(7 M NH$_3$ in MeOH), 98:2 and 99:1). The product fractions were combined and evaporated to dryness. The residue was dissolved in dry acetonitrile (5 ml), the solution was dried by freeze drying and the solid was then dissolved in methylene chloride (10 ml). Solid NaHCO$_3$ (approx. 500 mg) was added to this solution and the mixture was stirred for 1 hour. The mixture was then filtered and the filtrate was concentrated in vacuo. The yield was 105 mg (45% over 2 stages).
MS, R$_f$=3.0 min, m/z=550.1 [MH]$^+$ Example 56

N-[2-[2-[2-(Azetidin-1-yl-methyl)-4,5,6,7-tetrahydro-thieno[3,2-c]pyridin-5-yl]-2-oxo-ethoxy]-ethyl]-2-chloro-N-cyclopropyl-6-methyl-benzenesulfonic acid amide

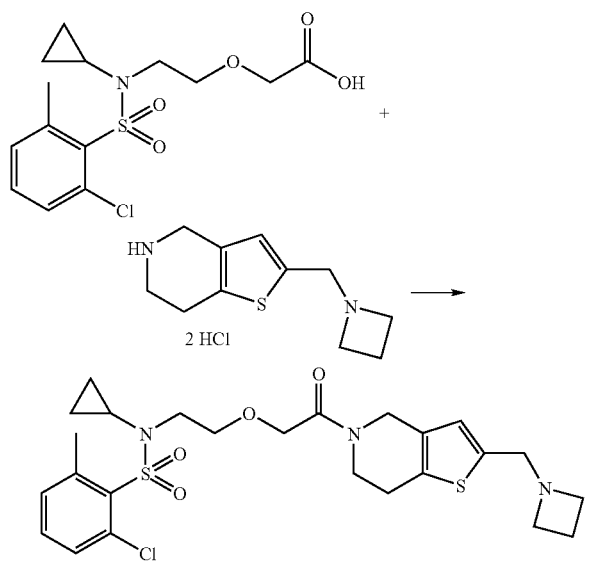

2-(2-(2-Chloro-N-cyclopropyl-6-methylphenylsulfonamido)ethoxy)acetic acid (AC27) (100 mg, 0.288 mmol), O-(1H-benzotriazol-1-yl)-N,N,N',N'-tetramethyl-uronium tetrafluoroborate (92 mg, 0.288 mmol) and 1-hydroxybenzotriazole hydrate (40 mg, 0.288 mmol) were dissolved in tetrahydrofuran (3.5 ml) and the mixture was stirred at room temperature for 30 min. A solution of 2-(azetidin-1-ylmethyl)-4,5,6,7-tetrahydrothieno[3,2-c]pyridine dihydrochloride (TP13) (97 mg, 0.346 mmol) and N-ethyl-diisopropylamine (146 µl, 0.864 mmol) in tetrahydrofuran (3.5 ml) was added and the mixture was stirred at room temperature overnight. The solvent was removed in vacuo, the residue was dissolved in ethyl acetate and saturated sodium hydrogen carbonate solution and the phases were separated. The aqueous phase was extracted with ethyl acetate (3×) and the combined organic layers were washed with saturated sodium chloride solution (1×), dried over sodium sulfate and concentrated in vacuo. The crude product was purified by column chromatography (silica) with ethyl acetate/methanol 5/1. Yield: 100 mg (64%).
MS, R$_f$=3.1 min, m/z=538.2 [MH]$^+$ Example 57

2-Chloro-N-cyclopropyl-N-[2-[2-[2-[(3,3-difluoro-azetidin-1-yl)-methyl]-4,5,6,7-tetrahydro-thieno[3,2-c]pyridin-5-yl]-2-oxo-ethoxy]-ethyl]-6-methyl-benzenesulfonic acid amide

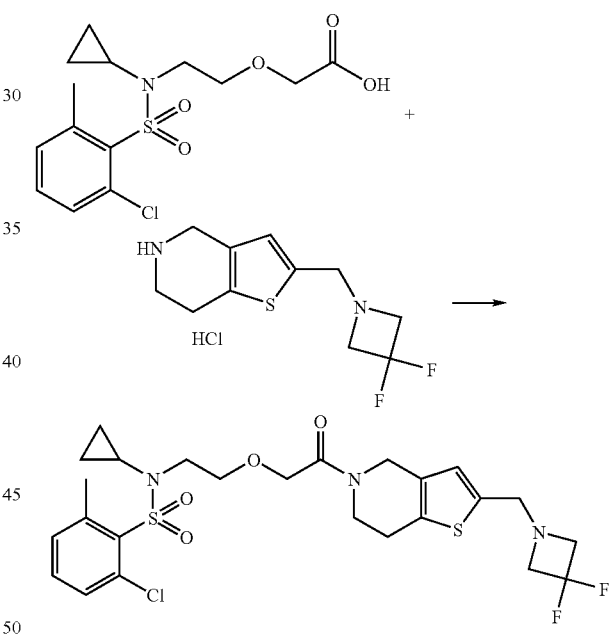

2-(2-(2-Chloro-N-cyclopropyl-6-methylphenylsulfonamido)ethoxy)acetic acid (AC27) (120 mg, 0.345 mmol), O-(1H-benzotriazol-1-yl)-N,N,N',N'-tetramethyl-uronium tetrafluoroborate (110 mg, 0.345 mmol) and 1-hydroxybenzotriazole hydrate (48 mg, 0.345 mmol) were dissolved in tetrahydrofuran (4 ml) and the mixture was stirred at room temperature for 30 min. A solution of 2-((3,3-difluoro-azetidin-1-yl)methyl)-4,5,6,7-tetrahydrothieno[3,2-c]pyridine hydrochloride (TP14) (116 mg, 0.414 mmol) and N-ethyl-diisopropylamine (175 µl, 1.035 mmol) in tetrahydrofuran (4 ml) was added and the mixture was stirred at room temperature overnight. The solvent was removed in vacuo, the residue was dissolved in ethyl acetate and saturated sodium hydrogen carbonate solution and the phases were separated. The aqueous phase was extracted with ethyl acetate (3×) and the combined organic layers were washed with saturated sodium chloride solution (1×), dried over sodium sulfate and concentrated in vacuo. The crude product was purified by column chromatography (silica) with ethyl acetate/hexane 2/1.

Yield: 130 mg (66%). MS, $R_t$=3.8 min, m/z=574.2 [MH]$^+$

B.) Synthesis of the Aminomethylated Thiophenepiperidines (Amines TP)

Synthesis of 2-(piperidin-1-ylmethyl)-4,5,6,7-tetrahydrothieno[3,2-c]pyridine (TP10)

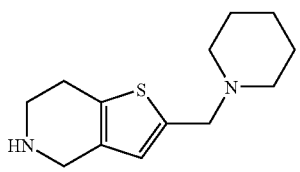

Stage 1. Tert-Butyl 2-(methoxy(methyl)carbamoyl)-6,7-dihydrothieno[3,2-c]pyridine-5(4H)-carboxylate 5-(tert-Butoxycarbonyl)-4,5,6,7-tetrahydrothieno[3,2-c] pyridine-2-carboxylic acid (968 mg, 3.42 mmol) and N,O-dimethylhydroxylamine hydrochloride (333 mg, 3.42 mmol) were dissolved in MC (50 ml) and the solution was cooled to 0° C. HOAt (46.5 mg, 0.34 mmol), diisopropylethylamine (0.66 ml, 3.76 mmol) and EDCI (720 mg, 3.76 mmol) were added to this mixture and the mixture was stirred at room temperature overnight. The reaction mixture was diluted with methylene chloride (50 ml) and washed with 0.5 M KHSO$_4$ solution (100 ml), NaHCO$_3$ solution and NaCl solution. The combined organic phases were dried with Na$_2$SO$_4$, filtered and concentrated in vacuo. The product obtained in this way (1.13 g) was employed in the next stage without further purification.

Stage 2. 5-(tert-Butoxycarbonyl)-4,5,6,7-tetrahydrothieno[3,2-c]pyridine-2-carbaldehyde The crude product of the precursor (1.04 g, 3.18 mmol) was dissolved in dry THF (30 ml) and the solution was cooled to −78° C. under a nitrogen atmosphere. LiAlH$_4$ (1 M in THF, 3.18 ml, 3.18 mmol) was added dropwise to this solution and the mixture was stirred at this temperature for 2 hours. Na$_2$SO$_4$.10×H$_2$O was then added until no further evolution of gas was to be observed, and the mixture was stirred for a further 24 hours. The solids were then filtered out and the residue was washed thoroughly with methylene chloride. The filtrate was concentrated in vacuo and the residue was purified by chromatography on silica gel (heptane/ethyl acetate, gradient 80:20 to 65:35). The yield was 580 mg (68%).

Stage 3. tert-Butyl 2-(piperidin-1-ylmethyl)-6,7-dihydrothieno[3,2-c]pyridine-5(4H)-carboxylate 5-(tert-Butoxycarbonyl)-4,5,6,7-tetrahydrothieno[3,2-c] pyridine-2-carbalde-hyde (440 mg, 1.65 mmol) and piperidine (0.18 ml, 1.81 mmol) were dissolved in THF (10 ml), and NaBH(OAc)$_3$ (523 mg, 2.47 mmol) and glacial acetic acid (94 µl, 1.65 mmol) were added. This mixture was stirred under a nitrogen atmosphere at room temperature for 24 hours. The solvent was then distilled off in vacuo and the residue was taken up in ethyl acetate (25 ml). The solution obtained was washed with NaHCO$_3$ solution and NaCl solution and the combined organic phases were dried with Na$_2$SO$_4$, filtered and concentrated in vacuo. The crude product (580 mg) was employed directly in the next stage without further purification.

Stage 4. 2-(Piperidin-1-ylmethyl)-4,5,6,7-tetrahydrothieno[3,2-c]pyridine (TP10)

The resulting crude product of the precursor (147 mg, max. 0.42 mmol) was dissolved in methylene chloride (6 ml), trifluoroacetic acid (1.68 ml, 21.84 mmol) was added and the mixture was stirred at room temperature for 4 hours. The mixture was then concentrated to dryness in vacuo and codistilled again with methylene chloride. The product obtained in this way was employed directly in the next stage. [The synthesis of 2-(piperidin-1-ylmethyl)-4,5,6,7-tetrahydrothieno [3,2-c]pyridine (TP10) may also be accomplished in analogy to 2-(pyrrolidin-1-ylmethyl)-4,5,6,7-tetrahydrothieno[3,2-c] pyridine TP11.]

Synthesis of 2-(Pyrrolidin-1-ylmethyl)-4,5,6,7-tetrahydrothieno[3,2-c]pyridine (TP11)

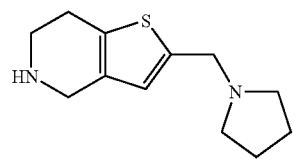

Step-1: Ethyl 4-chloro-3-formyl-5,6-dihydropyridine-1(2H)-carboxylate

POCl$_3$ (2.18 g, 23.4 mmol) was added very slowly to dry DMF (2.7 ml) at 0° C. and the resulting mixture was stirred at 25° C. for 15 min. The reaction mixture was again cooled to 0° C., and N-ethoxycarbonyl piperidone (11.7 mmol) was added. The resulting reaction mixture was stirred at 25° C. for 3 h. It was then stirred with sodium acetate (7 g) and water (8.5 ml) and extracted with benzene. The organic layer was successively washed with water, sodium hydrogencarbonate an brine and was finally dried over sodium sulfate. Evaporation of the organic layer under reduced pressure gave the crude product, which was used directly in the next step without further purification. Yield: 63%.

Step-2: Diethyl 6,7-dihydrothieno[3,2-c]pyridine-2,5 (4H)-dicarboxylate

To a solution of ethyl 4-chloro-3-formyl-5,6-dihydropyridine-1(2H)-carboxylate (7.4 mmol) in pyridine (3 ml) was added triethylamine (9.62 mmol) at 0° C. and the resulting reaction mixture was stirred at 25° C. for 3 h. 50% aqueous KOH solution (5 ml) was then added and the mixture stirred at the same temperature for 3 h. It was diluted with ethyl acetate and the organic layer was washed with water and brine. After drying over sodium sulfate the organic layer was evaporated under reduced pressure to give the crude product which was purified by column chromatography (50% ethyl acetate in hexane). Yield: 25%.

Step-3: 4,5,6,7-Tetrahydrothieno[3,2-c]pyridine-2-carboxylic acid hydrochloride

Diethyl 6,7-dihydrothieno[3,2-c]pyridine-2,5(4H)-dicarboxylate (1.76 mmol) in 3.5 N KOH solution (3 ml) was refluxed for 3 h (monitored by TLC). The reaction mixture was cooled to 0° C. and acidified with conc. HCl. The solid was collected by filtration and dried to give the desired product. Yield: 30%.

Step-4 and Step-5: 5-tert-Butyl 2-methyl 6,7-dihydrothieno[3,2-c]pyridine-2,5(4H)-dicarboxylate To a suspension of 4,5,6,7-tetrahydrothieno[3,2-c]pyridine-2-carboxylic acid hydrochloride (1.9 mmol) in methanol (10 ml) was added thionyl chloride (1.5 eq.) at 0° C. and the resulting reaction mixture was refluxed for 16 h. The solvent was completely evaporated off and the residue dissolved in dichloromethane (10 ml) and cooled to 0° C. To this cold mixture were added triethylamine (3 eq.) and Boc-anhydride (1.2 eqv) and the resulting reaction mixture was stirred at 25° C. for 12 h. The mixture was diluted with dichloromethane and successively washed with water and brine and finally dried over sodium sulfate. Evaporation of the organic layer under reduced pressure gave the crude product which was purified by column chromatography (10% ethyl acetate in hexane). Yield: 50%.

Step-6: tert-Butyl 2-(hydroxymethyl)-6,7-dihydrothieno[3,2-c]pyridine-5(4H)-carboxylate To a solution of 5-tert-butyl 2-methyl 6,7-dihydrothieno[3,2-c]pyridine-2,5(4H)-dicarboxylate (1.5 g, 5.3 mmol) in dry toluene (30 ml) was added DIBAL (1 M, 11.1 mmol) at −78° C. and the reaction mixture was stirred at this temperature for 1.5 h (monitored by TLC). The reaction was quenched with methanol (12 ml) and slowly brought to 25° C. Brine (25 ml) was added and it was filtered through a bed of Celite. The residue was washed with ethyl acetate and the combined organic layers were evaporated to give the crude aldehyde, which was used directly in the next step without further purification. Yield: 1.4 g.

Step-7: tert-Butyl 2-((methylsulfonyloxy)methyl)-6,7-dihydrothieno[3,2-c]pyridine-5(4H)-carboxylate To a dichloromethane solution (22 ml) of tert-butyl 2-(hydroxymethyl)-6,7-dihydrothieno[3,2-c]pyridine-5(4H)-carboxylate (5.3 mmol) was added triethylamine (21.2 mmol) and methane sulfonyl chloride (7.95 mmol) at 0° C. and the resulting reaction mixture was stirred at same temperature for 2 h (monitored by TLC). The reaction was diluted with dichloromethane, successively washed with water and brine and finally dried over sodium sulfate. Evaporation of the organic layer under reduced pressure gave the crude product which was used directly in the next step. Yield: quantitative

Step-8: tert-Butyl 2-(pyrrolidin-1-ylmethyl)-6,7-dihydrothieno[3,2-c]pyridine-5(4H)-carboxylate To a toluene solution (30 ml) of tert-butyl 2-((methylsulfonyloxy)methyl)-6,7-dihydrothieno[3,2-c]pyridine-5(4H)-carboxylate (5.3 mmol) was added potassium carbonate (26.5 mmol) and pyrrolidine (6.36 mmol) and the resulting reaction mixture was refluxed for 16 h. It was cooled to 25° C., diluted with ethyl acetate and the organic layer was successively washed with water and brine. After drying over sodium sulfate, the organic layer was evaporated under reduced pressure to give the crude product which was purified by column chromatography (5% methanol in dichloromethane). Yield: 35%.

Step-9: 2-(Pyrrolidin-1-ylmethyl)-4,5,6,7-tetrahydrothieno[3,2-c]pyridine (TP11)

tert-Butyl 2-(pyrrolidin-1-ylmethyl)-6,7-dihydrothieno[3,2-c]pyridine-5(4H)-carboxylate (0.235 mmol) was dissolved in dichloromethane and cooled to 0° C. Trifluoroacetic acid (2 ml/mmol) was added and the reaction mixture stirred for 2 h. The solvent was completely evaporated and kept under the high vacuum to give the desired product which was used in the next step without further purification. Yield: quantitative

Synthesis of 2-((4-methyl-1,4-diazepan-1-yl)methyl)-4,5,6,7-tetrahydrothieno[3,2-c]pyridine (TP12)

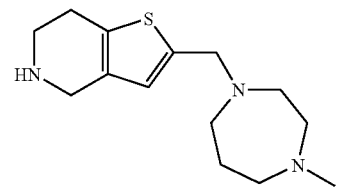

The preparation of this amine was carried out in analogy to that described for 2-(pyrrolidin-1-ylmethyl)-4,5,6,7-tetrahydrothieno[3,2-c]pyridine (TP1 1) employing 1-methyl-1,4-diazepane in step-8.

Synthesis of 2-(azetidin-1-ylmethyl)-4,5,6,7-tetrahydrothieno[3,2-c]pyridine Dihydrochloride (TP13)

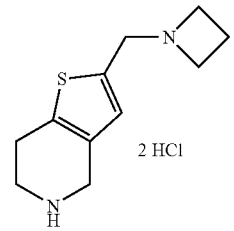

2 HCl

Step-1: Piperidin-4-one Hydrochloride

Methanolic HCl (50 ml) was added dropwise to a solution of N-Boc-4-piperidone (5 g) in dichloromethane (50 ml) over 5-10 min and the reaction mixture was stirred for 2-2.5 h at room temperature. Progress of the reaction was monitored by TLC (30% ethyl acetate/hexane). Upon completion of the reaction the reaction contents were concentrated under reduced pressure and the residue obtained was directly used for the next step. Yield: 4.4 g.

Step-2: Benzyl 4-oxopiperidine-1-carboxylate

To a solution of piperidin-4-one hydrochloride (32 g, 0.23 mol) in tetrahydrofuran (320 ml, 10×) was added $K_2CO_3$ (64.2 g) dissolved in water (160 ml) at room temperature. The mixture was cooled to 0-5° C. and then Cbz chloride (50%) (74.28 ml, 1.1 eq.) was added dropwise. The reaction mixture was warmed to room temperature and stirred for 1-2 h. Progress of the reaction was monitored by TLC (30% ethyl acetate/hexane). Upon disappearance of the starting material the mixture was filtered and the layers were separated. The aqueous layer was extracted with ethyl acetate (2×300 ml) and the combined organic layers were dried over sodium sulfate and concentrated under reduced pressure. The crude product was purified by column chromatography (silica, 12% ethyl acetate/hexane). Yield: 40.7 g (74%)

Step-3: Benzyl 4-chloro-3-formyl-5,6-dihydropyridine-1(2H)-carboxylate $POCl_3$ (26.35 g, 16.06 ml, 1.6 eq.) was added dropwise to DMF (16.4 ml, 2 eq.) at 0-5° C. To the mixture was added dichloromethane (50 ml) in a dropwise fashion and it was stirred for 2 h at room temperature. A solution of benzyl 4-oxopiperidine-1-carboxylate (25 g, 0.10 mol) in dichloromethane (200 ml) was added dropwise to the mixture and it was stirred for 2 h at room temperature. Progress of the reaction was monitored by TLC (30% ethyl acetate/hexane). Upon completion of the reaction the mixture was poured into crushed ice and basified to a pH~8 with sodium carbonate. Then the dichloromethane layer was separated and the aqueous layer was extracted with dichloromethane (2×200 ml). The combined organic layers were dried over sodium sulfate, concentrated under reduced pressure and the crude product obtained was purified by column chromatography (silica, 8% ethyl acetate/hexane). Yield: 14.5 g (48%).

Step-4: 5-Benzyl 2-ethyl 6,7-dihydrothieno[3,2-c]pyridine-2,5(4H)-dicarboxylate To a solution of Benzyl 4-chloro-3-formyl-5,6-dihydropyridine-1(2H)-carboxylate (14.5 g, 0.05 mol) in dichloromethane (145 ml, 10×) was added ethyl mercapto acetate (9.3 g, 8.56 ml, 1.09 mol, 1.5 eq.) followed by triethylamine (10.4 g, 14.35 ml, 0.73 mol, 2 eq.) dropwise at 0° C. The reaction mixture was warmed to room temperature and allowed stir for 4 h. Progress of the reaction was monitored by TLC (30% ethyl acetate/hexane). On completion of the reaction the mixture was diluted with water. Then the dichloromethane layer was separated and the aqueous layer was extracted with dichloromethane (2×150 ml). The combined organic layers were dried over sodium sulfate, concentrated under reduced pressure and the crude product obtained was purified by column chromatography (silica, 12% ethyl acetate/hexane). Yield: 9.12 g (51%).

Step-5: 5-tert-Butyl 2-ethyl 6,7-dihydrothieno[3,2-c]pyridine-2,5(4H)-dicarboxylate To 10% Pd/C (2 g) in ethanol (100 ml) was added 5-benzyl 2-ethyl 6,7-dihydrothieno[3,2-c]pyridine-2,5(4H)-dicarboxylate (12.5 g, 0.03 mol) dissolved in ethanol (400 ml). Then, Boc-anhydride (12.4 ml, 1.5 eq.) followed by triethylamine (7.5 ml, 1.5 eq.) were added slowly and the reaction mixture was hydrogenated for 13-14 h at 90 psi. Progress of the reaction was monitored by TLC (20% ethyl acetate/hexane). As the starting material had not been completely consumed, stirring was continued for another 14 h and the progress checked by TLC. Starting material was still present but hydrogenation was stopped and the reaction mixture filtered over a bed of celite. The filtration bed was washed with ethanol (200 ml) and the filtrate was concentrated under reduced pressure. The resulting crude product was purified by column chromatography (silica, 10% ethyl acetate/hexane). Yield: 2.5 g (22%). (Note: 7 g of starting material were recovered.)

Step-6: tert-Butyl 6,7-dihydro-2-(hydroxymethyl)thieno[3,2-c]pyridine-5(4H)-carboxylate Tetrahydrofuran (10 ml) was added dropwise to lithium aluminium hydride (0.46 g, 2 eq.) at 0° C. and the mixture was stirred for 10-15 min at the same temperature. Then a solution of 5-tert-butyl 2-ethyl 6,7-dihydrothieno[3,2-c]pyridine-2,5 (4H)-dicarboxylate (2 g, 0.006 mol) in tetrahydrofuran (10 ml) was added dropwise to the mixture at 0° C. and the resulting reaction mixture was stirred for 1-2 h at the same temperature. Progress of the reaction was monitored by TLC (30% ethyl acetate/hexane). Upon completion of the reaction the reaction mixture was poured into ice water and quenched with saturated sodium sulfate solution at 0° C. The mixture was filtered over a bed of Celite and the filtrate was extracted with ethyl acetate (2×150 ml). The combined organic layers were dried over sodium sulfate and concentrated under reduced pressure to yield the crude product as a pale yellow colored liquid. The crude product obtained was directly employed in the next step. Yield: 1.6 g (92%).

Step-7: tert-Butyl 2-formyl-6,7-dihydrothieno[3,2-c]pyridine-5(4H)-carboxylate To a solution of tert-butyl 6,7-dihydro-2-(hydroxymethyl)thieno[3,2-c]pyridine-5(4H)-carboxylate (1.6 g, 0.006 mol) in dichloromethane (18 ml), sodium hydrogen carbonate (1.06 g) dissolved in water was added and the resulting mixture was cooled to 0° C. Then a catalytic amount of TEMPO followed by NaOCl (18 ml, 10×) were added at 0° C. and the reaction mixture was stirred for 1-2 h at room temperature. Progress of the reaction was monitored by TLC (30% ethyl acetate/hexane). Upon completion of the reaction, the reaction mixture were diluted with water (20 ml) and dichloromethane (20 ml). Then the dichloromethane layer was separated and the aqueous layer was extracted with dichloromethane. The combined extract was dried over sodium sulfate, concentrated under reduced pressure and the crude so obtained was purified by column chromatography (silica, 7% ethyl acetate/hexane) to yield the titled compound as a pale yellow solid.
Yield: 1.1 g (70%)

Step-8: Tert-Butyl 2-(azetidin-1-ylmethyl)-6,7-dihydrothieno[3,2-c]pyridine-5(4H)-carboxylate tert-Butyl 2-formyl-6,7-dihydrothieno[3,2-c]pyridine-5 (4H)-carboxylate (0.3 g, 0.122 mmol) and azetidine (96 mg, 1.683 mmol) were dissolved in 1,2-dichloro-ethane (9 ml) and stirred at room temperature for 10 min. Sodium triacetoxyboro-hydride (0.331 g, 1.571 mmol) was added and the resulting mixture stirred at room temperature for 48 h. Saturated sodium hydrogen carbonate solution was added and the phases were separated. The aqueous phase was extracted with diethylether (3×) and the organics were washed with saturated sodium chloride solution (1×). The organic layer was dried over magnesium sulfate and concentrated in vacuo. The crude product was purified by column chromatography (ethyl acetate/methanol, 10:1). Yield: 0.28 g (81%).

Step-9: 2-(Azetidin-1-ylmethyl)-4,5,6,7-tetrahydrothieno[3,2-c]pyridine Dihydrochloride (TP13)

tert-Butyl 2-(azetidin-1-ylmethyl)-6,7-dihydrothieno[3,2-c]pyridine-5(4H)-carboxylate (0.28 g, 0.908 mmol) was dissolved in methanol (1 ml) and HCl in methanol (1.25 M, 3.63 ml, 4.54 mmol) was added. The reaction mixture was heated at reflux for 1 h. After cooling to room temperature the solvent was removed in vacuo. The crude product was re-dissolved in ethanol, diethylether was added and the mixture was stirred at 0° C. for 20 min. The solid was collected by filtration, washed with diethylether and dried in vacuo. Yield: 0.2 g (78%).

Synthesis of 2-((3,3-difluoroazetidin-1-yl)methyl)-4,5,6,7-tetrahydrothieno[3,2-c]pyridine hydrochloride (TP14)

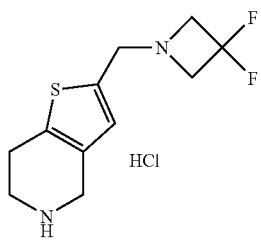

The synthesis of 2-((3,3-difluoroazetidin-1-yl)methyl)-4,5,6,7-tetrahydro-thieno[3,2-c]pyridine hydrochloride (TP14) was carried out analogously to the synthesis of 2-(Azetidin-1-ylmethyl)-4,5,6,7-tetrahydrothieno[3,2-c]pyridine dihydrochloride (TP13) employing 3,3-difluoroazetidine hydrochloride plus 3 eq. of triethylamine instead of azetidine in Step-7.

4.) Synthesis of Example Compounds by Reaction of Isoxazole Compounds with Carboxylic Acids A.) Reaction of Isoxazole Compounds with Carboxylic Acids

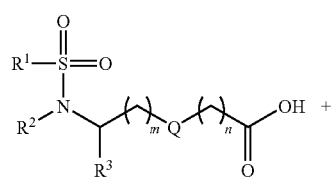

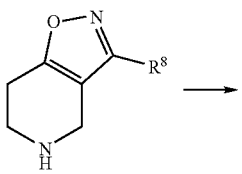

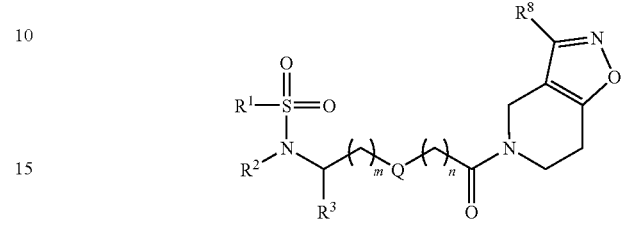

Method A

General Synthesis Instructions

A solution of 1,1'-carbonyldiimidazole (0.209 g, 1.29 mmol) and the particular acid (1.23 mmol) in MC (15 ml) was stirred at room temperature for 1 hour. A solution of triethylamine (2.46 mmol) and amine (isoxazole compound) (1.23 mmol) in MC was stirred in a second flask for 30 minutes and then added to the acid. The reaction mixture was stirred at room temperature for 16 hours and then diluted with methylene chloride and washed with NaHCO$_3$ solution and NaCl solution. The organic phase was dried with Na$_2$SO$_4$, filtered and concentrated in vacuo. Purification was carried out by chromatography on silica gel.

The example compounds listed in the following table were prepared from the corresponding carboxylic acids and amines (isoxazole compounds) in accordance with the general working instructions.

| Ex. No. | Structure | Acid | Amine | HPLC-MS |
|---|---|---|---|---|
| 04 | 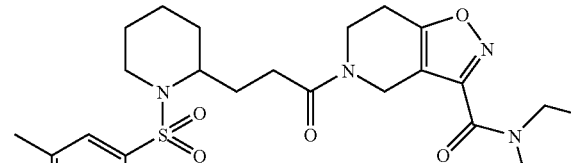 | AC3 | AM4 | MS, $R_t$ = 5.4 min, m/z = 577.3 [MH]$^+$ |
| 14 | 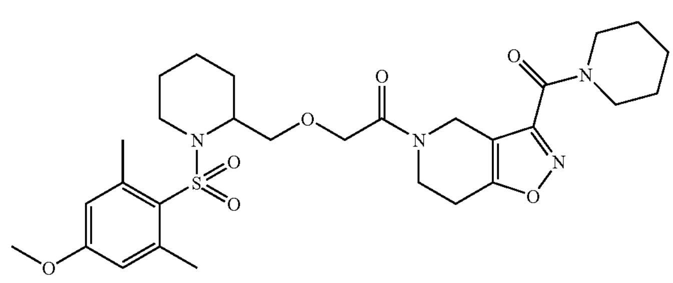 | AC5 | AM4 | MS, $R_t$ = 4.9 min, m/z = 589.3 [MH]$^+$ |

-continued

| Ex. No. | Structure | Acid | Amine | HPLC-MS |
|---|---|---|---|---|
| 05 | 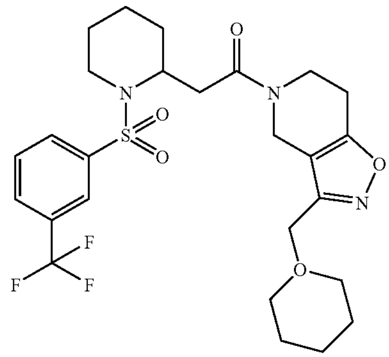 | AC2 | AM2 | MS, R$_t$ = 2.8 min, m/z = 555.3 [MH]$^+$ |
| 17 | 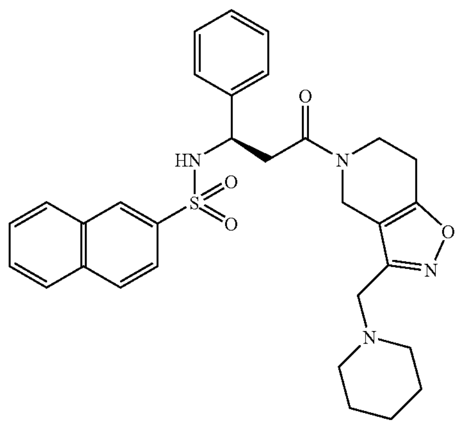 | AC1 | AM2 | MS, R$_t$ = 3.2 min, m/z = 559.2 [MH]$^+$ |
| 06 | 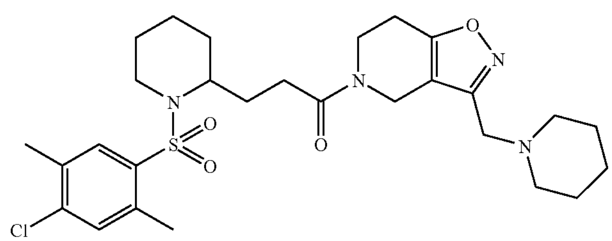 | AC3 | AM2 | MS, R$_t$ = 3.3 min, m/z = 563.3 [MH]$^+$ |
| 09 | 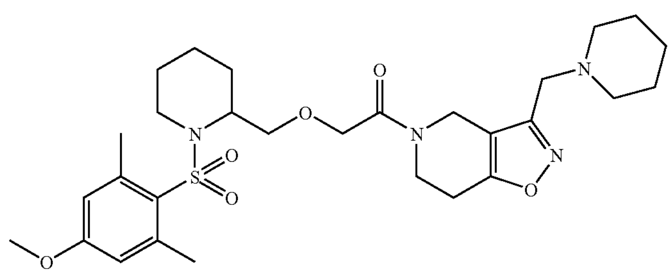 | AC5 | AM2 | MS, R$_t$ = 2.9 min, m/z = 575.3 [MH]$^+$ |
| 13 | 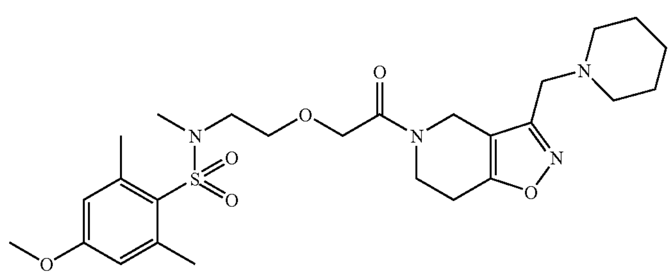 | AC6 | AM2 | MS, R$_t$ = 2.8 min, m/z = 535.2 [MH]$^+$ |

-continued
| Ex. No. | Structure | Acid | Amine | HPLC-MS |
|---|---|---|---|---|
| 32 | 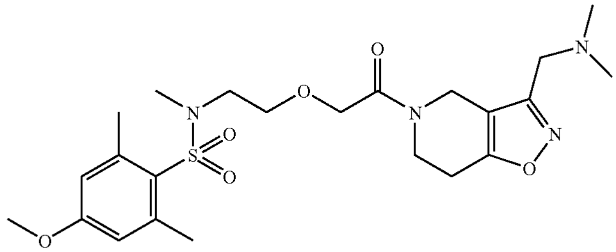 | AC6 | AM1 | MS, $R_t$ = 2.3 min, m/z = 495.1 $[MH]^+$ |
| 31 | 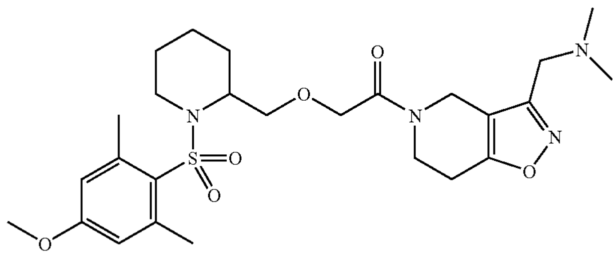 | AC5 | AM1 | MS, $R_t$ = 3.0 min, m/z = 535.1 $[MH]^+$ |
| 30 | 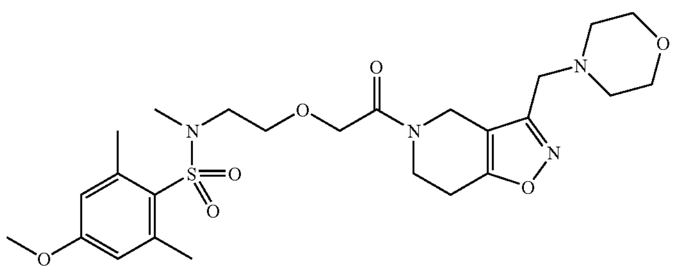 | AC6 | AM3 | MS, $R_t$ = 2.9 min, m/z = 537.1 $[MH]^+$ |
| 29 | 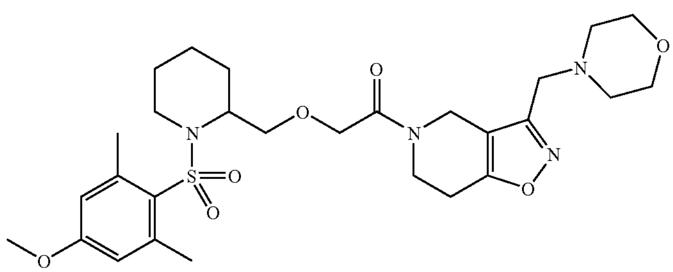 | AC5 | AM3 | MS, $R_t$ = 3.4 min, m/z = 577.1 $[MH]^+$ |
Method B
Example 01
3-(1-(4-Methoxy-2,6-dimethylphenylsulfonyl)piperidin-2-yl)-1-(3-(pyridin-4-yl)-6,7-dihydroisoxazolo[4,5-c]pyridin-5(4H)-yl)propan-1-one
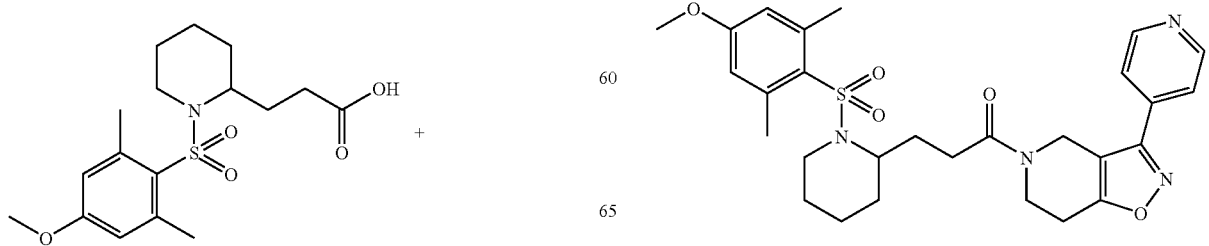

3-(1-(4-Methoxy-2,6-dimethylphenylsulfonyl)piperidin-2-yl)propionic acid (AC4) (0.15 g, 0.42 mmol) was dissolved in MC (5 ml) and 1,1'-carbonyldiimidazole (72 mg, 0.44 mmol) was added. After the mixture had been stirred at room temperature for 1 hour, 3-(pyridin-4-yl)-4,5,6,7-tetrahydroisoxazolo[4,5-c]pyridine (AM5) (84 mg, 0.42 mmol) in MC (5 ml) was added and the mixture was stirred at room temperature for 3 days. Saturated sodium bicarbonate solution (10 ml) was added to the reaction mixture, the aqueous phase was extracted with MC (3×30 ml) and the combined organic phases were washed with saturated sodium chloride solution, dried ($Na_2SO_4$) and concentrated in vacuo. The crude product was purified by column chromatography (silica gel) with ethyl acetate/hexane 10/1. The yield was 0.18 g (79%, white, finely crystalline). MS, $R_t$=4.0 min, m/z=539.3 [MH]$^+$ The example compounds listed in the following table were prepared from 3-(pyridin-4-yl)-4,5,6,7-tetrahydroisoxazolo[4,5-c]pyridine (AM5) by reaction of the corresponding acid units analogously to the process described for Example 01.

| Example no. | Structure | Acid | Yield (%) | HPLC-MS |
|---|---|---|---|---|
| 02 | 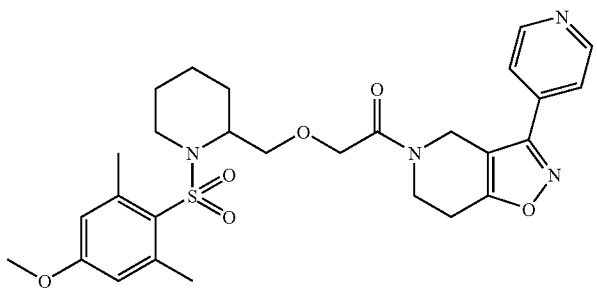 | 2-((1-(4-Methoxy-2,6-dimethylphenylsulfonyl)-piperidin-2-yl)methoxy)acetic acid (AC5) | 71 | MS, Rt = 3.9 min, m/z = 555.3 [MH]+ |
| 03 | 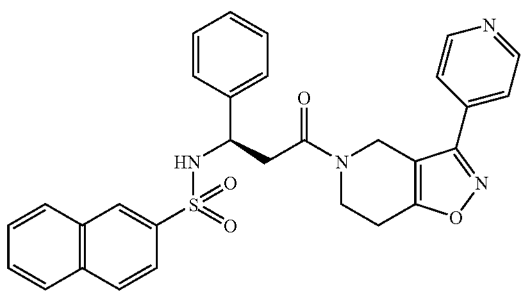 | (R)-3-(Naphthalene-2-sulfonamide)-3-phenylpropionic acid (AC1) | 70 | MS, Rt = 3.8 min, m/z = 539.2 [MH]+ |

The example compounds listed in the following table were prepared from 2-((1-(4-methoxy-2,6-dimethylphenylsulfonyl)piperidin-2-yl)methoxy)acetic acid AC5 by reaction with the corresponding amines analogously to the process described for Example 01.

| Example no. | Structure | Amine | Yield (%) | HPLC-MS |
|---|---|---|---|---|
| 24 | 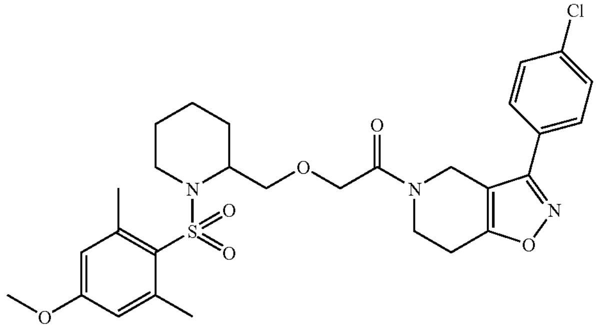 | 3-(4-Chlorophenyl)-4,5,6,7-tetrahydroisoxazolo-[4,5-c]pyridine | 71 | MS, $R_t$ = 6.0 min, m/z = 588.1 [MH]$^+$ |

-continued

| Example no. | Structure | Amine | Yield (%) | HPLC-MS |
|---|---|---|---|---|
| 25 | 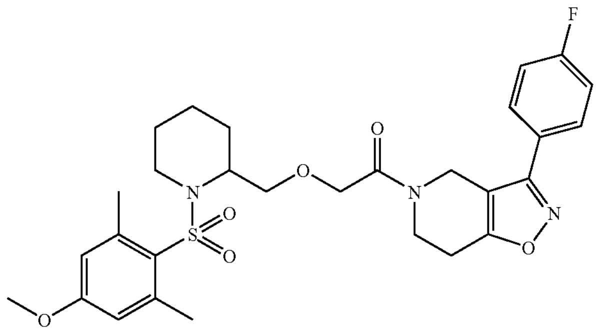 | 3-(4-Fluorophenyl)-4,5,6,7-tetra-hydroisoxazolo[4,5-c]pyridine | 82 | MS, $R_t$ = 5.7 min, m/z = 572.1 [MH]$^+$ |

Example 125

2-[[(2S)-1-[(4-Methoxy-2,6-dimethyl-phenyl)sulfonyl]-1,2,3,4-tetrahydro-quinolin-2-yl]-methoxy]-1-(3-pyridin-4-yl-4,5,6,7-tetrahydro-isoxazolo[4,5-c]pyridin-5-yl)-ethanone (S)-2-((1-(4-Methoxy-2,6-dimethylphenylsulfonyl)-1,2,3,4-tetrahydroquinolin-2-yl)methoxy)acetic acid (AC31) (0.13 g, 0.31 mmol) was dissolved in dichloromethane (4 ml) and 1,1'-carbonyldiimidazole (53 mg, 0.325 mmol) was added. After the mixture had been stirred at room temperature for 1 h, 3-(pyridin-4-yl)-4,5,6,7-tetrahydroisoxazolo[4,5-c]pyridine (AM5) (62 mg, 0.31 mmol) in dichloromethane (4 ml) was added and the mixture was stirred at room temperature overnight. Saturated sodium hydrogen carbonate solution was added to the reaction mixture, the aqueous phase was extracted with dichloromethane (2×) and the combined organic phases were washed with saturated sodium chloride solution, dried (MgSO$_4$) and concentrated in vacuo. The crude product was purified by column chromatography (silica) with ethyl acetate/hexane 20/1. Yield: 0.13 g (77%). MS, $R_t$=4.8 min, m/z=603.1 [MH]$^+$

Example 126

2-((1-(4-Methoxy-2,6-dimethylphenylsulfonyl)piperidin-2-yl)methoxy)-1-(4-phenyl-3-(piperidin-1-ylmethyl)-6,7-dihydroisoxazolo[4,5-c]pyridin-5(4H)-yl)ethanone

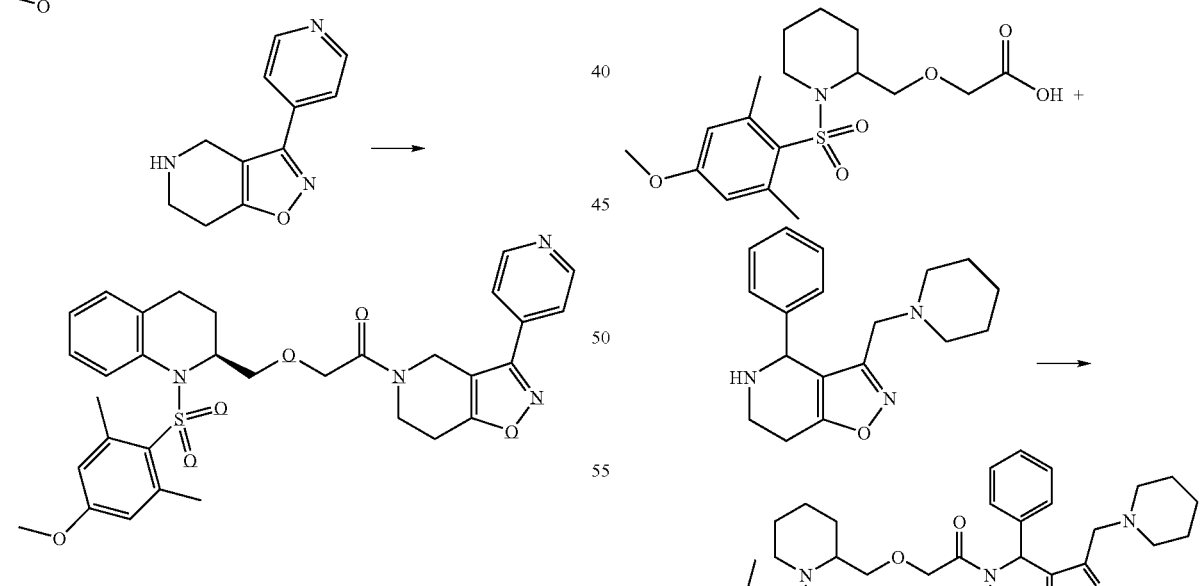

To a solution of 2-((1-(4-Methoxy-2,6-dimethylphenylsulfonyl)piperidin-2-yl)methoxy)acetic acid (AC5) (0.673 mmol, 1.0 eq.) in dichloromethane (10 ml/mmol) was added di-isopropyl ethylamine (5.0 eq.) at 0° C. followed by the addition of HOBT (1.0 eq.) and EDCI (1.5 eq.). The resultant solution was stirred at room temperature for 15 min. It was again cool to 0° C. and 4-phenyl-3-(piperidin-1-ylmethyl)-4,5,6,7-tetrahydroisoxazolo[4,5-c]pyridine (AM7) (1.0 eq.), dissolved in dichloromethane (1 ml/mmol), was added. The reaction mixture was stirred at room temperature for 24 h. The mixture was diluted with dichloromethane, washed with saturated ammonium chloride solution, brine, saturated sodium bicarbonate and finally again with brine. The organic layer was dried over sodium sulfate and evaporated to dryness under reduced pressure to give the crude product which was purified by column chromatography (neutral alumina). Yield: 35%. MS, $R_t$=3.7 min, m/z=651.5 [MH]$^+$ B.) Synthesis of the Isoxazole Compounds (Amines AM):

Synthesis of the amines AM1 to AM3

Stage 1. tert-Butyl 4-(pyrrolidin-1-yl)-5,6-dihydro-pyridine-1(2H)-carboxylate

Catalytic amounts of p-toluenesulfonic acid (0.47 g, 0.27 mmol) were added to a solution of N-Boc-4-piperidone (5 g, 25.12 mmol) and pyrrolidine (1.96 g, 27.63 mmol) in toluene (100 ml) and the mixture was stirred under reflux for 2 hours, using a water separator. The solution formed was concentrated to dryness in vacuo and the residue obtained was employed directly in the next stage.

Stage 2. 5-tert-Butyl 3-ethyl 7a-(pyrrolidin-1-yl)-3a,4,7,7a-tetrahydroisoxazolo[4,5-c]pyridine-3,5(6H)-dicarboxylate The crude product of the preceding stage was dissolved in methylene chloride (50 ml) and a solution of 2-chlorohydroxyiminoacetic acid ethyl ester (5.3 g, 35.17 mmol) followed by triethylamine (4.8 ml, 35.17 mmol) were added with vigorous stirring. The reaction was stirred at room temperature for 16 hours and ended by addition of 10% strength citric acid. The mixture was extracted with methylene chloride and the organic phases were washed with NaHCO$_3$ solution and NaCl solution, dried with Na$_2$SO$_4$ and concentrated in vacuo. Purification of the crude product was carried out by chromatography on silica gel (100-200 mesh silica gel, 8% acetone in hexane). The yield was 60%.

Stage 3. Ethyl 4,5,6,7-tetrahydroisoxazolo[4,5-c]pyridine-3-carboxylate

Trifluoroacetic acid (6.67 ml, 89.9 mmol) was added to a solution of 5-tert-Butyl 3-ethyl 7a-(pyrrolidin-1-yl)-3a,4,7,7a-tetrahydroisoxazolo[4,5-c]pyridine-3,5(6H)-dicarboxylate (5.5 g, 14.98 mmol) in MC (100 ml) at 0° C. and the mixture was stirred under reflux for 16 hours. Thereafter, the mixture was cooled to 0° C. and NaHCO$_3$ solution was added. The phases were separated and the aqueous phase was extracted with methylene chloride. The combined organic phases were dried with Na$_2$SO$_4$, filtered and concentrated in vacuo. The crude product obtained was employed directly in the next stage without further purification.
[The regiochemistry was assigned by NMR experiments.]

Stage 4. 5-tert-Butyl 3-ethyl 6,7-dihydroisoxazolo[4,5-c]pyridine-3,5(4H)-dicarboxylate Triethylamine (2.8 ml, 20.45 mmol) and Boc anhydride (3.5 ml, 16.36 mmol) were added to a solution of ethyl 5,6,7-tetrahydroisoxazolo[4,5-c]pyridine-3-carboxylate (2.7 g, 13.63 mmol) in MC (50 ml) at 0° C. and the mixture was stirred at room temperature for 3 hours. Water was then added and the mixture was extracted with MC. The combined organic phases were washed with water, dried with Na$_2$SO$_4$, filtered and concentrated in vacuo. The crude product was purified by chromatography on silica gel (100-200 silica gel, 10% ethyl acetate in hexane). The crude yield was 80%.

Stage 5. 5-(tert-Butoxycarbonyl)-4,5,6,7-tetrahydroisoxazolo[4,5-c]pyridine-3-carboxylic Acid An aqueous lithium hydroxide solution (0.54 g, 12.88 mol in 12.8 ml) was added dropwise to a solution of 5-tert-butyl 3-ethyl 6,7-dihydroisoxazolo[4,5-c]pyridine-3,5(4H)-dicarboxylate (3.2 g, 10.73 mmol) in ethanol (48 ml) at 0° C. and the mixture was stirred at room temperature for 3 hours. The mixture was then concentrated in vacuo, the residue was acidified with 10% strength citric acid and the mixture was extracted three times with ethyl acetate. The combined organic phases were dried with Na$_2$SO$_4$, filtered and concentrated in vacuo. The crude product was employed directly in the next stage without further purification.

General synthesis instructions 1 (explained by way of example for amine AM2)

Stage 6. tert-Butyl 3-(piperidine-1-carbonyl)-6,7-dihydroisoxazolo[4,5-c]pyridine-5(4H)-carboxylate Piperidine (1.1 ml, 11.18 mmol), N-methylmorpholine (3.68 ml, 33.54 mmol) and BOP reagent (6.42 g, 14.53 mmol) were added to a solution of 5-(tert-butoxycarbonyl)-4,5,6,7-tetrahydroisoxazolo[4,5-c]pyridine-3-carboxylic acid (3 g, 11.18 mmol) in dry dimethylformamide (100 ml) and the reaction mixture was stirred at room temperature for 16 hours. The solution was then concentrated in vacuo, the residue was taken up in ethyl acetate and the mixture was washed with NaHCO$_3$ solution and NaCl solution. The combined organic phases were dried with Na$_2$SO$_4$, filtered and concentrated in vacuo. Purification was carried out by chromatography on silica gel (100-200 mesh silica gel, 30% ethyl acetate in hexane). The yield was (71%).

General synthesis instructions 2 (explained by way of example for amine AM2)

Stage 7. 3-(Piperidin-1-ylmethyl)-4,5,6,7-tetrahydroisoxazolo[4,5-c]pyridine (AM2)

BH$_3$.5Me$_2$ (2 M in THF, 11.92 ml, 23.85 mmol) was added to a solution of tert-butyl 3-(piperidine-1-carbonyl)-6,7-dihydroisoxazolo[4,5-c]pyridine-5(4H)-carboxylate (2 g, 5.96 mmol) in dry THF (50 ml) and the solution was stirred under reflux for 6 hours. The reaction mixture was then cooled to 0° C., methanol (20 ml) was added and the mixture was stirred at room temperature for a further 16 hours. 6 N HCl was then added and the mixture was boiled under reflux for 1 hour. After cooling to room temperature, the mixture was concentrated to dryness in vacuo, the residue was taken up in ethyl acetate and the mixture was adjusted to pH=9-10 with NaHCO$_3$. The organic phase was separated off, washed with NaCl solution, dried with Na$_2$SO$_4$ and concentrated in vacuo. Purification was carried out by chromatography on silica gel (methanol/ethyl acetate, gradient 1/1 to 5/1).

The yield was 77%.

The following amines were prepared by the synthesis process described, dimethylamine being employed in stage 6 in the case of AM1 and morpholine in the case of AM3.

| Amine no. | Name | Structure |
|---|---|---|
| AM1 | N,N-Dimethyl-1-(4,5,6,7-tetrahydroisoxazolo[4,5-c]pyridin-3-yl)methanamine | 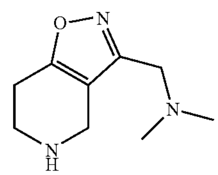 |
| AM2 | 3-(Piperidin-1-ylmethyl)-4,5,6,7-tetrahydroisoxazolo[4,5-c]pyridine | 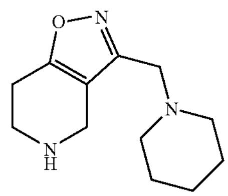 |
| AM3 | 3-(Morpholinomethyl)-4,5,6,7-tetrahydroisoxazolo[4,5-c]pyridine | 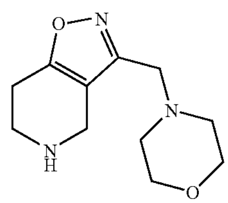 |

Stage 8. Piperidin-1-yl(4,5,6,7-tetrahydroisoxazolo[4,5-c]pyridin-3-yl)methanone (Amine AM4)

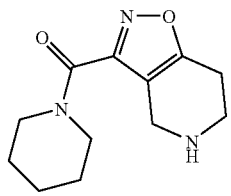

tert-Butyl 3-(piperidine-1-carbonyl)-6,7-dihydroisoxazolo[4,5-c]pyridine-5(4H)-carboxylate (0.3 g, 0.89 mmol) (product of stage 6) was dissolved in 7 ml of methanol, concentrated HCl (0.56 ml, 17.8 mmol) was added and the mixture was stirred at room temperature overnight. The solvent was then distilled off in vacuo, the residue was taken up in NaHCO$_3$ solution and the mixture was extracted with ethyl acetate. The combined organic phases were dried with MgSO$_4$, filtered and concentrated in vacuo. The crude product was employed in the next stage without further purification.

Synthesis of 3-(pyridin-4-yl)-4,5,6,7-tetrahydroisoxazolo[4,5-c]pyridine (AM5)

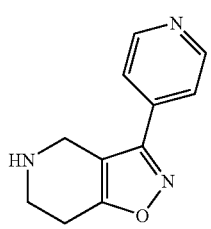

Stage (i): 1-(4-(Pyrrolidin-1-yl)-5,6-dihydropyridin-1(2H)-yl)ethanone

Pyridine-4-carbaldoxime (1 g, 8.19 mmol) was dissolved in DMF (10 ml), a solution of N-chlorosuccinimide (1.31 g, 9.83 mmol) in DMF (5 ml) was slowly added dropwise and the reaction mixture was stirred at room temperature. When the reaction was complete (thin layer chromatography control, here 6 h), diethyl ether (50 ml) and water (20 ml) were added, phase separation, extraction of the aqueous phase with diethyl ether (5×30 ml). The combined organic phases were washed with water (50 ml) and saturated sodium chloride solution (50 ml), dried (MgSO$_4$) and concentrated in vacuo. The crude yield was reacted without further purification and analysis. The yield was 0.74 g (>99%).

Stage (ii): 1-(3-(Pyridin-4-yl)-7a-(pyrrolidin-1-yl)-3a,4,7,7a-tetrahydro-isoxazolo[4,5-c]pyridin-5(6H)-yl)ethanone 1-(4-(Pyrrolidin-1-yl)-5,6-dihydropyridin-1(2H)-yl)ethanone (1.2 g, 6.176 mmol) (synthesis: see below) was dissolved in methylene chloride (10 ml) and the solution was cooled to 0° C. under an inert gas. (Z)-N-Hydroxyisonicotinimidoyl chloride (1.45 g, 9.264 mmol), dissolved in methylene chloride (5 ml), and triethyl-amine (2.1 ml, 14.82 mmol), dissolved in methylene chloride (5 ml), were added, stir for 15 h, during this allow to warm to room temperature. The mixture was diluted with methylene chloride (30 ml) and washed water (20 ml) and citric acid (10%, 20 ml). The aqueous phase was neutralized with sodium bicarbonate and extracted with methylene chloride and the combined organic phases were washed with saturated sodium chloride solution, dried (MgSO$_4$) and concentrated in vacuo. The crude product was purified by column chromatography (silica gel) with ethyl acetate/methanol/ammonia (25% eq.) 100/10/1. The yield was 0.64 g (33%).

Stage (iii): 3-(Pyridin-4-yl)-4,5,6,7-tetrahydroisoxazolo[4,5-c]pyridine (AM5)

1-(3-(Pyridin-4-yl)-7a-(pyrrolidin-1-yl)-3a,4,7,7a-tetrahydroisoxazolo[4,5-c]pyridin-5(6H)-yl)ethanone (0.63 g, 2 mmol) was initially introduced into water (14 ml) and sulfuric acid (95%, 14 ml) was added. The reaction mixture was refluxed for 5 hours, cooled with an ice bath, neutralized with sodium hydroxide solution (5 mol/l) and concentrated in vacuo. Ethyl acetate (10 ml) was added to the residue and the suspension was stirred at room temperature for 30 minutes. The precipitate was filtered out with suction and the mother liquor was extracted with ethyl acetate (4×20 ml). The combined organic phases were dried (MgSO$_4$) and concentrated in vacuo. The yield was 0.34 g (84%). [The regiochemistry was assigned in analogy to AM1-AM4.]

Preparation of 1-(4-(pyrrolidin-1-yl)-5,6-dihydropyridin-1(2H)-yl)ethanone (Employed in Stage (ii))

N-Acetyl-4-piperidinone (1.3 g, 9.2 mmol) was dissolved in toluene (10 ml), and pyrrolidine (0.72 g, 10.13 mmol) and p-toluenesulfonic acid hydrate (catalytic) were added. The reaction mixture was refluxed under an inert gas for 2 hours using a water separator, cooled slowly under an inert gas and concentrated in vacuo and the residue was dried. The crude product was employed immediately without purification. The yield was 1.87 g (>99%).

Synthesis of 4-phenyl-3-(piperidin-1-ylmethyl)-4,5,6,7-tetrahydroisoxazolo[4,5-c]pyridine (AM7)

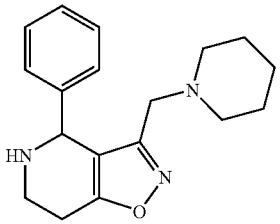

Step (i) and Step (ii): 1-Acetyl-2-phenyl-2,3-dihydropyridin-4(1H)-one

To a solution of 4-methoxypyridine (45.871 mmol, 1.0 eq.) in dry tetrahydro-furan (200 ml) was added acetyl chloride (45.871 mmol, 1.0 eq.), followed by TMSOTf (45.871 mmol, 1.0 eq.) at room temperature. The reaction mixture was cooled to −78° C. and stirred for 1 h. PhMgCl (3.0 eq., 2M solution in THF) was added dropwise to the reaction mixture at −78° C. and mixture was stirred at same temperature for additional 1 h. The reaction mixture was quenched with 2M HCl and warmed to room temperature. The mixture was extracted with ethyl acetate, dried over sodium sulfate and solvent was evaporated under reduced pressure to get crude product which was purified by column chromatography. Yield: 65%

Step (iii): 1-Acetyl-2-phenylpiperidin-4-one

To a solution of compound I-acetyl-2-phenyl-2,3-dihydropyridin-4(1H)-one (4.65 mmol, 1.0 eq.) in tetrahydrofuran (40 ml) was added a 1 M solution of L-selectride in THF (11.62 mmol, 2.5 eq.) at −78° C. The mixture was stirred at same temperature for 30 min and then allowed to warm to room temperature. After completion (progress monitored by TLC), tetrahydrofuran was evaporated under reduced pressure and the residue was dissolved in ethyl acetate. It was washed successively with water and brine, and dried over sodium sulfate. The solvent was evaporated under reduced pressure to give the crude product which was purified by gel column chromatography (silica). Yield: 73%

Step (iv): 1-(2-Phenyl-4-(pyrrolidin-1-yl)-5,6-dihydropyridin-1(2H)-yl)ethanone To a mixture of 1-acetyl-2-phenylpiperidin-4-one (3.364 mmol, 1.0 eq.) and pyrrolidine (3.7 mmol, 1.1 eq.) in toluene (16 ml) was added PTSA (0.336 mmol, 0.1 eq.) and the reaction mixture was heated to reflux for 5 h using a Dean-Stark apparatus. After completion of the reaction, the solvent was evaporated under reduced pressure to obtain the crude product which was used in the next step without further purification.

Step (v): Ethyl 5-acetyl-4-phenyl-7a-(pyrrolidin-1-yl)-3a,4,5,6,7,7a-hexahydroisoxazolo[4,5-c]pyridine-3-carboxylate To a solution of 1-(2-phenyl-4-(pyrrolidin-1-yl)-5,6-dihydropyridin-1(2H)-yl)ethanone in dichloromethane (15 mL) was added a solution of ethyl 2-chloro-2-(hydroxyimino) acetate (4.709 mmol, 1.4 eq.) in dichloromethane (5 ml) at 0° C. Then triethylamine (1.4 eq.) was added dropwise at same reaction conditions and the mixture was stirred at room temperature overnight. The reaction mixture was quenched with 10% citric acid solution and extracted with dichloromethane (3×). The combined organic layers were washed with saturated sodium bicarbonate solution and brine, dried over sodium sulfate, concentrated to dryness to give the desired product, which was used in the next step without further purification.
Yield: 80% (over two steps)

Step (vi): Ethyl 4-phenyl-4,5,6,7-tetrahydroisoxazolo[4,5-c]pyridine-3-carboxylate Conc. HCl (12 ml) was added to ethyl 5-acetyl-4-phenyl-7a-(pyrrolidin-1-yl)-3a,4,5,6,7,7a-hexahydroisoxazolo[4,5-c]pyridine-3-carboxylate (2 g) at 0° C., and the reaction mixture was heated to 130° C. for 5 h. The hydrochloric acid was evaporated under reduced pressure and the residue was dissolved in dichloromethane and basified with sodium carbonate solution. The organic layer was separated and the aqueous layer was extracted with dichloromethane. The combined organic layers were washed with brine solution and dried over sodium sulfate. The solvent was evaporated under reduced pressure to give the crude compound which was used in the next step without further purification. Yield: 50%.

Step (vii): 5-tert-Butyl 3-ethyl 4-phenyl-6,7-dihydroisoxazolo[4,5-c]pyridine-3,5(4H)-dicarboxylate To a solution of ethyl 4-phenyl-4,5,6,7-tetrahydroisoxazolo[4,5-c]pyridine-3-carboxylate (2.57 mmol, 1.0 eq.) and triethylamine (3.0 eq.) in dichloromethane (10 ml) was added Boc$_2$O (1.2 eq.) and the reaction mixture was stirred at room temperature for 2 h. After completion (progress monitored by TLC), the reaction mixture was diluted with dichloromethane and the organic layer was washed with water and brine, and dried over sodium sulfate. The solvent was evaporated under reduced pressure to give the crude compound which was purified by column chromatography (silica). Yield: 68%.

Step (viii): 5-(tert-Butoxycarbonyl)-4-phenyl-4,5,6,7-tetrahydroisoxazolo[4,5-c]pyridine-3-carboxylic Acid 5-tert-Butyl 3-ethyl 4-phenyl-6,7-dihydroisoxazolo[4,5-c]pyridine-3,5(4H)-dicarboxylate (1.75 mmol) was hydrolyzed to corresponding acid by using LiOH.H$_2$O (1.5 eq.) as a base in ethanol-water (10 ml, 4:1). Yield: quantitative.

Step (ix): Tert-Butyl 4-phenyl-3-(piperidine-1-carbonyl)-6,7-dihydroisoxazolo-[4,5-c]pyridine-5(4H)-carboxylate To a solution of 5-(tert-butoxycarbonyl)-4-phenyl-4,5,6,7-tetrahydroisoxazolo-[4,5-c]pyridine-3-carboxylic acid (1.747 mmol, 1.0 eq.) in DMF (2 ml) was added BOP reagent (2.27 mmol, 1.3 eq.) and N-methyl morpholine (5.24 mmol, 3.0 eq.). The reaction mixture was stirred at room temperature for 15 min. A solution of piperidine (1.747 mmol, 1.0 eq.) in DMF (0.5 ml) was added to the reaction mixture and it was stirred for 12 h. The mixture was poured into water and resulting aqueous solution was extracted with ethyl acetate. The organic layer was successively washed with water and brine, and dried over sodium sulfate. The solvent was evaporated under reduced pressure to give the crude product which was purified by column chromatography (silica). Yield: 23%.

Step (x): 4-Phenyl-3-(piperidin-1-ylmethyl)-4,5,6,7-tetrahydroisoxazolo[4,5-c]pyridine To solution of tert-butyl 4-phenyl-3-(piperidine-1-carbonyl)-6,7-dihydro-isoxazolo[4,5-c]pyridine-5(4H)-carboxylate (3.16 mmol, 1.0 eq.) in THF (6.5 ml) was added $BH_3$-DMS (1.2 ml, 4.0 eq.) and the reaction mixture was heated at 110° C. for 6 h. The mixture was cooled to room temperature and MeOH (5 ml) was added dropwise at 0° C. The reaction mixture was stirred at room temperature for overnight. 6N HCl (1.5 ml) was added and the mixture was again heated at 110° C. for 2 h. The reaction mixture was concentrated to dryness and the residue was dissolved in dichloromethane, and basified with saturated sodium carbonate solution. The organic layer was separated, dried over sodium sulfate and the solvent was evaporated under reduced pressure to give the crude product which was purified by column chromatography. Yield: 40%. [The regiochemistry was assigned by NMR experiments (COSY; HSQC, HMBC).]

5.) Synthesis of an Example Compound by Reaction of a Thiazolopiperidine with a Carboxylic Acid A.) Reaction of a Thiazolopiperidine Compound with a Carboxylic Acid Example 58

2-[[(2S)-1-[(4-Methoxy-2,6-dimethyl-phenyl)sulfonyl]-piperidin-2-yl]-methoxy]-1-[2-(piperidin-1-ylmethyl)-4,5,6,7-tetrahydro-thiazolo[5,4-c]pyridin-5-yl]-ethanone

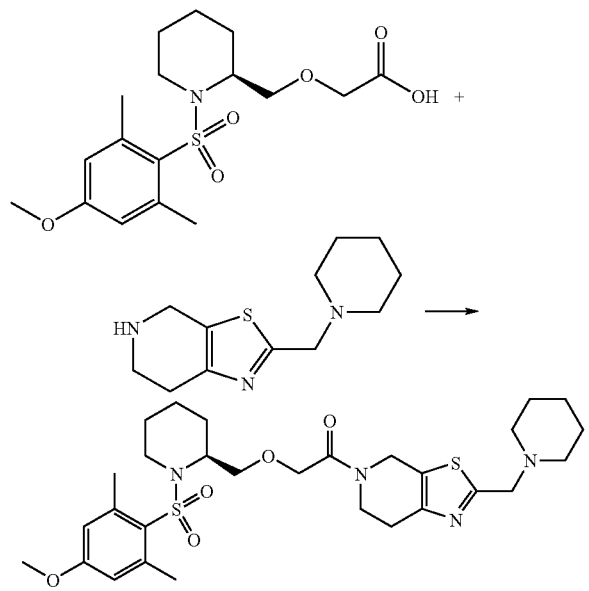

To a solution of (S)-2-((1-(4-methoxy-2,6-dimethylphenylsulfonyl)piperidin-2-yl)methoxy)acetic acid (AC28) (0.449 mmol, 1.0 eq.) in dichloromethane (10 ml/mmol) was added Diisopropyl ethylamine (3.0 eq.) at 0° C. followed by the addition of HOBT (1.0 eq.) and EDCI (1.5 eq.). The resultant solution was stirred at room temperature for 15 min. It was again cool to 0° C. and the 2-(piperidin-1-ylmethyl)-4,5,6,7-tetrahydrothiazolo[5,4-c]pyridine (AM6) (1.2 eq.) was added. The reaction mixture was stirred for 16 h at room temperature. The mixture was diluted with dichloromethane, washed with saturated ammonium chloride solution, brine, saturated sodium bicarbonate and finally with brine. The organic layer was dried over sodium sulfate and evaporated to dryness under reduced pressure to get the crude product. The crude material was purified by column chromatography.

Yield: 20%. MS, $R_t$=3.2 min, m/z=591.4 $[MH]^+$

B.) Synthesis of the Thiazolopiperidine (Amine AM6)

Synthesis of 2-(Piperidin-1-ylmethyl)-4,5,6,7-tetrahydrothiazolo[5,4-c]pyridine (AM6)

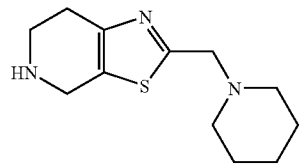

Step-1: Ethyl 3-bromo-4-oxopiperidine-1-carboxylate

To a refluxing solution of ethyl 4-oxopiperidine-1-carboxylate (2 g, 11.6 mmol) in 1:1 chloroform-ethyl acetate (23 ml) was added copper(II) bromide (5.2 g, 23.38 mmol) with a constant stream of nitrogen bubbling through the reaction mixture. After complete addition, the reaction mixture was heated for 45 min until the green color of the mixture and the dark solid had disappeared. The mixture was cooled to 25° C. and filtered. The filtrate was evaporated completely and the residue was dissolved in ethyl acetate. The ethyl acetate layer was washed with water, sodium bicarbonate solution and brine. After drying over sodium sulfate the organic layer was evaporated under reduced pressure to yield the crude product which was used in the next step without further purification. Yield: 70%.

Step-2: Diethyl 6,7-dihydrothiazolo[5,4-c]pyridine-2,5(4H)-dicarboxylate

To a 2-propanol solution (60 ml) of ethyl 3-bromo-4-oxopiperidine-1-carboxylate (5 g, 20 mmol) were added ethyl thiooxamate (18 mmol) (preparation: see below) and calcium carbonate (200 mmol) and the resulting reaction mixture was allowed to reflux for 48 h (monitored by TLC). The reaction mixture was cooled to 25° C., filtered through a bed of celite and the residue was washed repeatedly with ethyl acetate. The combined organic layers were evaporated completely, the residue again dissolved in ethyl acetate and the organics washed successively with water and brine and finally dried over sodium sulfate. Evaporation of the organic layer under reduced pressure gave the crude product which was purified by column chromatography (30% ethyl acetate in hexane). Yield: 30%.

Preparation of Ethyl Thiooxamate $H_2S$ gas was passed through a toluene solution (15 ml) of ethyl cyanoformate (10 g) for 10 min and triethylamine (2 ml)

was added to it. The resulting reaction mixture was stirred for 16 h at ambient temperature and then the solid was filtered out, washed with ether and finally dried to get the crude ethyl thiooxamate which was used directly in the next step without further purification. Yield: 6.2 g.

Step-3: 4,5,6,7-Tetrahydrothiazolo[5,4-c]pyridine-2-carboxylic Acid Hydrochloride Diethyl 6,7-dihydrothiazolo[5,4-c]pyridine-2,5(4H)-dicarboxylate (1.76 mmol) in 3.5 N KOH solution (3 ml) was refluxed for 3 h (monitored by TLC). The reaction mixture was cooled to 0° C. and acidified with conc. HCl. The solid was collected by filtration and dried to yield the desired product. Yield: 60%.

Step-4 and Step-5: 5-tert-Butyl 2-methyl 6,7-dihydrothiazolo[5,4-c]pyridine-2,5(4H)-dicarboxylate To a suspension of 4,5,6,7-tetrahydrothiazolo[5,4-c]pyridine-2-carboxylic acid hydrochloride (1.9 mmol) in methanol (10 ml) was added thionyl chloride (1.5 eq.) at 0° C. and the resulting reaction mixture was refluxed for 16 h. The solvent was completely evaporated and the residue dissolved in dichloromethane (10 ml) and cooled to 0° C. To this cold mixture were added triethylamine (3 eq.) and Boc-anhydride (1.2 eq.) and the resulting reaction mixture was stirred at 25° C. for 12 h. The mixture was diluted with dichloromethane, washed successively with water and brine and the organics finally dried over sodium sulfate. Evaporation of the organic layer under reduced pressure gave the crude product which was purified by column chromatography (10% ethyl acetate in hexane). Yield: 45%.

Step-6: tert-Butyl 2-(hydroxymethyl)-6,7-dihydrothiazolo[5,4-c]pyridine-5(4H)-carboxylate To a suspension of lithium aluminium hydride (3.986 mmol) in dry tetrahydrofuran (12 ml) was added 5-tert-butyl 2-methyl 6,7-dihydrothiazolo[5,4-c]pyridine-2,5(4H)-dicarboxylate (3.22 mmol) in tetrahydrofuran (10 ml) at 0° C. and the resulting reaction mixture was stirred at the same temperature for 1 h. It was quenched with saturated aqueous sodium sulfate solution, diluted with ethyl acetate and filtered. The filtrate was evaporated under reduced pressure to give the crude product which was used in the next step without further purification. Yield: 66%.

Step-7: tert-Butyl 2-((methylsulfonyloxy)methyl)-6,7-dihydrothiazolo[5,4-c]pyridine-5(4H)-carboxylate To a dichloromethane solution (15 ml) of tert-butyl 2-(hydroxymethyl)-6,7-dihydrothiazolo[5,4-c]pyridine-5(4H)-carboxylate (1 eq.) was added triethylamine (2.5 eq.) and methane sulfonylchloride (1.2 eq.) at 0° C. and the resulting reaction mixture was stirred at ambient temperature for 2 h. The reaction was quenched with ice and diluted with dichloromethane. The organic layer was successively washed with water and brine and finally dried over sodium sulfate. Evaporation of the organic layer under reduced pressure gave the crude product which was used directly in the next step without further purification. Yield: 80%.

Step-8: tert-Butyl 2-(piperidin-1-ylmethyl)-6,7-dihydrothiazolo[5,4-c]pyridine-5(4H)-carboxylate To a toluene solution (14 ml) of tert-butyl 2-((methylsulfonyloxy)methyl)-6,7-dihydrothiazolo[5,4-c]pyridine-5 (4H)-carboxylate (2.01 mmol) was added potassium carbonate (10 mmol) and piperidine (1.1 eq.) and the resulting reaction mixture was refluxed for 16 h. It was cooled to room temperature, diluted with ethyl acetate and the organic layer was washed successively with water and brine. After drying over sodium sulfate, the organic layer was evaporated under reduced pressure to give the crude product which was purified by column chromatography (silica). Yield: 30%.

Step-9: 2-(Piperidin-1-ylmethyl)-4,5,6,7-tetrahydrothiazolo[5,4-c]pyridine (AM6)

To a cooled (0° C.) solution of tert-butyl 2-(piperidin-1-ylmethyl)-6,7-dihydrothiazolo[5,4-c]pyridine-5(4H)-carboxylate (0.534 mmol) in dichloromethane (3 ml) was added trifluoroacetic acid (1 ml) and reaction mixture was stirred at room temperature for 2 h. Solvent was evaporated under reduced pressure and residue was azeotroped twice with dichloromethane and used in the next step.

II. Parallel Synthesis

General

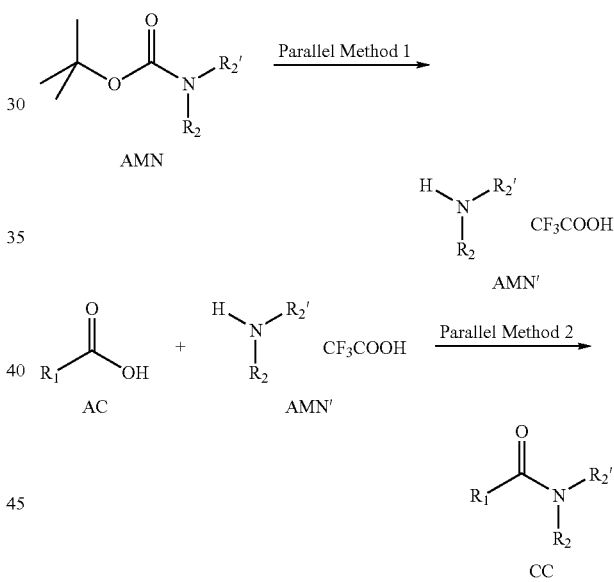

The amine units AMN' were prepared from the Boc-protected amines AMN by Parallel Method 1 in accordance with the above equation. The amine trifluoroacetic acid salts AMN' obtained in this way were reacted in parallel synthesis by Parallel Method 2 with the acids AC to give the amidic products CC.

Parallel Method 1: Amine Liberation

20% trifluoroacetic acid in MC (10 ml/mol) was added to the corresponding Boc-protected amine (1 eq., AMN) at 0° C. The reaction mixture obtained was stirred at 25° C. for 4 hours. The course of the reaction was monitored by thin layer chromatography. The solvent was then removed under reduced pressure and the residue was dried thoroughly in order to remove traces of trifluoroacetic acid. The crude product obtained in this way was used for synthesis of the libraries without further purification.

Parallel Method 2: Amide formation

EDCI (1.5 eq.), HOBT (1 eq.) and DIPEA (2.5 eq.) were added in succession to a solution of the corresponding acid unit (unit AC, 1 eq.) in MC (3 ml/mmol). The reaction mixture obtained was stirred at 25° C. for 15 minutes. A solution of the corresponding Boc-deprotected amine unit (AMN; 1.5 eq.) in MC (1 ml/mmol) was cooled in an ice bath in a further flask, and DIPEA (4 eq.) was added. The solutions from the two flasks were combined. The reaction mixture obtained in this way was stirred at 25° C. for 16 hours and then diluted with methylene chloride. The organic phase was washed successively with aqueous ammonium chloride solution, sodium carbonate and saturated sodium chloride solution. The organic phase was dried over sodium sulfate. After the solvent had been removed under reduced pressure, the crude product obtained was purified by column chromatography. The crude products of the parallel synthesis were purified by column chromatography. It was possible to demonstrate the identity of the products by analytical HPLC-MS measurements (cf. HPLC-MS data).

The example compounds described in the following table were prepared in this way from the corresponding acid units AC and the corresponding amines AMN.

| Example no. | Acid | Amine | MS, m/z (MH+) | Rt [min] |
|---|---|---|---|---|
| 37 | AC2 | AMN-01 | 551.1 | 2.98 |
| 38 | AC5 | AMN-02 | 585.2 | 2.84 |
| 39 | AC6 | AMN-02 | 545.2 | 2.71 |
| 40 | AC2 | AMN-02 | 565.2 | 2.85 |
| 41 | AC4 | AMN-02 | 569.2 | 2.87 |
| 42 | AC1 (racemate) | AMN-02 | 569.3 | 2.85 |
| 43 | AC7 | AMN-02 | 583.4 | 2.89 |
| 44 | AC2 | AMN-03 | 585.3 | 2.85 |
| 45 | AC4 | AMN-03 | 589.4 | 2.87 |
| 46 | AC1 (racemate) | AMN-03 | 589.3 | 2.86 |
| 47 | AC7 | AMN-03 | 603.3 | 2.90 |
| 48 | AC5 | AMN-01 | 571.2 | 3.00 |
| 49 | AC6 | AMN-01 | 531.2 | 2.94 |
| 50 | AC5 | AMN-03 | 605.3 | 2.92 |
| 51 | AC6 | AMN-03 | 565.3 | 2.81 |
| 52 | AC4 | AMN-01 | 555.2 | 9.96 |
| 53 | AC7 | AMN-01 | 569.3 | 5.12 |

Parallel Method 3

Parallel Synthesis Method for the Preparation of CC Amides

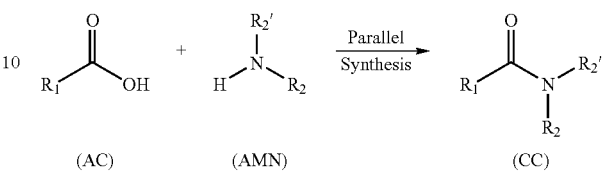

Acid building blocks AC were converted with amines AMN to amides CC in parallel fashion. The correlation between product and reagent, building block and method can be taken from the synthesis matrix. The crude products from the parallel synthesis were analyzed by HPLC_MS[1] and afterwards purified via reverse phase HPLC-MS[2]. The identification of the products was demonstrated by analytical HPLC-MS[1][1] measurements.

Parallelsynthesis: Protocol for the Synthesis of CC Amides

To a solution of acid AC (100 μmol) in 1 ml dichlormethane a solution of 1,1'-carbonyldiimidazole (150 μmol) in 1 ml dichlormethane was added and the reaction mixture was stirred at room temperature for 1.5 h. Afterwards a solution of amine AMN (150 μmol) and Hünigs base (500 μmol) in 1 ml dichlormethane was added. The mixture was stirred for 18 h at room temperature. The solvent was evaporated under reduced pressure in a vacuum centrifuge (brand: GeneVac). The final purification resulted from HPLC-MS[2]. The final analytics resulted from LC-MS[1].

[1] Equipment and Methods for HPLC-MS Analytics:

Parallelsynthesis Method: HPLC: Waters Alliance 2795 with PDA Waters 2996; MS: ZQ 2000 MassLynx Single Quadrupol MS Detector; Column: Atlantis dC18 30×2.1 mm, 3 μm; Col. temp:. 40° C., Eluent A: purified water+0.1% formic acid; Eluent B: methanol (gradient grade)+0.1% formic acid; Gradient: 0% B to 100% B in 2.3 min, 100% B for 0.4 min, 100% B to 0% B in 0.01 min, 0% B for 0.8 min; Flow: 1.0 mL/min; Ionisation: ES+, 25V; make up: 100 μL/min 70% methanol+0.2% formic acid; UV: 200-400 nm.

[2] Equipment and Methods for HPLC-MS Purification:

Prep Pump: Waters 2525; Make Up Pump: Waters 515; Auxiliary Detector: Waters DAD 2487; MS Detector: Waters Micromass ZQ; Injector/Fraction Collector: Waters Sample Manager 2767; Gradient: Initial: 60% Water 40% Methanol ->12-14.5 min: 0% Water 100% Methanol ->14.5-15 min: 60% Water 40% Methanol; Flow: 35 ml/min Column: Macherey-Nagel, C18 Gravity, 100×21 mm, 5μ. A variety of products was purified by a slightly modified method.

The example compounds described in the following table were prepared in this manner from the corresponding acid units and the corresponding amines.

| Example No. | Name | Acid (S) | Amine (A) | [M+] found | R.t. [min] |
|---|---|---|---|---|---|
| 66 | 4-Methoxy-N,2,6-trimethyl-N-[2-[2-oxo-2-(4-phenyl-4,5,6,7-tetrahydro-1H-imidazo[4,5-c]pyridin-5-yl)-ethoxy]-ethyl]-benzenesulfonic acid amide | 2-[2-[[(4-Methoxy-2,6-dimethyl-phenyl)sulfonyl]-methyl-amino]-ethoxy]-acetic acid (AC6) | 4-Pyridin-4-Yl-4,5,6,7-tetrahydro-1H-imidazo[4,5-c]pyridine (AMN-06) | | |

-continued

| Example No. | Name | Acid (S) | Amine (A) | [M+] found | R.t. [min] |
|---|---|---|---|---|---|
| 68 | 4-[1-[(2-Chloro-6-methyl-phenyl)sulfonyl]-piperidin-2-yl]-1-[2-[(4-methyl-piperazin-1-yl)-methyl]-4,5,6,7-tetrahydro-thieno[3,2-c]pyridin-5-yl]-butan-1-one | 4-[1-[(2-Chloro-6-methyl-phenyl)sulfonyl]-piperidin-2-yl]-butyric acid (AC-11) | 2-[(4-Methyl-Piperazin-1-yl)-methyl]-4,5,6,7-tetrahydro-thieno[3,2-c]pyridine trihydrochloride (AMN-03) | 593.2 | 1.80 |
| 69 | 4-[1-[(2-Chloro-6-methyl-phenyl)sulfonyl]-piperidin-2-yl]-1-(4-phenyl-4,5,6,7-tetrahydro-1H-imidazo[4,5-c]pyridin-5-yl)-butan-1-one | 4-[1-[(2-Chloro-6-methyl-phenyl)sulfonyl]-piperidin-2-yl]-butyric acid (AC-11) | 4-Pyridin-4-Yl-4,5,6,7-tetrahydro-1H-imidazo[4,5-c]pyridine (AMN-06) | 541.2 | 1.88 |
| 71 | 4-[1-[(4-Methoxy-2,6-dimethyl-phenyl)sulfonyl]-piperidin-2-yl]-1-(4-phenyl-4,5,6,7-tetrahydro-1H-imidazo[4,5-c]pyridin-5-yl)-butan-1-one | 4-[1-[(4-Methoxy-2,6-dimethyl-phenyl)sulfonyl]-piperidin-2-yl]-butyric acid (AC7) | 4-Pyridin-4-Yl-4,5,6,7-tetrahydro-1H-imidazo[4,5-c]pyridine (AMN-06) | 551.2 | 1.88 |
| 73 | 1-[2-[(4-Methyl-piperazin-1-yl)-methyl]-4,5,6,7-tetrahydro-thieno[3,2-c]pyridin-5-yl]-4-[1-(naphthalen-1-ylsulfonyl)-piperidin-2-yl]-butan-1-one | 4-[1-(Naphthalen-1-ylsulfonyl)-piperidin-2-yl]-butyric acid (AC-12) | 2-[(4-Methyl-Piperazin-1-yl)-methyl]-4,5,6,7-tetrahydro-thieno[3,2-c]pyridine trihydrochloride (AMN-03) | 595.3 | 1.83 |
| 74 | 4-[1-(Naphthalen-1-ylsulfonyl)-piperidin-2-yl]-1-(4-phenyl-4,5,6,7-tetrahydro-1H-imidazo[4,5-c]pyridin-5-yl)-butan-1-one | 4-[1-(Naphthalen-1-ylsulfonyl)-piperidin-2-yl]-butyric acid (AC-12) | 4-Pyridin-4-Yl-4,5,6,7-tetrahydro-1H-imidazo[4,5-c]pyridin (AMN-06) | 543.4 | 2.24 |
| 75 | 1-[2-[(4-Methyl-piperazin-1-yl)-methyl]-4,5,6,7-tetrahydro-thieno[3,2-c]pyridin-5-yl]-4-[1-(naphthalen-2-ylsulfonyl)-piperidin-2-yl]-butan-1-one | 4-[1-(Naphthalen-2-ylsulfonyl)-piperidin-2-yl]-butyric acid (AC-13) | 2-[(4-Methyl-Piperazin-1-yl)-methyl]-4,5,6,7-tetrahydro-thieno[3,2-c]pyridine trihydrochloride (AMN-03) | 595.3 | 1.88 |
| 76 | 4-[1-(Naphthalen-2-ylsulfonyl)-piperidin-2-yl]-1-(4-phenyl-4,5,6,7-tetrahydro-1H-imidazo[4,5-c]pyridin-5-yl)-butan-1-one | 4-[1-(Naphthalen-2-ylsulfonyl)-piperidin-2-yl]-butyric acid (AC-13) | 4-Pyridin-4-Yl-4,5,6,7-tetrahydro-1H-imidazo[4,5-c]pyridine (AMN-06) | 543.2 | 1.94 |
| 78 | N-(4H-[1,3]Benzodioxin-7-yl-methyl)-4-methoxy-2,6-dimethyl-N-[2-[2-[2-[(4-methyl-piperazin-1-yl)-methyl]-4,5,6,7-tetrahydro-thieno[3,2-c]pyridin-5-yl]-2-oxo-ethoxy]-ethyl]-benzenesulfonic acid amide | 2-[2-[4H-[1,3]Benzodioxin-7-yl-methyl-[(4-methoxy-2,6-dimethyl-phenyl)sulfonyl]-amino]-ethoxy]-acetic acid (AC-26) | 2-[(4-Methyl-Piperazin-1-yl)-methyl]-4,5,6,7-tetrahydro-thieno[3,2-c]pyridine trihydrochloride (AMN-03) | 699.3 | 1.85 |
| 81 | N-Benzyl-4-Methoxy-2,6-dimethyl-N-[2-[2-[2-[(4-methyl-piperazin-1-yl)-methyl]-4,5,6,7-tetrahydro-thieno[3,2-c]pyridin-5-yl]-2-oxo-ethoxy]-ethyl]-benzenesulfonic acid amide | 2-[2-[Benzyl-[(methoxy-2,6-dimethyl-phenyl)sulfonyl]-amino]-ethoxy]-acetic acid (AC-21) | 2-[(4-Methyl-Piperazin-1-yl)-methyl]4,5,6,7-tetrahydro-thieno[3,2-c]pyridine trihydrochloride (AMN-03) | 641.3 | 1.91 |
| 82 | N-Benzyl-4-Methoxy-2,6-dimethyl-N-[2-[2-oxo-2-(4-phenyl-4,5,6,7-tetrahydro-1H-imidazo[4,5-c]pyridin-5-yl)-ethoxy]-ethyl]-benzenesulfonic acid amide | 2-[2-[Benzyl-[(methoxy-2,6-dimethyl-phenyl)sulfonyl]-amino]-ethoxy]-acetic acid (AC-21) | 4-Pyridin-4-Yl-4,5,6,7-tetrahydro-1H-imidazo[4,5-c]pyridine (AMN-06) | 589.2 | 1.96 |
| 83 | 4-Methoxy-2,6-Dimethyl-N-[2-[2-[2-[(4-methyl-piperazin-1-yl)-methyl]-4,5,6,7-tetrahydro-thieno[3,2-c]pyridin-5-yl]-2-oxo-ethoxy]-ethyl]-N-phenyl-benzenesulfonic acid amide | 2-[2-(N-[(4-Methoxy-2,6-dimethyl-phenyl)sulfonyl-anilino)-ethoxy]-acetic acid (AC-20) | 2-[(4-Methyl-Piperazin-1-yl)-methyl]-4,5,6,7-tetrahydro-thieno[3,2-c]pyridine trihydrochloride (AMN-03) | 627.3 | 1.79 |
| 84 | 4-Methoxy-2,6-Dimethyl-N-[2-[2-oxo-2-(4-phenyl-4,5,6,7-tetrahydro-1H-imidazo[4,5-c]pyridin-5-yl)-ethoxy]-ethyl]-N-phenyl-benzenesulfonic acid amide | 2-[2-(N-[(4-Methoxy-2,6-dimethyl-phenyl)sulfonyl-anilino)-ethoxy]-acetic acid (AC-20) | 4-Pyridin-4-Yl-4,5,6,7-tetrahydro-1H-imidazo[4,5-c]pyridine (AMN-06) | 575.2 | 1.85 |
| 85 | 2-[[1-[(4-Methoxy-2,6-dimethyl-phenyl)sulfonyl]-1,2,3,4-tetrahydro-quinolin-2-yl]-methoxy]-1-[2-[(4-methyl-piperazin-1-yl)-methyl]-4,5,6,7-tetrahydro-thieno[3,2-c]pyridin-5-yl]-ethanone | 2-[[1-[(4-Methoxy-2,6-dimethyl-phenyl)sulfonyl]-1,2,3,4-tetrahydro-quinolin-2-yl]-methoxy]-acetic acid (AC-22) | 2-[(4-Methyl-Piperazin-1-yl)-methyl]-4,5,6,7-tetrahydro-thieno[3,2-c]pyridine trihydrochloride (AMN-03) | 653.3 | 1.88 |
| 86 | 2-[[1-[(4-Methoxy-2,6-dimethyl-phenyl)sulfonyl]-1,2,3,4-tetrahydro-quinolin-2-yl]-methoxy]-1-(4-phenyl-4,5,6,7-tetrahydro-1H-imidazo[4,5-c]pyridin-5-yl)-ethanone | 2-[[1-[(4-Methoxy-2,6-dimethyl-phenyl)sulfonyl]-1,2,3,4-tetrahydro-quinolin-2-yl]-methoxy]-acetic acid (AC-22) | 4-Pyridin-4-Yl-4,5,6,7-tetrahydro-1H-imidazo[4,5-c]pyridine (AMN-06) | 601.2 | 1.95 |
| 87 | 1-[2-[(4-Methyl-piperazin-1-yl)-methyl]-4,5,6,7-tetrahydro-thieno[3,2-c]pyridin-5-yl]-4-[1-[[2-(trifluoromethyl)-phenyl]sulfonyl]-piperidin-2-yl]-butan-1-one | 4-[1-[[2-(Trifluoromethyl)-phenyl]sulfonyl]-piperidin-2-yl]-butyric acid (AC-15) | 2-[(4-Methyl-Piperazin-1-yl)-methyl]-4,5,6,7-tetrahydro-thieno[3,2-c]pyridine trihydrochloride (AMN-03) | 613.2 | 1.77 |
| 88 | 1-(4-Phenyl-4,5,6,7-tetrahydro-1H-imidazo[4,5-c]pyridin-5-yl)-4-[1-[[2-(trifluoromethyl)-phenyl]sulfonyl]-piperidin-2-yl]-butan-1-one | 4-[1-[[2-(Trifluoromethyl)-phenyl]sulfonyl]-piperidin-2-yl]-butyric acid (AC-15) | 4-Pyridin-4-Yl-4,5,6,7-tetrahydro-1H-imidazo[4,5-c]pyridine (AMN-06) | 561.2 | 1.87 |
| 91 | 2-[[4-[(4-Methoxy-2,6-dimethyl-phenyl)sulfonyl]-3,4-dihydro-2H-[1,4]benzoxazin-3-yl]-methoxy]-1-[2-[(4-methyl-piperazin-1-yl)-methyl]-4,5,6,7-tetrahydro-thieno[3,2-c]pyridin-5-yl]-ethanone | 2-[[4-[(4-Methoxy-2,6-dimethyl-phenyl)sulfonyl]-3,4-dihydro-2H-[1,4]benzoxazin-3-yl]-methoxy]-acetic acid (AC-23) | 2-[(4-Methyl-Piperazin-1-yl)-methyl]-4,5,6,7-tetrahydro-thieno[3,2-c]pyridine trihydrochloride (AMN-03) | 655.3 | 1.89 |

-continued

| Example No. | Name | Acid (S) | Amine (A) | [M+] found | R.t. [min] |
|---|---|---|---|---|---|
| 92 | 2-[[4-[(4-Methoxy-2,6-dimethyl-phenyl)sulfonyl]-3,4-dihydro-2H-[1,4]benzoxazin-3-yl]-methoxy]-1-(4-phenyl-4,5,6,7-tetrahydro-1H-imidazo[4,5-c]pyridin-5-yl)-ethanone | 2-[[4-[(4-Methoxy-2,6-dimethyl-phenyl)sulfonyl]-3,4-dihydro-2H-[1,4]benzoxazin-3-yl]-methoxy]-acetic acid (AC-23) | 4-Pyridin-4-Yl-4,5,6,7-tetrahydro-1H-imidazo[4,5-c]pyridine (AMN-06) | 603.2 | 1.95 |
| 93 | 1-[2-[(4-Methyl-piperazin-1-yl)-methyl]-4,5,6,7-tetrahydro-thieno[3,2-c]pyridin-5-yl]-2-[[4-[[2-(trifluoromethyl)-phenyl]sulfonyl]-3,4-dihydro-2H-[1,4]benzoxazin-3-yl]-methoxy]-ethanone | 2-[[4-[[2-(Trifluoromethyl)-phenyl]sulfonyl]-3,4-dihydro-2H-[1,4]benzoxazin-3-yl]-methoxy]-acetic acid (AC-25) | 2-[(4-Methyl-Piperazin-1-yl)-methyl]-4,5,6,7-tetrahydro-thieno[3,2-c]pyridine trihydrochloride (AMN-03) | 665.2 | 1.83 |
| 94 | 1-(4-Phenyl-4,5,6,7-tetrahydro-1H-imidazo[4,5-c]pyridin-5-yl)-2-[[4-[[2-(trifluoromethyl)-phenyl]sulfonyl]-3,4-dihydro-2H-[1,4]benzoxazin-3-yl]-methoxy]-ethanone | 2-[[4-[[2-(Trifluoromethyl)-phenyl]sulfonyl]-3,4-dihydro-2H-[1,4]benzoxazin-3-yl]-methoxy]-acetic acid (AC-25) | 4-Pyridin-4-Yl-4,5,6,7-tetrahydro-1H-imidazo[4,5-c]pyridine (AMN-06) | 613.2 | 1.93 |
| 95 | 4-Methoxy-N,2,3,6-tetramethyl-N-[2-[2-[(4-methyl-piperazin-1-yl)-methyl]-4,5,6,7-tetrahydro-thieno[3,2-c]pyridin-5-yl]-2-oxo-ethoxy]-ethyl]-benzenesulfonic acid amide | 2-[2-[[(4-Methoxy-2,3,6-trimethyl-phenyl)sulfonyl]-methyl-amino]-ethoxy]-acetic acid (AC-10) | 2-[(4-Methyl-Piperazin-1-yl)-methyl]-4,5,6,7-tetrahydro-thieno[3,2-c]pyridine trihydrochloride (AMN-03) | 579.2 | 1.75 |
| 96 | 4-Methoxy-N,2,3,6-tetramethyl-N-[2-[2-oxo-2-(4-phenyl-4,5,6,7-tetrahydro-1H-imidazo[4,5-c]pyridin-5-yl)-ethoxy]-ethyl]-benzenesulfonic acid amide | 2-[2-[[(4-Methoxy-2,3,6-trimethyl-phenyl)sulfonyl]-methyl-amino]-ethoxy]-acetic acid (AC-10) | 4-Pyridin-4-Yl-4,5,6,7-tetrahydro-1H-imidazo[4,5-c]pyridine (AMN-06) | 527.2 | 1.83 |
| 97 | 1-[2-[(4-Methyl-piperazin-1-yl)-methyl]-4,5,6,7-tetrahydro-thieno[3,2-c]pyridin-5-yl]-2-[[1-[[2-(trifluoromethyl)-phenyl]sulfonyl]-piperidin-2-yl]-methoxy]-ethanone | 2-[[1-[[2-(Trifluoromethyl)-phenyl]sulfonyl]-piperidin-2-yl]-methoxy]-acetic acid (AC-16) | 2-[(4-Methyl-Piperazin-1-yl)-methyl]-4,5,6,7-tetrahydro-thieno[3,2-c]pyridine trihydrochloride (AMN-03) | 615.2 | 1.72 |
| 98 | 1-(4-Phenyl-4,5,6,7-tetrahydro-1H-imidazo[4,5-c]pyridin-5-yl)-2-[[1-[[2-(trifluoromethyl)-phenyl]sulfonyl]-piperidin-2-yl]-methoxy]-ethanone | 2-[[1-[[2-(Trifluoromethyl)-phenyl]sulfonyl]-piperidin-2-yl]-methoxy]-acetic acid (AC-16) | 4-Pyridin-4-Yl-4,5,6,7-tetrahydro-1H-imidazo[4,5-c]pyridine (AMN-06) | 563.1 | 1.74 |
| 99 | 3-[[1-[(4-Methoxy-2,6-dimethyl-phenyl)sulfonyl]-piperidin-2-yl]-methoxy]-1-[2-[(4-methyl-piperazin-1-yl)-methyl]-4,5,6,7-tetrahydro-thieno[3,2-c]pyridin-5-yl]-propan-1-one | 3-[[1-[(4-Methoxy-2,6-dimethyl-phenyl)sulfonyl]-piperidin-2-yl]-methoxy]-propionic acid (AC-19) | 2-[(4-Methyl-Piperazin-1-yl)-methyl]-4,5,6,7-tetrahydro-thieno[3,2-c]pyridine trihydrochloride (AMN-03) | 619.3 | 1.82 |
| 100 | 3-[[1-[(4-Methoxy-2,6-dimethyl-phenyl)sulfonyl]-piperidin-2-yl]-methoxy]-1-(4-phenyl-4,5,6,7-tetrahydro-1H-imidazo[4,5-c]pyridin-5-yl)-propan-1-one | 3-[[1-[(4-Methoxy-2,6-dimethyl-phenyl)sulfonyl]-piperidin-2-yl]-methoxy]-propionic acid (AC-19) | 4-Pyridin-4-Yl-4,5,6,7-tetrahydro-1H-imidazo[4,5-c]pyridine (AMN-06) | 567.2 | 1.90 |
| 101 | 2-[2-[1-[(4-Methoxy-2,6-dimethyl-phenyl)sulfonyl]-piperidin-2-yl]-ethoxy]-1-[2-[(4-methyl-piperazin-1-yl)-methyl]-4,5,6,7-tetrahydro-thieno[3,2-c]pyridin-5-yl]-ethanone | 2-[2-[1-[(4-Methoxy-2,6-dimethyl-phenyl)sulfonyl]-piperidin-2-yl]-ethoxy]-acetic acid (AC-18) | 2-[(4-Methyl-Piperazin-1-yl)-methyl]-4,5,6,7-tetrahydro-thieno[3,2-c]pyridine trihydrochloride (AMN-03) | 619.3 | 1.78 |
| 102 | 2-[2-[1-[(4-Methoxy-2,6-dimethyl-phenyl)sulfonyl]-piperidin-2-yl]-ethoxy]-1-(4-phenyl-4,5,6,7-tetrahydro-1H-imidazo[4,5-c]pyridin-5-yl)-ethanone | 2-[2-[1-[(4-Methoxy-2,6-dimethyl-phenyl)sulfonyl]-piperidin-2-yl]-ethoxy]-acetic acid (AC-18) | 4-Pyridin-4-Yl-4,5,6,7-tetrahydro-1H-imidazo[4,5-c]pyridine (AMN-06) | 567.2 | 1.90 |
| 103 | N-Methyl-N-[4-[2-[(4-methyl-piperazin-1-yl)-methyl]-4,5,6,7-tetrahydro-thieno[3,2-c]pyridin-5-yl]-4-oxo-butyl]-3-(trifluoromethyl)-benzenesulfonic acid amide | 4-[Methyl-[[3-(trifluoromethyl)phenyl]sulfonyl]-amino]-butyric acid (AC-08) | 2-[(4-Methyl-Piperazin-1-yl)-methyl]-4,5,6,7-tetrahydro-thieno[3,2-c]pyridine trihydrochloride (AMN-03) | 559.2 | 1.70 |
| 104 | N-Methyl-N-[4-Oxo-4-(4-phenyl-4,5,6,7-tetrahydro-1H-imidazo[4,5-c]pyridin-5-yl)-butyl]-3-(trifluoromethyl)-benzenesulfonic acid amide | 4-[Methyl-[[3-(trifluoromethyl)phenyl]sulfonyl]-amino]-butyric acid (AC-08) | 4-Pyridin-4-Yl-4,5,6,7-tetrahydro-1H-imidazo[4,5-c]pyridine (AMN-06) | 507.1 | 1.78 |
| 105 | 1-[2-[(4-Methyl-piperazin-1-yl)-methyl]-4,5,6,7-tetrahydro-thieno[3,2-c]pyridin-5-yl]-2-[4-(naphthalen-2-ylsulfonyl)-3,4-dihydro-2H-[1,4]benzoxazin-3-yl]-ethanone | 2-[4-(Naphthalen-2-ylsulfonyl)-3,4-dihydro-2H-[1,4]benzoxazin-3-yl]-acetic acid (AC-17) | 2-[(4-Methyl-Piperazin-1-yl)-methyl]-4,5,6,7-tetrahydro-thieno[3,2-c]pyridine trihydrochloride (AMN-03) | 617.2 | 1.93 |
| 106 | 2-[4-(Naphthalen-2-ylsulfonyl)-3,4-dihydro-2H-[1,4]benzoxazin-3-yl]-1-(4-phenyl-4,5,6,7-tetrahydro-1H-imidazo[4,5-c]pyridin-5-yl)-ethanone | 2-[4-(Naphthalen-2-ylsulfonyl)-3,4-dihydro-2H-[1,4]benzoxazin-3-yl]-acetic acid (AC-17) | 4-Pyridin-4-Yl-4,5,6,7-tetrahydro-1H-imidazo[4,5-c]pyridine (AMN-06) | 565.2 | 1.98 |
| 107 | 4-Methoxy-N,2,6-trimethyl-N-[2-[2-oxo-2-(2-phenyl-4,5,6,7-tetrahydro-oxazolo[5,4-c]pyridin-5-yl)-ethoxy]-ethyl]-benzenesulfonic acid amide | 2-[2-[[(4-Methoxy-2,6-dimethyl-phenyl)sulfonyl]-methyl-amino]-ethoxy]-acetic acid (AC6) | 2-Phenyl-4,5,6,7-tetrahydro-oxazolo[5,4-c]pyridine hydrochloride (AMN-04) | 514.1 | 2.30 |
| 108 | 4-Methoxy-N,2,6-trimethyl-N-[2-[2-[1-methyl-3-(trifluoromethyl)-1,4,5,6-tetrahydro-pyrrolo[3,4-c]pyrazol-5-yl]-2-oxo-ethoxy]-ethyl]-benzenesulfonic acid amide | 2-[2-[[(4-Methoxy-2,6-dimethyl-phenyl)sulfonyl]-methyl-amino]-ethoxy]-acetic acid (AC6) | 1-Methyl-3-(Trifluoromethyl)-1,4,5,6-tetrahydro-pyrrolo[3,4-c]pyrazole hydrochloride (AMN-09) | 505.1 | 2.14 |

-continued

| Example No. | Name | Acid (S) | Amine (A) | [M+] found | R.t. [min] |
|---|---|---|---|---|---|
| 109 | 2-[[1-[(4-Methoxy-2,6-dimethyl-phenyl)sulfonyl]-piperidin-2-yl]-methoxy]-1-(2-phenyl-4,5,6,7-tetrahydro-oxazolo[5,4-c]pyridin-5-yl)-ethanone | 2-[[1-[(4-Methoxy-2,6-dimethyl-phenyl)sulfonyl]-piperidin-2-yl]-methoxy]-acetic acid (AC5) | 2-Phenyl-4,5,6,7-tetrahydro-oxazolo[5,4-c]pyridine hydrochloride (AMN-04) | 554.2 | 2.39 |
| 110 | 2-[[1-[(4-Methoxy-2,6-dimethyl-phenyl)sulfonyl]-piperidin-2-yl]-methoxy]-1-[1-methyl-3-(trifluoromethyl)-1,4,5,6-tetrahydro-pyrrolo[3,4-c]pyrazol-5-yl]-ethanone | 2-[[1-[(4-Methoxy-2,6-dimethyl-phenyl)sulfonyl]-piperidin-2-yl]-methoxy]-acetic acid (AC5) | 1-Methyl-3-(Trifluoromethyl)-1,4,5,6-tetrahydro-pyrrolo[3,4-c]pyrazole hydrochloride (AMN-09) | 545.1 | 2.27 |
| 111 | 4-[1-[(2-Chloro-6-methyl-phenyl)sulfonyl]-piperidin-2-yl]-1-(2-phenyl-4,5,6,7-tetrahydro-oxazolo[5,4-c]pyridin-5-yl)-butan-1-one | 4-[1-[(2-Chloro-6-methyl-phenyl)sulfonyl]-piperidin-2-yl]-butyric acid (AC-11) | 2-Phenyl-4,5,6,7-tetrahydro-oxazolo[5,4-c]pyridine hydrochloride (AMN-04) | 542.1 | 2.43 |
| 112 | 4-[1-[(2-Chloro-6-methyl-phenyl)sulfonyl]-piperidin-2-yl]-1-[1-phenyl-3-(trifluoromethyl)-1,4,5,6-tetrahydro-pyrrolo[3,4-c]pyrazol-5-yl]-butan-1-one | 4-[1-[(2-Chloro-6-methyl-phenyl)sulfonyl]-piperidin-2-yl]-butyric acid (AC-11) | 1-Phenyl-3-(Trifluoromethyl)-1,4,5,6-tetrahydro-pyrrolo[3,4-c]pyrazole hydrochloride (AMN-08) | 595.1 | 2.57 |
| 113 | 4-[1-[(2-Chloro-6-methyl-phenyl)sulfonyl]-piperidin-2-yl]-1-[1-methyl-3-(trifluoromethyl)-1,4,5,6-tetrahydro-pyrrolo[3,4-c]pyrazol-5-yl]-butan-1-one | 4-[1-[(2-Chloro-6-methyl-phenyl)sulfonyl]-piperidin-2-yl]-butyric acid (AC-11) | 1-Methyl-3-(Trifluoromethyl)-1,4,5,6-tetrahydro-pyrrolo[3,4-c]pyrazole hydrochloride (AMN-09) | 533.1 | 2.33 |
| 114 | 4-[1-[(4-Methoxy-2,6-dimethyl-phenyl)sulfonyl]-piperidin-2-yl]-1-(2-phenyl-4,5,6,7-tetrahydro-oxazolo[5,4-c]pyridin-5-yl)-butan-1-one | 4-[1-[(4-Methoxy-2,6-dimethyl-phenyl)sulfonyl]-piperidin-2-yl]-butyric acid (AC7) | 2-Phenyl-4,5,6,7-tetrahydro-oxazolo[5,4-c]pyridine hydrochloride (AMN-04) | 552.2 | 2.43 |
| 115 | 4-[1-[(4-Methoxy-2,6-dimethyl-phenyl)sulfonyl]-piperidin-2-yl]-1-[1-phenyl-3-(trifluoromethyl)-1,4,5,6-tetrahydro-pyrrolo[3,4-c]pyrazol-5-yl]-butan-1-one | 4-[1-[(4-Methoxy-2,6-dimethyl-phenyl)sulfonyl]-piperidin-2-yl]-butyric acid (AC7) | 1-Phenyl-3-(Trifluoromethyl)-1,4,5,6-tetrahydro-pyrrolo[3,4-c]pyrazole hydrochloride (AMN-08) | 605.2 | 2.58 |
| 116 | 4-[1-[(4-Methoxy-2,6-dimethyl-phenyl)sulfonyl]-piperidin-2-yl]-1-[1-methyl-3-(trifluoromethyl)-1,4,5,6-tetrahydro-pyrrolo[3,4-c]pyrazol-5-yl]-butan-1-one | 4-[1-[(4-Methoxy-2,6-dimethyl-phenyl)sulfonyl]-piperidin-2-yl]-butyric acid (AC7) | 1-Methyl-3-(Trifluoromethyl)-1,4,5,6-tetrahydro-pyrrolo[3,4-c]pyrazole hydrochloride (AMN-09) | 543.2 | 2.35 |
| 117 | 4-[1-(Naphthalen-1-ylsulfonyl)-piperidin-2-yl]-1-(2-phenyl-4,5,6,7-tetrahydro-oxazolo[5,4-c]pyridin-5-yl)-butan-1-one | 4-[1-(Naphthalen-1-ylsulfonyl)-piperidin-2-yl]-butyric acid (AC-12) | 2-Phenyl-4,5,6,7-tetrahydro-oxazolo[5,4-c]pyridine hydrochloride (AMN-04) | 544.2 | 2.41 |
| 118 | 1-[1-Methyl-3-(trifluoromethyl)-1,4,5,6-tetrahydro-pyrrolo[3,4-c]pyrazol-5-yl]-4-[1-(naphthalen-1-ylsulfonyl)-piperidin-2-yl]-butan-1-one | 4-[1-(Naphthalen-1-ylsulfonyl)-piperidin-2-yl]-butyric acid (AC-12) | 1-Methyl-3-(Trifluoromethyl)-1,4,5,6-tetrahydro-pyrrolo[3,4-c]pyrazole hydrochloride (AMN-09) | 535.2 | 2.32 |
| 119 | 4-[1-(Naphthalen-2-ylsulfonyl)-piperidin-2-yl]-1-(2-phenyl-4,5,6,7-tetrahydro-oxazolo[5,4-c]pyridin-5-yl)-butan-1-one | 4-[1-(Naphthalen-2-ylsulfonyl)-piperidin-2-yl]-butyric acid (AC-13) | 2-Phenyl-4,5,6,7-tetrahydro-oxazolo[5,4-c]pyridine hydrochloride (AMN-04) | 544.2 | 2.45 |
| 120 | 1-[1-Methyl-3-(trifluoromethyl)-1,4,5,6-tetrahydro-pyrrolo[3,4-c]pyrazol-5-yl]-4-[1-(naphthalen-2-ylsulfonyl)-piperidin-2-yl]-butan-1-one | 4-[1-(Naphthalen-2-ylsulfonyl)-piperidin-2-yl]-butyric acid (AC-13) | 1-Methyl-3-(Trifluoromethyl)-1,4,5,6-tetrahydro-pyrrolo[3,4-c]pyrazole hydrochloride (AMN-09) | 535.1 | 2.33 |
| 121 | N-[(1-Ethyl-1H-imidazol-2-yl)-methyl]-4-methoxy-2,6-dimethyl-N-[2-[2-oxo-2-(2-phenyl-4,5,6,7-tetrahydro-oxazolo[5,4-c]pyridin-5-yl)-ethoxy]-ethyl]-benzenesulfonic acid amide | 2-[2-[(1-Ethyl-1H-imidazol-2-yl)-methyl-[(4-methoxy-2,6-dimethyl-phenyl)sulfonyl]-amino]-ethoxy]-acetic acid (AC-24) | 2-Phenyl-4,5,6,7-tetrahydro-oxazolo[5,4-c]pyridine hydrochloride (AMN-04) | 608.2 | 1.87 |
| 122 | N-[(1-Ethyl-1H-imidazol-2-yl)-methyl]-4-methoxy-2,6-dimethyl-N-[2-[2-oxo-2-[1-phenyl-3-(trifluoromethyl)-1,4,5,6-tetrahydro-pyrrolo[3,4-c]pyrazol-5-yl]-ethoxy]-ethyl]-benzenesulfonic acid amide | 2-[2-[(1-Ethyl-1H-imidazol-2-yl)-methyl-[(4-methoxy-2,6-dimethyl-phenyl)sulfonyl]-amino]-ethoxy]-acetic acid (AC-24) | 1-Phenyl-3-(Trifluoromethyl)-1,4,5,6-tetrahydro-pyrrolo[3,4-c]pyrazole hydrochloride (AMN-08) | 661.2 | 2.03 |
| 123 | N-[(1-Ethyl-1H-imidazol-2-yl)-methyl]-4-methoxy-2,6-dimethyl-N-[2-[2-[1-methyl-3-(trifluoromethyl)-1,4,5,6-tetrahydro-pyrrolo[3,4-c]pyrazol-5-yl]-2-oxo-ethoxy]-ethyl]-benzenesulfonic acid amide | 2-[2-[(1-Ethyl-1H-imidazol-2-yl)-methyl-[(4-methoxy-2,6-dimethyl-phenyl)sulfonyl]-amino]-ethoxy]-acetic acid (AC-24) | 1-Methyl-3-(Trifluoromethyl)-1,4,5,6-tetrahydro-pyrrolo[3,4-c]pyrazole hydrochloride (AMN-09) | 599.2 | 1.76 |
| 124 | N-(4H-[1,3]Benzodioxin-7-yl-methyl)-4-methoxy-2,6-dimethyl-N-[2-[2-oxo-2-(2-phenyl-4,5,6,7-tetrahydro-oxazolo[5,4-c]pyridin-5-yl)-ethoxy]-ethyl]-benzenesulfonic acid amide | 2-[2-[4H-[1,3]Benzodioxin-7-yl-methyl-[(4-methoxy-2,6-dimethyl-phenyl)sulfonyl]-amino]-ethoxy]-acetic acid (AC-26) | 2-Phenyl-4,5,6,7-tetrahydro-oxazolo[5,4-c]pyridine hydrochloride (AMN-04) | 648.2 | 2.43 |

| Synthesis of the acid units for the parallel synthesis | | |
|---|---|---|
| Acid | Structure | Name |
| AC-08 | | 4-[Methyl-[[3-(trifluoromethyl)phenyl]sulfonyl]-amino]-butyric acid |
| AC-10 | | 2-[2-[[(4-Methoxy-2,3,6-trimethyl-phenyl)sulfonyl]-methyl-amino]-ethoxy]-acetic acid |
| AC-11 | | 4-[1-[(2-Chloro-6-methyl-phenyl)sulfonyl]-piperidin-2-yl]-butyric acid |
| AC-12 | | 4-[1-(Naphthalen-1-ylsulfonyl)-piperidin-2-yl]-butyric acid |
| AC-13 | | 4-[1-(Naphthalen-2-ylsulfonyl)-piperidin-2-yl]-butyric acid |
| AC-15 | | 4-[1-[[2-(Trifluoromethyl)-phenyl]sulfonyl]-piperidin-2-yl]-butyric acid |

Synthesis of the acid units for the parallel synthesis

| Acid | Structure | Name |
|---|---|---|
| AC-16 | 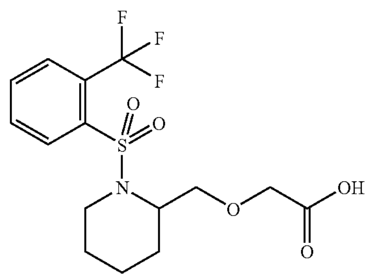 | 2-[[1-[[2-(Trifluoromethyl)-phenyl]sulfonyl]-piperidin-2-yl]-methoxy]-acetic acid |
| AC-17 | 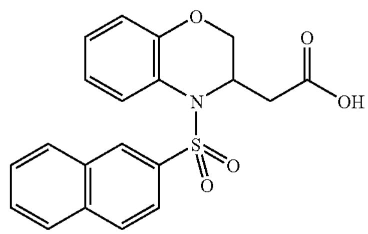 | 2-[4-(Naphthalen-2-ylsulfonyl)-3,4-dihydro-2H-[1,4]benzoxazin-3-yl]-acetic acid |
| AC-18 | 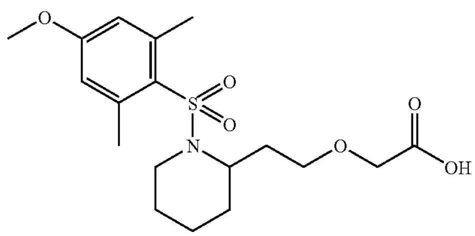 | 2-[2-[1-[(4-Methoxy-2,6-dimethyl-phenyl)sulfonyl]-piperidin-2-yl]-ethoxy]-acetic acid |
| AC-19 | 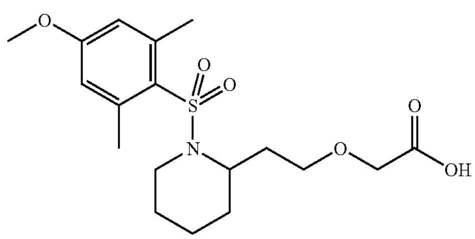 | 3-[[1-[(4-Methoxy-2,6-dimethyl-phenyl)sulfonyl]-piperidin-2-yl]-methoxy]-propionic acid |
| AC-20 | 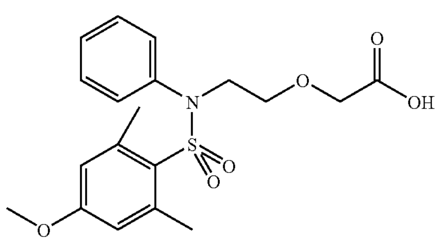 | 2-[2-(N-[(4-Methoxy-2,6-dimethyl-phenyl)sulfonyl]-anilino)-ethoxy]-acetic acid |
| AC-21 | 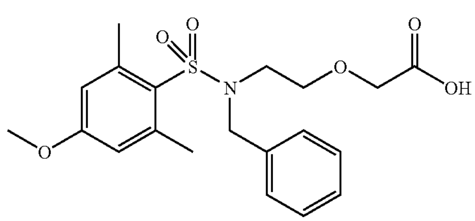 | 2-[2-[Benzyl-[(4-methoxy-2,6-dimethyl-phenyl)sulfonyl]-amino]-ethoxy]-acetic acid |

-continued

Synthesis of the acid units for the parallel synthesis

| Acid | Structure | Name |
| --- | --- | --- |
| AC-22 | 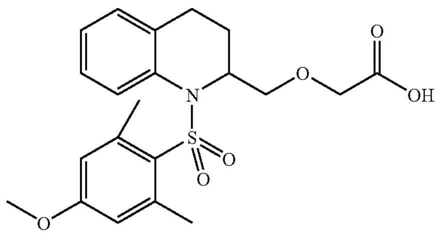 | 2-[[1-[(4-Methoxy-2,6-dimethyl-phenyl)sulfonyl]-1,2,3,4-tetrahydro-quinolin-2-yl]-methoxy]-acetic acid |
| AC-23 | 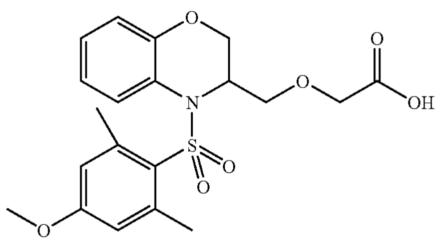 | 2-[[4-[(4-Methoxy-2,6-dimethyl-phenyl)sulfonyl]-3,4-dihydro-2H-[1,4]benzoxazin-3-yl]-methoxy]-acetic acid |
| AC-24 | 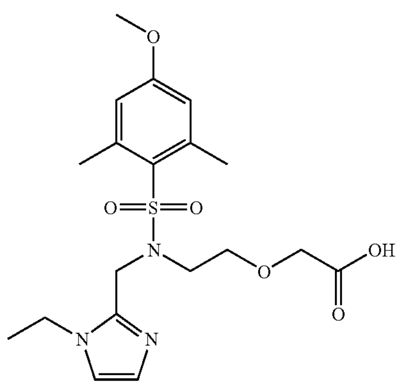 | 2-[2-[(1-Ethyl-1H-imidazol-2-yl)-methyl-[(4-methxoy-2,6-dimethyl-phenyl)sulfonyl]-amino]-ethoxy]-acetic acid |
| AC-25 | 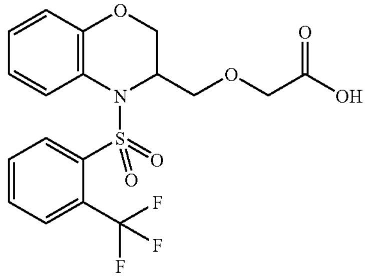 | 2-[[4-[[2-(Trifluoromethyl)-phenyl]sulfonyl]-3,4-dihydro-2H-[1,4]benzoxazin-3-yl]-methoxy]-acetic acid |

| Acid | Structure | Name |
|---|---|---|
| AC-26 | 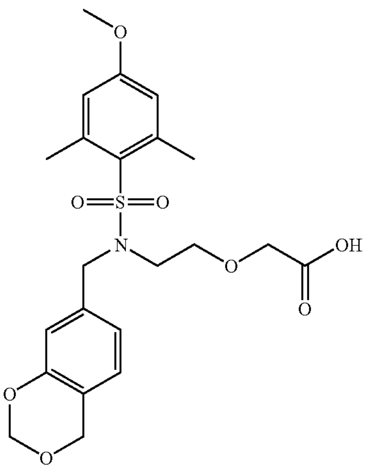 | 2-[2-[4H-[1,3]Benzodioxin-7-yl-methyl-[(4-methoxy-2,6-dimethyl-phenyl)sulfonyl]-amino]-ethoxy]-acetic acid |

Synthesis of acid building block AC-08: 4-[Methyl-[[3-(trifluoromethyl)phenyl]-sulfonyl]-amino]-butyric Acid (AC-08)

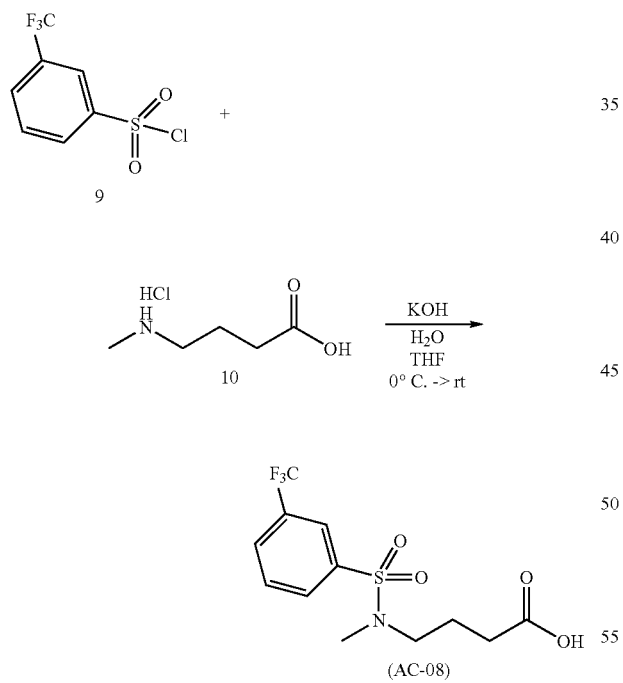

(AC-08)

To a solution of KOH (16.5 g, 294 mmol) in H₂O (75 ml) was added 4-(methylamino)butyric acid hydrochloride (10, 15.1 g, 98.1 mmol) and the reaction mixture was cooled with an icebath. A solution of 3-(trifluoromethyl)benzenesulfonyl chloride (9, 12.0 g, 49.1 mmol) in THF (75 ml) was dropwise added to the reaction mixture and stirring was continued at room temperature overnight. Aqueous 6 M HCl (75 ml) was added to the reaction mixture while cooling with an icebath, after which CH₂Cl₂ was added. The organic layer was separated, washed with brine, dried (Na₂SO₄), concentrated and co-evaporated with a minimal amount of Et₂O. Crystallization of the residue out of EtOAc/heptane resulted in AC-08 (11.32 g, 71%).

Synthesis of acid building block AC-10: 2-[2-[[(4-Methoxy-2,3,6-trimethyl-phenyl)sulfonyl]-methyl-amino]-ethoxy]-acetic Acid (AC-10)

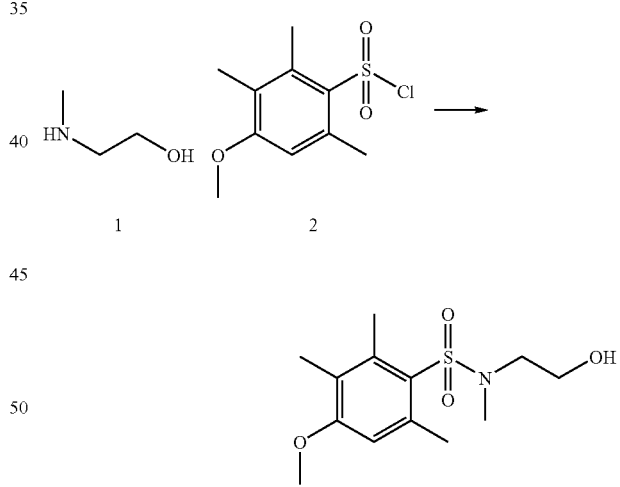

Step-1: To a solution of 2-Methylaminoethanol 1 (1 eq., 79.9 mmol) in 500 ml Dichlormethane was added triethylamine (1.2 eq., 95.9 mmol) and a solution of sulfonylchloride 2 (1.2 eq., 95.9 mmol) in 60 ml dichloromethane. The reaction mixture was stirred for 4 h at room temperature (TLC control). H₂O (100 ml) and sat. NaHCO₃-solution (100 ml) were added. After separation of the two phases, the aqueous phase was extracted 3× with Dichloromethane (250 ml). The combined organic phases were dried over Na₂SO₄, filtered and concentrated. The residue was purified by column chromatography (Silica, Diethyl ether/Hexane 8:2% 9:1), to afford the alcohol 3 (66.3 mmol, 83% yield).

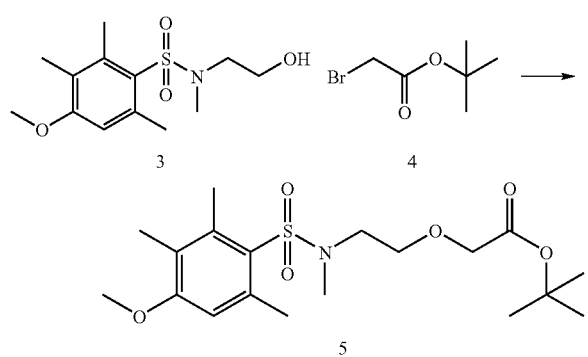

Step-2: A mixture of alcohol 3 (1 eq., 74.8 mmol), tert.-butylbromacetate (2.1 eq., 157 mmol), tetrabutylammonium-hydrogensulfate (0.1 eq., 7.48 mmol), 50% NaOH-solution and toluene was stirred vigorously for 3.5 h at room temperature. After separation of the two phases, the aqueous phase was extracted 2× with diethyl ether (450 ml). The combined organic phases were dried over $Na_2SO_4$ and concentrated. Product 5 (67.3 mmol, 90%) was obtained and it was used in the next step without further purification.

Step-3: Product 5 (1 eq., 67.3 mmol) was dissolved in dichlormethane and TFA (20 eq., 1345 mmol) was added. The reaction mixture was stirred for 4 h at room temperature (TLC controlled). The reaction mixture was dried over $MgSO_4$, filtered and completely evaporated. The residue was co-evaporated 2× with toluene (300 ml). The residue was then washed 3× with diisopropylether, whereas diisopropylether was decanted from the residue. The residue was suspended in Dichloromethane and was evaporated to dryness, to afford product AC-1 0 (101.9 mmol, '151%').

Synthesis of acid building blocks AC-11, AC-15, AC-13: 4-(1-(2-Chloro-6-methylphenylsulfonyl) piperidin-2-yl)butanoic Acid (AC-11), 4-(1-(2-(trifluoromethyl)phenylsulfonyl)piperidin-2-yl)butanoic Acid (AC-15) and 4-(1-(naphthalen-2-ylsulfonyl) piperidin-2-yl)butanoic Acid (AC-13)

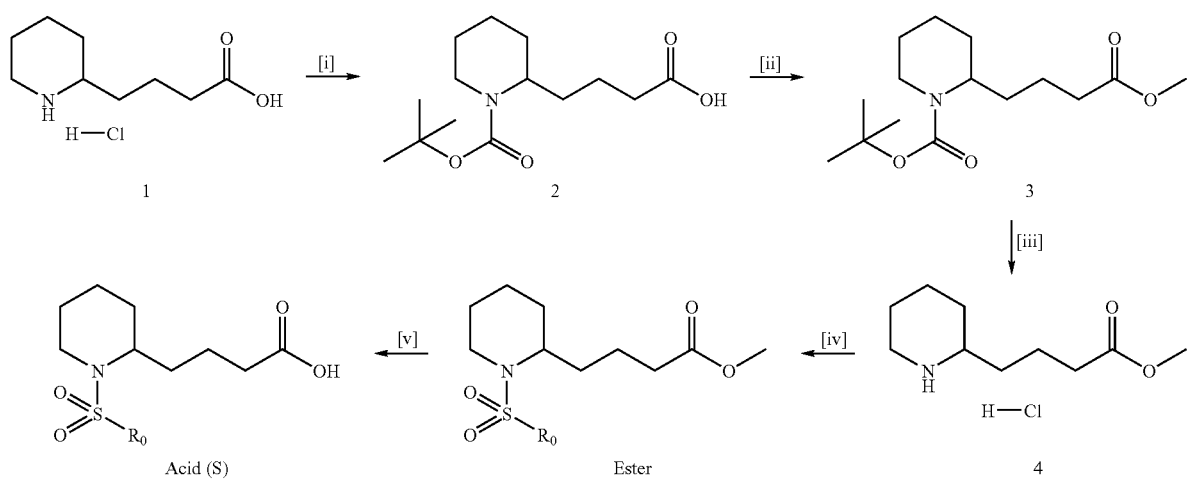

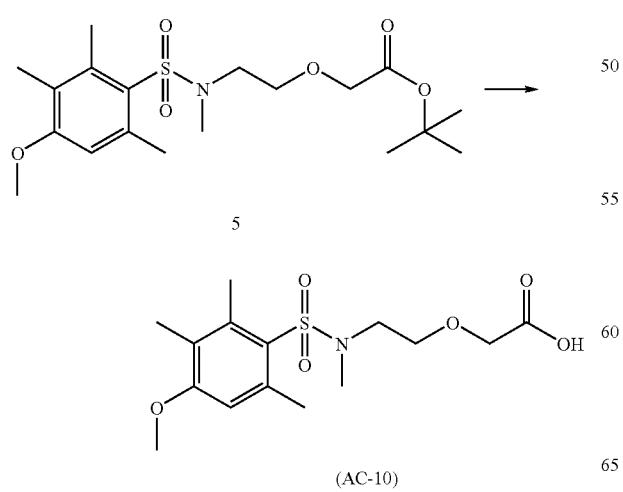

Step (i): 4-(1-tert-Butoxycarbonyl)piperidin-2-yl) butanoic Acid (2)

4-Piperidin-2-ylbutanoic acid hydrochloride (10.0 g, 48.3 mmol), and $K_2CO_3$ (26.6 g, 193.1 mmol) was dissolved in dest. water (70 ml) and dioxane (124 ml). The reaction mixture was cooled to 0° C. and at this temperature di-tert-butyldi-carbonate (11.4 g, 53.1 mmol) was added slowly. The reaction mixture was stirred for 24 h at room temperature. After completion of the reaction, water and ethyl acetate were added, and the two phases were separated. The aqueous Phase was extracted once with ethylacetate. Afterwards the aqueous Phase was triturated with 2 M HCL (aqueous) to reach pH=2. At this pH the aqueous phase was extracted 4× with dichloromethane. The combined organic layers were dried over magnesium sulfate, filtered out and evaporated to complete dryness to give (2) (13.13 g, 100%).

Step (ii): tert-Butyl-2-(4-methoxy-4-oxobutyl)piperidine-1-carboxylate (3)

To a solution of 4-(1-tert-Butoxycarbonyl)piperidin-2-yl) butanoic acid (2) (26 g, 95.8 mmol) in Dichloromethane 1,1'-carbonyldiimidazole (23.3 g, 143.7 mmol) was added. The reaction mixture was stirred for 1 h at room temperature. Subsequently Methanol (19.4 ml, 479 mmol) was added and the reaction mixture was stirred over night. The completion of the reaction was controlled via Thin-layer chromatography.

After completion the reaction mixture was washed 3× with saturated solution NH₄CL (aqueous) and 2× with brine. The organic layer was dried over Magnesium sulfate, filtered and evaporated in vacuum to afford tert-Butyl-2-(4-methoxy-4-oxobutyl)piperidine-1-carboxylate (3) (25.67 g, 94%).

Step (iii): Methyl 4-(piperidin-2-yl)butanoate Hydrochloride (4)

To a solution of tert-Butyl-2-(4-methoxy-4-oxobutyl)piperidine-1-carboxylate (3) (25.67 g, 89.9 mmol) in Methanol was added dropwise acetyl chloride. The reaction mixture was stirred for 5 h at room temperature. The completion of the reaction was controlled via Thin-layer chromatography. After completion the reaction mixture was evaporated in vacuum to give Methyl 4-(piperidin-2-yl)butanoate hydrochloride (4) (20.14 g, 100%)

General Procedure GP 1-Sulfonylation
(Ester 11, 13 & 15)

Step (iv): To a solution of methyl 4-(piperidin-2-yl)butanoate hydrochloride (4) (1 Equiv.) in Dichloromethane the sulfonyl chloride (3 Equiv.) was added. Subsequently N-Ethyl-diisopropylamine (3 Equiv.) was added dropwise. The reaction mixture was stirred overnight at room temperature. The completion of the reaction was controlled via Thin-layer chromatography. After completion the reaction mixture was made acidic with 1 M HCl (aqueous) and the aqueous phase was saturated with brine and then extracted 3× with Dichloromethane. The combined organics layers were dried over Magnesium sulfate, filtered and evaporated in vacuum. Purification by columnchromatography (Aluminiumoxide; Hexan/Ethylacetate) gave us the desired product.

TABLE 1

Synthesis of the sulfonylated amino acid ester

| Ester No. | Structure | Name | Aminoacid ester (4) | Sulfonylchloride |
|---|---|---|---|---|
| Ester 13 | 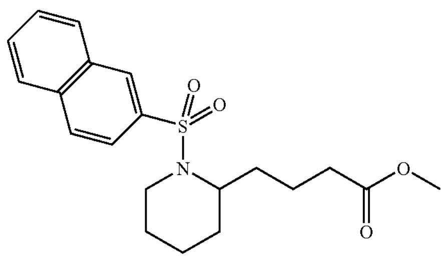 | Methyl 4-(1-(naphthalene-2-ylsulfonyl)piperidin-2-yl)butanoate (iv-01) | Methyl 4-(piperidin-2-yl)butanoate hydrochloride (40 | Naphthalene-2-sulfonylchloride |
| Ester 11 | 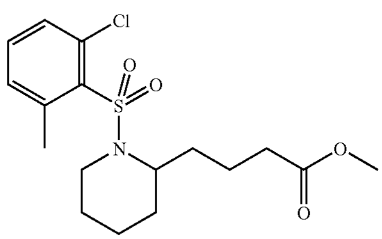 | Methyl 4-(1-(2-chloro-6-methylphenylsulfonyl)piperidin-2-yl)butanoate (iv-03) | Methyl 4-(piperidin-2-yl)butanoate hydrochloride (40 | 2-Chloro-6-methylbenzene-1-sulfonylchloride |
| Ester 15 | 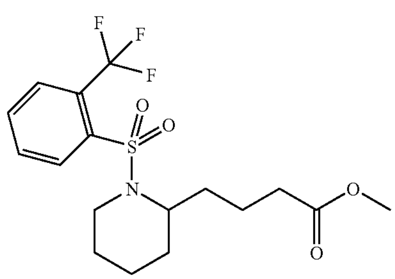 | Methyl 4-(1-(2-(trifluoromethyl)phenylsulfonyl)-piperidin-2-yl)butanoate (iv-04) | Methyl 4-(piperidin-2-yl)butanoate hydrochloride (40 | 2-(trifluroomethyl)-benzene-1-sulfonylchloride |

| Ester No. | Snthesis according to | Yield | Comment |
|---|---|---|---|
| Ester 13 | GP I | 80% (18.1 mmol) | Columnchromatography; Aluminiumoxide; Hexane/Ethylacetate 5:1 → 4:1 |
| Ester 11 | GP I | 93% (10.4 mmol) | Columnchromatography: Aluminiumoxide; Hexane/Ethylacetate 98:2 → 8:2 |

TABLE 1-continued

| | | | | |
|---|---|---|---|---|
| Ester 15 | GP I | 61% (11.5 mmol) | Columnchromatography: Aluminiumoxide; Hexane/Ethylacetate 95:5 → 8:2 | |

General Procedure GP III—Saponification (AC-11, AC-13 & AC-15)

Step (v):

To a solution of (Ester 11, 13 & 15) (1 Equiv.) in Methanol/Water Lithiumhydroxide was added and the reaction mixture was stirred over night at room temperature. The completion of the reaction was controlled via Thin-layer chromatography. After completion the Methanol was evaporated in vacuum, and the residue was triturated with Ethylacetate. The mixture was made acidic with diluted HCl. The aqueous layer was extracted 2× with Ethylacetate, the combined organic layers were dried over sodium sulfate and were evaporated in vacuum to give the desired Product (AC-1 3, AC-11 & AC-15).

Synthesis of acid building block AC-12: 4-[1-(Naphthalen-1-ylsulfonyl)-piperidin-2-yl]-butyric Acid (AC-12)

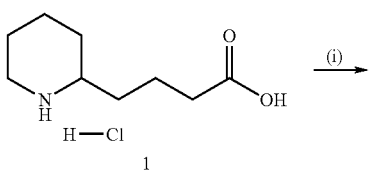

TABLE 2

Synthesis of Sulfonamide acids

| Acid No. | Structure | Name | Sulfonamidester (Ester) | Synthesis according to | Yield |
|---|---|---|---|---|---|
| AC-13 | 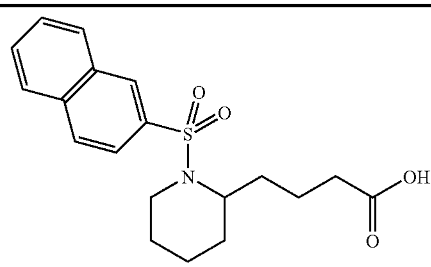 | 4-(1-naphthalen-2-ylsulfonyl)-piperidin-2-yl)butanoic acid | Methyl 4-(1-(naphthalene-2-ylsulfonyl)-piperidin-2-yl)butanoate (Ester 30) | GP II | 102% (23.2 mmol) |
| AC-11 | 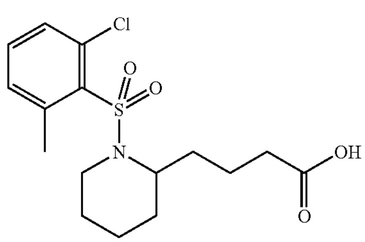 | 4-(1-(2-chloro-6-methylphenylsulfonyl)piperidin-2-yl)butanoic acid (v-01) | Methyl 4-(1-(2-chloro-6-methylphenyl-sulfonyl)piperidin-2-yl)butanoate (Ester 32) | GP II | 112% (8.22 mmol) |
| AC-15 | 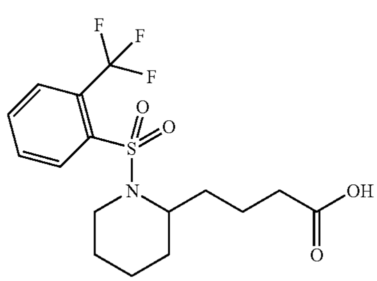 | 4-(1-(2-(trifluormethyl)phenylsulfonyl)piperidin-2-yl)butanoic acid | Methyl 4-(1-(2-(trifluoromethyl)-phenylsulfonyl)piperidin-2-yl)butanoate (Ester 34) | GP II | 125% (11.1 mmol) |

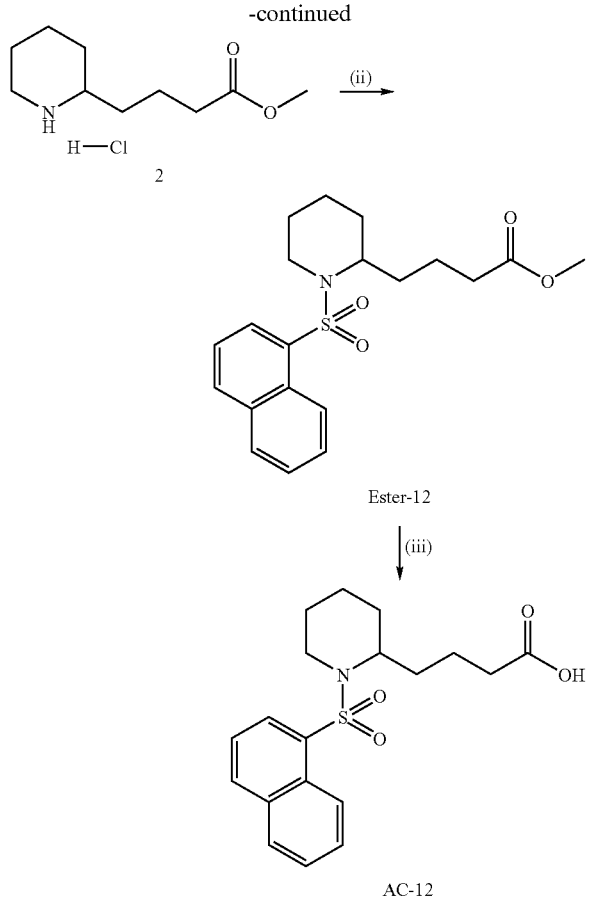

Step (iii): 4-(1-(Naphthalen-1-ylsulfonyl)piperidin-2-yl)butanoic Acid (AC-12)

To a solution of methyl 4-(1-(naphthalene-1-ylsulfonyl) piperidin-2-yl)butanoate (Ester-12) (4.95 g, 13.18 mmol.) in Methanol/Water (54 ml/36 ml) lithiumhydroxide (1.58 g, 65.9 mmol) was added and the reaction mixture was stirred over night at room temperature. The completion of the reaction was controlled via thin-layer chromatography. After completion the methanol was evaporated in vacuum, and the residue was triturated with ethyl acetate. The mixture was made acidic with diluted HCl. The aqueous layer was extracted 2× with ethyl acetate, the combined organic layers were dried over sodium sulfate and were evaporated in vacuum to give the desired product 4-(1-(Naphthalen-1-yl-sulfonyl)piperidin-2-yl)butanoic acid (AC-12) (4.38 g, 91%).

Synthesis of acid building block AC-16: 2-[[1-[[2-(Trifluoromethyl)-phenyl]sulfonyl]-piperidin-2-yl]-methoxy]-acetic Acid (AC-16)

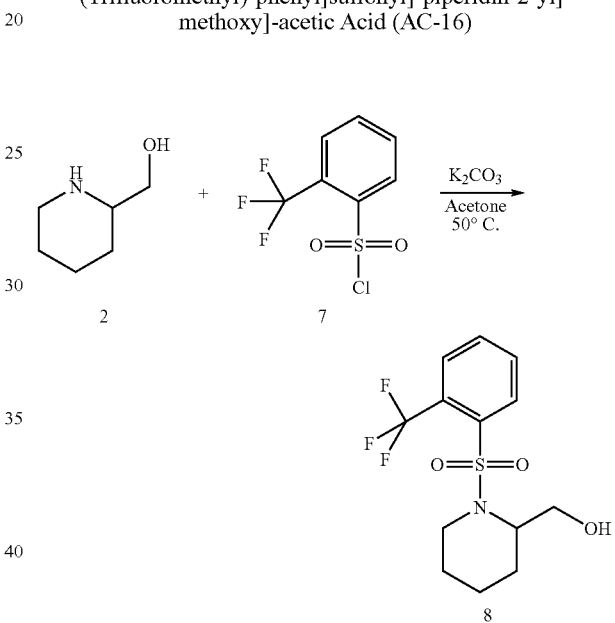

Step (i): Methyl 4-(piperidin-2-yl)butanoate hydrochloride (2)

A solution of 4-(2-piperidinyl)butanoic acid hydrochloride (5.95 g, 34.8 mmol) in Methanol (104 ml) is cooled to 0° C. At this temperature thionylchloride (7.54 ml, 104.3 mmol) is added slowly. The reaction mixture is heated to reflux for 12 h. The solvent is evaporated in vacuum. The residue is suspended in ethylacetate and is heated to reflux. The suspension is filtered while it is still hot. In the filtrate a white solid dropped out, which was filtered out and dried in vacuum to give Methyl 4-(piperidin-2-yl)butanoate hydrochloride (2) (3.49 g, 45%).

Step (ii): Methyl 4-(1-(naphthalene-1-ylsulfonyl) piperidin-2-yl)butanoate (Ester-21)

To a solution of methyl 4-(piperidin-2-yl)butanoate hydrochloride (2) (3.74 g, 20.2 mmol) in dichloromethane (143 ml) naphthalene-1-sulfonylchloride (13.7 g, 60.55 mmol) was added. Subsequently N-ethyl-diisopropylamine (10.2 ml, 60 55 mmol.) was added dropwise. The reaction mixture was stirred overnight at room temperature. The completion of the reaction was controlled via thin-layer chromatography. After completion the reaction mixture was made acidic with 1 M HCl (aqueous) and the aqueous phase was saturated with brine and then extracted 4× with dichloromethane. The combined organic layers were dried over magnesium sulfate, filtered and evaporated in vacuum. Purification by columnchromatography (Aluminiumoxid; Hexan/Ethylacetate 97:3-9:1) gave us the desired Product Methyl 4-(1-(naphthalene-1-yl-sulfonyl)piperidin-2-yl)butanoate (Ester 12) (4.95 g, 65%)

8. Alcohol 2 (4.3 g, 37.2 mmol) was suspended in acetone (150 ml). K₂CO₃ (10.27 g, 74.3 mmol) and 2-(trifluoromethyl)benzenesulfonyl chloride (7.10 g, 40.9 mmol) were subsequently added. The mixture was stirred overnight at 50° C. The reaction mixture was filtered after cooling to room temperature and the filtrate was evaporated to dryness under reduced pressure. The crude product was purified by column chromatography (silica, heptane/EtOAc 2:1) to afford 8.95 g (75%) of alcohol 8.

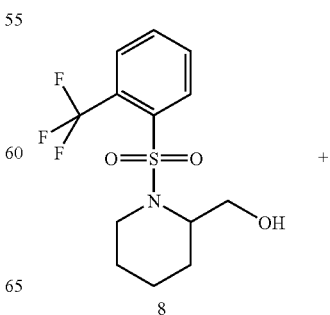

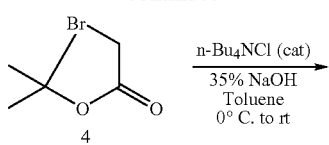

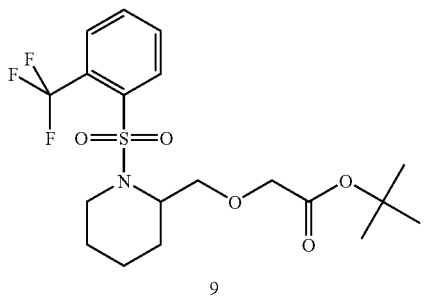

9. To a solution of alcohol 8 (8.95 g, 27.7 mmol) in toluene (100 ml) was added n-Bu₄NCl (2.54 g, 9.1 mmol). The reaction mixture was cooled to 0° C. after which aqueous 35% NaOH (100 ml) was added, followed by the addition of tert-butyl bromoacetate (4, 6.05 ml, 41.5 mmol). After stirring for 3 h at room temperature no more starting material was seen on TLC (silica, heptane/EtOAc, 2:1). The organic layer was separated and washed with H₂O (4×200 ml) and brine (200 ml) until neutral, dried (Na₂SO₄) and concentrated under reduced pressure. Purification by column chromatography (silica, heptane/EtOAc 4:1) afforded 11.57 g (96%) of ester 9.

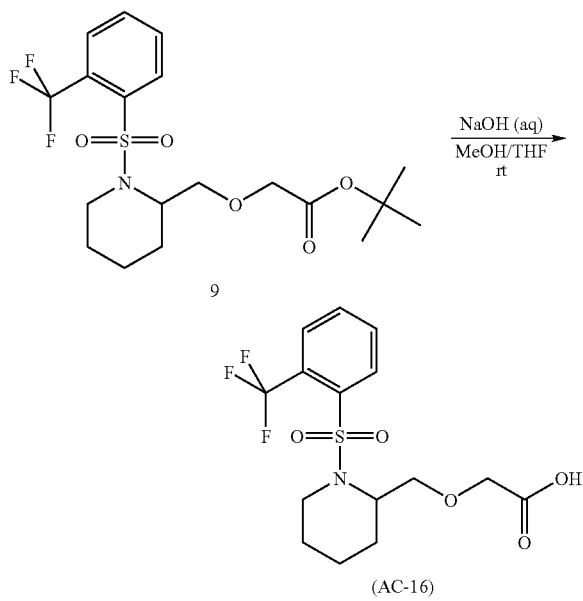

A mixture of ester 9 (11.57 g, 26.4 mmol), aqueous 6 M NaOH (88 ml, 528 mmol), MeOH (85 ml) and THF (85 ml) was stirred at room temperature for 30 min. The reaction was complete according to TLC (silica, heptane/EtOAc 2:1). The solution was then concentrated under reduced pressure to remove MeOH. The resulting suspension was acidified with aqueous 6 M HCl (120 ml) at 0° C. CH₂Cl₂ (300 ml) was added and after separation of the layers, the aqueous layer was extracted with CH₂Cl₂ (100 ml). The combined organic layers were dried (Na₂SO₄) and evaporated to dryness under reduced pressure affording 9.89 g (98%) of carboxylic acid AC-16.

Synthesis of acid building block AC-17: 2-[4-(Naphthalen-2-ylsulfonyl)-3,4-dihydro-2H-[1,4]benzoxazin-3-yl]-acetic Acid (AC-17)

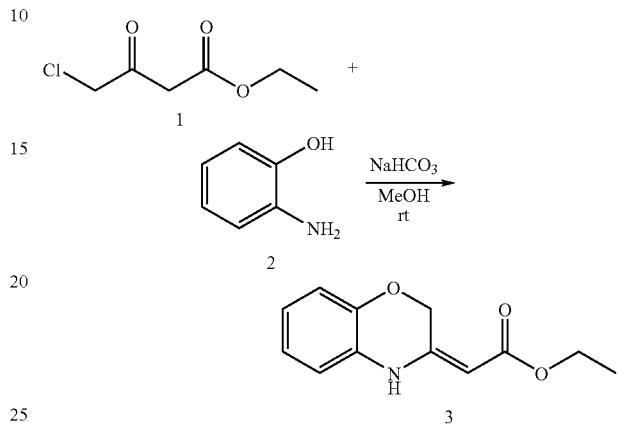

3. NaHCO₃ (35.1 g, 418 mmol) was added to a suspension of 2-aminophenol (2, 30.4 g, 279 mmol) and ethyl 4-chloro-3-oxobutanoate (1, 45.9 g, 279 mmol) in MeOH (280 ml) and the reaction mixture was stirred at room temperature for 2 days. After the addition of H₂O (280 ml), the reaction mixture was extracted with Et₂O (2×), washed with brine, dried (Na₂SO₄) and concentrated. The residue was purified by column chromatography (silica, heptane/EtOAc, 6:1) to yield 3 (33.71 g, 55%).

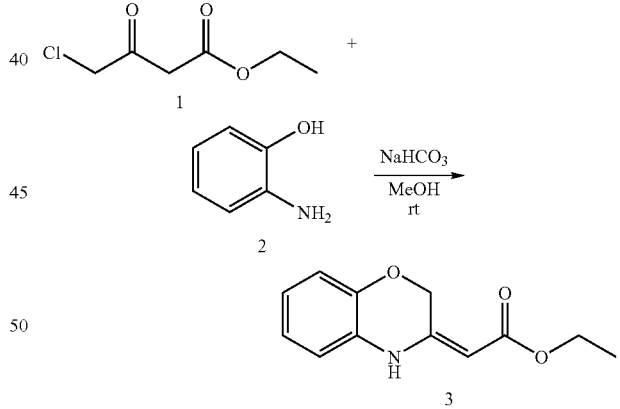

4. A suspension of Raney nickel 50% slurry in water (~3 ml) was added to a solution of 3 (16.0 g, 73.0 mmol) in THF (150 ml) and the reaction mixture was stirred under an hydrogen atmosphere of 9 bar at 40° C. for 2 days. The reaction mixture was filtered over Celite, eluted with THF and the combined filtrate was concentrated. A suspension of Raney nickel 50% slurry in water (~3 ml) was added to the residue in THF (150 ml) and the reaction mixture was stirred under an hydrogen atmosphere of 9 bar at 40° C. overnight. The reaction mixture was filtered over Celite, eluted with THF and the combined filtrate was concentrated and purified by column chromatography (silica, heptane/EtOAc, 6:1->4:1) to give 4 (13.73 g, 85%).

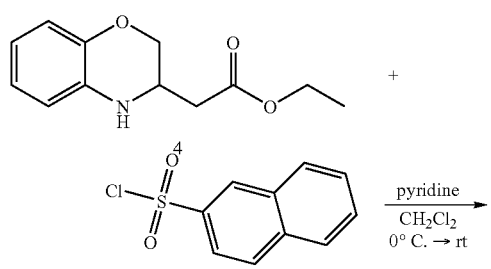

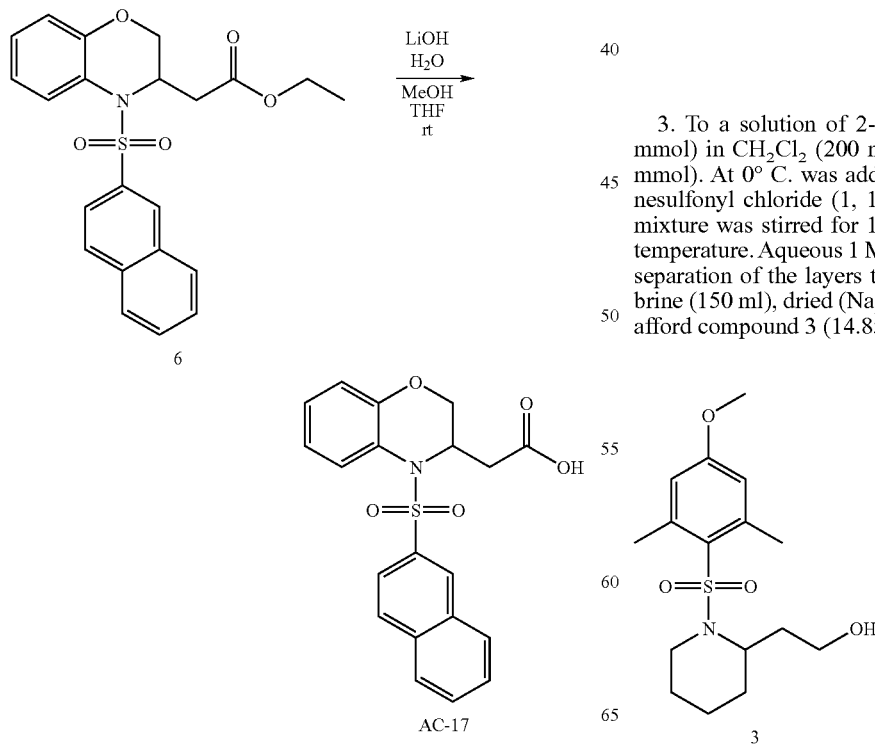

6. A solution of 2-naphthalenesulfonyl chloride (5, 9.22 g, 40.7 mmol) in $CH_2Cl_2$ (40 ml) was added to a solution of 4 (9.00 g, 40.7 mmol) and pyridine (4.93 ml, 61.0 mmol) in $CH_2Cl_2$ (80 ml) while cooling with an icebath. The reaction mixture was stirred at room temperature overnight, and extra 2-naphthalenesulfonyl chloride (5, 0.92 g, 4.07 mmol) in $CH_2Cl_2$ (5 ml) and extra pyridine (4.93 ml, 61.0 mmol) were added. The reaction mixture was stirred at room temperature overnight, after which aqueous 1 M HCl was added. The organic layer was separated, washed with brine, dried ($Na_2SO_4$), concentrated, purified by column chromatography (silica, heptane/EtOAc, 4:1) and co-evaporated with $CH_2Cl_2$ (2×) resulting in 6 (13.08 g, 75%).

Respectively $H_2O$ (60.0 ml) and $LiOH.H_2O$ (5.20 g, 124 mmol) were added to a solution of 6 (12.74 g, 31.0 mmol) in MeOH (60 ml) and THF (60.0 ml). The reaction mixture was stirred at room temperature overnight, acidified with aqueous 1 M HCl and extracted with $CH_2Cl_2$. The organic layer was washed with brine, dried ($Na_2SO_4$), concentrated and co-evaporated with $CH_2Cl_2$ to yield AC-17 (11.63 g, 98%).

Synthesis of acid building block AC-18: 2-[2-[1-[(4-Methoxy-2,6-dimethyl-phenyl)sulfonyl]-piperidin-2-yl]-ethoxy]-acetic Acid (AC-18)

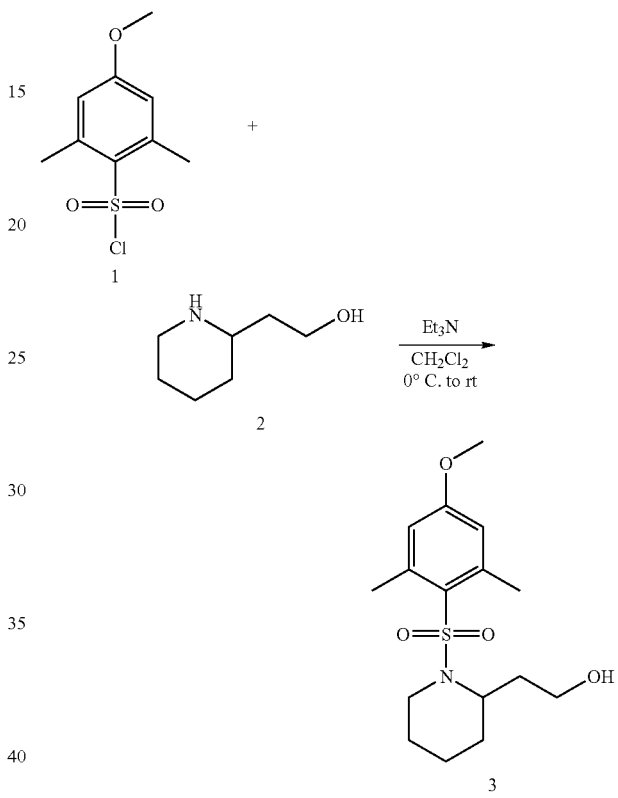

3. To a solution of 2-piperidineethanol (2, 5.63 g, 43.6 mmol) in $CH_2Cl_2$ (200 ml) was added $Et_3N$ (14.1 ml, 109 mmol). At 0° C. was added 4-methoxy-2,6-dimethylbenzenesulfonyl chloride (1, 10.23 g, 43.6 mmol). The reaction mixture was stirred for 1 h at 0° C. and overnight at room temperature. Aqueous 1 M HCl (150 ml) was added and after separation of the layers the organic layer was washed with brine (150 ml), dried ($Na_2SO_4$) and evaporated to dryness to afford compound 3 (14.85 g, '104%').

-continued

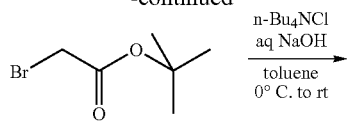

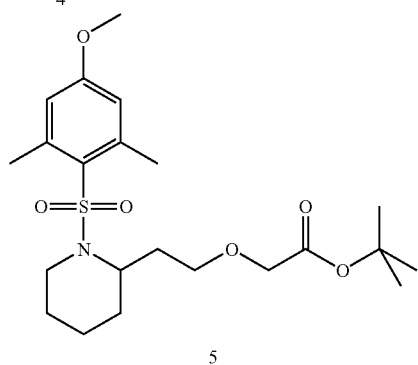

5. To a solution of alcohol 3 (14.8 g, max. 43.6 mmol) in toluene (200 ml) was added n-Bu₄NCl (4.04 g, 14.5 mmol). After cooling to 0° C., an aqueous 35% NaOH solution (200 ml) was added, followed by a dropwise addition of tert-butyl bromoacetate (4, 9.53 ml, 65.4 mmol). The reaction mixture was stirred at room temperature for 3 h. The organic layer was separated and washed with H₂O (3×200 ml), dried (Na₂SO₄) and evaporated to dryness. Purification by column chromatography (silica, heptane/EtOAc, 4:1) yielded compound 5 (12.90 g, 67%, 2 steps).

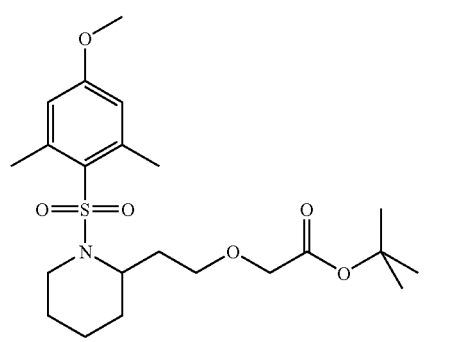

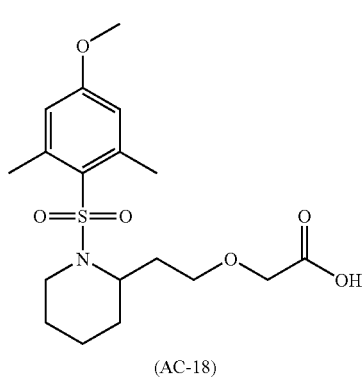

(AC-18)

To a solution of ester 5 (12.90 g, 29.2 mmol) in THF (95 ml) and MeOH (95 ml) was added aqueous 6 M NaOH (95 ml). After 1 h organic solvents were evaporated and aqueous 6 M HCl (95 ml) was added at 0° C. The mixture was extracted with EtOAc (500 ml), dried (Na₂SO₄) and co-evaporated with Et₂O (2×) to afford compound AC-18 (11.07 g, 98%).

Synthesis of acid building block AC-19: 3-((1-(4-Methoxy-2,6-dimethylphenylsulfonyl)piperidin-2-yl)methoxy)propanoic Acid (AC-19)

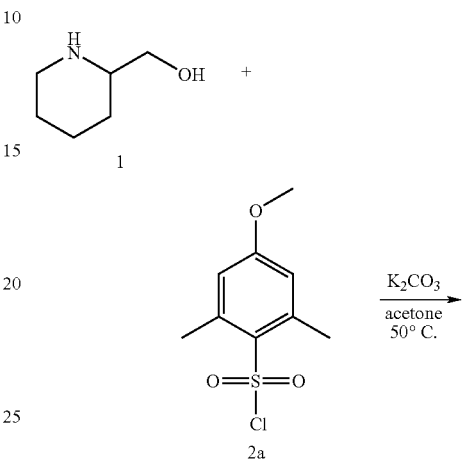

3. 2-Piperidinemethanol (1, 8.1 g, 70.11 mmol) was suspended in acetone (350 ml). K₂CO₃ (19.4 g, 140.22 mmol) was added followed by sulfonyl chloride 2a (18.1 g, 77.12 mmol). The mixture was stirred overnight at 50° C. After cooling to room temperature, the reaction mixture was filtered and the filtrate was evaporated to dryness. Purification by column chromatography (silica, heptane/EtOAc 2:1) gave 3 (12.9 g, 59%) as a white solid.

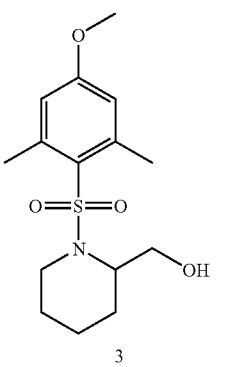

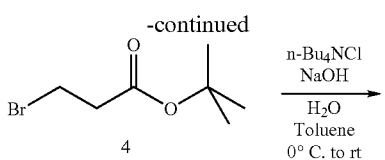

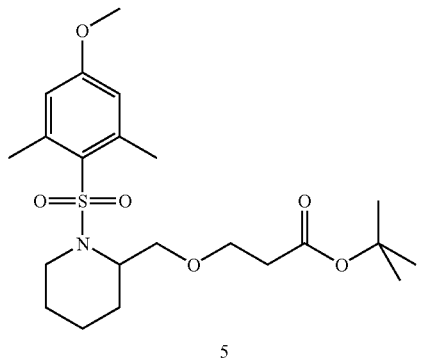

5. To a solution of alcohol 3 (12.8 g, 40.84 mmol) in toluene (200 ml) was added Bu₄NCl (3.7 g, 13.48 mmol). The reaction mixture was cooled to 0° C. after which aqueous 35% NaOH (250 ml) was added followed by a dropwise addition of tert-butyl 3-bromopropionate (4, 8.2 ml, 49.01 mmol) in toluene (50 ml). The mixture was stirred overnight at room temperature. The organic layer was separated and washed with H₂O until neutral, dried (Na₂SO₄), concentrated and co-evaporated with CH₂Cl₂ (3×). Purification by column chromatography (silica, heptane/EtOAc 4:1) gave 5 (11.2 g, 62%) as a yellow oil.

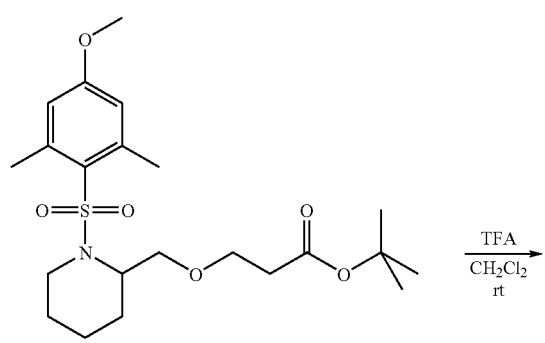

tert-Butyl ester 5 (10.9 g, 24.68 mmol) was dissolved in CH₂Cl₂ (150 ml). TFA (75 ml) was added and the mixture was stirred overnight at room temperature. The reaction mixture was concentrated in vacuo and co-evaporated with toluene (3×) and CH₂Cl₂ (3×). The crude product was purified by column chromatography (silica, heptane/EtOAc 2:1+2% HOAc). Co-evaporation with toluene (2×) and CH₂Cl₂ (3×) gave AC-19 (9.2 g, 97%) as a yellow oil.

Synthesis of acid building block AC-20: 2-[2-(N-[(4-Methoxy-2,6-dimethyl-phenyl)sulfonyl]-anilino)-ethoxy]-acetic Acid (AC-20)

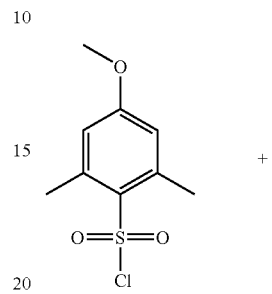

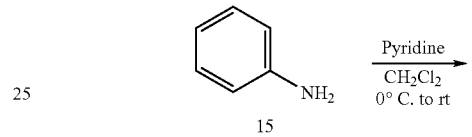

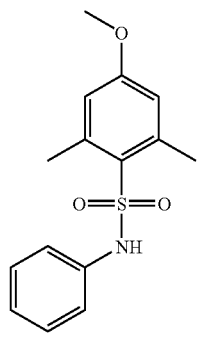

16. A solution of sulfonyl chloride 8 (10.1 g, 43.0 mmol) in CH₂Cl₂ (100 ml) was added dropwise to a stirred and cooled (0° C.) solution of aniline (15, 3.92 ml, 43.0 mmol) and pyridine (10.4 ml, 129 mmol) in CH₂Cl₂ (250 ml) and the reaction mixture was stirred at room temperature for 3 h. The mixture was washed with aqueous 0.5 M KHSO₄ (100 ml) and saturated aqueous NaHCO₃ (100 ml), dried (Na₂SO₄) and evaporated to dryness to afford crude sulfonamide 16 (14.87 g, '119%').

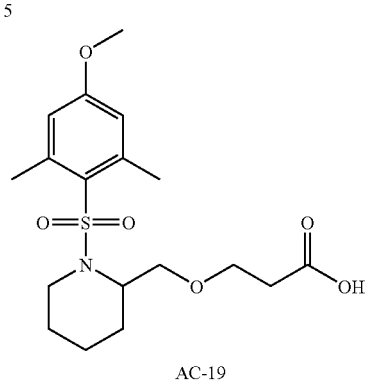

-continued

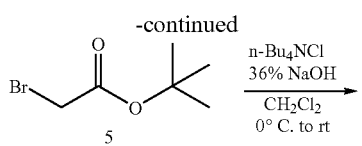

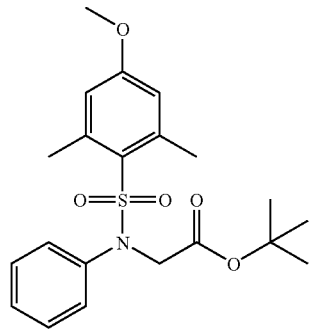
17

17. A solution of sulfonamide 16 (14.72 g, max. 43.0 mmol) and n-Bu₄NCl (1.50 g, 5.40 mmol) in CH₂Cl₂ (150 ml) was cooled to 0° C. and aqueous 35% NaOH (150 ml) was added. After 10 min tert-butyl bromoacetate (5, 11.2 ml, 76.0 mmol) was added and the mixture was stirred at room temperature for 3 h. The layers were separated and the organic layer was washed with H₂O (3×200 ml). The organic layer was dried (Na₂SO₄) and evaporated to dryness to afford crude ester 17 (22.6 g, '130%').

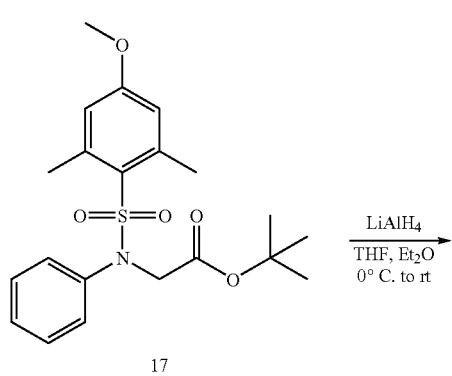
17

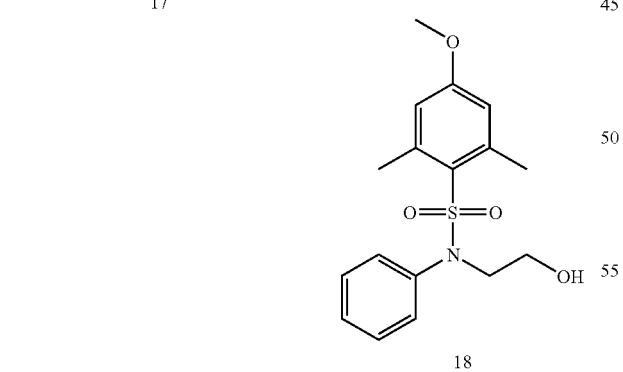
18

18. A solution of 4 M LiAlH₄ in Et₂O (20.9 ml, 84.0 mmol) was added dropwise to a stirred and cooled (0° C.) solution of ester 17 (22.6 g, max. 43.0 mmol) in THF (225 ml). The reaction mixture was stirred for 15 min at 0° C. after complete addition and Na₂SO₄.10H₂O was added until gas evolution stopped and was stirred at room temperature overnight. The mixture was filtered over a small pad of Na₂SO₄ and the filtrate was evaporated to dryness. The crude product was purified by column chromatography (silica, heptane/EtOAc, 2:1) to afford alcohol 18 (11.25 g, 78% over 3 steps).

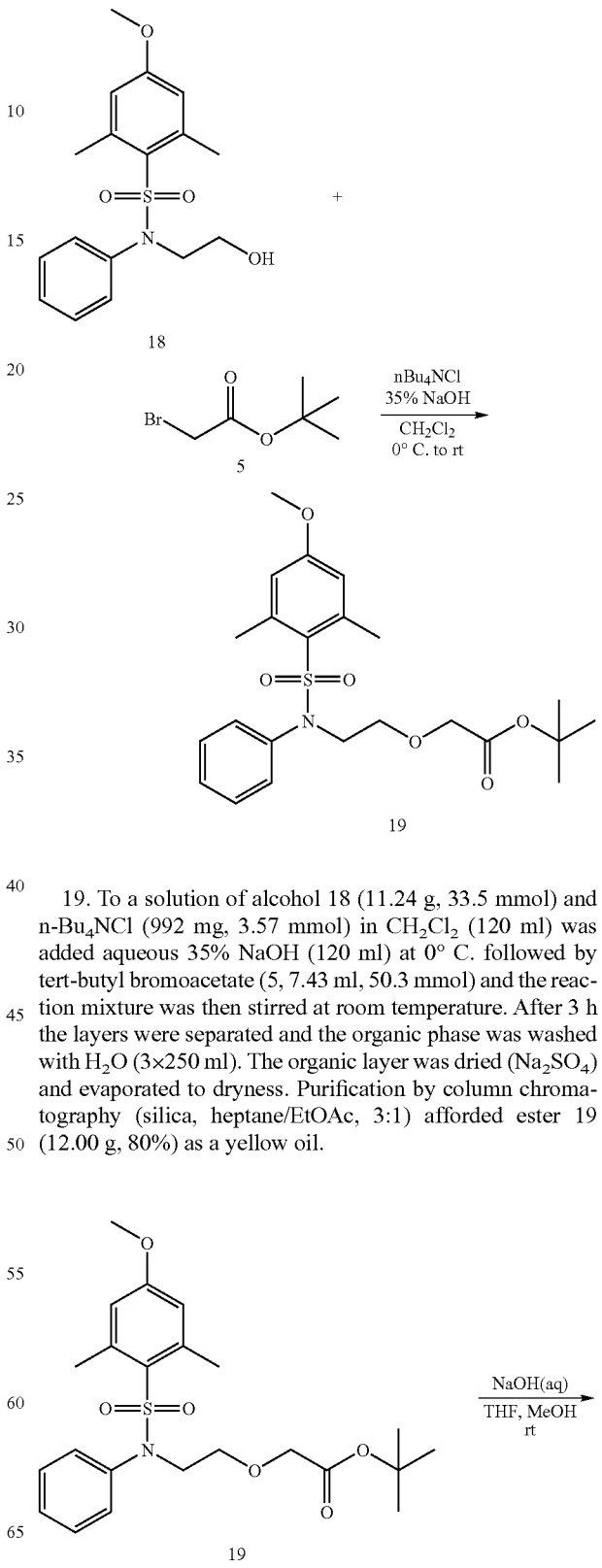

19. To a solution of alcohol 18 (11.24 g, 33.5 mmol) and n-Bu₄NCl (992 mg, 3.57 mmol) in CH₂Cl₂ (120 ml) was added aqueous 35% NaOH (120 ml) at 0° C. followed by tert-butyl bromoacetate (5, 7.43 ml, 50.3 mmol) and the reaction mixture was then stirred at room temperature. After 3 h the layers were separated and the organic phase was washed with H₂O (3×250 ml). The organic layer was dried (Na₂SO₄) and evaporated to dryness. Purification by column chromatography (silica, heptane/EtOAc, 3:1) afforded ester 19 (12.00 g, 80%) as a yellow oil.

-continued

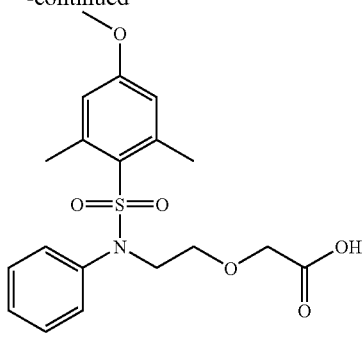

(AC-20)

To a solution of ester 19 (12.00 g, 26.70 mmol) in MeOH (200 ml) and THF (200 ml) was added aqueous 4 M NaOH (200 ml, 800 mmol) and the reaction mixture was stirred at room temperature. After 3 h the organic solvents were evaporated and the aqueous layer was acidified with aqueous 6 M HCl (250 ml). The aqueous layer was extracted with $CH_2Cl_2$ (200 ml) and the combined organic layers were dried ($Na_2SO_4$) and evaporated to dryness to afford building block AC-20 (11.27 g, '107%').

Synthesis of acid building block AC-21: 2-[2-[Benzyl-[(4-methoxy-2,6-dimethyl-phenyl)sulfonyl]-amino]-ethoxy]-acetic Acid (AC-21)

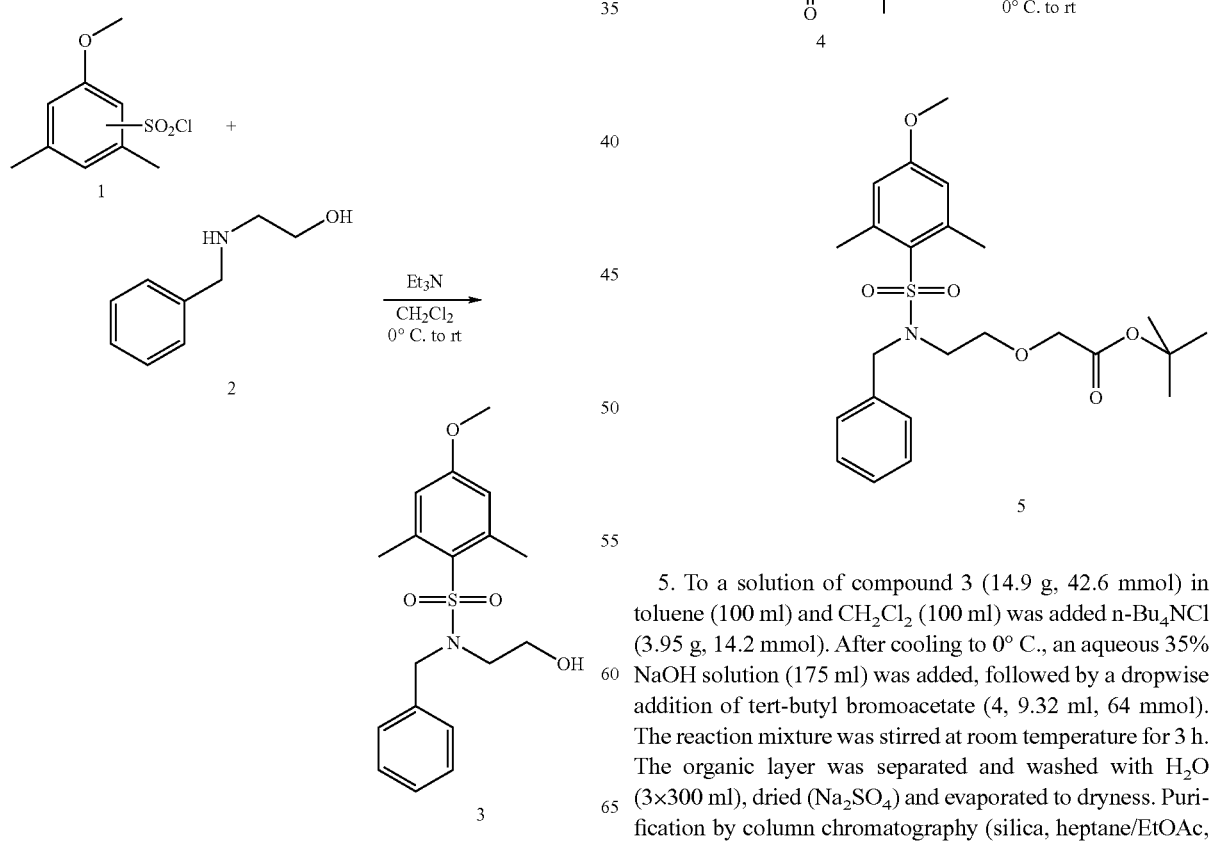

3. To a solution of N-benzylaminoethanol (2, 10.0 ml, 70.3 mmol) in $CH_2Cl_2$ (200 ml) was added $Et_3N$ (22.5 ml, 160 mmol). The mixture was cooled to 0° C. after which a solution of compound 1 (15.0 g, 63.9 mmol) in $CH_2Cl_2$ (100 ml) was added dropwise. The mixture was stirred for 3 h at room temperature. Aqueous 1 M HCl (150 ml) was added. After phase separation the organic layer was washed with water (100 ml), dried ($Na_2SO_4$) and evaporated under reduced pressure. Purification by column chromatography (silica, heptane/EtOAc, 2:1) afforded sulfonamide 3 (14.93 g, 67%).

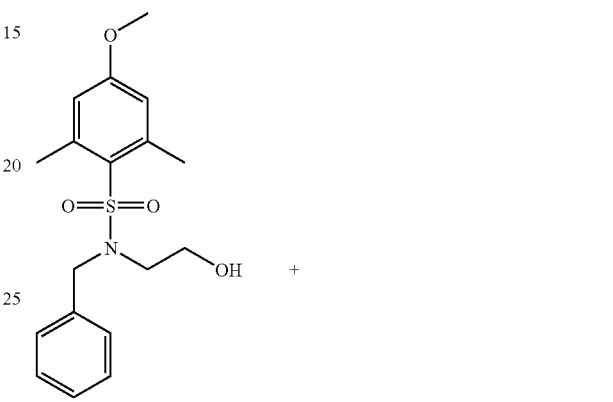

5. To a solution of compound 3 (14.9 g, 42.6 mmol) in toluene (100 ml) and $CH_2Cl_2$ (100 ml) was added n-$Bu_4NCl$ (3.95 g, 14.2 mmol). After cooling to 0° C., an aqueous 35% NaOH solution (175 ml) was added, followed by a dropwise addition of tert-butyl bromoacetate (4, 9.32 ml, 64 mmol). The reaction mixture was stirred at room temperature for 3 h. The organic layer was separated and washed with $H_2O$ (3×300 ml), dried ($Na_2SO_4$) and evaporated to dryness. Purification by column chromatography (silica, heptane/EtOAc, 3:1) afforded compound 5 (19.40 g, 98%).

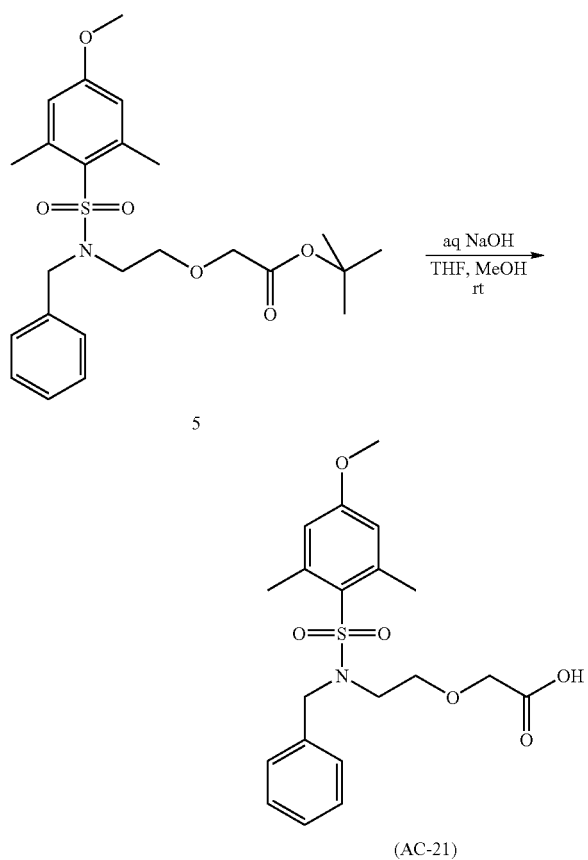

To a solution of compound 5 (19.4 g, 41.8 mmol) in THF (165 ml) and MeOH (150 ml) was added aqueous 6 M NaOH (150 ml, 900 mmol). The reaction mixture was stirred at room temperature. After 1 h the organic solvents were evaporated and aqueous 6 M HCl (155 ml) was added at 0° C. The aqueous layer was extracted with EtOAc (2×150 ml). The organic layers were combined, dried (Na$_2$SO$_4$) and evaporated to dryness. The product was co-evaporated with Et$_2$O and i-Pr$_2$O (2×) to yield compound AC-21 (17.05 g, 100%).

Synthesis of Acid Building Block AC-22: 2-[[1-[(4-Methoxy-2,6-dimethyl-phenyl)sulfonyl]-1,2,3,4-tetrahydro-quinolin-2-yl]-methoxy]-acetic Acid (AC-22)

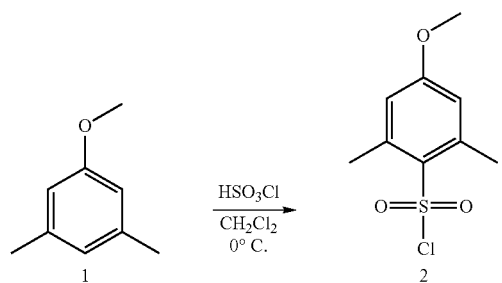

2. A solution of chlorosulfonic acid (247 ml, 3687 mmol) in CH$_2$Cl$_2$ (250 ml) was added dropwise to a solution of 3,5-dimethylanisole (1, 100.44 g, 737 mmol) in CH$_2$Cl$_2$ (1 L) at 0° C. After 15 min, the reaction mixture was poured into ice-water (1.5 L) and extracted with CH$_2$Cl$_2$ (250 ml). The organic layer was quickly washed with ice-cold H$_2$O (1 L), ice-cold aqueous saturated NaHCO$_3$ (1 L), dried (Na$_2$SO$_4$) and concentrated under reduced pressure. Purification by column chromatography (silica, heptane/CH$_2$Cl$_2$, 5:1) afforded sulfonyl chloride 2 (79.64 g, 46%) as a yellow oil which crystallised at −20° C. in the freezer overnight. The product was stored under argon in a freezer due to instability issues.

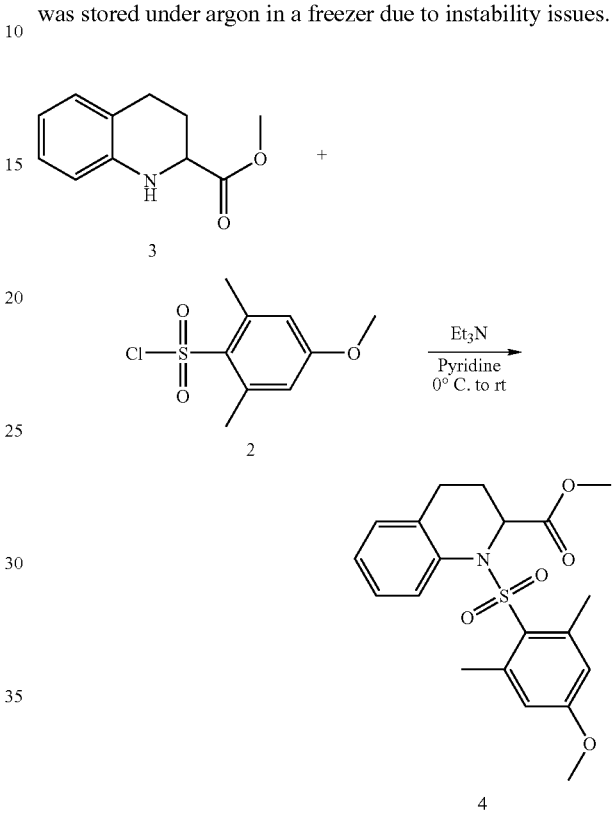

4. To a mixture of ester 3 (8.24 g, 43.1 mmol) in dry pyridine (10.5 ml, 129 mmol) was added sulfonyl chloride 2 (20.23 g, 86 mmol) and the mixture was stirred overnight at 40° C. CH$_2$Cl$_2$ (100 ml) was added and the reaction mixture was washed with aqueous 1 M HCl (100 ml), dried (Na$_2$SO$_4$) and evaporated to dryness under reduced pressure. Purification by column chromatography (silica, toluene/EtOAc, 24:1) afforded sulfonamide 4 (14.39 g, 86%).

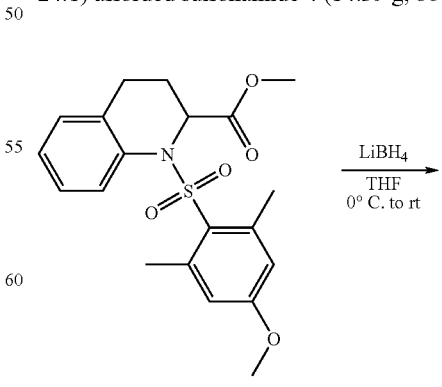

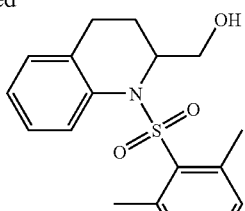

5

5. Sulfonamide 4 (14.29 g, 36.7 mmol) was dissolved in dry THF (100 ml). After cooling to 0° C. a solution of 2 M LiBH₄ in THF (33.0 ml, 66.0 mmol) was added dropwise slowly and the reaction mixture was stirred at room temperature overnight. The reaction was not complete according to TLC (silica, heptane/EtOAc, 1:1), additional 2 M LiBH₄ in THF (18.35 ml, 36.7 mmol) was added and the reaction mixture was stirred at room temperature overnight. The reaction was complete according to TLC. The reaction mixture was quenched by adding Na₂SO₄.10H₂O and H₂O, additional Na₂SO₄ was added to remove any residual H₂O, filtered, dried (Na₂SO₄) and evaporated to dryness under reduced pressure. The residue was dissolved in CH₂Cl₂ (100 ml), washed with H₂O (100 ml) and evaporated to dryness under reduced pressure to afford alcohol 5 (14.01 g, '106'%).

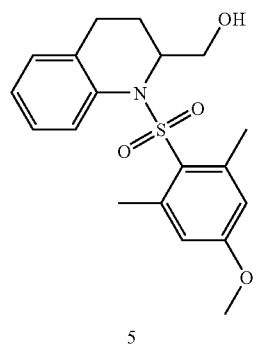

5

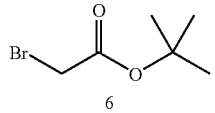

6

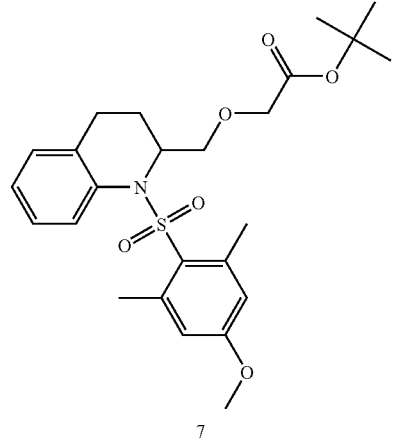

7

7. To a solution of alcohol 5 (13.23 g, max 34.7 mmol) in CH₂Cl₂ (80 ml) was added n-Bu₄NCl (3.36 g, 12.1 mmol). The reaction mixture was cooled to 0° C. after which aqueous 35% NaOH (84 ml) was added, followed by the addition of tert-butyl 2-bromoacetate (6, 6.40 ml, 43.9 mmol). After stirring for 4 h at room temperature no more starting material was observed on TLC (silica, heptane/EtOAc, 1:1). The organic layer was separated, washed with H₂O (3×150 ml) and brine (150 ml) until neutral, dried (Na₂SO₄) and concentrated under reduced pressure. Purification was carried out by subjecting the crude compound twice to column chromatography (silica, heptane/EtOAc, 4:1) and afforded ester 7 (14.90 g, 90% over 2 steps).

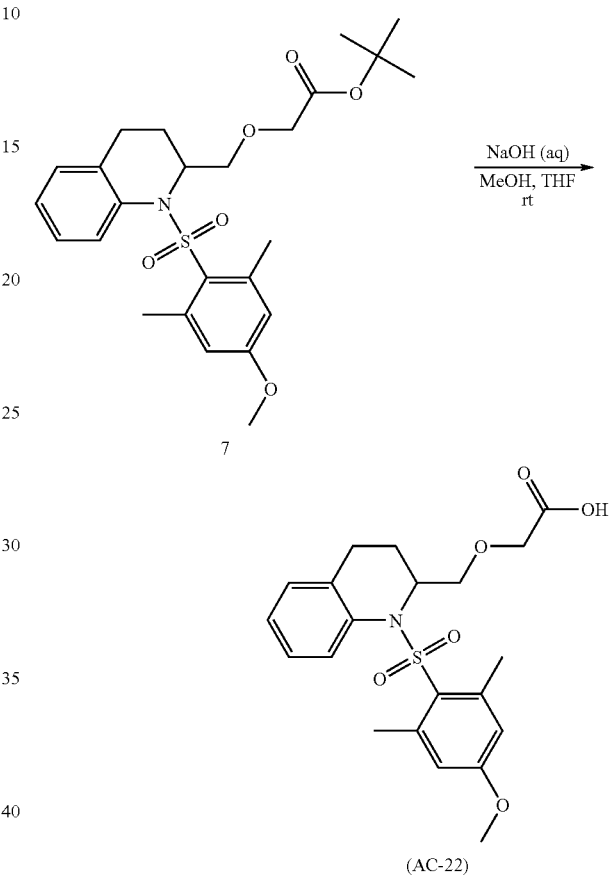

(AC-22)

A mixture of ester 7 (14.82 g, 31.2 mmol), MeOH (110 ml), THF (110 ml) and aqueous 4 M NaOH (117 ml, 467 mmol) was stirred at room temperature for 2 h. The reaction was complete according to TLC (silica, heptane/EtOAc 2:1). The solution was then concentrated under reduced pressure to remove the organic solvents. The resulting suspension was acidified with aqueous 6 M HCl (120 ml) while cooling at 0° C. CH₂Cl₂ (250 ml) was added and after separation of the layers, the organic layer was dried (Na₂SO₄) and evaporated to dryness under reduced pressure affording carboxylic acid AC-22 (12.64 g, 97%).

Synthesis of Acid Building Block AC-23: 2-[[4-[(4-Methoxy-2,6-dimethyl-phenyl)sulfonyl]-3,4-dihydro-2H-[1,4]benzoxazin-3-yl]-methoxy]-acetic Acid (AC-23)

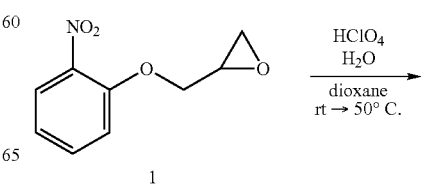

1

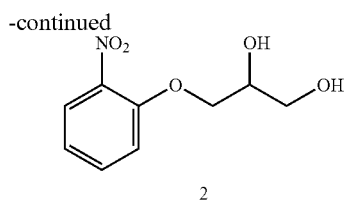

2. Perchloric acid (3.30 ml, 38.2 mmol) was added to a solution of 1 (37.3 g, 191 mmol) in dioxane (746 ml) and H₂O (568 ml) and the reaction mixture was stirred at 50° C. overnight. The reaction mixture was concentrated to half its volume and aqueous saturated NaHCO₃ was added. The H₂O layer was extracted with CH₂Cl₂ (2×) and the combined organic layer was washed with brine, dried (Na₂SO₄) and concentrated. Purification by column chromatography (silica, heptane/EtOAc, 2:3) yielded 2 (30.6 g, 75%).

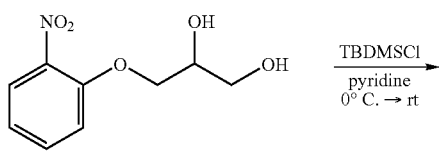

3. To a solution of 2 (30.6 g, 143 mmol) in pyridine (75 ml) was added tert-butyldimethylsilyl chloride (23.8 g, 158 mmol) while cooling with an icebath. The reaction mixture was stirred at room temperature for 2 h and afterwards concentrated and co-evaporated with toluene. The residue was dissolved in EtOAc, washed with H₂O, brine, dried (Na₂SO₄) and concentrated to give 3 (46.7 g, 99%).

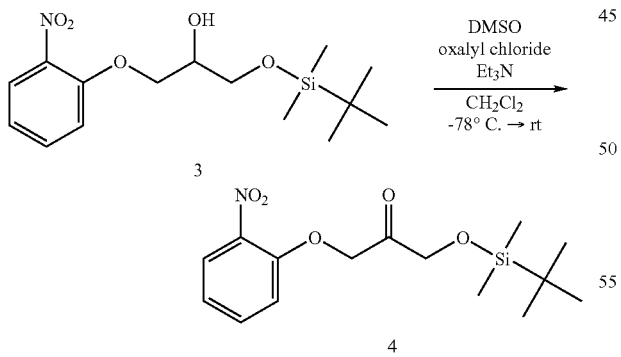

4. A solution of DMSO (21.24 ml, 299 mmol) in CH₂Cl₂ (600 ml) was dropwise added to a solution of oxalyl chloride (15.0 ml, 171 mmol) in CH₂Cl₂ (300 ml) in 30 min while maintaining the internal temperature below −65° C. A solution of 3 (46.7 g, 142 mmol) in CH₂Cl₂ (300 ml) was added dropwise in 15 min. while maintaining the temperature below −65° C. The reaction mixture was stirred an additional 45 minutes at −78° C., after which Et₃N (99.0 ml, 712 mmol) was added. After the reaction mixture was stirred at −78° C. for 45 min, the reaction mixture was allowed to warm to room temperature and stirring was continued for an additional hour. The reaction mixture was washed with H₂O and brine, dried (Na₂SO₄) and concentrated. The residue was dissolved in Et₂O, filtered and the filtrate was concentrated and crystallized (Et₂O/heptane) to result in 4 (30.9 g, 67%). The mother liquor was concentrated and crystallized (Et₂O/heptane) and gave extra 4 (2.27 g, 5%).

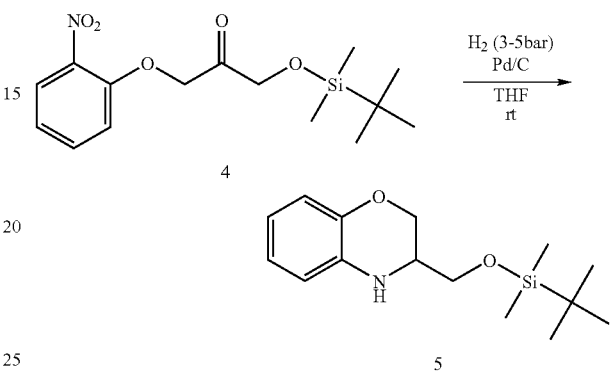

5. A mixture of 4 (18 g, 55.3 mmol) and 10% Pd/C (1.8 g, 1.7 mmol) in dry THF (150 ml) was stirred under an hydrogen atmosphere of ~3 bar for 2 days and then under an hydrogen atmosphere of 5 bar for 1 d. The reaction mixture was filtered over Celite and eluted with THF. The filtrate was concentrated and 10% Pd/C (1.8 g, 1.7 mmol) was added to the residue in dry THF (150 ml) and the resulting reaction mixture was stirred under an hydrogen atmosphere of ~5 bar for 1 d. The reaction mixture was filtered over Celite and eluted with THF. The filtrate was concentrated and purified by column chromatography (silica, heptane/Et₂O, 9:1) to yield 5 (7.11 g, 46%).

Another batch of 4 (15.06 g, 46.3 mmol) and Pd/C 10% Pd/C (1.5 g, 1.4 mmol) in dry THF (150 ml) was stirred under an hydrogen atmosphere (~5 bar) for 2 days. The reaction mixture was filtered over Celite and eluted with THF. The filtrate was concentrated and purified by column chromatography (silica, heptane/Et₂O, 9:1) to yield extra 5 (3.20 g, 25%).

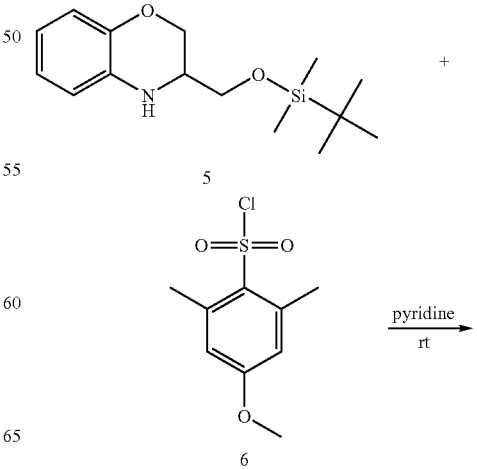

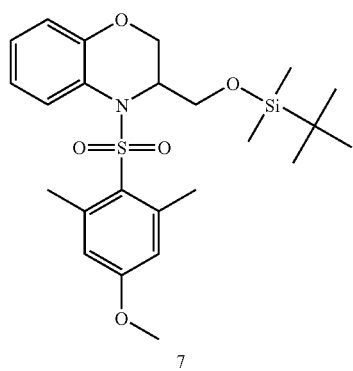

7

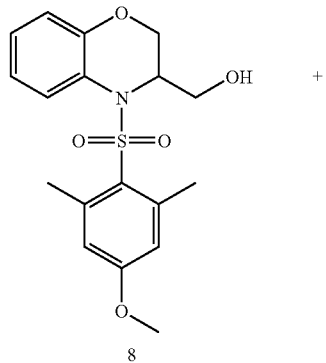

8

7. Sulfonyl chloride 6 (8.96 g, 38.2 mmol) was added to a solution of 5 (9.70 g, 34.7 mmol) in pyridine (8.42 ml) and the reaction mixture was stirred at room temperature for 2 d. The reaction mixture was concentrated, dissolved in CH₂Cl₂ and washed with H₂O, brine, dried (Na₂SO₄) and concentrated to give crude 7, which was directly used in the next step.

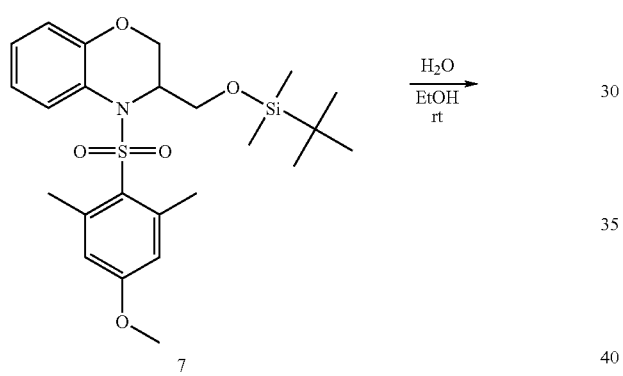

7

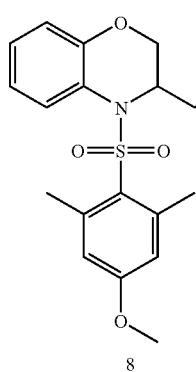

8

8. Crude 7 was dissolved in EtOH (~100 ml) and H₂O (~100 ml) with heating and was left standing overnight. The reaction mixture was concentrated, dissolved in CH₂Cl₂, washed with aqueous saturated NaHCO₃, brine, dried (Na₂SO₄) and concentrated. The residue was solidified with EtOAc/heptane (2:1) and some CH₂Cl₂. The resulting precipitate was washed with EtOAc/heptane (2:1) and dried on filter to yield 8 (9.68 g, 77% over 2 steps).

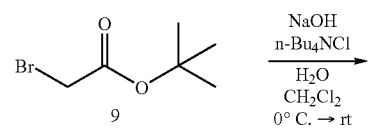

9

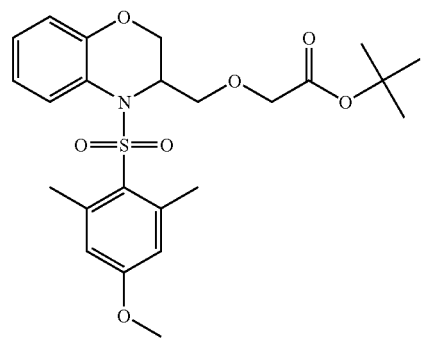

10

10. To an ice-cooled solution of 8 (9.68 g, 26.6 mmol) and n-Bu₄NCl (2.44 g, 8.79 mmol) in CH₂Cl₂ (130 ml) was sequentially added aqueous 35% NaOH solution (130 ml) and tert-butyl bromoacetate (9, 11.6 ml, 80.0 mmol). The reaction mixture was stirred at room temperature for 4.5 h, after which H₂O was added. The organic layer was separated, washed with H₂O (2×), dried (Na₂SO₄) and concentrated. The residue was purified by column chromatography (silica, heptane/EtOAc, 4:1->3:1) to provide 10 (11.9 g, 94%).

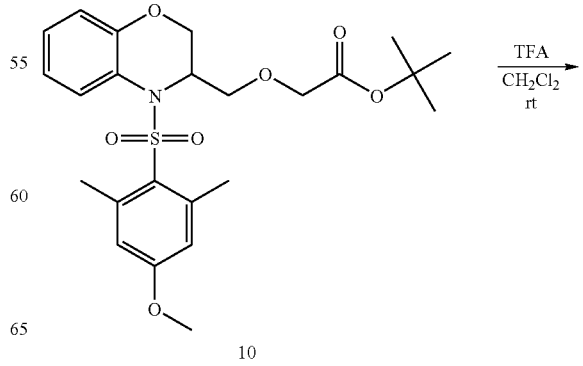

10

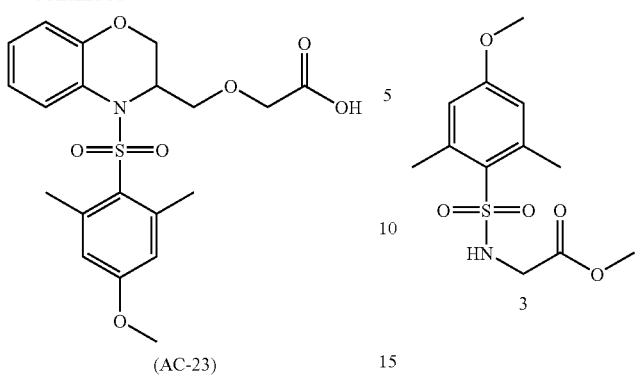

(AC-23)

A solution of 10 (11.80 g, 24.7 mmol) and TFA (25 ml, 324 mmol) in CH₂Cl₂ (125 ml) was stirred at room temperature for 2.5 h. The reaction mixture was concentrated, co-evaporated with toluene (2×) and CH₂Cl₂ (2×). The residue was dried under vacuum for 1 day to furnish AC-23 (10.26 g, 99%).

Synthesis of Acid Building Block AC-24: 2-[2-[(1-Ethyl-1H-imidazol-2-yl)-methyl-[(4-methoxy-2,6-dimethyl-phenyl)sulfonyl]-amino]-ethoxy]-acetic Acid (AC-24)

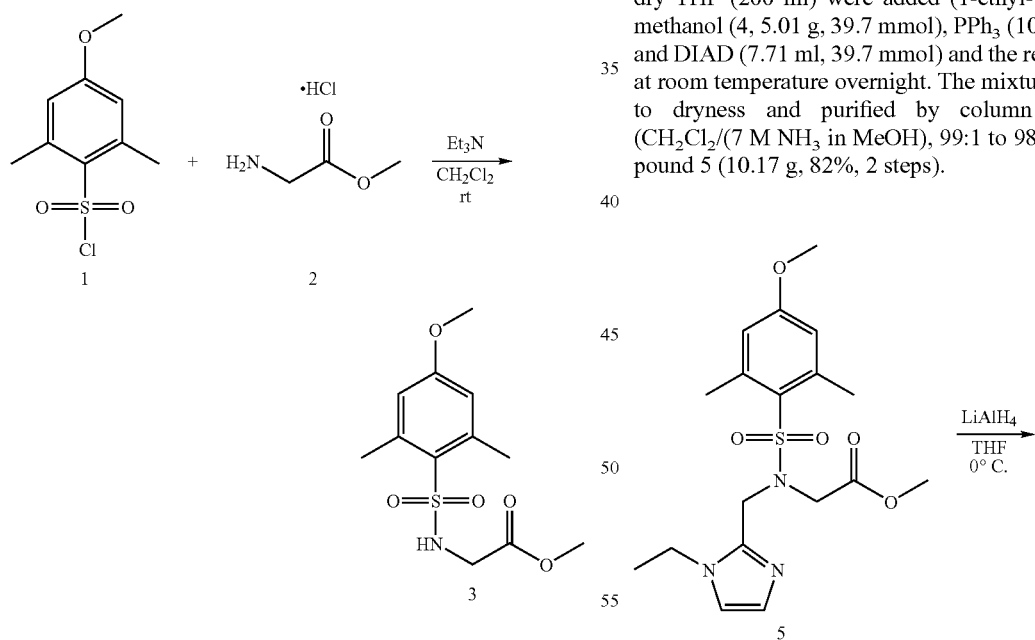

3. A solution of sulfonyl chloride 1 (15.0 g, 63.9 mmol) in CH₂Cl₂ (100 ml) was added dropwise to a stirred solution of methyl 2-aminoacetate hydrochloride (2, 8.83 g, 70.3 mmol) and Et₃N (31.2 ml, 224 mmol) in CH₂Cl₂ (200 ml). The reaction mixture was stirred at room temperature for 2 h and washed with aqueous 1 M HCl (100 ml). The organic layer was dried (Na₂SO₄) and evaporated to dryness to afford compound 3 (19.3 g, '105%').

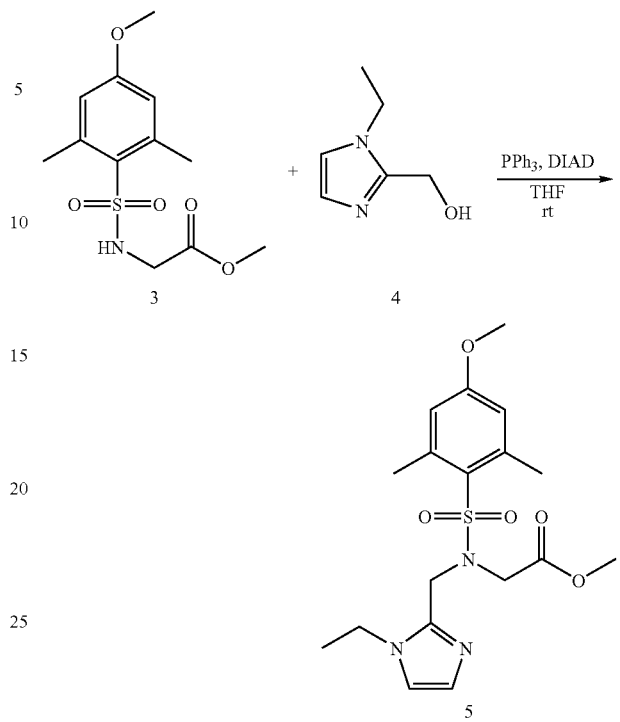

5. To a solution of compound 3 (9.50 g, max. 31.5 mmol) in dry THF (200 ml) were added (1-ethyl-1H-imidazol-2-yl) methanol (4, 5.01 g, 39.7 mmol), PPh₃ (10.41 g, 39.7 mmol) and DIAD (7.71 ml, 39.7 mmol) and the reaction was stirred at room temperature overnight. The mixture was evaporated to dryness and purified by column chromatography (CH₂Cl₂/(7 M NH₃ in MeOH), 99:1 to 98:2) to afford compound 5 (10.17 g, 82%, 2 steps).

-continued

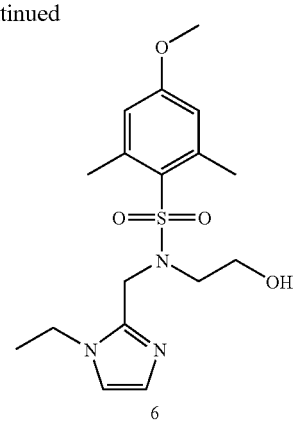

6

6. A solution of ester 5 (10.17 g, 25.7 mmol) in dry THF (50 ml) was added dropwise to a stirred and cooled (0° C.) solution of LiAlH₄ (2.4 M in THF, 36 ml, 86 mmol) in THF (50 ml). After 15 min the reaction mixture was quenched with a mixture of THF/H₂O (1:1, 36 ml). The suspension was filtered over a small pad of Na₂SO₄. The residue was refluxed in THF (500 ml) for 1 h and the warm mixture was filtered over a small path of Na₂SO₄. The combined filtrates were evaporated to dryness to afford alcohol 6 (8.17 q, 86%).

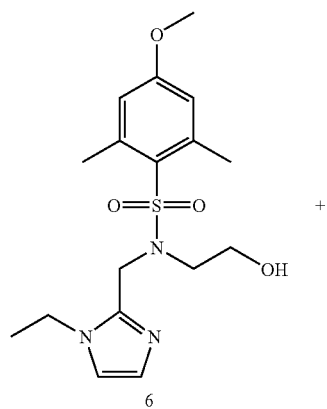

6

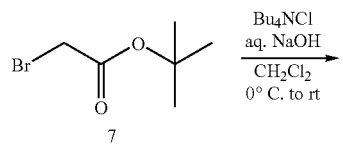

7

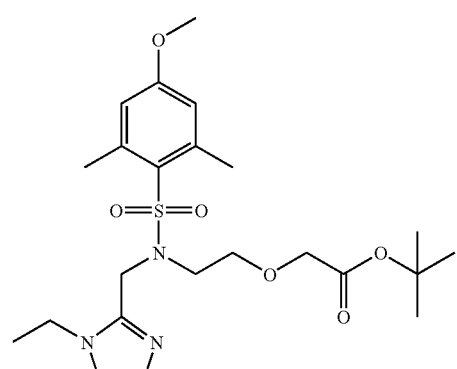

8

8. To a solution of alcohol 6 (8.17 g, 22.2 mmol) and Bu₄NCl (2.04 g, 7.34 mmol) in CH₂Cl₂ (100 ml) was added aqueous 35% NaOH (50.8 ml) at 0° C. followed by tert-butyl bromoacetate (7, 6.48 ml, 44.5 mmol). The reaction mixture was stirred at room temperature and after 1 h more tert-butyl bromoacetate (3.24 ml, 22.2 mmol) was added. After 1 h the layers were separated. The organic layer was washed with H₂O (500 ml), dried (Na₂SO₄) and directly purified by column chromatography (silica, CH₂Cl₂/(7 M NH₃ in MeOH), 98:2) to afford ester 8 (6.50 g, 61%).

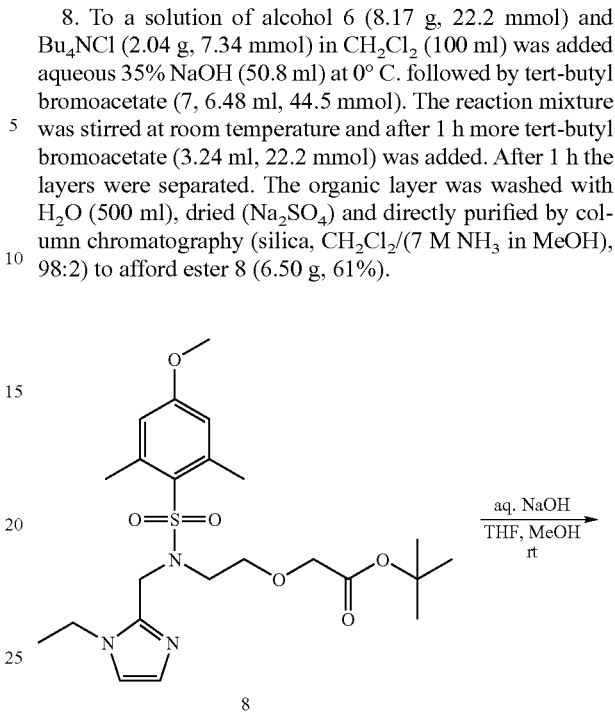

Ac-24

To a solution of ester 8 (6.50 g, 13.50 mmol) in THF (50 ml) and MeOH (50 ml) was added aqueous 6 M NaOH (45.0 ml, 270 mmol) and the reaction mixture was stirred at room temperature. After 1 h the organic solvents were evaporated and the residue was acidified with aqueous 6 M HCl (50 ml). The mixture was extracted with CH₂Cl₂ (2×150 ml). The combined organic layers were dried (Na₂SO₄) and evaporated to dryness. Crystallization from i-PrOH afforded building block AC-24 (4.30 g, 75%).

Synthesis of Acid Building Block AC-25: 2-[[4-[[2-(Trifluoromethyl)-phenyl]sulfonyl]-3,4-dihydro-2H-[1,4]benzoxazin-3-yl]-methoxy]-acetic Acid (AC-25)

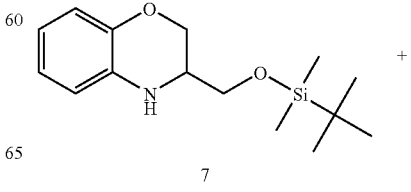

7

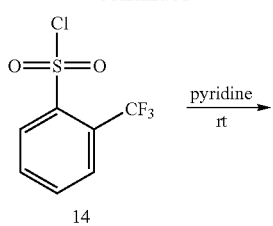

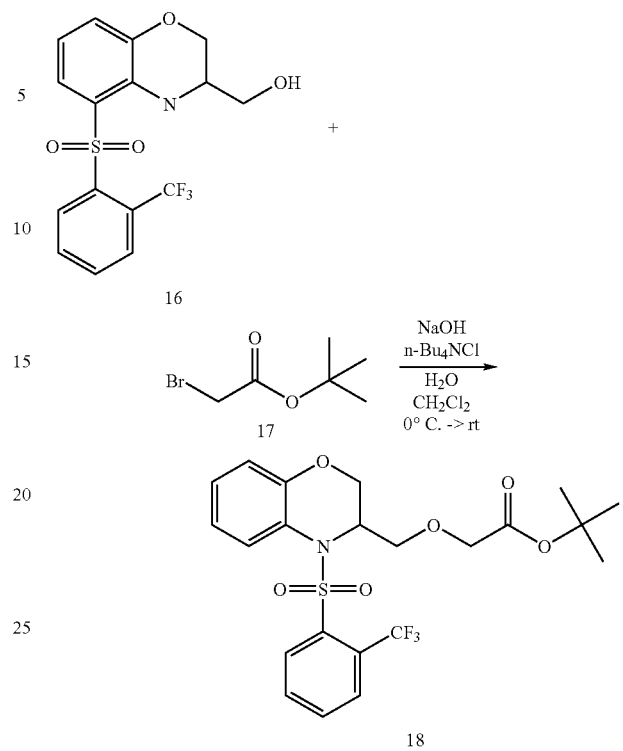

15. 2-(trifluoromethyl)benzenesulfonyl chloride (14, 8.50 g, 34.8 mmol) was added to a solution of 7 (8.83 g, 31.6 mmol) in pyridine (7.67 ml, 95.0 mmol) and the reaction mixture was stirred at room temperature overnight. $CH_2Cl_2$ and $H_2O$ were added to the reaction mixture and the organic layer was separated, washed with brine and concentrated to give crude 15, which was directly used as such in the next step.

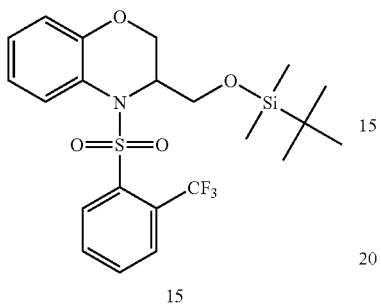

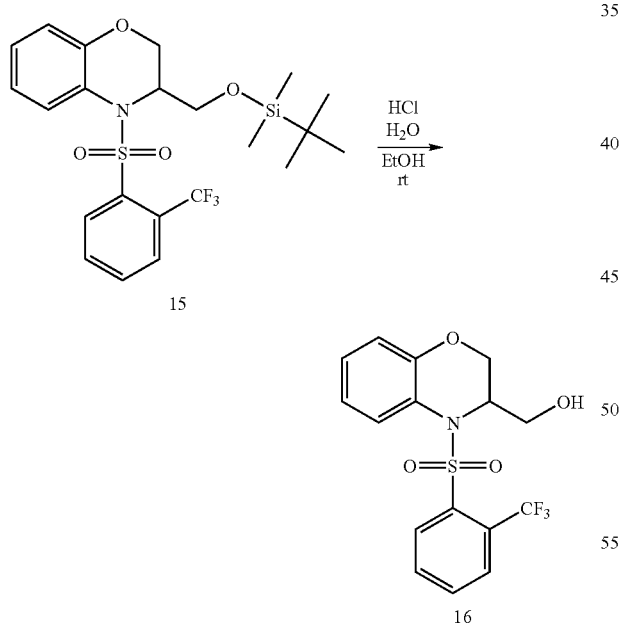

16. Aqueous 1 M HCl (50 ml, 50 mmol) was added to crude 15 in EtOH (200 ml) and the reaction mixture was stirred at room temperature overnight. The reaction mixture was concentrated, dissolved in $CH_2Cl_2$, washed with aqueous saturated $NaHCO_3$, dried ($Na_2SO_4$) and concentrated. The residue was purified by column chromatography (silica, heptane/EtOAc: 2:1) to yield 16 (10.29 g, 78%, 2 steps).

18. To an ice-cooled solution of 16 (10.29 g, 24.81 mmol) and n-Bu$_4$NCl (2.28 g, 8.19 mmol) in $CH_2Cl_2$ (125 ml) was sequentially added aqueous 35% NaOH solution (125 ml) and tert-butyl bromoacetate (17, 10.83 ml, 74.4 mmol). The reaction mixture was stirred at room temperature for 4 h, after which $H_2O$ was added. The organic layer was separated, washed with $H_2O$ and brine, dried ($Na_2SO_4$) and concentrated. The residue was purified by column chromatography (silica, heptane/EtOAc, 4:1) to provide 18 (11.65 g, 93%).

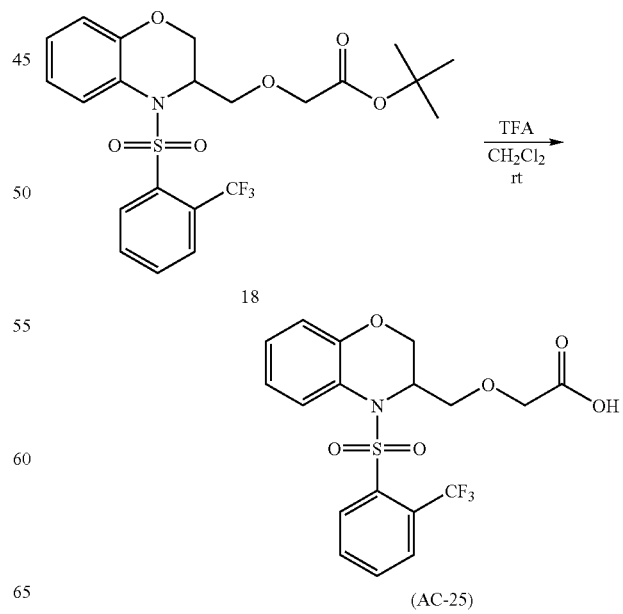

A solution of 18 (11.55 g, 22.98 mmol) and TFA (20 ml, 260 mmol) in CH$_2$Cl$_2$ (100 ml) was stirred at room temperature for 2 h. The reaction mixture was concentrated, co-evaporated with toluene (2×) and CH$_2$Cl$_2$ (2×). The residue was transferred to a jar with CH$_2$Cl$_2$, concentrated and dried under vacuum overnight to furnish AC-25 (10.18 g, '103'%).

Synthesis of Acid Building Block AC-26: 2-[2-[4H-[1,3]Benzodioxin-7-yl-methyl-[(4-methoxy-2,6-dimethyl-phenyl)sulfonyl]-amino]-ethoxy]-acetic Acid (AC-26)

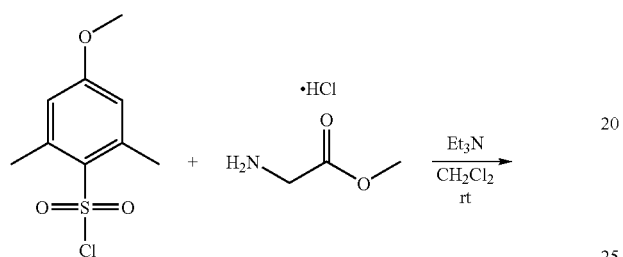

3. A solution of sulfonyl chloride 1 (15.0 g, 63.9 mmol) in CH$_2$Cl$_2$ (100 ml) was added dropwise to a stirred solution of methyl 2-aminoacetate hydrochloride (2, 8.83 g, 70.3 mmol) and Et$_3$N (31.2 ml, 224 mmol) in CH$_2$Cl$_2$ (200 ml). The reaction mixture was stirred at room temperature for 2 h and washed with aqueous 1 M HCl (100 ml). The organic layer was dried (Na$_2$SO$_4$) and evaporated to dryness to afford compound 3 (19.3 g, '105%').

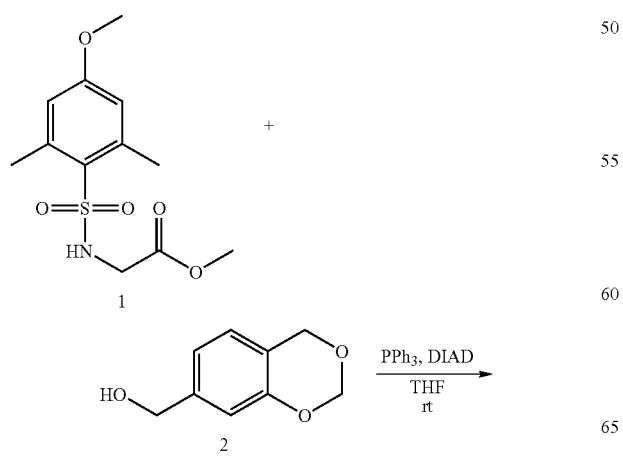

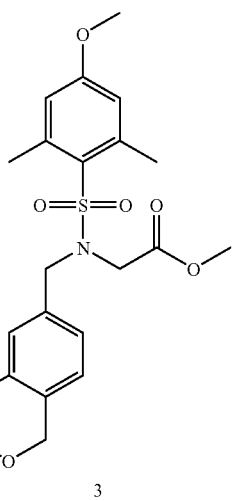

3. To a solution of compound 1 (9.08 g, max. 30.1 mmol), (4H-benzo[d][1,3]dioxin-7-yl)methanol (2, 5.25 g, 31.6 mmol) and PPh$_3$ (9.95 g, 37.9 mmol) in dry THF (200 ml) was added DIAD (7.37 ml, 37.9 mmol) and the mixture was stirred at room temperature overnight. The mixture was filtered and the filtrate was evaporated to dryness. Purification by column chromatography twice (silica, heptane/EtOAc, 3:1 and silica, toluene/EtOAc, 23:2) afforded sulfonamide 3 (5.29 g, 40%, 2 steps).

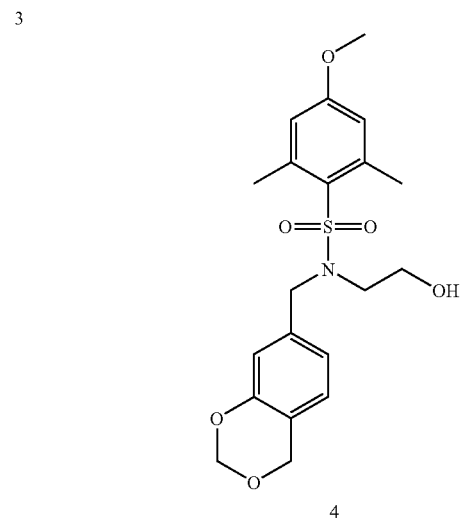

4. To a cooled (0° C.) and stirred solution of LiAlH₄ (2.4 M in THF, 15.2 ml, 36.4 mmol) in dry THF (50 ml), a solution of sulfonamide 3 (5.29 g, 12.2 mmol) in dry THF (100 ml) was added dropwise. After 5 min the reaction mixture was quenched with a mixture of THF/H₂O (1:1,16 ml). The mixture was filtered over a small pad of Na₂SO₄ and rinsed with THF. The filtrate was evaporated to dryness to afford alcohol 4 (5.03 g, '102%').

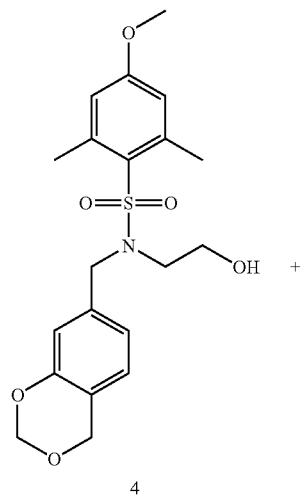
4

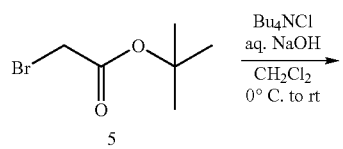
5

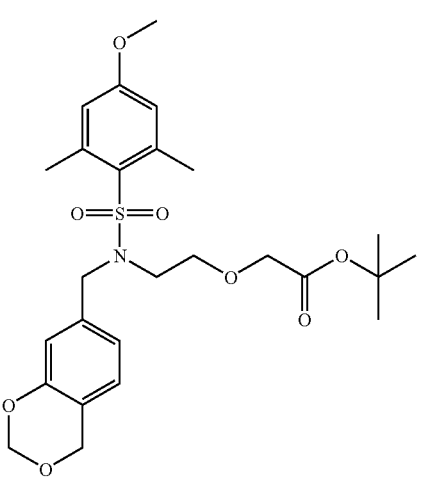
6

6. To a cooled (0° C.) solution of alcohol 4 (5.03 g, max 12.2 mmol) and Bu₄NCl (1.10 g, 3.97 mmol) in CH₂Cl₂ (50 ml) was added aqueous 35% NaOH (27.5 ml) followed by tert-butyl bromoacetate (5, 2.63 ml, 18.04 mmol). The reaction mixture was then stirred at room temperature. After 2 h more tert-butyl bromoacetate (5, 438 μL, 3.01 mmol) was added. After 2 h the layers were separated and the organic layer was washed with H₂O (3×100 ml). The organic layer was dried (Na₂SO₄) and evaporated to dryness. Purification by column chromatography (silica, toluene/EtOAc, 23:2) afforded ester 6 (6.29 g, 99%, 2 steps).

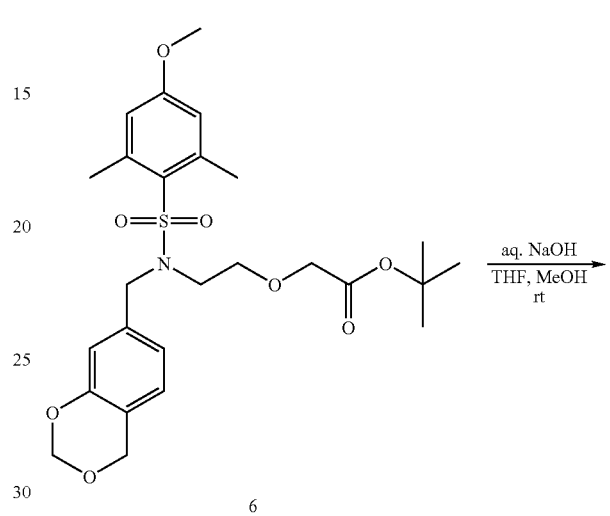
6

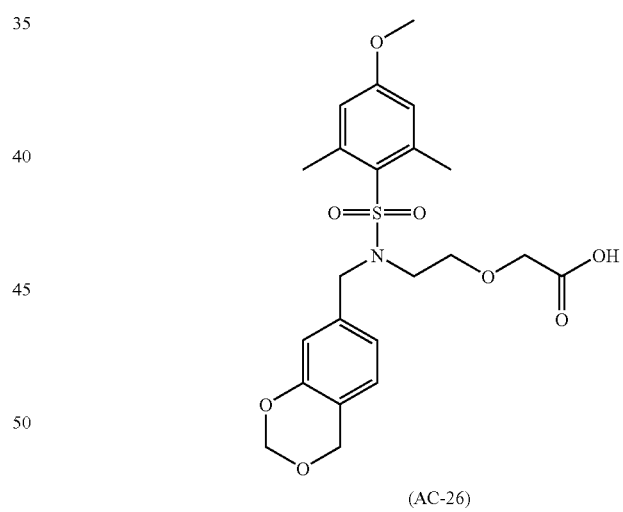
(AC-26)

To a solution of ester 6 (6.25 g, 12.0 mmol) in THF (45 ml) and MeOH (45 ml) was added aqueous 6 M NaOH (39.9 ml, 240 mmol) and the reaction mixture was stirred at room temperature. After 1 h the organic solvents were evaporated. The residue was acidified with aqueous 6 M HCl (45 ml) and the mixture was extracted with CH₂Cl₂ (2×100 ml). The combined organic layers were dried (Na₂SO₄) and evaporated to dryness. Purification by column chromatography (silica, CH₂Cl₂/MeOH, 98:2+1% AcOH) afforded building block AC-26 (4.40 g, 79%)

| Amine Building Block No. | Structure | Name |
|---|---|---|
| AMN-01 | (structure) · HCl | 2-(Pyridin-4-yl)-4,5,6,7-tetrahydrothiazolo[5,4-c]pyridine hydrochloride |
| AMN-02 | (structure) · HCl | 2-(Pyridin-4-ylmethyl)-4,5,6,7-tetrahydrothiazolo[5,4-c]pyridine hydrochloride |
| AMN-03 | (structure) | tert-Butyl 2-((4-methylpiperazin-1-yl)methyl)-6,7-dihydrothieno[3,2-c]pyridine-5(4H)-carboxylate |
| AMN-04 | (structure) · H—Cl | 2-Phenyl-4,5,6,7-tetrahydro-oxazolo[5,4-c]pyridine hydrochloride (AMN-04) |
| AMN-05 | (structure) · H—Cl · H—Cl | 3-(4-Chlorophenyl)-4,5,6,7-tetrahydro-1H-pyraozlo[4,3-c]pyridine dihydrochloride (AMN-05) |
| AMN-06 | (structure) | 4-Pyridin-4-Yl-4,5,6,7-tetrahydro-1H-imidazo[4,5-c]pyridine (AMN-06) |
| AMN-07 | (structure) | 4-Phenyl-4,5,6,7-tetrahydro-1H-imidazo[4,5-c]pyridine (AMN-07) |
| AMN-08 | (structure) · H—Cl | 1-Phenyl-3-(Trifluoromethyl)-1,4,5,6-tetrahydro-pyrrolo[3,4-c]pyrazole hydrochloride (AMN-08) |

Synthesis of the amine units for the parallel synthesis

| Synthesis of the amine units for the parallel synthesis | | | |
|---|---|---|---|
| Amine Building Block No. | Structure | | Name |
| AMN-09 | [Structure: 1-Methyl-3-(trifluoromethyl)-1,4,5,6-tetrahydro-pyrrolo[3,4-c]pyrazole hydrochloride, shown with HN-containing ring fused to pyrazole with CF₃ group, N-methyl, and H-Cl] | | 1-Methyl-3-(Trifluoromethyl)-1,4,5,6-tetrahydro-pyrrolo[3,4-c]pyraozle hydrochloride (AMN-09) |

2-(Pyridin-4-yl)-4,5,6,7-tetrahydrothiazolo[5,4-c]pyridine Hydrochloride (AMN-01)

Stage 1: Ethyl 3-bromo-4-oxopiperidine-1-carboxylate

Copper(II) bromide (5.2 g; 23.38 mmol) was added to a refluxing solution of N-ethoxycarbonylpiperidone (2 g; 11.6 mmol) in a chloroform/ethanol mixture (1:1, 23 ml) under an inert gas atmosphere. When the addition was complete, the reaction mixture was heated for 45 minutes until the green color and the dark solid disappeared. Thereafter, the reaction mixture was cooled to 25° C. and filtered and the filtrate was concentrated under reduced pressure. For working up, the residue was taken up in ethyl acetate and the mixture was washed with water, sodium carbonate solution and saturated sodium chloride solution. After the organic phase had been dried over sodium sulfate, the solvent was removed under reduced pressure. The crude product obtained was employed in the next stage without further purification. The crude yield was 70%.

Stage 2: Ethyl 2-(pyridin-4-yl)-6,7-dihydrothiazolo[5,4-c]pyridine-5(4H)-carboxylate Thioisonicotinamide (18 mmol) and calcium carbonate (200 mmol) were added to a solution of ethyl 3-bromo-4-oxopiperidine-1-carboxylate (5 g; 20 mmol) in 2-propanol (60 ml). The reaction mixture obtained was heated under reflux for 48 hours. The course of the reaction was monitored by thin layer chromatography. The reaction mixture was then cooled to 25° C. and filtered over Celite and the filter cake was washed several times with ethyl acetate. The organic phase was concentrated under reduced pressure, the residue was taken up in ethyl acetate and the mixture was washed successively with water and saturated sodium chloride solution. After the organic phase had been dried over sodium sulfate, the solvent was removed under reduced pressure. The crude product obtained was purified by column chromatography (30% ethyl acetate in hexane). The desired product was obtained in a yield of 20%.

Stage 3: 2-(Pyridin-4-yl)-4,5,6,7-tetrahydrothiazolo[5,4-c]pyridine Hydrochloride (AMN-01)

A solution of ethyl 2-(pyridin-4-yl)-6,7-dihydrothiazolo[5,4-c]pyridine-5(4H)-carboxylate (1.8 mmol) in a 3.5 N potassium hydroxide solution (3 ml) was heated under reflux for 3 hours. The course of the reaction was monitored by thin layer chromatography. The reaction mixture was then cooled to 0° C. and acidified with concentrated hydrochloric acid. The solid which had precipitated was filtered out and dried. The product was obtained in the form of the HCl salt. The yield was 30%.

2-(Pyridin-4-ylmethyl)-4,5,6,7-tetrahydrothiazolo[5,4-c]pyridine hydrochloride (AMN-02)

Stage 1: 2-(Pyridin-4-yl)Ethanethioamide

Hydrogen sulfide was passed through a solution of 2-(pyridin-4-yl)acetonitrile (2.5 g) in 30% strength ammoniacal methanol (12 ml) at 0° C. for 30 minutes. The resulting reaction mixture was stirred at 25° C. for 16 hours. The solid which had precipitated was filtered out, washed with ether and dried. The desired product was obtained in a yield of 76%.

Stage 2: Ethyl 2-(pyridin-4-ylmethyl)-6,7-dihydrothiazolo[5,4-c]pyridine-5(4H)-carboxylate 2-(Pyridin-4-yl)ethanethioamide (6 mmol) and 20 mmol of calcium carbonate were added to a solution of ethyl 3-bromo-4-oxopiperidine-1-carboxylate (1 g; 4 mmol; cf. AMN-01) in 20 ml of 2-propanol. The reaction mixture obtained was heated under reflux for 20 hours. The course of the reaction was monitored by thin layer chromatography. The reaction mixture was then cooled to 25° C. and filtered over Celite. The filter cake was washed several times with ethyl acetate. The organic phase was concentrated under reduced pressure, the residue was taken up in ethyl acetate and the mixture was washed successively with water and saturated sodium chloride solution. After the organic phase had been dried over sodium sulfate, the solvent was removed under reduced pressure. The crude product obtained was purified by column chromatography (30% ethyl acetate in hexane). The desired product was obtained in a yield of 70%.

Stage 3: 2-(Pyridin-4-ylmethyl)-4,5,6,7-tetrahydrothiazolo[5,4-c]pyridine hydrochloride A solution of ethyl 2-(pyridin-4-ylmethyl)-6,7-dihydrothiazolo[5,4-c]pyridine-5(4H)-carboxylate (3.7 mmol) in a 3.5 N potassium hydroxide solution (7 ml) was heated under reflux for 3 hours. The course of the reaction was monitored by thin layer chromatography. The reaction mixture was then cooled to 0° C. and acidified with concentrated hydrochloric acid. The solid which precipitated was filtered out and dried. The product was obtained in the form of the HCl salt. The desired product was obtained in a yield of 35%.

tert-Butyl 2-((4-methylpiperazin-1-yl)methyl)-6,7-dihydrothieno[3,2-c]pyridine-5(4H)-carboxylate (AMN-03)

Stage 1: Ethyl 4-chloro-3-formyl-5,6-dihydropyridine-1(2H)-carboxylate $POCl_3$ (2.18 g, 23.4 mmol) was added very slowly to 2.7 ml of dry DMF at 0° C. The mixture obtained was stirred at 25° C. for 15 minutes. After the reaction temperature had been reduced again to 0° C., N-ethoxycarbonylpiperidone (11.7 mmol) was added. The reaction mixture obtained was stirred at 25° C. for 3 hours. Thereafter, sodium acetate (7 g) and water (8.5 ml) were added and the mixture was stirred. The reaction mixture was extracted with benzene. The organic phase was washed successively with water, sodium carbonate and saturated sodium chloride solution. After the organic phase had been dried over sodium sulfate, the solvent was removed under reduced pressure. The crude product obtained was employed in the next stage without further purification. The crude yield was 63%.

Stage 2: Diethyl 6,7-dihydrothieno[3,2-c]pyridine-2,5(4H)-dicarboxylate

Triethylamine (9.62 mmol) was added to a ° C. cold solution of ethyl 4-chloro-3-formyl-5,6-dihydropyridine-1(2H)-carboxylate (7.4 mmol) in pyridine (3 ml) and the reaction mixture obtained was stirred at 25° C. for 3 hours. 50% strength aqueous potassium hydroxide solution (5 ml) was then added. The reaction mixture obtained was stirred at 25° C. for 3 hours and then diluted with ethyl acetate. The reaction mixture was washed with water and saturated sodium chloride solution and dried over sodium sulfate. After the solvent had been removed under reduced pressure, the crude product obtained was purified by column chromatography (50% ethyl acetate in hexane). The desired product was obtained in a yield of 25%.

Stage 3: 4,5,6,7-Tetrahydrothieno[3,2-c]pyridine-2-carboxylic Acid Hydrochloride A solution of diethyl 6,7-dihydrothieno[3,2-c]pyridine-2,5(4H)-dicarboxylate (1.76 mmol) in 3.5 N potassium hydroxide solution (3 ml) was heated under reflux for 3 hours. The course of the reaction was monitored by thin layer chromatography. The reaction mixture was then cooled to 0° C. and acidified with concentrated hydrochloric acid. The solid which had precipitated was filtered out and dried. The desired product was obtained in a yield of 30%.

Stage 4 and 5: 5-tert-Butyl 2-methyl 6,7-dihydrothieno[3,2-c]pyridine-2,5(4H)-dicarboxylate Thionyl chloride (1.5 eq.) was added to a 0° C. cold suspension of 4,5,6,7-tetrahydrothieno[3,2-c]pyridine-2-carboxylic acid hydrochloride (1.9 mmol) in methanol (10 ml). The reaction mixture obtained was heated under reflux for 16 hours and the solvent was then removed under reduced pressure. The residue was taken up in methylene chloride (10 ml) and cooled to 0° C. Triethylamine (3 eq.) and Boc anhydride (1.2 eq.) were added to this ice-cold mixture. The reaction mixture obtained was stirred at 25° C. for 12 hours and then diluted with methylene chloride. The reaction mixture was washed with water and saturated sodium chloride solution and dried over sodium sulfate. After the solvent had been removed under reduced pressure, the crude product was purified by column chromatography (10% ethyl acetate in hexane). The desired product was obtained in a yield of 50%.

Stage 6: tert-Butyl 2-(hydroxymethyl)-6,7-dihydrothieno[3,2-c]pyridine-5(4H)-carboxylate DIBAL-H (11.1 mmol) was added to a −78° C. cold solution of 5-tert-butyl 2-methyl 6,7-dihydrothieno[3,2-c]pyridine-2,5(4H)-dicarboxylate (1.5 g, 5.3 mmol) in dry toluene (30 ml). The reaction mixture obtained was stirred at −78° C. for 1.5 hours. The course of the reaction was monitored by thin layer chromatography. Methanol (12 ml) was then added to the reaction mixture, the mixture was warmed slowly to 25° C. and thereafter saturated sodium chloride solution was added. The reaction mixture was filtered over Celite and the filter cake was washed with ethyl acetate. The organic phases were concentrated under reduced pressure. The crude product obtained in this way was employed in the next stage without further purification. The crude yield was 1.4 g.

Stage 7: tert-Butyl 2-((methylsulfonyloxy)methyl)-6,7-dihydrothieno[3,2-c]pyridine-5(4H)-carboxylate Triethylamine (21.2 mmol) and methanesulfonyl chloride (7.95 mmol) were added to a 0° C. cold solution of tert-butyl 2-(hydroxymethyl)-6,7-dihydrothieno[3,2-c]pyridine-5(4H)-carboxylate (5.3 mmol) in methylene chloride (22 ml). The reaction mixture obtained was stirred at 0° C. for 2 hours. The course of the reaction was monitored by thin layer chromatography. The reaction mixture was then diluted with methylene chloride and washed successively with water and saturated sodium chloride solution. After the organic phase had been dried over sodium sulfate, the solvent was removed under reduced pressure. The crude product obtained was employed in the next stage without further purification.

Stage 8: tert-Butyl 2-((4-methylpiperazin-1-yl)methyl)-6,7-dihydrothieno[3,2-c]pyridine-5(4H)-carboxylate (AMN-03)

Potassium carbonate (26.5 mmol) and N-methylpiperazine (6.36 mmol) was added to a solution of tert-butyl 2-((methylsulfonyloxy)methyl)-6,7-dihydrothieno-[3,2-c]pyridine-5(4H)-carboxylate (5.3 mmol) in toluene (30 ml). The reaction mixture obtained was heated under reflux for 16 hours. The reaction temperature was then reduced to 25° C. and the reaction mixture was diluted with ethyl acetate. The reaction mixture was washed with water and saturated sodium chloride solution and dried over sodium sulfate. After the solvent had been removed under reduced pressure, the crude product obtained was purified by column chromatography (5% methanol in methylene chloride). The desired product was obtained in a yield of 50%.

Amine-04: 2-Phenyl-4,5,6,7-tetrahydro-oxazolo[5,4-c]pyridine [885272-73-1] commercially available at e.g. ChemImpex.

Amine-05: 3-(4-Chlorophenyl)-4,5,6,7-tetrahydro-1h-pyrazolo[4,3-c]pyridine Hydrochloride [MFCD09763695] commercially available at e.g. Otava-BB.

Amine-06: 4-Pyridin-4-yl-4,5,6,7-tetrahydro-3h-imidazo[4,5-c]pyridine [MFCD09749722] commercially available at e.g. Otava-BB.

Amine-07: 4-Phenyl-4,5,6,7-tetrahydro-1h-imidazo[4,5-c]pyridine [4875-39-2] commercially available at e.g. BBB-SCl.

Amine-08: 1,4,5,6-Tetrahydro-1-phenyl-3-(trifluoromethyl)pyrrolo-[3,4-c]-pyrazole [MFCD08447382] commercially available at e.g. BBB-SCl.

Amine-09: 1,4,5,6-Tetrahydro-1-methyl-3-(trifluoromethyl)pyrrolo-[3,4-c]-pyrazole [MFCD08447379] commercially available at e.g. BBB-SCl.

Pharmacological Studies

The agonistic and antagonistic action of the compounds according to the invention on the bradykinin 1 receptor (B1R) of the human and rat species were determined as described above. Antagonists lead to a suppression of the $Ca^{2+}$ inflow. % inhibition compared with the maximum achievable inhibition was calculated. The compounds according to the invention show a good activity on the human and on the rat receptor.

| Example | B1R antagonism, rat [10 µM] % inhibition | B1R antagonism, human (10 µM) % inhibition |
|---|---|---|
| 01 | 98 | 46 |
| 02 | 101 | 100 |
| 03 | 102 | 83 |
| 04 | 56 | — |
| 05 | 27 | 48 |
| 06 | 57 | 93 |
| 07 | 104 | 69 |
| 08 | 106 | 48 |
| 09 | 105 | 100 |
| 10 | 105 | 78 |
| 11 | 60 | 7 |
| 12 | 104 | 64 |
| 13 | 99 | 56 |
| 14 | 99 | 85 |
| 15 | 98 | 69 |
| 16 | 81 | 43 |
| 17 | 55 | 49 |
| 18 | 109 | 99 |
| 19 | 83 | 35 |
| 20 | 96 | 11 |
| 21 | 70 | 34 |
| 22 | 100 | 96 |
| 23 | 105 | 91 |
| 24 | 100 | 73 |
| 25 | 103 | 86 |
| 26 | 101 | 97 |
| 27 | 106 | 100 |
| 28 | 109 | 100 |
| 29 | 101 | 99 |
| 30 | 104 | 99 |
| 31 | 105 | 100 |
| 32 | 104 | 99 |
| 33 | 35 | 40 |
| 34 | 57 | 29 |
| 35 | 3 | 41 |
| 36 | 100 | 100 |
| 37 | 97 | 28 |
| 38 | 97 | 99 |
| 39 | 99 | 100 |
| 40 | 90 | 51 |
| 41 | 99 | 64 |
| 42 | 79 | 14 |
| 43 | 99 | 99 |
| 44 | 59 | 83 |
| 45 | 99 | 98 |
| 46 | 102 | 100 |
| 47 | 101 | 100 |
| 48 | 94 | 100 |
| 49 | 95 | 99 |
| 50 | 102 | 100 |
| 51 | 103 | 100 |
| 52 | 95 | 76 |
| 53 | 98 | 96 |
| 54 | 101 | 16 |
| 55 | 103 | 88 |

-continued

| Example | B1R antagonism, rat [10 µM] % inhibition | B1R antagonism, human (10 µM) % inhibition |
|---|---|---|
| 56 | 105 | 100 |
| 57 | 99 | 100 |
| 58 | 103 | 100 |
| 59 | 104 | 100 |
| 60 | 106 | 100 |
| 61 | 106 | 100 |
| 62 | 107 | 100 |
| 63 | 106 | 99 |
| 64 | | 100 |
| 66 | 97 | |
| 68 | 103 | |
| 69 | 64 | |
| 71 | 101 | |
| 73 | 99 | |
| 74 | 95 | |
| 75 | 103 | |
| 76 | 48 | |
| 78 | 98 | |
| 81 | 102 | |
| 82 | 100 | |
| 83 | 101 | |
| 84 | 97 | |
| 85 | 102 | |
| 86 | 96 | |
| 87 | 103 | |
| 88 | 65 | |
| 91 | 103 | |
| 92 | 94 | |
| 93 | 93 | |
| 94 | 36 | |
| 95 | 99 | |
| 96 | 54 | |
| 97 | 96 | |
| 98 | 98 | |
| 99 | 98 | |
| 100 | 101 | |
| 125 | 102 | 75 |
| 126 | 104 | 90 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:
1. A substituted sulfonamide compound corresponding to formula I:

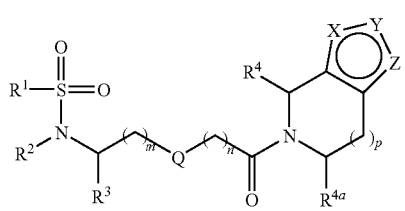

wherein
m and n each independently represent 0, 1 or 2;
p represents 0, 1 or 2;
Q represents —O—;
X represents N, $NR^5$, O, S or $CR^8$;
Y represents N, $NR^6$, O, S or $CR^9$;
Z represents N, $NR^7$, O, S or $CR^{10}$;

$R^1$ represents phenyl or naphthyl, unsubstituted or mono- or poly-substituted by identical or different substituents independently selected from the group consisting of methyl, methoxy, $CF_3$, $OCF_3$, F, Cl, and Br;

$R^2$ represents H, $C_{1-6}$-alkyl, $C_{3-8}$-cycloalkyl, bicyclic 8- to 12-membered carbocyclyl, $CH(aryl)_2$, aryl or heteroaryl; or a $C_{3-8}$-cycloalkyl, bicyclic 8- to 12-membered carbocyclyl, $CH(aryl)_2$, aryl or heteroaryl bonded via a $C_{1-6}$-alkylene group, $C_{2-6}$-alkenylene group or $C_{2-6}$-alkynylene group;

$R_3$ represents H, —C(=O)—$NR^{11}R^{12}$, —C(=O)—$OR^{13}$, $C_{1-6}$-alkyl, aryl or heteroaryl; or an aryl or heteroaryl bonded via a $C_{1-6}$-alkylene group, $C_{2-6}$-alkenylene group or $C_{2-6}$-alkynylene group, wherein $R^2$ and $R^3$ are not simultaneously H; or $R^2$ and $R^3$ together with the —N—(CH—)— group joining them form an unsubstituted or mono- or polysubstituted 4-, 5-, 6- or 7-membered heterocyclic ring, which optionally may be fused with an aryl or heteroaryl group, wherein said heterocyclic ring may be saturated or mono- or polyunsaturated but not aromatic, and optionally may contain, in addition to the N hetero atom to which $R^2$ is bonded, one or more further hetero atoms or hetero atom groups selected from the group consisting of N, $NR^{14}$, O, S, S=O or $S(=O)_2$; wherein
$R^{14}$ denotes H, $C_{1-6}$-alkyl, —C(=O)—$R^{15}$, $C_{3-8}$-cycloalkyl, aryl, heteroaryl, or a $C_{3-8}$-cycloalkyl, aryl or heteroaryl bonded via a $C_{1-3}$-alkylene group, and
$R^{15}$ denotes $C_{1-6}$-alkyl, $C_{3-8}$-cycloalkyl, aryl, heteroaryl, or a $C_{3-8}$-cycloalkyl, aryl or heteroaryl bonded via a $C_{1-3}$-alkylene group;

$R^4$ and $R^{4a}$ each independently represent H, $C_{1-6}$-alkyl, $C_{3-8}$-cycloalkyl, aryl, heteroaryl, or a $C_{3-8}$-cycloalkyl, aryl or heteroaryl bonded via a $C_{1-3}$-alkylene group;

$R^5$, $R^6$ and $R^7$ each independently represent H, $C_{1-6}$-alkyl, aryl or heteroaryl;

$R^8$, $R^9$ and $R^{10}$ each independently represent H, —$CF_3$, —C(=O)—$NR^{11}R^{12}$, —$C_{1-6}$-alkylene-C(=O)—$NR^{11}R^{12}$, —$C_{1-6}$-alkylene-$NR^{11}R^{12}$ $C_{3-8}$-cycloalkyl, 3- to 8-membered heterocycloalkyl, aryl or heteroaryl, or a $C_{3-8}$-cycloalkyl, 3- to 8-membered heterocycloalkyl, aryl or heteroaryl bonded via a $C_{1-6}$-alkylene group;
wherein at least one of $R^4$, $R^{4a}$, $R^5$, $R^6$, $R^7$, $R^8$, $R^9$ and $R^{10}$ is not H;

$R^{11}$ and $R^{12}$ each independently denote H, $C_{1-6}$-alkyl, $C_{2-6}$-alkenyl, $C_{3-8}$-cycloalkyl, 3- to 8-membered heterocycloalkyl, aryl or heteroaryl, or a $C_{3-8}$-cycloalkyl, 3- to 8-membered heterocycloalkyl, aryl or heteroaryl bonded via a $C_{1-3}$-alkylene group; or $R^{11}$ and $R^{12}$ together with the nitrogen atom joining them form an unsubstituted or mono- or polysubstituted 4-, 5-, 6- or 7-membered heterocyclic ring, which optionally may be fused with a saturated, mono- or polyunsaturated or aromatic, unsubstituted or mono- or polysubstituted, 4-, 5-, 6- or 7-membered ring system, wherein
said heterocyclic ring may be saturated or mono- or polyunsaturated but not aromatic, and optionally may contain, in addition to the N hetero atom to which $R^{11}$ and $R^{12}$ are bonded, one or more further hetero atoms or hetero atom groups selected from the group consisting of N, $NR^{16}$, O, S, S=O and $S(=O)_2$, and
said ring system optionally may contain one or more hetero atoms or hetero atom groups selected from the group consisting of N, $NR^{17}$, O, S, S=O and $S(=O)_2$;

$R^{16}$ represents H, $C_{1-6}$-alkyl, $C_{3-8}$-cycloalkyl, aryl, heteroaryl, or an aryl, heteroaryl or $C_{3-8}$-cycloalkyl bonded via a $C_{1-3}$-alkylene group; and $R^{17}$ represents H, $C_{1-6}$-alkyl, $C_{3-8}$-cycloalkyl, aryl, heteroaryl, or an aryl, heteroaryl or $C_{3-8}$-cycloalkyl bonded via a $C_{1-3}$-alkylene group;

$R^{13}$ denotes H, $C_{1-6}$-alkyl, $C_{3-8}$-cycloalkyl, 3- to 8-membered heterocycloalkyl, aryl, heteroaryl, or a $C_{3-8}$-cycloalkyl, 3- to 8-membered heterocycloalkyl, aryl or heteroaryl bonded via a $C_{1-3}$-alkylene group;

wherein
said $C_{1-6}$-alkyl, $C_{2-6}$-alkenyl, $C_{1-3}$-alkylene, $C_{1-6}$-alkylene, $C_{2-6}$-alkenylene, $C_{2-6}$-alkynylene, and $C_{3-8}$-cycloalkyl, groups may be unsubstituted or substituted one or more times by identical or different substituents selected from the group consisting of F, Cl, Br, I, CN, $NH_2$, NH—$C_{1-6}$-alkyl, NH—$C_{1-6}$-alkylene-OH, $C_{1-6}$-alkyl, $N(C_{1-6}$-alkyl$)_2$, $N(C_{1-6}$-alkylene-OH$)_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$alkyl, $CO_2H$, $CO_2$-$C_{1-6}$alkyl and benzyl;

said 3- to 8-membered heterocycloalkyl groups may be unsubstituted or substituted one or more times by identical or different substituents selected from the group consisting of F, Cl, Br, I, —CN, $NH_2$, NH—$C_{1-6}$-alkyl, NH—$C_{1-6}$-alkylene-OH, $C_{1-6}$-alkyl, $N(C_{1-6}$-alkyl$)_2$, $N(C_{1-6}$-alkylene-OH$)_2$, pyrrolinyl, piperazinyl, morpholinyl, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$alkyl, $CO_2H$, $CO_2$-$C_{1-6}$alkyl and benzyl; or, if a N heteroatom is present, the N heteroatom can be substituted by a $C_{1-6}$-alkyl, $C_{3-8}$-cycloalkyl, aryl, heteroaryl, or a $C_{3-8}$-cycloalkyl, aryl or heteroaryl bonded via a $C_{1-3}$-alkylene group, wherein these alkyl, cycloalkyl, alkylene and aryl and heteroaryl groups may each be unsubstituted or substituted one or more times by identical or different substituents;

said bicyclic 8- to 12-membered carbocyclyl groups may be unsubstituted, substituted on a saturated or partly unsaturated ring of the carbocyclyl one or more times by identical or different substituents selected from the group consisting of F, Cl, Br, I, CN, $NH_2$, NH—$C_{1-6}$-alkyl, NH—$C_{1-6}$-alkylene-OH, $C_{1-6}$-alkyl, $N(C_{1-6}$-alkyl$)_2$, $N(C_{1-6}$-alkylene-OH$)_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O) $C_{1-6}$alkyl, $CO_2H$, $CO_2$-$C_{1-6}$alkyl and benzyl, or substituted on an aromatic ring of the carbocyclyl one or more times by identical or different substituents selected from the group consisting of F, Cl, Br, I, CN, $NH_2$, NH—$C_{1-6}$-alkyl, NH—$C_{1-6}$-alkylene-OH, $N(C_{1-6}$-alkyl$)_2$, $N(C_{1-6}$-alkylene-OH$)_2$, NH-aryl$^1$, $N(aryl^1)_2$, $N(C_{1-6}$-alkyl)aryl$^1$, pyrrolinyl, piperazinyl, morpholinyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—$C(CH_3)_2$—$CH_2$—, unsubstituted $C_{1-6}$-alkyl, pyrrolidinyl, imidazolyl, piperidinyl, benzyloxy, phenoxy, phenyl, naphthyl, pyridinyl, —$C_{1-3}$-alkylene-aryl$^1$, benzyl, thienyl, and furyl, wherein aryl$^1$ represents phenyl, furyl, thienyl or pyridinyl and the abovementioned substituents can optionally be substituted by the same substituents;

said aryl and heteroaryl groups may be unsubstituted or substituted one or more times by identical or different substituents selected from the group consisting of F, Cl, Br, I, CN, $NH_2$, NH—$C_{1-6}$-alkyl, NH—$C_{1-6}$-alkylene-OH, $N(C_{1-6}$-alkyl$)_2$, $N(C_{1-6}$-alkylene-OH$)_2$, NH-aryl$^1$, N(aryl$^1)_2$, $N(C_{1-6}$-alkyl)aryl$^1$, pyrrolinyl, piperazinyl, morpholinyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—C($CH_3)_2$—$CH_2$—O—$CH_2$—O—, —O—$Ch_2$—O—$CH_2$, unsubstituted $C_{1-6}$-alkyl, pyrrolidinyl, imidazolyl, piperidinyl, benzyloxy, phenoxy, phenyl, naphthyl, pyridinyl, —$C_{1-3}$-alkylene-aryl$^1$, benzyl, thienyl, and furyl, wherein aryl$^1$ represents phenyl, furyl, thienyl or pyridinyl and the abovementioned substituents can optionally be substituted by the same substituents;

the substituents of a substituted heterocyclic ring are independently selected from the group consisting of F, Cl, Br, I, CN, $NH_2$, NH—$C_{1-6}$-alkyl, NH—$C_{1-6}$-alkylene-OH, $C_{1-6}$-alkyl, $N(C_{1-6}$-alkyl$)_2$, $N(C_{1-6}$-alkylene-OH$)_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$alkyl, $CO_2H$, $CO_2$-$C_{1-6}$alkyl and benzyl;

the substituents of a substituted, saturated or at least partly unsaturated ring system which is fused with a heterocyclic ring formed by $R^{11}$ and $R^{12}$ are independently selected from the group consisting of F, Cl, Br, I, CN, $NH_2$, NH—$C_{1-6}$-alkyl, NH—$C_{1-6}$-alkylene-OH, $C_{1-6}$-alkyl, $N(C_{1-6}$-alkyl$)_2$, $N(C_{1-6}$-alkylene-OH$)_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$alkyl, $CO_2H$, $CO_2$-$C_{1-6}$alkyl and benzyl;

the substituents of a substituted aromatic ring system which is fused with a heterocyclic ring formed by $R^{11}$ and $R^{12}$ are independently selected from the group consisting of F, Cl, Br, I, CN, $NH_2$, NH—$C_{1-6}$-alkyl, NH—$C_{1-6}$-alkylene-OH, $N(C_{1-6}$-alkyl$)_2$, $N(C_{1-6}$-alkylene-OH$)_2$, NH-aryl$^1$, N(aryl$^1)_2$, $N(C_{1-6}$-alkyl)aryl$^1$, pyrrolinyl, piperazinyl, morpholinyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—C($CH_3)_2$—$CH_2$—$CH_2$—, —$CH_2$—O—$CH_2$—O—, —O—$CH_2$—O—$CH_2$—, unsubstituted $C_{1-6}$-alkyl, pyrrolidinyl, imidazolyl, piperidinyl, benzyloxy, phenoxy, phenyl, naphthyl, pyridinyl, —$C_{1-3}$-alkylene-aryl$^1$, benzyl, thienyl, and furyl, wherein aryl$^1$ represents phenyl, furyl, thienyl or pyridinyl and the abovementioned substituents can optionally be substituted by the same substituents; and said $C_{1-6}$-alkyl, $C_{2-6}$-alkenyl, $C_{1-3}$-alkylene, $C_{1-6}$-alkylene, $C_{2-6}$-alkenylene and $C_{2-6}$-alkynylene groups may each be branched or unbranched;

or a physiologically acceptable salt or N-oxide thereof.

2. A compound as claimed in claim 1, wherein said compound is in the form of a mixture of stereoisomers in any mixing ratio.

3. A compound as claimed in claim 2, wherein said mixture is a racemic mixture.

4. A compound as claimed in claim 1, wherein said compound is in the form of an individual stereoisomer.

5. A compound as claimed in claim 1, wherein $R^2$ represents H, $C_{1-6}$-alkyl, $C_{3-6}$-cycloalkyl, 8- to 10-membered benzo-fused cycloalkyl, CH(phenyl)$_2$, aryl, heteroaryl, or a $C_{3-6}$-cycloalkyl, benzo-fused cycloalkyl, CH(phenyl)$_2$, aryl or heteroaryl bonded via a $C_{1-6}$-alkylene group, $C_{2-6}$-alkenylene group or $C_{2-6}$-alkynylene group; wherein said $C_{1-6}$-alkyl, $C_{3-6}$-cycloalkyl, $C_{1-6}$-alkylene, $C_{2-6}$-alkenylene, and $C_{2-6}$-alkynylene, groups may each be unsubstituted or mono- or polysubstituted by identical or different substituents independently selected from the group consisting of $C_{1-6}$-alkyl, $C_{1-6}$-alkyl-O—, F, Cl, Br, I, OH and SH; and said aryl and heteroaryl groups may each be unsubstituted or mono- or polysubstituted by identical or different substituents independently selected from the group consisting of —$CH_2$—O—$CH_2$—O—, —O—$CH_2$—O—$CH_2$—, $C_{1-6}$-alkyl, $C_{1-6}$-alkyl-O—, F, Cl, Br, I, $CF_3$, $OCF_3$, OH and SH.

6. A compound as claimed in claim 1, wherein $R^3$ represents H, —C(=O)—$NR^{11}R^{12}$, —C(=O)—$OR^{13}$, $C_{1-6}$-alkyl, aryl or heteroaryl; wherein said $C_{1-6}$-alkyl group may be unsubstituted or mono- or polysubstituted by identical or different substituents independently selected from the group consisting of $C_{1-6}$-alkyl, $C_{1-6}$-alkyl-O—, F, Cl, Br, I, OH and SH; and said aryl and heteroaryl groups may each be unsubstituted or mono- or polysubstituted by identical or different substituents independently selected from the group consisting of $C_{1-6}$-alkyl, $C_{1-6}$-alkyl-O—, F, Cl, Br, I, $CF_3$, $OCF_3$, OH and SH.

7. A substituted sulfonamide compound corresponding to formula I:

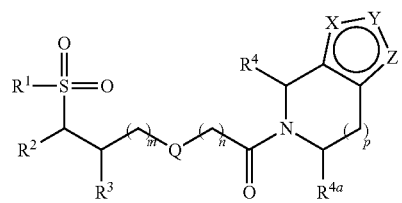

wherein m and n each independently represent 0, 1 or 2;

p represents 0, 1 or 2;

Q represents a single bond —$CH_2$—or —O—;

X represents N, $NR^5$, O, S or $CR^8$;

Y represents N, $NR^6$, O, S or $CR^9$;

Z represents N, $NR^7$, O, S or $CR^{10}$;

$R^1$ represents phenyl or naphthyl, unsubstituted or mono- or poly-substituted by identical or different substituents independently selected from the group consisting of methyl, methoxy, $CF_3$, $OCF_3$, F, Cl, and Br;

$R^2$ and $R^3$ together with the —N—(CH—)—group joining them form a 4-, 5-, 6- or 7-membered, unsubstituted or mono- or polysubstituted heterocyclic ring, wherein said heterocyclic ring may be saturated or mono- or polyunsaturated but not aromatic, which optionally may contain an oxygen atom as a ring-member, and which optionally may be fused with one or two 6-membered aromatic rings;

$R^4$ and $R^{4a}$ each independently represent H, $C_{1-6}$-alkyl, $C_{3-8}$-cycloalkyl, aryl, heteroaryl, or a $C_{3-8}$-cycloalkyl, aryl or heteroaryl bonded via a $C_{1-3}$-alkylene group;

$R^5$, $R^6$ and $R^7$ each independently represent H, $C_{1-6}$-alkyl, aryl or heteroaryl;

$R^8$, $R^9$ and $R^{10}$ each independently represent H, —$CF_3$, —C(=O)—$NR^{11}R^{12}$, —$C_{1-6}$-alkylene-C(=O)—$NR^{11}R^{12}$, —$C_{1-6}$-alkylene-$NR^{11}R^{12}$, $C_{3-8}$-cycloalkyl, 3- to 8-membered heterocycloalkyl, aryl or heteroaryl, or a $C_{3-8}$-cycloalkyl, 3- to 8-membered heterocycloalkyl, aryl or heteroaryl bonded via a $C_{3-6}$-alkylene group;

wherein at least one of $R^4$, $R^{4a}$, $R^5$, $R^6$, $R^7$, $R^8$, $R^9$ and $R^{10}$ is not H;

$R^{11}$ and $R^{12}$ each independently denote H, $C_{1-6}$-alkyl, $C_{2-6}$-alkenyl, $C_{3-8}$-cycloalkyl, 3- to 8-membered heterocycloalkyl, aryl or heteroaryl, or a $C_{3-8}$-cycloalkyl, 3-to 8-membered heterocycloalkyl, aryl or heteroaryl bonded via a $C_{1-3}$-alkylene group; or $R^{11}$ and $R^{12}$ together with the nitrogen atom joining them form an unsubstituted or mono- or polysubstituted 4-, 5-, 6- or 7-membered heterocyclic ring, which optionally may be fused with a saturated, mono- or polyunsaturated or aromatic, unsubstituted or mono- or polysubstituted, 4-, 5-, 6- or 7-membered ring system, wherein said heterocyclic ring may be saturated or mono- or polyunsaturated but not aromatic, and optionally may contain, in addition to the N hetero atom to which $R^{11}$ and $R^{12}$ are bonded, one or more further hetero atoms or hetero atom groups selected from the group consisting of N, $NR^{16}$, O, S, S=O and S(=O)$_2$, and said ring system optionally may contain one or more hetero atoms or hetero atom groups selected from the group consisting of N, $NR^{17}$, O, S, S=O and S(=O)$_2$;

$R^{16}$ represents H, $C_{1-6}$-alkyl, $C_{3-8}$-cycloalkyl, aryl, heteroaryl, or an aryl, heteroaryl or $C_{3-8}$-cycloalkyl bonded via a $C_{1-3}$-alkylene group; and $R^{17}$ represents H, $C_{3-8}$-cycloalkyl, aryl, heteroaryl, or an aryl, heteroaryl or $C_{3-8}$-cycloalkyl bonded via a $C_{1-3}$-alkylene group;

wherein
said $C_{1-6}$-alkyl, $C_{2-6}$-alkenyl, $C_{1-3}$-alkylene, $C_{1-6}$-alkylene, $C_{2-6}$-alkenylene, $C_{2-6}$-alkynylene, and $C_{3-8}$-cycloalkyl, groups may be unsubstituted or substituted one or more times by identical or different substituents selected from the group consisting of F, Cl, Br, I, CN, $NH_2$, NH—$C_{1-6}$-alkyl, NH—$C_{1-6}$-alkylene-OH, $C_{1-6}$-alkyl, N($C_{1-6}$-alkyl)$_2$, N($C_{1-6}$-alkylene-OH)$_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$alkyl, $CO_2H$, $CO_2$-$C_{1-6}$alkyl and benzyl;

said 3- to 8-membered heterocycloalkyl groups may be unsubstituted or substituted one or more times by identical or different substituents selected from the group consisting of F, Cl, Br, I, —CN, $NH_2$, NH—$C_{1-6}$-alkyl, NH—$C_{1-6}$-alkylene-OH, $C_{1-6}$-alkyl, N($C_{1-6}$-alkyl)$_2$, N($C_{1-6}$-alkylene-OH)$_2$, pyrrolinyl, piperazinyl, morpholinyl, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$alkyl, $CO_2H$, $CO_2$-$C_{1-6}$alkyl and benzyl; or, if a N heteroatom is present, the N heteroatom can be substituted by a $C_{1-6}$-alkyl, $C_{3-8}$-cycloalkyl, aryl, heteroaryl, or a $C_{3-8}$-cycloalkyl, aryl or heteroaryl bonded via a $C_{1-3}$-alkylene group, wherein these alkyl, cycloalkyl, alkylene and aryl and heteroaryl groups may each be unsubstituted or substituted one or more times by identical or different substituents;

said bicyclic 8- to 12-membered carbocyclyl groups may be unsubstituted, substituted on a saturated or partly unsaturated ring of the carbocyclyl one or more times by identical or different substituents selected from the group consisting of F, Cl, Br, I, CN, $NH_2$, NH—$C_{1-6}$-alkyl, NH—$C_{1-6}$-alkylene-OH, $C_{1-6}$-alkyl, N($C_{1-6}$-alkyl)$_2$, N($C_{1-6}$-alkylene-OH)$_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$alkyl, $CO_2H$, $CO_2$-$C_{1-6}$alkyl and benzyl, or substituted on an aromatic ring of the carbocyclyl one or more times by identical or different substituents selected from the group consisting of F, Cl, Br, I, CN, $NH_2$, NH—$C_{1-6}$-alkyl, NH—$C_{1-6}$-alkylene-OH, N($C_{1-6}$-alkyl)$_2$, N($C_{1-6}$-alkylene-OH)$_2$, NH-aryl$^1$, N(aryl$^1$)$_2$, N($C_{1-6}$-alkyl)aryl$^1$, pyrrolinyl, piperazinyl, morpholinyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—C($CH_3$)$_2$—$CH_2$—, unsubstituted $C_{1-6}$-alkyl, pyrrolidinyl, imidazolyl, piperidinyl, benzyloxy, phenoxy, phenyl, naphthyl, pyridinyl, —$C_{1-3}$-alkylene-aryl$^1$, benzyl, thienyl, and furyl, wherein aryl$^1$ represents phenyl, furyl, thienyl or pyridinyl and the abovementioned substituents can optionally be substituted by the same substituents;

said aryl and heteroaryl groups may be unsubstituted or substituted one or more times by identical or different substituents selected from the group consisting of F, Cl, Br, I, CN, $NH_2$, NH—$C_{1-6}$-alkyl, NH—$C_{1-6}$-alkylene-OH, N($C_{1-6}$-alkyl)$_2$, N($C_{1-6}$-alkylene-OH)$_2$, NH-aryl$^1$, N(aryl$^1$)$_2$, N($C_{1-6}$-alkyl)aryl$^1$, pyrrolinyl, piperazinyl, morpholinyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—C($CH_3$)$_2$—$CH_2$—O—$CH_2$—O—, —O—$Ch_2$—O—$CH_2$, unsubstituted $C_{1-6}$-alkyl, pyrrolidinyl, imidazolyl, piperidinyl, benzyloxy, phenoxy, phenyl, naphthyl, pyridinyl, —$C_{1-3}$-alkylene-aryl$^1$, benzyl, thienyl, and furyl, wherein aryl$^1$ represents phenyl, furyl, thienyl or pyridinyl and the abovementioned substituents can optionally be substituted by the same substituents;

the substituents of a substituted heterocyclic ring are independently selected from the group consisting of F, Cl, Br, I, CN, $NH_2$, NH—$C_{1-6}$-alkyl, NH—$C_{1-6}$-alkylene-OH, $C_{1-6}$-alkyl, N($C_{1-6}$-alkyl)$_2$, N($C_{1-6}$-alkylene-OH)$_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$alkyl, $CO_2H$, $CO_2$-$C_{1-6}$alkyl and benzyl;

the substituents of a substituted, saturated or at least partly unsaturated ring system which is fused with a heterocyclic ring formed by $R^{11}$ and $R^{12}$ are independently selected from the group consisting of F, Cl, Br, I, CN, $NH_2$, NH—$C_{1-6}$-alkyl, NH—$C_{1-6}$-alkylene-OH, $C_{1-6}$-alkyl, N($C_{1-6}$-alkyl)$_2$, N($C_{1-6}$-alkylene-OH)$_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$alkyl, $CO_2H$, $CO_2$-$C_{1-6}$alkyl and benzyl;

the substituents of a substituted aromatic ring system which is fused with a heterocyclic ring formed by $R^{11}$ and $R^{12}$ are independently selected from the group consisting of F, Cl, Br, I, CN, $NH_2$, $NH$—$C_{1-6}$-alkyl, $NH$—$C_{1-6}$-alkylene-OH, $N(C_{1-6}$-alkyl$)_2$, $N(C_{1-6}$-alkylene-OH$)_2$, $NH$-aryl$^1$, $N($aryl$^1)_2$, $N(C_{1-6}$-alkyl)aryl$^1$, pyrrolinyl, piperazinyl, morpholinyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—$C(CH_3)_2$—$CH_2$—$CH_2$—, —$CH_2$—O—$CH_2$—O—, —O—$CH_2$—O—$CH_2$—, unsubstituted $C_{1-6}$-alkyl, pyrrolidinyl, imidazolyl, piperidinyl, benzyloxy, phenoxy, phenyl, naphthyl, pyridinyl, —$C_{1-3}$-alkylene-aryl$^1$, benzyl, thienyl, and furyl, wherein aryl$^1$ represents phenyl, furyl, thienyl or pyridinyl and the abovementioned substituents can optionally be substituted by the same substituents; and said $C_{1-6}$-alkyl, $C_{2-6}$-alkenyl, $C_{1-3}$-alkylene, $C_{1-6}$-alkylene, $C_{2-6}$-alkenylene and $C_{2-6}$-alkynylene groups may each be branched or unbranched;

or a physiologically acceptable salt or N-oxide thereof.

8. A substituted sulfonamide compound corresponding to formula I:

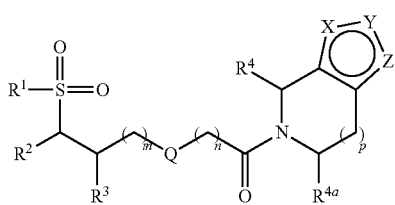

I wherein m and n each independently represent 0, 1 or 2;

p represents 0, 1 or 2;

Q represents a single bond —$CH_2$— or —O—;

X represents N, $NR^5$, O, S or $CR^8$;

Y represents N, $NR^6$, O, S or $CR^9$;

Z represents N, $NR^7$, O, S or $CR^{10}$;

$R^1$ represents phenyl or naphthyl, unsubstituted or mono- or poly-substituted by identical or different substituents independently selected from the group consisting of methyl, methoxy, $CF_3$, $OCF_3$, F, Cl, and Br;

$R^2$ represents H, $C_{1-6}$-alkyl, $C_{3-8}$-cycloalkyl, bicyclic 8- to 12-membered carbocyclyl, CH(aryl)$_2$, aryl or heteroaryl; or a $C_{3-8}$-cycloalkyl, bicyclic 8- to 12-membered carbocyclyl, CH(aryl)$_2$, aryl or heteroaryl bonded via a $C_{1-6}$-alkylene group, $C_{2-6}$-alkenylene group or $C_{2-6}$-alkynylene group;

$R^3$ represents H, =C(=O)—$NR^{11}R^{12}$, —C(=O)—$OR^{13}$, $C_{1-6}$-alkyl, aryl or heteroaryl; or an aryl or heteroaryl bonded via a $C_{1-6}$-alkylene group, $C_{2-6}$-alkenylene group or $C_{2-6}$-alkynylene group, wherein $R^2$ and $R^3$ are not simultaneously H; or $R^2$ and $R^3$ together with the —N—(CH—)—group joining them form an unsubstituted or mono- or polysubstituted 4-, 5-, 6-, 7-membered heterocyclic ring, which optionally may be fused with an aryl or heteroaryl group, wherein said heterocyclic ring may be saturated or mono- or polyunsaturated but not aromatic, and optionally may contain, in addition to the N hetero atom to which $R^2$ is bonded, one or more further hetero atoms or hetero atom groups selected from the group consisting of N, $NR^{14}$, O, S, S=O or S(=O)$_2$; wherein $R^{14}$ denotes H, $C_{1-6}$-alkyl, =C(=O)—$R^{15}$, $C_{3-8}$-cycloalkyl, aryl, heteroaryl, or a $C_{3-8}$-cycloalkyl, aryl or heteroaryl bonded via a $C_{1-3}$-alkylene group, and $R^{15}$ denotes $C_{1-6}$-alkyl, $C_{3-8}$-cycloalkyl, aryl, heteroaryl, or a $C_{3-8}$-cycloalkyl, aryl or heteroaryl bonded via a $C_{1-3}$-alkylene group;

$R^4$ and $R^{4a}$ each independently represent H, $C_{1-6}$-alkyl, $C_{3-8}$-cycloalkyl, phenyl, naphthyl, furyl, thienyl, pyridinyl, or a phenyl, naphthyl, furyl, thienyl or pyridinyl bonded via a C1_3-alkylene group: wherein said phenyl, naphthyl, furyl, thienyl and pyridinyl may each be unsubstituted or mono- or polysubstituted by identical or different substituents independently selected from the group consisting of —O—$C_{1-3}$-alkyl, —$C_{1-6}$-alkyl, —F, —Cl, —Br, —I, —$CF_3$, —$OCF_3$, —OH, —SH, phenyl, naphthyl, furyl, thienyl and pyridinyl;

$R^5$, $R^6$ and $R^7$ each independently represent H, $C_{1-6}$-alkyl, aryl or heteroaryl;

$R^8$, $R^9$ and $R^{10}$ each independently represent H, —$CF_3$, —C(=O)—$NR^{11}R^{12}$, —$C_{1-6}$-alkylene-C(=O)—$NR^{11}R^{12}$, —$C_{1-6}$-alkylene-$NR^{11}R^{12}$, $C_{3-8}$-cycloalkyl, 3- to 8-membered heterocycloalkyl, aryl or heteroaryl, or a $C_{3-8}$-cycloalkyl, 3- to 8-membered heterocycloalkyl, aryl or heteroaryl bonded via a $C_{3-6}$-alkylene group;

wherein at least one of $R^4$, $R^{4a}$, $R^5$, $R^6$, $R^7$, $R^8$, $R^9$ and $R^{10}$ is not H;

$R^{11}$ and $R^{12}$ each independently denote H, $C_{1-6}$-alkyl, $C_{2-6}$-alkenyl, $C_{3-8}$-cycloalkyl, 3- to 8-membered heterocycloalkyl, aryl or heteroaryl, or a $C_{3-8}$-cycloalkyl, 3-to 8-membered heterocycloalkyl, aryl or heteroaryl bonded via a $C_{1-3}$-alkylene group; or $R^{11}$ and $R^{12}$ together with the nitrogen atom joining them form an unsubstituted or mono- or polysubstituted 4-, 5-, 6- or 7-membered heterocyclic ring, which optionally may be fused with a saturated, mono- or polyunsaturated or aromatic, unsubstituted or mono- or polysubstituted, 4-, 5-, 6- or 7-membered ring system, wherein said heterocyclic ring may be saturated or mono- or polyunsaturated but not aromatic, and optionally may contain, in addition to the N hetero atom to which $R^{11}$ and $R^{12}$ are bonded, one or more further hetero atoms or hetero atom groups selected from the group consisting of N, $NR^{16}$, O, S, S=O and S(=O)$_2$, and said ring system optionally may contain one or more hetero atoms or hetero atom groups selected from the group consisting of N, $NR^{17}$, O, S, S=O and S(=O)$_2$;

$R^{16}$ represents H, $C_{1-6}$-alkyl, $C_{3-8}$-cycloalkyl, aryl, heteroaryl, or an aryl, heteroaryl or $C_{3-8}$-cycloalkyl bonded via a $C_{1-3}$-alkylene group; and $R^{17}$ represents H, $C_{3-8}$-cycloalkyl, aryl, heteroaryl, or an aryl, heteroaryl or $C_{3-8}$-cycloalkyl bonded via a $C_{1-3}$-alkylene group;

$R^{13}$ denotes H, $C_{1-6}$-alkyl, $C_{3-8}$-cycloalkyl, 3- to 8-membered heterocycloalkyl, aryl, heteroaryl, or a $C_{3-8}$-cycloalkyl, 3- to 8-membered heterocycloalkyl, aryl or heteroaryl bonded via a $C_{1-3}$-alkylene group;

wherein said $C_{1-6}$-alkyl, $C_{2-6}$-alkenyl, $C_{1-3}$-alkylene, $C_{1-6}$-alkylene, $C_{2-6}$-alkenylene, $C_{2-6}$-alkynylene, and $C_{3-8}$-cycloalkyl, groups may be unsubstituted or substituted one or more times by identical or different substituents selected from the group consisting of F, Cl, Br, I, CN, $NH_2$, $NH$—$C_{1-6}$-alkyl, $NH$—$C_{1-6}$-alkylene-OH, $C_{1-6}$-alkyl, $N(C_{1-6}$-alkyl$)_2$, $N(C_{1-6}$-alkylene-OH$)_2$, NO$_2$, SH, S—C$_{1-6}$-alkyl, S-benzyl, O—C$_{1-6}$-alkyl, OH, O—C$_{1-6}$-alkylene-OH, =O, O-benzyl, C(=O) C$_{1-6}$alkyl, CO$_2$H, CO$_2$-C$_{1-6}$alkyl and benzyl;

said 3- to 8-membered heterocycloalkyl groups may be unsubstituted or substituted one or more times by identical or different substituents selected from the group consisting of F, Cl, Br, I, —CN, NH$_2$, NH—C$_{1-6}$-alkyl, NH—C$_{1-6}$-alkylene-OH, C$_{1-6}$-alkyl, N(C$_{1-6}$-alkyl)$_2$, N(C$_{1-6}$-alkylene-OH)$_2$, pyrrolinyl, piperazinyl, morpholinyl, NO$_2$, SH, S—C$_{1-6}$-alkyl, S-benzyl, O—C$_{1-6}$-alkyl, OH, O—C$_{1-6}$-alkylene-OH, =O, O-benzyl, C(=O)C$_{1-6}$alkyl, CO$_2$H, CO$_2$-C$_{1-6}$alkyl and benzyl; or, if a N heteroatom is present, the N heteroatom can be substituted by a C$_{1-6}$-alkyl, C$_{3-8}$-cycloalkyl, aryl, heteroaryl, or a C$_{3-8}$-cycloalkyl, aryl or heteroaryl bonded via a C$_{1-3}$-alkylene group, wherein these alkyl, cycloalkyl, alkylene and aryl and heteroaryl groups may each be unsubstituted or substituted one or more times by identical or different substituents;

said bicyclic 8- to 12-membered carbocyclyl groups may be unsubstituted, substituted on a saturated or partly unsaturated ring of the carbocyclyl one or more times by identical or different substituents selected from the group consisting of F, Cl, Br, I, CN, NH$_2$, NH—C$_{1-6}$-alkyl, NH—C$_{1-6}$-alkylene-OH, C$_{1-6}$-alkyl, N(C$_{1-6}$-alkyl)$_2$, N(C$_{1-6}$-alkylene-OH)$_2$, NO$_2$, SH, S—C$_{1-6}$-alkyl, S-benzyl, O—C$_{1-6}$-alkyl, OH, O—C$_{1-6}$-alkylene-OH, =O, O-benzyl, C(=O) C$_{1-6}$alkyl, CO$_2$H, CO$_2$-C$_{1-6}$alkyl and benzyl, or substituted on an aromatic ring of the carbocyclyl one or more times by identical or different substituents selected from the group consisting of F, Cl, Br, I, CN, NH$_2$, NH—C$_{1-6}$-alkyl, NH—C$_{1-6}$-alkylene-OH, N(C$_{1-6}$-alkyl)$_2$, N(C$_{1-6}$-alkylene-OH)$_2$, NH-aryl$^1$, N(aryl$^1$)$_2$, N(C$_{1-6}$-alkyl)aryl$^1$, pyrrolinyl, piperazinyl, morpholinyl, NO$_2$, SH, S—C$_{1-6}$-alkyl, OH, O—C$_{1-6}$-alkyl, O—C$_{1-6}$-alkyl-OH, C(=O)C$_{1-6}$-alkyl, NHSO$_2$C$_{1-6}$-alkyl, NHCOC$_{1-6}$-alkyl, CO$_2$H, CH$_2$SO$_2$-phenyl, CO$_2$—C$_{1-6}$-alkyl, OCF$_3$, CF$_3$, —O—CH$_2$—O—, —O—CH$_2$—CH$_2$—O—, —O—C(CH$_3$)$_2$—CH$_2$—, unsubstituted C$_{1-6}$-alkyl, pyrrolidinyl, imidazolyl, piperidinyl, benzyloxy, phenoxy, phenyl, naphthyl, pyridinyl, —C$_{1-3}$-alkylene-aryl$^1$, benzyl, thienyl, and furyl, wherein aryl$^1$ represents phenyl, furyl, thienyl or pyridinyl and the abovementioned substituents can optionally be substituted by the same substituents;

said aryl and heteroaryl groups may be unsubstituted or substituted one or more times by identical or different substituents selected from the group consisting of F, Cl, Br, I, CN, NH$_2$, NH—C$_{1-6}$-alkyl, NH—C$_{1-6}$-alkylene-OH, N(C$_{1-6}$-alkyl)$_2$, N(C$_{1-6}$-alkylene-OH)$_2$, NH-aryl$^1$, N(aryl$^1$)$_2$, N(C$_{1-6}$-alkyl)aryl$^1$, pyrrolinyl, piperazinyl, morpholinyl, NO$_2$, SH, S—C$_{1-6}$-alkyl, OH, O—C$_{1-6}$-alkyl, O—C$_{1-6}$-alkyl-OH, C(=O)C$_{1-6}$-alkyl, NHSO$_2$C$_{1-6}$-alkyl, NHCOC$_{1-6}$-alkyl, CO$_2$H, CH$_2$SO$_2$-phenyl, CO$_2$—C$_{1-6}$-alkyl, OCF$_3$, CF$_3$, —O—CH$_2$—O—, —O—CH$_2$—CH$_2$—O—, —O—C(CH$_3$)$_2$—CH$_2$—O—CH$_2$—O—, —O—Ch$_2$—O—CH$_2$—, unsubstituted C$_{1-6}$-alkyl, pyrrolidinyl, imidazolyl, piperidinyl, benzyloxy, phenoxy, phenyl, naphthyl, pyridinyl, —C$_{1-3}$-alkylene-aryl$^1$, benzyl, thienyl, and furyl, wherein aryl$^1$ represents phenyl, furyl, thienyl or pyridinyl and the abovementioned substituents can optionally be substituted by the same substituents;

the substituents of a substituted heterocyclic ring are independently selected from the group consisting of F, Cl, Br, I, CN, NH$_2$, NH—C$_{1-6}$-alkyl, NH—C$_{1-6}$-alkylene-OH, C$_{1-6}$-alkyl, N(C$_{1-6}$-alkyl)$_2$, N(C$_{1-6}$-alkylene-OH)$_2$, NO$_2$, SH, S—C$_{1-6}$-alkyl, S-benzyl, O—C$_{1-6}$-alkyl, OH, O—C$_{1-6}$-alkylene-OH, =O, O-benzyl, C(=O)C$_{1-6}$alkyl, CO$_2$H, CO$_2$-C$_{1-6}$alkyl and benzyl;

the substituents of a substituted, saturated or at least partly unsaturated ring system which is fused with a heterocyclic ring formed by R$^{11}$ and R$^{12}$ are independently selected from the group consisting of F, Cl, Br, I, CN, NH$_2$, NH—C$_{1-6}$-alkyl, NH—C$_{1-6}$-alkylene-OH, C$_{1-6}$-alkyl, N(C$_{1-6}$-alkyl)$_2$, N(C$_{1-6}$-alkylene-OH)$_2$, NO$_2$, SH, S—C$_{1-6}$-alkyl, S-benzyl, O—C$_{1-6}$-alkyl, OH, O—C$_{1-6}$-alkylene-OH, =O, O-benzyl, C(=O)C$_{1-6}$alkyl, CO$_2$H, CO$_2$-C$_{1-6}$alkyl and benzyl;

the substituents of a substituted aromatic ring system which is fused with a heterocyclic ring formed by R$^{11}$ and R$^{12}$ are independently selected from the group consisting of F, Cl, Br, I, CN, NH$_2$, NH—C$_{1-6}$-alkyl, NH—C$_{1-6}$-alkylene-OH, N(C$_{1-6}$-alkyl)$_2$, N(C$_{1-6}$-alkylene-OH)$_2$, NH-aryl$^1$, N(aryl$^1$)$_2$, N(C$_{1-6}$-alkyl)aryl$^1$, pyrrolinyl, piperazinyl, morpholinyl, NO$_2$, SH, S—C$_{1-6}$-alkyl, OH, O—C$_{1-6}$-alkyl, O—C$_{1-6}$-alkyl-OH, C(=O)C$_{1-6}$-alkyl, NHSO$_2$C$_{1-6}$-alkyl, NHCOC$_{1-6}$-alkyl, CO$_2$H, CH$_2$SO$_2$-phenyl, CO$_2$—C$_{1-6}$-alkyl, OCF$_3$, CF$_3$, —O—CH$_2$—O—, —O—CH$_2$—CH$_2$—O—, —O—C(CH$_3$)$_2$—CH$_2$—CH$_2$—, —CH$_2$—O—CH$_2$—O—, —O—CH$_2$—O—CH$_2$—, unsubstituted C$_{1-6}$-alkyl, pyrrolidinyl, imidazolyl, piperidinyl, benzyloxy, phenoxy, phenyl, naphthyl, pyridinyl, —C$_{1-3}$-alkylene-aryl$^1$, benzyl, thienyl, and furyl, wherein aryl$^1$ represents phenyl, furyl, thienyl or pyridinyl and the abovementioned substituents can optionally be substituted by the same substituents; and said C$_{1-6}$-alkyl, C$_{2-6}$-alkenyl, C$_{1-3}$-alkylene, C$_{1-6}$-alkylene, C$_{2-6}$-alkenylene and C$_{2-6}$-alkynylene groups may each be branched or unbranched;

or a physiologically acceptable salt or N-oxide thereof.

9. A compound as claimed in claim 1, wherein R$^5$, R$^6$ and R$^7$ each independently represent H, C$_{1-4}$-alkyl or phenyl.

10. A compound as claimed in claim 1, wherein R$^8$, R$^9$ and R$^{10}$ each independently represent H, —CF$_3$, —C(=O)—NR$^{11}$R$^{12}$, —C$_{1-6}$-alkylene-C(=O)—NR$^{11}$R$^{12}$, —C$_{1-6}$-alkylene-NR$^{11}$R$^{12}$, phenyl, naphthyl, furyl, thienyl, pyridinyl, or a phenyl, naphthyl, furyl, thienyl or pyridinyl bonded via a C$_{1-6}$-alkylene group; wherein said phenyl, naphthyl, furyl, thienyl or pyridinyl may each be unsubstituted or mono- or polysubstituted by identical or different substituents independently selected from the group consisting of —O—C$_{1-3}$-alkyl, —C$_{1-6}$-alkyl, —F, —Cl, —Br, —I, —CF$_3$, —OCF$_3$, —OH, —SH, phenyl, naphthyl, furyl, thienyl and pyridinyl.

11. A substituted sulfonamide compound corresponding to formula I:

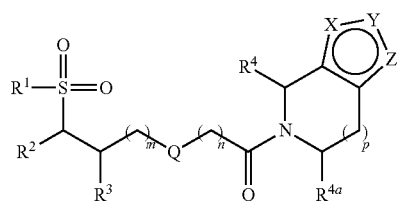

wherein m and n each independently represent 0, 1 or 2;

p represents 0, 1 or 2;

Q represents a single bond —CH$_2$— or —O—;

X represents N, NR$^5$, O, S or CR$^8$;
Y represents N, NR$^6$, O, S or CR$^9$;
Z represents N, NR$^7$, O, S or CR$^{10}$;
R$^1$ represents phenyl or naphthyl, unsubstituted or mono- or poly-substituted by identical or different substituents independently selected from the group consisting of methyl, methoxy, CF$_3$, OCF$_3$, F, Cl, and Br;
R$^2$ represents H, C$_{1-6}$-alkyl, C$_{3-8}$-cycloalkyl, bicyclic 8- to 12-membered carbocyclyl, CH(aryl)$_2$, aryl or heteroaryl; or a C$_{3-8}$-cycloalkyl, bicyclic 8- to 12-membered carbocyclyl, CH(aryl)$_2$, aryl or heteroaryl bonded via a C$_{1-6}$-alkylene group, C$_{2-6}$-alkenylene group or C$_{2-6}$-alkynylene group;
R$^3$ represents H, =C(=O)—NR$^{11}$R$^{12}$, —C(=O)—OR$^{13}$, C$_{1-6}$-alkyl, aryl or heteroaryl; or an aryl or heteroaryl bonded via a C$_{1-6}$-alkylene group, C$_{2-6}$-alkenylene group or C$_{2-6}$-alkynylene group, wherein R$^2$ and R$^3$ are not simultaneously H; or
R$^2$ and R$^3$ together with the —N—(CH—)—group joining them form an unsubstituted or mono- or polysubstituted 4-, 5-, 6-, 7-membered heterocyclic ring, which optionally may be fused with an aryl or heteroaryl group, wherein said heterocyclic ring may be saturated or mono- or polyunsaturated but not aromatic, and optionally may contain, in addition to the N hetero atom to which R$^2$ is bonded, one or more further hetero atoms or hetero atom groups selected from the group consisting of N, NR$^{14}$, O, S, S=O or S(=O)$_2$; wherein
R$^{14}$ denotes H, C$_{1-6}$-alkyl, =C(=O)—R$^{15}$, C$_{3-8}$-cycloalkyl, aryl, heteroaryl, or a C$_{3-8}$-cycloalkyl, aryl or heteroaryl bonded via a C$_{1-3}$-alkylene group, and
R$^{15}$ denotes C$_{1-6}$-alkyl, C$_{3-8}$-cycloalkyl, aryl, heteroaryl, or a C$_{3-8}$-cycloalkyl, aryl or heteroaryl bonded via a C$_{1-3}$-alkylene group;
R$^4$ and R$^{4a}$ each independently represent H, C$_{1-6}$-alkyl, C$_{3-8}$-cycloalkyl, aryl, heteroaryl, or a C$_{3-8}$-cycloalkyl, aryl or heteroaryl bonded via a C$_{1-3}$-alkylene group;
R$^5$, R$^6$ and R$^7$ each independently represent H, C$_{1-6}$-alkyl, aryl or heteroaryl;
R$^8$, R$^9$ and R$^{10}$ each independently represent H, —CF$_3$, —C(=O)—NR$^{11}$R$^{12}$, —C$_{1-6}$-alkylene-C(=O)—NR$^{11}$R$^{12}$, —C$_{1-6}$-alkylene-NR$^{11}$R$^{12}$, C$_{3-8}$-cycloalkyl, 3- to 8-membered heterocycloalkyl, aryl or heteroaryl, or a C$_{3-8}$-cycloalkyl, 3- to 8-membered heterocycloalkyl, aryl or heteroaryl bonded via a C$_{3-6}$-alkylene group;
wherein at least one of R$^4$, R$^{4a}$, R$^5$, R$^6$, R$^7$, R$^8$, R$^9$ and R$^{10}$ is not H;
R$^{11}$ and R$^{12}$ each independently represent H, or substituted or unsubstituted C$_{1-6}$-alkyl or C$_{3-8}$-cycloalkyl; or the group —NR$^{11}$R$^{12}$ represents a heterocylic group corresponding to formula IIaa

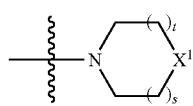

wherein
X$^1$ represents O, S, NR$^{18}$CH$_2$, C(H)(halogen) or C(halogen)$_2$;
R$^{18}$ represents H, C$_{1-6}$-alkyl, C$_{3-8}$-cycloalkyl, aryl, heteroaryl, or a C$_{3-8}$-cycloalkyl, aryl or heteroaryl bonded via a C$_{1-3}$-alkylene group; and s and t each independently represent 0, 1 or 2, with the proviso that s+t=0, 1, 2 or 3,
wherein
said C$_{1-6}$-alkyl and C$_{1-3}$-alkylene groups may each be unsubstituted or mono- or polysubstituted by identical or different substituents independently selected from the group consisting of —O—C$_{1-3}$-alkyl, —C$_{1-6}$-alkyl, —F, —Cl, —Br, —I, —OH, and —SH; and
said aryl and heteroaryl groups may each be unsubstituted or mono- or polysubstituted by identical or different substituents independently selected from the group consisting of —O—C$_{1-3}$-alkyl, —C$_{1-6}$-alkyl, —F, —Cl, —Br, —I, —CF$_3$, —OCF$_3$, —OH, —SH, phenyl, naphthyl, furyl, thienyl and pyridinyl; and
wherein
said C$_{1-6}$-alkyl, C$_{2-6}$-alkenyl, C$_{1-3}$-alkylene, C$_{1-6}$-alkylene, C$_{2-6}$-alkenylene, C$_{2-6}$-alkynylene, and C$_{3-8}$-cycloalkyl, groups may be unsubstituted or substituted one or more times by identical or different substituents selected from the group consisting of F, Cl, Br, I, CN, NH$_2$, NH—C$_{1-6}$-alkyl, NH—C$_{1-6}$-alkylene-OH, C$_{1-6}$-alkyl, N(C$_{1-6}$-alkyl)$_2$, N(C$_{1-6}$-alkylene-OH)$_2$, NO$_2$,SH, S—C$_{1-6}$-alkyl, S-benzyl, O—C$_{1-6}$-alkyl, OH, O—C$_{1-6}$-alkylene-OH, =O, O-benzyl, C(=O)C$_{1-6}$alkyl, CO$_2$H, CO$_2$-C$_{1-6}$alkyl and benzyl;
said 3- to 8-membered heterocycloalkyl groups may be unsubstituted or substituted one or more times by identical or different substituents selected from the group consisting of F, Cl, Br, I, —CN, NH$_2$, NH—C$_{1-6}$-alkyl, NH—C$_{1-6}$-alkylene-OH, C$_{1-6}$-alkyl, N(C$_{1-6}$-alkyl)$_2$, N(C$_{1-6}$-alkylene-OH)$_2$, pyrrolinyl, piperazinyl, morpholinyl, NO$_2$, SH, S—C$_{1-6}$-alkyl, S-benzyl, O—C$_{1-6}$-alkyl, OH, O—C$_{1-6}$-alkylene-OH, =O, O-benzyl, C(=O)C$_{1-6}$alkyl, CO$_2$H, CO$_2$-C$_{1-6}$alkyl and benzyl; or, if a N heteroatom is present, the N heteroatom can be substituted by a C$_{1-6}$-alkyl, C$_{3-8}$-cycloalkyl, aryl, heteroaryl, or a C$_{3-8}$-cycloalkyl, aryl or heteroaryl bonded via a C$_{1-3}$-alkylene group, wherein these alkyl, cycloalkyl, alkylene and aryl and heteroaryl groups may each be unsubstituted or substituted one or more times by identical or different substituents;
said bicyclic 8- to 12-membered carbocyclyl groups may be unsubstituted, substituted on a saturated or partly unsaturated ring of the carbocyclyl one or more times by identical or different substituents selected from the group consisting of F, Cl, Br, I, CN, NH$_2$, NH—C$_{1-6}$-alkyl, NH—C$_{1-6}$-alkylene-OH, C$_{1-6}$-alkyl, N(C$_{1-6}$-alkyl)$_2$, N(C$_{1-6}$-alkylene-OH)$_2$, NO$_2$, SH, S—C$_{1-6}$-alkyl, S-benzyl, O—C$_{1-6}$-alkyl, OH, O—C$_{1-6}$-alkylene-OH, =O, O-benzyl, C(=O)C$_{1-6}$alkyl, CO$_2$H, CO$_2$-C$_{1-6}$alkyl and benzyl, or substituted on an aromatic ring of the carbocyclyl one or more times by identical or different substituents selected from the group consisting of F, Cl, Br, I, CN, NH$_2$, NH—C$_{1-6}$-alkyl, NH—C$_{1-6}$-alkylene-OH, N(C$_{1-6}$-alkyl)$_2$, N(C$_{1-6}$-alkylene-OH)$_2$, NH-aryl$^1$, N(aryl$^1$)$_2$, N(C$_{1-6}$-alkyl)aryl$^1$, pyrrolinyl, piperazinyl, morpholinyl, NO$_2$, SH, S—C$_{1-6}$-alkyl, OH, O—C$_{1-6}$-alkyl, O—C$_{1-6}$-alkyl-OH, C(=O)C$_{1-6}$-alkyl, NHSO$_2$C$_{1-6}$-alkyl, NHCOC$_{1-6}$-alkyl, CO$_2$H, CH$_2$SO$_2$-phenyl, CO$_2$—C$_{1-6}$-alkyl, OCF$_3$, CF$_3$, —O—CH$_2$—O—, —O—CH$_2$—CH$_2$—O—, —O—C(CH$_3$)$_2$—CH$_2$—, unsubstituted C$_{1-6}$-alkyl, pyrrolidinyl, imidazolyl, piperidinyl, benzyloxy, phenoxy, phenyl, naphthyl, pyridinyl, —C$_{1-3}$-alkylenearyl¹, benzyl, thienyl, and furyl, wherein aryl¹ represents phenyl, furyl, thienyl or pyridinyl and the abovementioned substituents can optionally be substituted by the same substituents;

said aryl and heteroaryl groups may be unsubstituted or substituted one or more times by identical or different substituents selected from the group consisting of F, Cl, Br, I, CN, $NH_2$, NH—$C_{1-6}$-alkyl, NH—$C_{1-6}$-alkylene-OH, $N(C_{1-6}$-alkyl$)_2$, $N(C_{1-6}$-alkylene-OH$)_2$, NH-aryl¹, N(aryl¹$)_2$, N($C_{1-6}$-alkyl)aryl¹, pyrrolinyl, piperazinyl, morpholinyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—C($CH_3)_2$—$CH_2$—O—$CH_2$—O—, —O—$Ch_2$—O—$CH_2$, unsubstituted $C_{1-6}$-alkyl, pyrrolidinyl, imidazolyl, piperidinyl, benzyloxy, phenoxy, phenyl, naphthyl, pyridinyl, —$C_{1-3}$-alkylene-aryl¹, benzyl, thienyl, and furyl, wherein aryl¹ represents phenyl, furyl, thienyl or pyridinyl and the abovementioned substituents can optionally be substituted by the same substituents;

the substituents of a substituted heterocyclic ring are independently selected from the group consisting of F, Cl, Br, I, CN, $NH_2$, NH—$C_{1-6}$-alkyl, NH—$C_{1-6}$-alkylene-OH, $C_{1-6}$-alkyl, $N(C_{1-6}$-alkyl$)_2$, $N(C_{1-6}$-alkylene-OH$)_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$alkyl, $CO_2H$, $CO_2$-$C_{1-6}$alkyl and benzyl;

the substituents of a substituted, saturated or at least partly unsaturated ring system which is fused with a heterocyclic ring formed by $R^{11}$ and $R^{12}$ are independently selected from the group consisting of F, Cl, Br, I, CN, $NH_2$, NH—$C_{1-6}$-alkyl, NH—$C_{1-6}$-alkylene-OH, $C_{1-6}$-alkyl, $N(C_{1-6}$-alkyl$)_2$, $N(C_{1-6}$-alkylene-OH$)_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2H$, $CO_2$-$C_{1-6}$alkyl and benzyl;

the substituents of a substituted aromatic ring system which is fused with a heterocyclic ring formed by $R^{11}$ and $R^{12}$ are independently selected from the group consisting of F, Cl, Br, I, CN, $NH_2$, NH—$C_{1-6}$-alkyl, NH—$C_{1-6}$-alkylene-OH, $N(C_{1-6}$-alkyl$)_2$, $N(C_{1-6}$-alkylene-OH$)_2$, NH-aryl¹, N(aryl¹$)_2$, N($C_{1-6}$-alkyl)aryl¹, pyrrolinyl, piperazinyl, morpholinyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—C($CH_3)_2$—$CH_2$—$CH_2$—, —$CH_2$—O—$CH_2$—O—, —O—$CH_2$—O—$CH_2$—, unsubstituted $C_{1-6}$-alkyl, pyrrolidinyl, imidazolyl, piperidinyl, benzyloxy, phenoxy, phenyl, naphthyl, pyridinyl, —$C_{1-3}$-alkylene-aryl¹, benzyl, thienyl, and furyl, wherein aryl¹ represents phenyl, furyl, thienyl or pyridinyl and the abovementioned substituents can optionally be substituted by the same substituents; and said $C_{1-6}$-alkyl, $C_{2-6}$-alkenyl, $C_{1-3}$-alkylene, $C_{1-6}$-alkylene, $C_{2-6}$-alkenylene and $C_{2-6}$-alkynylene groups may each be branched or unbranched;

or a physiologically acceptable salt or N-oxide thereof.

12. A compound as claimed in claim 11, wherein halogen denotes F, Cl or Br; and $R^{18}$ represents phenyl, naphthyl, a 5- to 6-membered heteroaryl containing 1 or 2 N hetero atoms, or a phenyl, naphthyl or 5- to 6-membered heteroaryl containing 1 or 2 N hetero atoms bonded via a $C_{1-3}$-alkylene group.

13. A compound as claimed in claim 1, wherein $R_{13}$ represents H, $C_{1-6}$-alkyl, or a phenyl bonded via a $C_{1-3}$alkylene group.

14. A substituted sulfonamide compound corresponding to formula I:

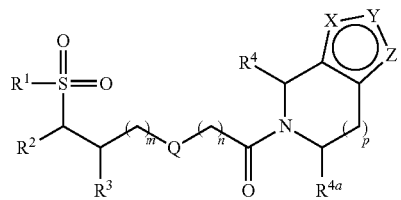

wherein
m and n each independently represent 0, 1 or 2;
p represents 0, 1 or 2;
Q represents a single bond —$CH_2$—or —O—;
X represents N, $NR^5$, O, S or $CR^8$;
Y represents N, $NR^6$, O, S or $CR^9$;
Z represents N, $NR^7$, O, S or $CR^{10}$;
$R^1$ represents phenyl or naphthyl, unsubstituted or mono- or poly-substituted by identical or different substituents independently selected from the group consisting of methyl, methoxy, —F, —Cl, —Br, —$CF_3$, and —$OCF_3$;
$R^2$ represents H, $C_{1-6}$-alkyl, $C_{3-6}$-cycloalkyl, 8- to 10-membered benzo-fused cycloalkyl, CH(phenyl$)_2$, aryl or heteroaryl; or a $C_{3-6}$-cycloalkyl, 8- to 12-membered benzo-fused cycloalkyl, CH(phenyl$)_2$, aryl or heteroaryl bonded via a $C_{1-6}$-alkylene group, $C_{2-6}$-alkenylene group or $C_{2-6}$-alkynylene group; wherein
said $C_{1-6}$-alkyl, $C_{3-6}$-cycloalkyl, $C_{1-6}$-alkylene, $C_{2-6}$-alkenylene, and $C_{2-6}$-alkynylene groups may each be unsubstituted or mono- or polysubstituted by identical or different substituents independently selected from the group consisting of $C_{1-6}$-alkyl, $C_{1-6}$-alkyl-O—, F, Cl, Br, I, OH and SH; and
said aryl groups may each be unsubstituted or mono- or polysubstituted by identical or different substituents independently selected from the group consisting of —$CH_2$—O—$CH_2$—O—, —O—$CH_2$—O—-$CH_2$—, $C_{1-6}$-alkyl, $C_{1-6}$-alkyl-O—, F, Cl, Br, I, $CF_3$, $OCF_3$, OH and SH;
$R^3$ represents H, =C(=O)—$NR^{11}R^{12}$, —C(=O)—$OR^{13}$, $C_{1-6}$-alkyl, aryl or heteroaryl; wherein
said $C_{1-6}$-alkyl group may be unsubstituted or mono- or polysubstituted by identical or different substituents independently selected from the group consisting of $C_{1-6}$-alkyl, $C_{1-6}$-alkyl-O—, F, Cl, Br, I, OH and SH; and
said aryl and heteroaryl groups may each be unsubstituted or mono- or polysubstituted by identical or different substituents independently selected from the group consisting of $C_{1-6}$-alkyl, $C_{1-6}$-alkyl-O—, F, Cl, Br, I, $CF_3$, $OCF_3$, OH and SH;
wherein $R^2$ and $R^3$ are not simultaneously H; or
$R^2$ and $R^3$ together with the —N—(CH—)—group joining them form an 4-, 5-, 6-, 7-membered unsubstituted or mono- or polysubstituted heterocyclic ring, which optionally may contain oxygen atom as a ring-member, and which optionally may be fused with one or two 6-membered aromatic rings;

$R^4$ and $R^{4a}$ each independently represent H, $C_{1-6}$-alkyl, $C_{3-8}$-cycloalkyl, phenyl, naphthyl, furyl, thienyl, pyridinyl, or a phenyl, naphthyl, furyl, thienyl or pyridinyl bonded via a $C_{1-3}$-alkylene group, wherein said phenyl, naphthyl, furyl, thienyl or pyridinyl may each be unsubstituted or mono- or polysubstituted by identical or different substituents independently selected from the group consisting of —O—$C_{1-3}$-alkyl, $C_{1-6}$-alkyl, —F, —Cl, —Br, —I, —CF$_3$, —OCF$_3$, —OH, —SH, phenyl, naphthyl, furyl, thienyl and pyridinyl;

$R^5$, $R^6$ and $R^7$ each independently represent H, $C_{1-4}$-alkyl, or phenyl;

$R^8$, $R^9$ and $R^{10}$ each independently represent H, —CF$_3$, —C(=O)—NR$^{11}$R$^{12}$, —C$_{1-6}$-alkylene-C(=O)—NR$^{11}$R$^{12}$, —C$_{1-6}$-alkylene-NR$^{11}$R$^{12}$, phenyl, naphthyl, furyl, thienyl, pyridinyl, or a phenyl, naphthyl, furyl, thienyl or pyridinyl bonded via a C1_6-alkylene group, wherein said phenyl, naphthyl, furyl, thienyl or pyridinyl may each be unsubstituted or mono- or polysubstituted by identical or different substituents independently selected from the group consisting of —O—$C_{1-3}$-alkyl, $C_{1-6}$-alkyl, —F, —Cl, —Br, —I, —CF$_3$, —OCF$_3$, —OH, —SH, phenyl, naphthyl, furyl, thienyl and pyridinyl;

wherein at least one of $R^4$, $R^{4a}$, $R^5$, $R^6$, $R^7$, $R^8$, $R^9$ and $R^{10}$ is not H;

$R^{11}$ and $R^{12}$ each independently represent H, or substituted or unsubstituted $C_{1-6}$-alkyl or $C_{3-8}$-cycloalkyl; or the group —NR$^{11}$R$^{12}$ represents a heterocylic ring corresponding to formula IIaa

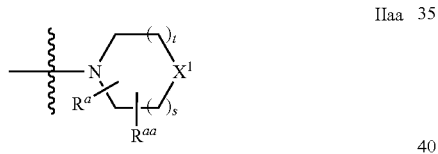

IIaa wherein $X^1$ represents O, S, NR$^{18}$CH$_2$, C(H)(halogen) or C(halogen)$_2$; represents H; $C_{1-6}$-alkyl, $C_{3-8}$-cycloalkyl, aryl, heteroaryl, or a $C_{3-8}$-cycloalkyl, aryl or heteroaryl bonded via a $C_{1-3}$-alkylene group, wherein
said $C_{1-6}$-alkyl, $C_{3-8}$-cycloalkyl, and $C_{1-3}$-alkylene groups may each be unsubstituted or mono- or polysubstituted by identical or different substituents independently selected from the group consisting of —O—$C_{1-3}$-alkyl, —F, —Cl, —Br, —I, —OH, and —SH; and
said aryl and heteroaryl groups may each be unsubstituted or mono- or polysubstituted by identical or different substituents independently selected from the group consisting of —O—$C_{1-3}$-alkyl, $C_{1-6}$-alkyl, —F, —Cl, —Br, —I, —CF3, —OCF3, —OH, —SH, phenyl, naphthyl, furyl, thienyl and pyridinyl;

$R^a$ and $R^{aa}$ each independently represent H, methyl, ethyl, F, Cl or Br, and s and t each independently represent 0, 1 or 2, with the proviso that s+t=0, 1, 2 or 3, and $R^{13}$ represents H, methyl, ethyl, n-propyl, iso-propyl, n-butyl, iso-butyl, sec-butyl, tert-butyl, benzyl or phenethyl;

wherein
said $C_{1-6}$-alkyl, $C_{2-6}$-alkenyl, $C_{1-3}$-alkylene, $C_{1-6}$-alkylene, $C_{2-6}$-alkenylene, $C_{2-6}$-alkynylene, and $C_{3-8}$-cycloalkyl, groups may be unsubstituted or substituted one or more times by identical or different substituents selected from the group consisting of F, Cl, Br, I, CN, NH$_2$, NH—$C_{1-6}$-alkyl, NH—$C_{1-6}$-alkylene-OH, $C_{1-6}$-alkyl, N($C_{1-6}$-alkyl)$_2$, N($C_{1-6}$-alkylene-OH)$_2$, NO$_2$,SH, S—$C_{1-6}$-alkyl, S-benzyl, O—$C_{1-6}$-alkyl, OH, O—$C_{1-6}$-alkylene-OH, =O, O-benzyl, C(=O) $C_{1-6}$alkyl, CO$_2$H, CO$_2$-$C_{1-6}$alkyl and benzyl;

said 3- to 8-membered heterocycloalkyl groups may be unsubstituted or substituted one or more times by identical or different substituents selected from the group consisting of F, Cl, Br, I, —CN, NH$_2$, NH—$C_{1-6}$-alkyl, NH—$C_{1-6}$-alkylene-OH, $C_{1-6}$-alkyl, N($C_{1-6}$-alkyl)$_2$, N($C_{1-6}$-alkylene-OH)$_2$, pyrrolinyl, piperazinyl, morpholinyl, NO$_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$alkyl, CO$_2$H, CO$_2$-$C_{1-6}$alkyl and benzyl; or, if a N heteroatom is present, the N heteroatom can be substituted by a $C_{1-6}$-alkyl, $C_{3-8}$-cycloalkyl, aryl, heteroaryl, or a $C_{3-8}$-cycloalkyl, aryl or heteroaryl bonded via a $C_{1-3}$-alkylene group, wherein these alkyl, cycloalkyl, alkylene and aryl and heteroaryl groups may each be unsubstituted or substituted one or more times by identical or different substituents;

said bicyclic 8- to 12-membered carbocyclyl groups may be unsubstituted, substituted on a saturated or partly unsaturated ring of the carbocyclyl one or more times by identical or different substituents selected from the group consisting of F, Cl, Br, I, CN, NH$_2$, NH—$C_{1-6}$-alkyl, NH—$C_{1-6}$-alkylene-OH, $C_{1-6}$-alkyl, N($C_{1-6}$-alkyl)$_2$, N($C_{1-6}$-alkylene-OH)$_2$, NO$_2$, SH, S—$C_{1-6}$-alkyl, S-benzyl, O—$C_{1-6}$-alkyl, OH, O—$C_{1-6}$-alkylene-OH, =O, O-benzyl, C(=O) $C_{1-6}$alkyl, CO$_2$H, CO$_2$-$C_{1-6}$alkyl and benzyl, or substituted on an aromatic ring of the carbocyclyl one or more times by identical or different substituents selected from the group consisting of F, Cl, Br, I, CN, NH$_2$, NH—$C_{1-6}$-alkyl, NH—$C_{1-6}$-alkylene-OH, N($C_{1-6}$-alkyl)$_2$, N($C_{1-6}$-alkylene-OH)$_2$, NH-aryl$^1$, N(aryl$^1$)$_2$, N($C_{1-6}$-alkyl)aryl$^1$, pyrrolinyl, piperazinyl, morpholinyl, NO$_2$, SH, S—$C_{1-6}$-alkyl, OH, O—$C_{1-6}$-alkyl, O—$C_{1-6}$-alkyl-OH, C(=O)$C_{1-6}$-alkyl, NHSO$_2$$C_{1-6}$-alkyl, NHCOC$_{1-6}$-alkyl, CO$_2$H, CH$_2$SO$_2$-phenyl, CO$_2$—$C_{1-6}$-alkyl, OCF$_3$, CF$_3$, —O—CH$_2$—O—, —O—CH$_2$—CH$_2$—O—, —O—C(CH$_3$)$_2$—CH$_2$—, unsubstituted $C_{1-6}$-alkyl, pyrrolidinyl, imidazolyl, piperidinyl, benzyloxy, phenoxy, phenyl, naphthyl, pyridinyl, —$C_{1-3}$-alkylene-aryl$^1$, benzyl, thienyl, and furyl, wherein aryl$^1$ represents phenyl, furyl, thienyl or pyridinyl and the abovementioned substituents can optionally be substituted by the same substituents;

said aryl and heteroaryl groups may be unsubstituted or substituted one or more times by identical or different substituents selected from the group consisting of F, Cl, Br, I, CN, NH$_2$, NH—$C_{1-6}$-alkyl, NH—$C_{1-6}$-alkylene-OH, N($C_{1-6}$-alkyl)$_2$, N($C_{1-6}$-alkylene-OH)$_2$, NH-aryl$^1$, N(aryl$^1$)$_2$, N($C_{1-6}$-alkyl)aryl$^1$, pyrrolinyl, piperazinyl, morpholinyl, NO$_2$, SH, S—$C_{1-6}$-alkyl, OH, O—$C_{1-6}$-alkyl, O—$C_{1-6}$-alkyl-OH, C(=O)$C_{1-6}$-alkyl, NHSO$_2$$C_{1-6}$-alkyl, NHCOC$_{1-6}$-alkyl, CO$_2$H, CH$_2$SO$_2$-phenyl, CO$_2$—$C_{1-6}$-alkyl, OCF$_3$, CF$_3$, —O—CH$_2$—O—, —O—CH$_2$—CH$_2$—O—, —O—C(CH$_3$)$_2$—CH$_2$—O—CH$_2$—O—, —O—Ch$_2$—O—CH$_2$, unsubstituted $C_{1-6}$-alkyl, pyrrolidinyl, imidazolyl, piperidinyl, benzyloxy, phenoxy, phenyl, naphthyl, pyridinyl, —$C_{1-3}$-alkylenearyl¹, benzyl, thienyl, and furyl, wherein aryl¹ represents phenyl, furyl, thienyl or pyridinyl and the abovementioned substituents can optionally be substituted by the same substituents;

the substituents of a substituted heterocyclic ring are independently selected from the group consisting of F, Cl, Br, I, CN, $NH_2$, NH—$C_{1-6}$-alkyl, NH—$C_{1-6}$-alkylene-OH, $C_{1-6}$-alkyl, N($C_{1-6}$-alkyl)$_2$, N($C_{1-6}$-alkylene-OH)$_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$alkyl, $CO_2H$, $CO_2$-$C_{1-6}$alkyl and benzyl;

the substituents of a substituted, saturated or at least partly unsaturated ring system which is fused with a heterocyclic ring formed by $R^{11}$ and $R^{12}$ are independently selected from the group consisting of F, Cl, Br, I, CN, $NH_2$, NH—$C_{1-6}$-alkyl, NH—$C_{1-6}$-alkylene-OH, $C_{1-6}$-alkyl, N($C_{1-6}$-alkyl)$_2$, N($C_{1-6}$-alkylene-OH)$_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$alkyl, $CO_2H$, $CO_2$-$C_{1-6}$alkyl and benzyl;

the substituents of a substituted aromatic ring system which is fused with a heterocyclic ring formed by $R^{11}$ and $R^{12}$ are independently selected from the group consisting of F, Cl, Br, I, CN, $NH_2$, NH—$C_{1-6}$-alkyl, NH—$C_{1-6}$-alkylene-OH, N($C_{1-6}$-alkyl)$_2$, N($C_{1-6}$-alkylene-OH)$_2$, NH-aryl¹, N(aryl¹)$_2$, N($C_{1-6}$-alkyl)aryl¹, pyrrolinyl, piperazinyl, morpholinyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—C($CH_3$)$_2$—$CH_2$—, —$CH_2$—O—$CH_2$—O—, —O—$CH_2$—O—$CH_2$—, unsubstituted $C_{1-6}$-alkyl, pyrrolidinyl, imidazolyl, piperidinyl, benzyloxy, phenoxy, phenyl, naphthyl, pyridinyl, —$C_{1-3}$-alkylene-aryl¹, benzyl, thienyl, and furyl, wherein aryl¹ represents phenyl, furyl, thienyl or pyridinyl and the abovementioned substituents can optionally be substituted by the same substituents; and said $C_{1-6}$-alkyl, $C_{2-6}$-alkenyl, $C_{1-3}$-alkylene, $C_{1-6}$-alkylene, $C_{2-6}$-alkenylene and $C_{2-6}$-alkynylene groups may each be branched or unbranched;

or a physiologically acceptable salt or N-oxide thereof.

15. A compound as claimed in claim 1, wherein:
X represents $CR^8$,
Y represents $CR^9$, and
Z represents S;
or
X represents S,
Y represents $CR^9$, and
Z represents N;
or
X represents $CR^8$,
Y represents N, and
Z represents O;
or
X represents $CR^8$,
Y represents $CR^9$, and
Z represents $NR^7$;
or
X represents S,
Y represents $CR^9$, and
Z represents $CR^{10}$;
or X represents N,
Y represents $CR^9$, and
Z represents $NR^7$;
or
X represents O,
Y represents $CR^9$, and
Z represents N;
or
X represents $NR^5$,
Y represents N, and
Z represents $CR^{10}$;
or
X represents $CR^8$,
Y represents N, and
Z represents $NR^7$.

16. A compound as claimed in claim 1, wherein p represents 0 or 1.

17. A compound as claimed in claim 1, selected from the group consisting of:

1  3-(1-(4-methoxy-2,6-dimethylphenylsulfonyl)piperidin-2-yl)-1-(3-(pyridin-4-yl)-6,7-dihydroisoxazolo[4,5-c]pyridin-5(4H)-yl)propan-1-one 2  2-((1-(4-methoxy-2,6-dimethylphenylsulfonyl)piperidin-2-yl)methoxy)-1-(3-(pyridin-4-yl)-6,7-dihydroisoxazolo[4,5-c]pyridin-5(4H)-yl)ethanone 3  (R)—N-(3-oxo-1-phenyl-3-(3-(pyridin-4-yl)-6,7-dihydroisoxazolo[4,5-c]pyridin-5(4H)-yl)propyl)naphthalene-2-sulfonamide 4  3-(1-(4-chloro-2,5-dimethylphenylsulfonyl)piperidin-2-yl)-1-(3-(piperidine-1-carbonyl)-6,7-dihydroisoxazolo[4,5-c]pyridin-5(4H)-yl)propan-1-one 5  1-(3-(piperidin-1-ylmethyl)-6,7-dihydroisoxazolo[4,5-c]pyridin-5(4H)-yl)-2-(1-(3-(trifluormethyl)phenylsulfonyl)piperidin-2-yl)ethanone 6  3-(1-(4-chloro-2,5-dimethylphenylsulfonyl)piperidin-2-yl)-1-(3-(piperidin-1-ylmethyl)-6,7-dihydroisoxazolo[4,5-c]pyridin-5(4H)-yl)propan-1-one 7  2-((1-(4-methoxy-2,6-dimethylphenylsulfonyl)piperidin-2-yl)methoxy)-1-(4-p-tolyl-6,7-dihydrothieno[3,2-c]pyridin-5(4H)-yl)ethanone 8  2-((1-(4-methoxy-2,6-dimethylphenylsulfonyl)piperidin-2-yl)methoxy)-1-(4-m-tolyl-6,7-dihydrothieno[3,2-c]pyridin-5(4H)-yl)ethanone 9  2-((1-(4-methoxy-2,6-dimethylphenylsulfonyl)piperidin-2-yl)methoxy)-1-(3-(piperidin-1-ylmethyl)-6,7-dihydroisoxazolo[4,5-c]pyridin-5(4H)-yl)ethanone 10  3-(1-(4-chloro-2,5-dimethylphenylsulfonyl)piperidin-2-yl)-1-(4-m-tolyl-6,7-dihydrothieno[3,2-c]pyridin-5(4H)-yl)propan-1-one 11  3-(1-(4-chloro-2,5-dimethylphenylsulfonyl)piperidin-2-yl)-1-(4-o-tolyl-6,7-dihydrothieno[3,2-c]pyridin-5(4H)-yl)propan-1-one 12  2-((1-(4-methoxy-2,6-dimethylphenylsulfonyl)piperidin-2-yl)methoxy)-1-(4-o-tolyl-6,7-dihydrothieno[3,2-c]pyridin-5(4H)-yl)ethanone 13  4-methoxy-N,2,6-trimethyl-N-(2-(2-oxo-2-(3-(piperidin-1-ylmethyl)-6,7-dihydroisoxazolo[4,5-c]pyridin-5(4H)-yl)ethoxy)ethyl)benzenesulfonamide 14  2-((1-(4-methoxy-2,6-dimethylphenylsulfonyl)piperidin-2-yl)methoxy)-1-(3-(piperidin-1-carbonyl)-6,7-dihydroisoxazolo[4,5-c]pyridin-5(4H)-yl)ethanone 15  2-((1-(4-methoxy-2,6-dimethylphenylsulfonyl)piperidin-2-yl)methoxy)-1-(4-phenyl-6,7-dihydrothieno[3,2-c]pyridin-5(4H)-yl)ethanone 16 3-(1-(4-chloro-2,5-dimethylphenylsulfonyl)piperidin-2-yl)-1-(4-phenyl-6,7-dihydrothieno[3,2-c]pyridin-5(4H)-yl)propan-1-one 17 (R)—N-(3-oxo-1-phenyl-3-(3-(piperidin-1-ylmethyl)-6,7-dihydroisoxazolo[4,5-c]pyridin-5(4H)-yl)propyl)naphthalene-2-sulfonamide 18 N-(2-(2-(4-ethyl-6,7-dihydrothieno[3,2-c]pyridin-5(4H)-yl)-2-oxoethoxy)ethyl)-4-methoxy-N,2,6-trimethylbenzenesulfonamide 19 1-(4-(4-fluorophenyl)-6,7-dihydrothieno[3,2-c]pyridin-5(4H)-yl)-2-(1-(3-(trifluoromethyl)phenylsulfonyl)piperidin-2-yl)ethanone 20 N-((1R)-3-oxo-1-phenyl-3-(4-p-tolyl-6,7-dihydrothieno[3,2-c]pyridin-5(4H) -yl)propyl)naphthalene-2-sulfonamide 21 N-((1R)-3-(4-(4-fluorophenyl)-6,7-dihydrothieno[3,2-c]pyridin-5(4H)-yl)-3-oxo-1-phenylpropyl)naphthalene-2-sulfonamide 22 1-(4-(4-fluorophenyl)-6,7-dihydrothieno[3,2-c]pyridin-5(4H)-yl)-2-((1-(4-methoxy-2,6-dimethylphenylsulfonyl)piperidin-2-yl)methoxy)ethanone 23 1-(4-ethyl-6,7-dihydrothieno[3,2-c]pyridin-5(4H)-yl)-4-(1-(4-methoxy-2,6-dimethylphenylsulfonyl)piperidin-2-yl)butan-1-one 24 1-(3-(4-chlorophenyl)-6,7-dihydroisoxazolo[4,5-c]pyridin-5(4H)-yl)-2-((1-(4-methoxy-2,6-dimethylphenylsulfonyl)piperidin-2-yl)methoxy)ethanone 25 1-(3-(4-fluorophenyl)-6,7-dihydroisoxazolo[4,5-c]pyridin-5(4H)-yl)-2-((1-(4-methoxy-2,6-dimethylphenylsulfonyl)piperidin-2-yl)methoxy)ethanone 26 (R)—N-(3-oxo-1-phenyl-3-(2-(piperidin-1-ylmethyl)-6,7-dihydrothieno[3,2-c]pyridin-5(4H)-yl)propyl)naphthalene-2-sulfonamide 27 2-((1-(4-methoxy-2,6-dimethylphenylsulfonyl)piperidin-2-yl)methoxy)-1-(2-(piperidin-1-ylmethyl)-6,7-dihydrothieno[3,2-c]pyridin-5(4H)-yl)ethanone 28 4-methoxy-N,2,6-trimethyl-N-(2-(2-oxo-2-(2-(piperidin-1-ylmethyl)-6,7-dihydrothieno[3,2-c]pyridin-5(4H)-yl)ethoxy)ethyl)benzenesulfonamide 29 2-((1-(4-methoxy-2,6-dimethylphenylsulfonyl)piperidin-2-yl)methoxy)-1-(3-(morpholinomethyl)-6,7-dihydroisoxazolo[4,5-c]pyridin-5(4H)-yl)ethanone 30 4-methoxy-N,2,6-trimethyl-N-(2-(2-(3-(morpholinomethyl)-6,7-dihydroisoxazolo[4,5-c]pyridin-5(4H)-yl)-2-oxoethoxy)ethyl)benzenesulfonamide 31 1-(3-((dimethylamino)methyl)-6,7-dihydroisoxazolo[4,5-c]pyridin-5(4H)-yl)-2-((1-(4-methoxy-2,6-dimethylphenylsulfonyl)piperidin-2-yl)methoxy)ethanone 32 N-(2-(2-(3-((dimethylamino)methyl)-6,7-dihydroisoxazolo[4,5-c]pyridin-5(4H)-yl)-2-oxoethoxy)ethyl)-4-methoxy-N,2,6-trimethylbenzenesulfonamide 33 3-(1-(4-chloro-2,5-dimethylphenylsulfonyl)piperidin-2-yl)-1-(4-(6-chloropyridin-3-yl)-6,7-dihydrothieno[3,2-c]pyridin-5(4H)-yl)propan-1-one 34 3-(1-(4-chloro-2,5-dimethylphenylsulfonyl)piperidin-2-yl)-1-(4-(3-(trifluoromethyl)phenyl)-6,7-dihydrothieno[3,2-c]pyridin-5(4H)-yl)propan-1-one 35 3-(1-(4-chloro-2,5-dimethylphenylsulfonyl)piperidin-2-yl)-1-(4-(3-fluorophenyl)-6,7-dihydrothieno[3,2-c]pyridin-5(4H)-yl)propan-1-one 36 2-((1-(4-methoxy-2,6-dimethylphenylsulfonyl)piperidin-2-yl)methoxy)-1-(4-(pyridin-4-yl)-6,7-dihydrothieno[3,2-c]pyridin-5(4H)-yl)ethanone 37 1-(2-(pyridin-4-yl)-6,7-dihydrothiazolo[5,4-c]pyridin-5(4H)-yl)-2-(1-(3-(trifluoromethyl)phenylsulfonyl)piperidin-2-yl)ethan-1-one 38 2-((1-(4-methoxy-2,6-dimethylphenylsulfonyl)piperidin-2-yl)methoxy)-1-(2-(pyridin-4-ylmethyl)-6,7-dihydrothiazolo[5,4-c]pyridin-5(4H)-yl)ethan-1-one 39 4-methoxy-N,2,6-trimethyl-N-(2-(2-oxo-2-(2-(pyridin-4-ylmethyl)-6,7-dihydrothiazolo[5,4-c]pyridin-5(4H)-yl)ethoxy)ethyl)benzenesulfonamide 40 1-(2-(pyridin-4-ylmethyl)-6,7-dihydrothiazolo[5,4-c]pyridin-5(4H)-yl)-2-(1-(3-(trifluoromethyl)phenylsulfonyl)piperidin-2-yl)ethan-1-one 41 3-(1-(4-methoxy-2,6-dimethylphenylsulfonyl)piperidin-2-yl)-1-(2-(pyridin-4-ylmethyl)-6,7-dihydrothiazolo[5,4-c]pyridin-5(4H)-yl)propan-1-one 42 N-(3-oxo-1-phenyl-3-(2-(pyridin-4-ylmethyl)-6,7-dihydrothiazolo[5,4-c]pyridin-5(4H)-yl)propyl)naphthalene-2-sulfonamide 43 4-(1-(4-methoxy-2,6-dimethylphenylsulfonyl)piperidin-2-yl)-1-(2-(pyridin-4-ylmethyl)-6,7-dihydrothiazolo[5,4-c]pyridin-5(4H)-yl)butan-1-one 44 1-(2-((4-methylpiperazin-1-yl)methyl)-6,7-dihydrothieno[3,2-c]pyridin-5(4H)-yl)-2-(1-(3-(trifluoromethyl)phenylsulfonyl)piperidin-2-yl)ethan-1-one 45 3-(1-(4-methoxy-2,6-dimethylphenylsulfonyl)piperidin-2-yl)-1-(2-((4-methylpiperazin-1-yl)methyl)-6,7-dihydrothieno[3,2-c]pyridin-5(4H) -yl)propan-1-one 46 N-(3-(2-((4-methylpiperazin-1-yl)methyl)-6,7-dihydrothieno[3,2-c]pyridin-5(4H)-yl)-3-oxo-1-phenylpropyl)naphthalene-2-sulfonamide 47 4-(1-(4-methoxy-2,6-dimethylphenylsulfonyl)piperidin-2-yl)-1-(2-((4-methylpiperazin-1-yl)methyl)-6,7-dihydrothieno[3,2-c]pyridin-5(4H) -yl)butan-1-one 48 2-((1-(4-methoxy-2,6-dimethylphenylsulfonyl)piperidin-2-yl)methoxy)-1-(2-(pyridin-4-yl)-6,7-dihydrothiazolo[5,4-c]pyridin-5(4H)-yl)ethan-1-one 49 4-methoxy-N,2,6-trimethyl-N-(2-(2-oxo-2-(2-(pyridin-4-yl)-6,7-dihydrothiazolo[5,4-c]pyridin-5(4H)-yl)ethoxy)ethyl)benzenesulfonamide 50 2-((1-(4-methoxy-2,6-dimethylphenylsulfonyl)piperidin-2-yl)methoxy)-1-(2-((4-methylpiperazin-1-yl)methyl)-6,7-dihydrothieno[3,2-c]pyridin-5(4H) -yl)ethan-1-one 51 4-methoxy-N,2,6-trimethyl-N-(2-(2-(2-((4-methylpiperazin-1-yl)methyl)-6,7-dihydrothieno[3,2-c]pyridin-5(4H)-yl)-2-oxoethoxy)ethyl)benzenesulfonamide 52 3-(1-(4-methoxy-2,6-dimethylphenylsulfonyl)piperidin-2-yl)-1-(2-(pyridin-4-yl)-6,7-dihydrothiazolo[5,4-c]pyridin-5(4H)-yl)propan-1-one 53 4-(1-(4-methoxy-2,6-dimethylphenylsulfonyl)piperidin-2-yl)-1-(2-(pyridin-4-yl)-6,7-dihydrothiazolo[5,4-c]pyridin-5(4H)-yl)butan-1-one 54 1-(4-pyridin-4-yl-4,5,6,7-tetrahydro-thieno[3,2-c]pyridin-5-yl)-2-[1-[[3-(trifluoromethyl)phenyl]sulfonyl]-piperidin-2-yl]-ethanone 55 3-[1-[(4-chloro-2,5-dimethyl-phenyl)sulfonyl]-piperidin-2-yl]-1-(4-pyridin-4-yl-4,5,6,7-tetrahydro-thieno[3,2-c]pyridin-5-yl)-propan-1-one 56 N-[2-[2-[2-(azetidin-1-yl-methyl)-4,5,6,7-tetrahydro-thieno[3,2-c]pyridin-5-yl]-2-oxo-ethoxy]-ethyl]-2-chloro-N-cyclopropyl-6-methyl-benzenesulfonic acid amide 57 2-chloro-N-cyclopropyl-N-[2-[2-[2-[(3,3-difluoro-azetidin-1-yl)-methyl]-4,5,6,7-tetra-hydro-thieno[3,2-c]pyridin-5-yl]-2-oxo-ethoxy]-ethyl]-6-methyl -benzenesulfonic acid amide 58  2-[[(2S)-1-[(4-methoxy-2,6-dimethyl-phenyl)sulfonyl]-piperidin-2-yl]-methoxy]-1-[2-(piperidin-1-yl-methyl)-4,5,6,7-tetrahydro-thiazolo[5,4-c]pyridin-5-yl]-ethanone 59  2-[[(2S)-1-[(2-chloro-6-methyl-phenyl)sulfonyl]-piperidin-2-yl]-methoxy]-1-[2-(piperidin-1-yl-methyl)-4,5,6,7-tetrahydro-thieno[3,2-c]pyridin-5-yl]-ethanone 60  2-chloro-N-cyclopropyl-6-methyl-N-[2-[2-oxo-2-[2-(piperidin-1-yl-methyl)-4,5,6,7-tetrahydro-thieno[3,2-c]pyridin-5-yl]-ethoxy]-ethyl]-benzenesulfonic acid amide 61  2-[[(2S)-1-[(4-methoxy-2,6-dimethyl-phenyl)sulfonyl]-1,2,3,4-tetrahydro -quinolin-2-yl]-methoxy]-1-[2-(piperidin-1-yl-methyl)-4,5,6,7-tetrahydro -thieno[3,2-c]pyridin-5-yl]-ethanone 62  2-[[(2S)-[(4-methoxy-2,6-dimethyl-phenyl)sulfonyl]-piperidin-2-yl]-methoxy]-1-[2-(pyrrolidin-1-yl-methyl)-4,5,6,7-tetrahydro-thieno[3,2-c]pyridin-5-yl]-ethanone 63  2-[[(2S)-[(4-methoxy-2,6-dimethyl-phenyl)sulfonyl]-pyrrolidin-2-yl]-methoxy]-[2-(piperidin-1-yl -methyl)-4,5,6,7-tetrahydro-thieno[3,2-c]pyridin-5-yl]-ethanone 64  2-[[(2S)-1-[(4-methoxy-2,6-dimethyl-phenyl)sulfonyl]-piperidin-2-yl]-methoxy]-1-[2-[(4-methyl-[1,4]diazepan-1-yl)-methyl]-4,5,6,7-tetrahydro -thieno[3,2-c]pyridin-5-yl]-ethanone 66  4-Methoxy-N,2,6-trimethyl-N-[2-[2-oxo-2-(4-phenyl-4,5,6,7-tetrahydro-1H -imidazo[4,5-c]pyridin-5-yl)-ethoxy]-ethyl]-benzenesulfonic acid amide 68  4-[1-[(2-Chloro-6-methyl-phenyl)sulfonyl]-piperidin-2-yl]-1-[2-[(4-methyl -piperazin-1-yl)-methyl]-4,5,6,7-tetrahydro-thieno[3,2-c]pyridin-5-yl]-butan-1-one 69  4-[1-[(2-Chloro-6-methyl-phenyl)sulfonyl]-piperidin-2-yl]-1-(4-phenyl-4,5,6,7-tetrahydro-1H-imidazo[4,5-c]pyridin-5-yl)-butan-1-one 71  4-[1-[(4-Methoxy-2,6-dimethyl-phenyl)sulfonyl]-piperidin-2-yl]-1-(4-phenyl-4,5,6,7-tetrahydro-1H-imidazo[4,5-c]pyridin-5-yl)-butan-1-one 73  1-[2-[(4-Methyl-piperazin-1-yl)-methyl]-4,5,6,7-tetrahydro-thieno[3,2-c]pyridin-5-yl]-4-[1-(naphthalen-1-yl-sulfonyl)-piperidin-2-yl]-butan-1-one 74  4-[1-(Naphthalen-1-ylsulfonyl)-piperidin-2-yl]-1-(4-phenyl-4,5,6,7-tetrahydro-1H-imidazo[4,5-c]pyridin-5-yl)-butan-1-one 75  1-[2-[(4-Methyl-piperazin-1-yl)-methyl]-4,5,6,7-tetrahydro-thieno[3,2-c]pyridin-5-yl]-4-[1-(naphthalen-2-yl-sulfonyl)-piperidin-2-yl]-butan-1-one 76  4-[1-(Naphthalen-2-ylsulfonyl)-piperidin-2-yl]-1-(4-phenyl-4,5,6,7-tetrahydro-1H-imidazo[4,5-c]pyridin-5-yl)-butan-1-one 78  N-(4H-[1,3]Benzodioxin-7-yl-methyl)-4-methoxy-2,6-dimethyl-N-[2-[2-[2-[(4-methyl-piperazin-1-yl)-methyl]-4,5,6,7-tetrahydro-thieno[3,2-c]pyridin-5-yl]-2-oxo-ethoxy]-ethyl]-benzenesulfonic acid amide 81  N-Benzyl-4-Methoxy-2,6-dimethyl-N-[2-[2-[2-[(4-methyl-piperazin-1-yl)  -methyl]-4,5,6,7-tetrahydro-thieno[3,2-c]pyridin-5-yl]-2-oxo-ethoxy]-ethyl]-benzenesulfonic acid amide 82  N-Benzyl-4-Methoxy-2,6-dimethyl-N-[2-[2-oxo-2-(4-phenyl-4,5,6,7-tetrahydro-1H-imidazo[4,5-c]pyridin-5-yl)-ethoxy]-ethyl]-benzenesulfonic acid amide 83  4-Methoxy-2,6-Dimethyl-N-[2-[2-[2-[(4-methyl-piperazin-1-yl)-methyl]-4,5,6,7-tetrahydro-thieno[3,2-c]pyridin-5-yl]-2-oxo-ethoxy]-ethyl]-N-phenyl -benzenesulfonic acid amide 84  4-Methoxy-2,6-Dimethyl-N-[2-[2-oxo-2-(4-phenyl-4,5,6,7-tetrahydro-1H -imidazo[4,5-c]pyridin-5-yl)-ethoxy]-ethyl]-N-phenyl-benzenesulfonic acid amide 85  2-[[1-[(4-Methoxy-2,6-dimethyl-phenyl)sulfonyl]-1,2,3,4-tetrahydro -quinolin-2-yl]-methoxy]-1-[2-[(4-methyl-piperazin-1-yl)-methyl]-4,5,6,7-tetrahydro-thieno[3,2-c]pyridin-5-yl]-ethanone 86  2-[[1-[(4-Methoxy-2,6-dimethyl-phenyl)sulfonyl]-1,2,3,4-tetrahydro -quinolin-2-yl]-methoxy]-1-(4-phenyl-4,5,6,7-tetrahydro-1H-imidazo[4,5-c]pyridin-5-yl)-ethanone 87  1-[2-[(4-Methyl-piperazin-1-yl)-methyl]-4,5,6,7-tetrahydro-thieno[3,2-c]pyridin-5-yl]-4-[1-[[2-(trifluoromethyl)-phenyl]sulfonyl]-piperidin-2-yl]-butan-1-one 88  1-(4-Phenyl-4,5,6,7-tetrahydro-1H-imidazo[4,5-c]pyridin-5-yl)-4-[1-[[2-(trifluoromethyl)-phenyl]sulfonyl]-piperidin-2-yl]-butan-1-one 91  2-[[4-[(Methoxy-2,6-dimethyl-phenyl)sulfonyl]-3,4-dihydro-2H -[1,4]benzoxazin-3-yl]-methoxy]-1-[2-[(4-methyl-piperazin-1-yl)-methyl]-4,5,6,7-tetrahydro-thieno[3,2-c]pyridin-5-yl]-ethanone 92  2-[[4-[(4-Methoxy-2,6-dimethyl-phenyl)sulfonyl]-3,4-dihydro-2H -[1,4]benzoxazin-3-yl]-methoxy]-1-(4-phenyl-4,5,6,7-tetrahydro-1H -imidazo[4,5-c]pyridin-5-yl)-ethanone 93  1-[2-[(4-Methyl-piperazin-1-yl)-methyl]-4,5,6,7-tetrahydro-thieno[3,2-c]pyridin-5-yl]-2-[[4-[[2-(trifluoromethyl)-phenyl]sulfonyl]-3,4-dihydro-2H -[1,4]benzoxazin-3-yl]-methoxy]-ethanone 94  1-(4-Phenyl-4,5,6,7-tetrahydro-1H-imidazo[4,5-c]pyridin-5-yl)-2-[[4-[[2-(trifluoromethyl)-phenyl]sulfonyl]-3,4-dihydro-2H-[1,4]benzoxazin-3-yl]-methoxy]-ethanone 95  4-Methoxy-N,2,3,6-tetramethyl-N-[2-[2-[2-[(4-methyl-piperazin-1-yl) -methyl]-4,5,6,7-tetrahydro-thieno[3,2-c]pyridin-5-yl]-2-oxo-ethoxy]-ethyl]-benzenesulfonic acid amide 96  4-Methoxy-N,2,3,6-tetramethyl-N-[2-[2-oxo-2-(4-phenyl-4,5,6,7-tetrahydro-1H-imidazo[4,5-c]pyridin-5-yl)-ethoxy]-ethyl]-benzenesulfonic acid amide 97  1-[2-[(4-Methyl-piperazin-1-yl)-methyl]-4,5,6,7-tetrahydro-thieno[3,2-c]pyridin-5-yl]-2-[[1-[[2-(trifluoromethyl)-phenyl]sulfonyl]-piperidin-2-yl]-methoxy]-ethanone 98  1-(4-Phenyl-4,5,6,7-tetrahydro-1H-imidazo[4,5-c]pyridin-5-yl)-2-[[1-[[2-(trifluoromethyl)-phenyl]sulfonyl]-piperidin-2-yl]-methoxy]-ethanone 99  3-[[1-[(4-Methoxy-2,6-dimethyl-phenyl)sulfonyl]-piperidin-2-yl]-methoxy]-1-[2-[(4-methyl-piperazin-1-yl)-methyl]-4,5,6,7-tetrahydro-thieno[3,2-c]pyridin-5-yl]-propan-1-one 100  3-[[1-[(4-Methoxy-2,6-dimethyl-phenyl)sulfonyl]-piperidin-2-yl]-methoxy]-1-(4-phenyl-4,5,6,7-tetrahydro-1H-imidazo[4,5-c]pyridin-5-yl)-propan-1-one 101  2-[2-[1-[(4-Methoxy-2,6-dimethyl-phenyl)sulfonyl]-piperidin-2-yl]-ethoxy]-1-[2-[(4-methyl-piperazin-1-yl)-methyl]-4,5,6,7-tetrahydro-thieno[3,2-c]pyridin-5-yl]-ethanone 102  2-[2-[1-[(4-Methoxy-2,6-dimethyl-phenyl)sulfonyl]-piperidin-2-yl]-ethoxy]-1-(4-phenyl-4,5,6,7-tetrahydro-1H-imidazo[4,5-c]pyridin-5-yl)-ethanone 103  N-Methyl-N-[4-[2-[(4-methyl-piperazin-1-yl)-methyl]-4,5,6,7-tetrahydro -thieno[3,2-c]pyridin-5-yl]-4-oxo-butyl]-3-(trifluoromethyl)-benzenesulfonic acid amide 104  N-Methyl-N-[4-Oxo-4-(4-phenyl-4,5,6,7-tetrahydro-1H-imidazo[4,5-c]pyridin-5-yl)-butyl]-3-(trifluoromethyl)-benzenesulfonic acid amide 105  1-[2-[(4-Methyl-piperazin-1-yl)-methyl]-4,5,6,7-tetrahydro-thieno[3,2-c]pyridin-5-yl]-2-[4-(naphthalen-2-yl-sulfonyl)-3,4-dihydro-2H -[1,4]benzoxazin-3-yl]-ethanone 106  2-[4-(Naphthalen-2-ylsulfonyl)-3,4-dihydro-2H-[1,4]benzoxazin-3-yl]-1-(4-phenyl-4,5,6,7-tetrahydro-1H-imidazo[4,5-c]pyridin-5-yl)-ethanone 107 4-Methoxy-N,2,6-trimethyl-N-[2-[2-oxo-2-(2-phenyl-4,5,6,7-tetrahydro-oxazolo[5,4-c]pyridin-5-yl)-ethoxy]-ethyl]-benzenesulfonic acid amide 108 4-Methoxy-N,2,6-trimethyl-N-[2-[2-[1-methyl-3-(trifluoromethyl)-1,4,5,6-tetrahydro-pyrrolo[3,4-c]pyrazol-5-yl]-2-oxo-ethoxy]-ethyl]-benzenesulfonic acid amide 109 2-[[1-[(4-Methoxy-2,6-dimethyl-phenyl)sulfonyl]-piperidin-2-yl]-methoxy]-1-(2-phenyl-4,5,6,7-tetrahydro-oxazolo[5,4-c]pyridin-5-yl)-ethanone 110 2-[[1-[(4-Methoxy-2,6-dimethyl-phenylsulfonyl]-piperidin-2-yl]-methoxy]-1-[1-methyl-3-(trifluoromethyl)-1,4,5,6-tetrahydro-pyrrolo[3,4-c]pyrazol-5-yl]-ethanone 111 4-[1-[(2-Chloro-6-methyl-phenyl)sulfonyl]-piperidin-2-yl]-1-(2-phenyl-4,5,6,7-tetrahydro-oxazolo[5,4-c]pyridin-5-yl)-butan-1-one 112 4-[1-[(2-Chloro-6-methyl-phenyl)sulfonyl]-piperidin-2-yl]-1-[1-phenyl-3-(trifluoromethyl)-1,4,5,6-tetrahydro-pyrrolo[3,4-c]pyrazol-5-yl]-butan-1-one 113 4-[1-[(2-Chloro-6-methyl-phenyl)sulfonyl]-piperidin-2-yl]-1-[1-methyl-3-(trifluoromethyl)-1,4,5,6-tetrahydro-pyrrolo[3,4-c]pyrazol-5-yl]-butan-1-one 114 4-[1-[(4-Methoxy-2,6-dimethyl-phenyl)sulfonyl]-piperidin-2-yl]-1-(2-phenyl-4,5,6,7-tetrahydro-oxazolo[5,4-c]pyridin-5-yl)-butan-1-one 115 4-[1-[(4-Methoxy-2,6-dimethyl-phenyl)sulfonyl]-piperidin-2-yl]-1-[1-phenyl-3-(trifluoromethyl)-1,4,5,6-tetrahydro-pyrrolo[3,4-c]pyrazol-5-yl]-butan-1-one 116 4-[1-[(4-Methoxy-2,6-dimethyl-phenyl)sulfonyl]-piperidin-2-yl]-1-[1-methyl-3-(trifluoromethyl)-1,4,5,6-tetrahydro-pyrrolo[3,4-c]pyrazol-5-yl]-butan-1-one 117 4-[1-(Naphthalen-1-ylsulfonyl)-piperidin-2-yl]-1-(2-phenyl-4,5,6,7-tetrahydro-oxazolo[5,4-c]pyridin-5-yl)-butan-1-one 118 1-[1-Methyl-3-(trifluoromethyl)-1,4,5,6-tetrahydro-pyrrolo[3,4-c]pyrazol-5-yl]-4-[1-(naphthalen-1-ylsulfonyl)-piperidin-2-yl]-butan-1-one 119 4-[1-(Naphthalen-2-ylsulfonyl)-piperidin-2-yl]-1-(2-phenyl-4,5,6,7-tetrahydro-oxazolo[5,4-c]pyridin-5-yl)-butan-1-one 120 1-[1-Methyl-3-(trifluoromethyl)-1,4,5,6-tetrahydro-pyrrolo[3,4-c]pyrazol-5-yl]-4-[1-(naphthalen-2-ylsulfonyl)-piperidin-2-yl]-butan-1-one 121 N-[(1-Ethyl-1H-imidazol-2-yl)-methyl]-4-methoxy-2,6-dimethyl-N-[2-[2-oxo-2-(2-phenyl-4,5,6,7-tetrahydro-oxazolo[5,4-c]pyridin-5-yl)-ethoxy]-ethyl]-benzenesulfonic acid amide 122 N-[(1-Ethyl-1H-imidazol-2-yl)-methyl]-4-methoxy-2,6-dimethyl-N-[2-[2-oxo-2-[1-phenyl-3-(trifluoromethyl)-1,4,5,6-tetrahydro-pyrrolo[3,4-c]pyrazol-5-yl]-ethoxy]-ethyl]-benzenesulfonic acid amide 123 N-[(1-Ethyl-1H-imidazol-2-yl)-methyl]-4-methoxy-2,6-dimethyl-N-[2-[2-[1-methyl-3-(trifluoromethyl)-1,4,5,6-tetrahydro-pyrrolo[3,4-c]pyrazol-5-yl]-2-oxo-ethoxy]-ethyl]-benzenesulfonic acid amide 124 N-(4H-[1,3]Benzodioxin-7-yl-methyl)-4-methoxy-2,6-dimethyl-N-[2-[2-oxo-2-(2-phenyl-4,5,6,7-tetrahydro-oxazolo[5,4-c]pyridin-5-yl)-ethoxy]-ethyl]-benzenesulfonic acid amide 125 2-[[(2S)-1-[(4-methoxy-2,6-dimethyl-phenyl)sulfonyl]-1,2,3,4-tetrahydro-quinolin-2-yl]-methoxy]-1-(3-pyridin-4-yl-4,5,6,7-tetrahydro-isoxazolo[4,5-c]pyridin-5-yl)-ethanone 126 2-((1-(4-methoxy-2,6-dimethylphenylsulfonyl)piperidin-2-yl)methoxy)-1-(4-phenyl-3-(piperidin-1-ylmethyl)-6,7-dihydroisoxazolo[4,5-c]pyridin-5(4H)-yl)ethanone and a physiologically acceptable salt thereof.

18. A pharmaceutical composition comprising a substituted sulfonamide compound corresponding to formula I:

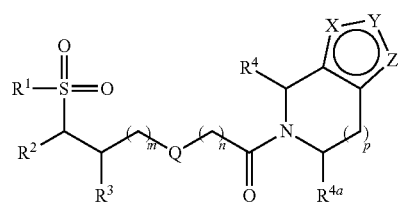

wherein m and n each independently represent 0, 1 or 2;

p represents 0, 1 or 2;

Q represents a single bond —CH$_2$— or —O—;

X represents N, NR$^5$, O, S or CR$^8$;

Y represents N, NR$^6$, O, S or CR$^9$;

Z represents N, NR$^7$, O, S or CR$^{10}$;

R$^1$ represents phenyl or naphthyl, unsubstituted or mono- or poly-substituted by identical or different substituents independently selected from the group consisting of methyl, methoxy, CF$_3$, OCF$_3$, F, Cl, and Br;

R$^2$ represents H, C$_{1-6}$-alkyl, C$_{3-8}$-cycloalkyl, bicyclic 8- to 12-membered carbocyclyl, CH(aryl)$_2$, aryl or heteroaryl; or a C$_{3-8}$-cycloalkyl, bicyclic 8- to 12-membered carbocyclyl, CH(aryl)$_2$, aryl or heteroaryl bonded via a C$_{1-6}$-alkylene group, C$_{2-6}$-alkenylene group or C$_{2-6}$-alkynylene group;

R$^3$ represents H, =C(=O)—NR$^{11}$R$^{12}$, —C(=O)—OR$^{13}$, C$_{1-6}$-alkyl, aryl or heteroaryl; or an aryl or heteroaryl bonded via a C$_{1-6}$-alkylene group, C$_{2-6}$-alkenylene group or C$_{2-6}$-alkynylene group, wherein R$^2$ and R$^3$ are not simultaneously H; or R$^2$ and R$^3$ together with the —N—(CH—)—group joining them form an unsubstituted or mono- or polysubstituted 4-, 5-, 6-, 7-membered heterocyclic ring, which optionally may be fused with an aryl or heteroaryl group, wherein said heterocyclic ring may be saturated or mono- or polyunsaturated but not aromatic, and optionally may contain, in addition to the N hetero atom to which R$^2$ is bonded, one or more further hetero atoms or hetero atom groups selected from the group consisting of N, NR$^{14}$, O, S, S=O or S(=O)$_2$; wherein R$^{14}$ denotes H, C$_{1-6}$-alkyl, =C(=O)—R$^{15}$, C$_{3-8}$-cycloalkyl, aryl, heteroaryl, or a C$_{3-8}$-cycloalkyl, aryl or heteroaryl bonded via a C$_{1-3}$-alkylene group, and R$^{15}$ denotes C$_{1-6}$-alkyl, C$_{3-8}$-cycloalkyl, aryl, heteroaryl, or a C$_{3-8}$-cycloalkyl, aryl or heteroaryl bonded via a C$_{1-3}$-alkylene group;

R$^4$ and R$^{4a}$ each independently represent H, C$_{1-6}$-alkyl, C$_{3-8}$-cycloalkyl, aryl, heteroaryl, or a C$_{3-8}$-cycloalkyl, aryl or heteroaryl bonded via a C$_{1-3}$-alkylene group;

R$^5$, R$^6$ and R$^7$ each independently represent H, C$_{1-6}$-alkyl, aryl or heteroaryl;

R$^8$, R$^9$ and R$^{10}$ each independently represent H, —CF$_3$, —C(=O)—NR$^{11}$R$^{12}$, —C$_{1-6}$-alkylene-C(=O)—NR$^{11}$R$^{12}$, —C$_{1-6}$-alkylene-NR$^{11}$R$^{12}$, C$_{3-8}$-cycloalkyl, 3- to 8-membered heterocycloalkyl, aryl or heteroaryl, or a C$_{3-8}$-cycloalkyl, 3- to 8-membered heterocycloalkyl, aryl or heteroaryl bonded via a C$_{3-6}$-alkylene group;

wherein at least one of $R^4$, $R^{4a}$, $R^5$, $R^6$, $R^7$, $R^8$, $R^9$ and $R^{10}$ is not H;

$R^{11}$ and $R^{12}$ each independently denote H, $C_{1-6}$-alkyl, $C_{2-6}$-alkenyl, $C_{3-8}$-cycloalkyl, 3- to 8-membered heterocycloalkyl, aryl or heteroaryl, or a $C_{3-8}$-cycloalkyl, 3- to 8-membered heterocycloalkyl, aryl or heteroaryl bonded via a $C_{1-3}$-alkylene group; or $R^{11}$ and $R^{12}$ together with the nitrogen atom joining them form an unsubstituted or mono- or polysubstituted 4-, 5-, 6- or 7-membered heterocyclic ring, which optionally may be fused with a saturated, mono- or polyunsaturated or aromatic, unsubstituted or mono- or polysubstituted, 4-, 5-, 6- or 7-membered ring system, wherein said heterocyclic ring may be saturated or mono- or polyunsaturated but not aromatic, and optionally may contain, in addition to the N hetero atom to which $R^{11}$ and $R^{12}$ are bonded, one or more further hetero atoms or hetero atom groups selected from the group consisting of N, $NR^{16}$, O, S, S=O and S(=O)$_2$, and said ring system optionally may contain one or more hetero atoms or hetero atom groups selected from the group consisting of N, $NR^{17}$, O, S, S=O and S(=O)$_2$;

$R^{16}$ represents H, $C_{1-6}$-alkyl, $C_{3-8}$-cycloalkyl, aryl, heteroaryl, or an aryl, heteroaryl or $C_{3-8}$-cycloalkyl bonded via a $C_{1-3}$-alkylene group; and $R^{17}$ represents H, $C_{3-8}$-cycloalkyl, aryl, heteroaryl, or an aryl, heteroaryl or $C_{3-8}$-cycloalkyl bonded via a $C_{1-3}$-alkylene group;

$R^{13}$ denotes H, $C_{1-6}$-alkyl, $C_{3-8}$-cycloalkyl, 3- to 8-membered heterocycloalkyl, aryl, heteroaryl, or a $C_{3-8}$-cycloalkyl, 3- to 8-membered heterocycloalkyl, aryl or heteroaryl bonded via a $C_{1-3}$-alkylene group;

wherein said $C_{1-6}$-alkyl, $C_{2-6}$-alkenyl, $C_{1-3}$-alkylene, $C_{1-6}$-alkylene, $C_{2-6}$-alkenylene, $C_{2-6}$-alkynylene, and $C_{3-8}$-cycloalkyl, groups may be unsubstituted or substituted one or more times by identical or different substituents selected from the group consisting of F, Cl, Br, I, CN, $NH_2$, NH—$C_{1-6}$-alkyl, NH—$C_{1-6}$-alkylene-OH, $C_{1-6}$-alkyl, $N(C_{1-6}$-alkyl)$_2$, $N(C_{1-6}$-alkylene-OH)$_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$alkyl, $CO_2H$, $CO_2$-$C_{1-6}$alkyl and benzyl;

said 3- to 8-membered heterocycloalkyl groups may be unsubstituted or substituted one or more times by identical or different substituents selected from the group consisting of F, Cl, Br, I, —CN, $NH_2$, NH—$C_{1-6}$-alkyl, NH—$C_{1-6}$-alkylene-OH, $C_{1-6}$-alkyl, $N(C_{1-6}$-alkyl)$_2$, $N(C_{1-6}$-alkylene-OH)$_2$, pyrrolinyl, piperazinyl, morpholinyl, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$alkyl, $CO_2H$, $CO_2$-$C_{1-6}$alkyl and benzyl; or, if a N heteroatom is present, the N heteroatom can be substituted by a $C_{1-6}$-alkyl, $C_{3-8}$-cycloalkyl, aryl, heteroaryl, or a $C_{3-8}$-cycloalkyl, aryl or heteroaryl bonded via a $C_{1-3}$-alkylene group, wherein these alkyl, cycloalkyl, alkylene and aryl and heteroaryl groups may each be unsubstituted or substituted one or more times by identical or different substituents;

said bicyclic 8- to 12-membered carbocyclyl groups may be unsubstituted, substituted on a saturated or partly unsaturated ring of the carbocyclyl one or more times by identical or different substituents selected from the group consisting of F, Cl, Br, I, CN, $NH_2$, NH—$C_{1-6}$-alkyl, NH—$C_{1-6}$-alkylene-OH, $C_{1-6}$-alkyl, $N(C_{1-6}$-alkyl)$_2$, $N(C_{1-6}$-alkylene-OH)$_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$alkyl, $CO_2H$, $CO_2$-$C_{1-6}$alkyl and benzyl, or substituted on an aromatic ring of the carbocyclyl one or more times by identical or different substituents selected from the group consisting of F, Cl, Br, I, CN, $NH_2$, NH—$C_{1-6}$-alkyl, NH—$C_{1-6}$-alkylene-OH, $N(C_{1-6}$-alkyl)$_2$, $N(C_{1-6}$-alkylene-OH)$_2$, NH-aryl$^1$, $N(aryl^1)_2$, $N(C_{1-6}$-alkyl)aryl$^1$, pyrrolinyl, piperazinyl, morpholinyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—$C(CH_3)_2$—$CH_2$—, unsubstituted $C_{1-6}$-alkyl, pyrrolidinyl, imidazolyl, piperidinyl, benzyloxy, phenoxy, phenyl, naphthyl, pyridinyl, —$C_{1-3}$-alkylene-aryl$^1$, benzyl, thienyl, and furyl, wherein aryl$^1$ represents phenyl, furyl, thienyl or pyridinyl and the abovementioned substituents can optionally be substituted by the same substituents;

said aryl and heteroaryl groups may be unsubstituted or substituted one or more times by identical or different substituents selected from the group consisting of F, Cl, Br, I, CN, $NH_2$, NH—$C_{1-6}$-alkyl, NH—$C_{1-6}$-alkylene-OH, $N(C_{1-6}$-alkyl)$_2$, $N(C_{1-6}$-alkylene-OH)$_2$, NH-aryl$^1$, $N(aryl^1)_2$, $N(C_{1-6}$-alkyl)aryl$^1$, pyrrolinyl, piperazinyl, morpholinyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—$C(CH_3)_2$—$CH_2$—O—$CH_2$—O—, —O—$Ch_2$—O—$CH_2$, unsubstituted $C_{1-6}$-alkyl, pyrrolidinyl, imidazolyl, piperidinyl, benzyloxy, phenoxy, phenyl, naphthyl, pyridinyl, —$C_{1-3}$-alkylene-aryl$^1$, benzyl, thienyl, and furyl, wherein aryl$^1$ represents phenyl, furyl, thienyl or pyridinyl and the abovementioned substituents can optionally be substituted by the same substituents;

the substituents of a substituted heterocyclic ring are independently selected from the group consisting of F, Cl, Br, I, CN, $NH_2$, NH—$C_{1-6}$-alkyl, NH—$C_{1-6}$-alkylene-OH, $C_{1-6}$-alkyl, $N(C_{1-6}$-alkyl)$_2$, $N(C_{1-6}$-alkylene-OH)$_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$alkyl, $CO_2H$, $CO_2$-$C_{1-6}$alkyl and benzyl;

the substituents of a substituted, saturated or at least partly unsaturated ring system which is fused with a heterocyclic ring formed by $R^{11}$ and $R^{12}$ are independently selected from the group consisting of F, Cl, Br, I, CN, $NH_2$, NH—$C_{1-6}$-alkyl, NH—$C_{1-6}$-alkylene-OH, $C_{1-6}$-alkyl, $N(C_{1-6}$-alkyl)$_2$, $N(C_{1-6}$-alkylene-OH)$_2$, $NO_2$, SH, S—$C_{1-6}$-alkyl, S-benzyl, O—$C_{1-6}$-alkyl, OH, O—$C_{1-6}$-alkylene-OH, =O, O-benzyl, C(=O)$C_{1-6}$alkyl, $CO_2H$, $CO_2$-$C_{1-6}$alkyl and benzyl;

the substituents of a substituted aromatic ring system which is fused with a heterocyclic ring formed by $R^{11}$ and $R^{12}$ are independently selected from the group consisting of F, Cl, Br, I, CN, $NH_2$, NH—$C_{1-6}$-alkyl, NH—$C_{1-6}$-alkylene-OH, $N(C_{1-6}$-alkyl)$_2$, $N(C_{1-6}$-alkylene-OH)$_2$, NH-aryl$^1$, $N(aryl^1)_2$, $N(C_{1-6}$-alkyl)aryl$^1$, pyrrolinyl, piperazinyl, morpholinyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—$C(CH_3)_2$—$CH_2$—$CH_2$—, —$CH_2$—O—$CH_2$—O—, —O—$CH_2$—O—$CH_2$—, unsubstituted $C_{1-6}$-alkyl, pyrrolidinyl, imidazolyl, piperidinyl, benzyloxy, phenoxy, phenyl, naphthyl, pyridinyl, —$C_{1-3}$-alkylene-$aryl^1$, benzyl, thienyl, and furyl, wherein $aryl^1$ represents phenyl, furyl, thienyl or pyridinyl and the abovementioned substituents can optionally be substituted by the same substituents; and said $C_{1-6}$-alkyl, $C_{2-6}$-alkenyl, $C_{1-3}$-alkylene, $C_{1-6}$-alkylene, $C_{2-6}$-alkenylene and $C_{2-6}$-alkynylene groups may each be branched or unbranched;

or a physiologically acceptable salt or N-oxide thereof, and at least one pharmaceutically acceptable carrier or auxiliary substance.

19. A method of treating or inhibiting a condition selected from the group consisting of pain, migraine, diabetes, respiratory tract diseases, inflammatory intestinal diseases, neurological diseases, skin inflammations, rheumatic diseases, septic shock, reperfusion syndrome and obesity, or of inhibiting angiogenesis, in a subject in need thereof, said method comprising administering to said human a pharmacologically effective amount of a compound as claimed in claim 1.

20. A method as claimed in claim 19, wherein said condition is pain selected from the group consisting of acute pain, visceral pain, neuropathic pain, chronic pain and inflammatory pain.

* * * * *